United States Patent
Kugimiya et al.

(10) Patent No.: US 8,993,763 B2
(45) Date of Patent: *Mar. 31, 2015

(54) SULFONAMIDE DERIVATIVE HAVING PGD2 RECEPTOR ANTAGONISTIC ACTIVITY

(75) Inventors: Akira Kugimiya, Osaka (JP); Masahiko Fujioka, Osaka (JP); Yuki Tachibana, Osaka (JP); Takami Murashi, Osaka (JP); Naohiro Onodera, Osaka (JP)

(73) Assignee: Shionogi & Co., Ltd., Osaka (JP)

( * ) Notice: Subject to any disclaimer, the term of this patent is extended or adjusted under 35 U.S.C. 154(b) by 821 days.

This patent is subject to a terminal disclaimer.

(21) Appl. No.: 11/992,602

(22) PCT Filed: Sep. 25, 2006

(86) PCT No.: PCT/JP2006/318917
§ 371 (c)(1),
(2), (4) Date: Mar. 26, 2008

(87) PCT Pub. No.: WO2007/037187
PCT Pub. Date: Apr. 5, 2007

(65) Prior Publication Data
US 2010/0063040 A1 Mar. 11, 2010

(30) Foreign Application Priority Data

Sep. 27, 2005 (JP) .................. 2005-280532
Mar. 8, 2006 (JP) .................. 2006-062617

(51) Int. Cl.
*C07D 295/26* (2006.01)
*C07D 417/12* (2006.01)
(Continued)

(52) U.S. Cl.
CPC ............ *C07D 207/14* (2013.01); *C07D 207/48* (2013.01); *C07D 211/58* (2013.01); *C07D 211/70* (2013.01); *C07D 211/96* (2013.01); *C07D 213/38* (2013.01); *C07D 213/40* (2013.01); *C07D 213/64* (2013.01); *C07D 213/71* (2013.01); *C07D 213/74* (2013.01); *C07D 231/12* (2013.01); *C07D 231/40* (2013.01); *C07D 235/08* (2013.01); *C07D 235/30* (2013.01); *C07D 235/32* (2013.01); *C07D 243/08* (2013.01); *C07D 261/08* (2013.01); *C07D 261/18* (2013.01); *C07D 263/32* (2013.01); *C07D 263/58* (2013.01); *C07D 265/36* (2013.01); *C07D 271/10* (2013.01); *C07D 277/24* (2013.01); *C07D 277/28* (2013.01); *C07D 285/12* (2013.01); *C07D 285/135* (2013.01);
(Continued)

(58) Field of Classification Search
CPC .. C07D 295/26; C07D 417/12; C07D 413/10; C07D 407/10

USPC .......................... 544/383, 369, 379
See application file for complete search history.

(56) References Cited

U.S. PATENT DOCUMENTS 4,616,086 A 10/1986 Witte et al.
5,411,972 A 5/1995 Komoto et al.
(Continued)

FOREIGN PATENT DOCUMENTS

EP 0 076 996 4/1983
EP 0 607 536 11/1993
(Continued)

OTHER PUBLICATIONS

Vippagunta et al.; "Crystalline solids"; 2001; Advanced Drug Delivery Reviews; 48: 3-26.*
(Continued)

*Primary Examiner* — Timothy Thomas
(74) *Attorney, Agent, or Firm* — Wenderoth, Lind & Ponack, L.L.P.

(57) ABSTRACT

The present invention provides an sulfonamide derivative having DP receptor antagonistic activity and a pharmaceutical composition comprising the said compound as an active ingredient, and further a therapeutic agent for treating allergic diseases.
A compound of the general formula (II):

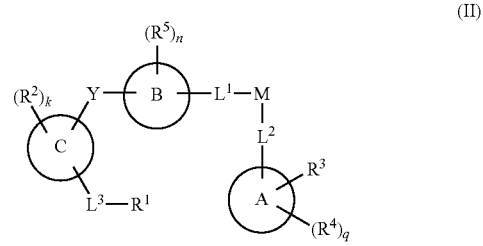

wherein the ring A is an aromatic carbocyclic ring etc.; the ring B is a nitrogen-containing non-aromatic heterocyclic ring etc.; the ring C is an aromatic carbocyclic ring etc.; R1 is carboxy etc.; R2 is independently a halogen atom etc.; R3 is optionally substituted alkyloxy etc.; R4 is independently a halogen atom etc.; R5 is independently optionally substituted alkyl etc.; M is sulfonyl etc.; Y is a single bond etc.; L1 is a single bond etc.; L2 is a single bond etc.; k is 0, 1, 2, 3 or 4; n is 0, 1 or 2; and q is 0, 1, 2 or 3; provided that a) k is not 0 when the ring B is a 6-membered nitrogen-containing heterocyclic ring containing one or two nitrogen atom(s) and the ring C is a benzene ring, etc.;
a pharmaceutically acceptable salt or a hydrate thereof.

4 Claims, No Drawings

(51) Int. Cl.

| | | |
|---|---|---|
| *C07D 413/10* | (2006.01) | |
| *C07D 407/10* | (2006.01) | |
| *C07D 207/14* | (2006.01) | |
| *C07D 207/48* | (2006.01) | |
| *C07D 211/58* | (2006.01) | |
| *C07D 211/70* | (2006.01) | |
| *C07D 211/96* | (2006.01) | |
| *C07D 213/38* | (2006.01) | |
| *C07D 213/40* | (2006.01) | |
| *C07D 213/64* | (2006.01) | |
| *C07D 213/71* | (2006.01) | |
| *C07D 213/74* | (2006.01) | |
| *C07D 231/12* | (2006.01) | |
| *C07D 231/40* | (2006.01) | |
| *C07D 235/08* | (2006.01) | |
| *C07D 235/30* | (2006.01) | |
| *C07D 235/32* | (2006.01) | |
| *C07D 243/08* | (2006.01) | |
| *C07D 261/08* | (2006.01) | |
| *C07D 261/18* | (2006.01) | |
| *C07D 263/32* | (2006.01) | |
| *C07D 263/58* | (2006.01) | |
| *C07D 265/36* | (2006.01) | |
| *C07D 271/10* | (2006.01) | |
| *C07D 277/24* | (2006.01) | |
| *C07D 277/28* | (2006.01) | |
| *C07D 285/12* | (2006.01) | |
| *C07D 285/135* | (2006.01) | |
| *C07D 295/096* | (2006.01) | |
| *C07D 295/155* | (2006.01) | |
| *C07D 307/42* | (2006.01) | |
| *C07D 307/52* | (2006.01) | |
| *C07D 307/56* | (2006.01) | |
| *C07D 307/68* | (2006.01) | |
| *C07D 333/36* | (2006.01) | |
| *C07D 401/12* | (2006.01) | |
| *C07D 413/12* | (2006.01) | |

(52) U.S. Cl.
 CPC ....... *C07D 295/096* (2013.01); *C07D 295/155* (2013.01); *C07D 295/26* (2013.01); *C07D 307/42* (2013.01); *C07D 307/52* (2013.01); *C07D 307/56* (2013.01); *C07D 307/68* (2013.01); *C07D 333/36* (2013.01); *C07D 401/12* (2013.01); *C07D 413/12* (2013.01)
 USPC ............................ 544/383; 544/369; 544/379

(56) References Cited

U.S. PATENT DOCUMENTS

| 5,532,371 | A | 7/1996 | Komoto et al. | |
|---|---|---|---|---|
| 5,753,658 | A | 5/1998 | Ogata et al. | |
| 7,179,912 | B2 | 2/2007 | Halbrook et al. | |
| 2001/0051624 | A1 | 12/2001 | Jones | |
| 2003/0055077 | A1 | 3/2003 | Jones | |
| 2005/0113373 | A1* | 5/2005 | Van Emelen et al. | 514/242 |
| 2006/0223829 | A1 | 10/2006 | Aertgeerts et al. | |

FOREIGN PATENT DOCUMENTS

| EP | 1 486 491 | 12/2004 |
|---|---|---|
| EP | 1 505 061 | 2/2005 |
| EP | 1 820 798 | 8/2007 |
| JP | 57-77676 | 5/1982 |
| JP | 58-83678 | 5/1983 |
| JP | 58-88314 | 5/1983 |
| JP | 61-44817 | 3/1986 |
| JP | 63-146871 | 6/1988 |
| JP | 64-61468 | 3/1989 |
| JP | 1-117865 | 5/1989 |
| JP | 3-141258 | 6/1991 |
| JP | 7-219168 | 8/1995 |
| JP | 2009-55295 | 3/2009 |
| JP | 2009-55298 | 3/2009 |
| WO | 93/12086 | 6/1993 |
| WO | 98/50029 | 11/1998 |
| WO | 99/37304 | 7/1999 |
| WO | 99/47508 | 9/1999 |
| WO | 01/07050 | 2/2001 |
| WO | 01/07436 | 2/2001 |
| WO | 01/12186 | 2/2001 |
| WO | 01/46164 | 6/2001 |
| WO | 01/78697 | 12/2001 |
| WO | 02/06221 | 1/2002 |
| WO | 02/06255 | 1/2002 |
| WO | 02/20500 | 3/2002 |
| WO | 03/007954 | 1/2003 |
| WO | 03/076422 | 9/2003 |
| WO | 2004/073606 | 9/2004 |
| WO | 2004/089884 | 10/2004 |
| WO | 2004/089885 | 10/2004 |
| WO | WO 2004092117 A1 * | 10/2004 |
| WO | 2004/106302 | 12/2004 |
| WO | 2006/016680 | 2/2006 |
| WO | 2006/021418 | 3/2006 |
| WO | 2006/056752 | 6/2006 |
| WO | 2006/095822 | 9/2006 |
| WO | 2006/105127 | 10/2006 |
| WO | 2006/124875 | 11/2006 |

OTHER PUBLICATIONS

Kabashima et al.; "The DP receptor, allergic inflammation and asthma"; 2003; Prostaglandins, Leukotrienes and Essential Fatty Acids; 69: 187-194.*

Rodriguez-Vita et al.; "Resolution of inflammation and cancer"; 2010; Cytokine & Growth Factor Reviews; 21: 61-75.*

Wermuth; "13. Molecular Variations Based on Isosteric Replacements"; 1996; The Practice of Medicinal Chemistry; Academic Press Limited ISBN 0-12-744640-0; pp. 203-237.*

Hawcroft et al.; "Expression of prostaglandin D2 receptors DP1 and DP2 by human colorectal cancer cells"; 2004; Cancer Letters; 210: 81-84.*

Fuk-Wah Sum et al., "Cyclic Amine Sulfonamides as Linkers in the Design and Synthesis of Novel Human $\beta_3$ Adrenergic Receptor Agonists", Bioorganic & Medicinal Chemistry Letters, vol. 13, No. 13, pp. 2191-2194, 2003.

Ahmed Kamal et al., "Synthesis and DNA-Binding Affinity of A-C8/C-C2 Alkoxyamido-Linked Pyrrolo[2,1-c] [1,4]benzodiazepine Dimers", Bioorganic & Medicinal Chemistry Letters, vol. 13, No. 22, pp. 3955-3958, 2003.

Scott L. Cockroft et al., "Electrostatic Control of Aromatic Stacking Interactions", J. Am. Chem. Soc., vol. 127, No. 24, pp. 8594-8595, 2005.

Complete English translation of JP 2002-506859 published Mar. 5, 2002.

International Search Report issued Dec. 26, 2006 in the International (PCT) Application PCT/JP2006/318917 of which the present application is the U.S. National Stage.

Robert A. Coleman et al., "VIII. International Union of Pharmacology Classification of Prostanoid Receptors: Properties, Distribution, and Structure of the Receptors and Their Subtypes", Pharmacological Reviews, vol. 46, No. 2, pp. 205-229, 1994.

Masakazu Sato et al., "Synthesis and Evaluation of Novel Thiazolidine Derivatives as Thromboxane $A_2$ Receptor Antagonists", Chem. Pharm. Bull., 42(3), pp. 521-529, 1994.

Teruo Komoto et al., "New Strong Fibrates with Piperidine Moiety", Chem. Pharm. Bull., 48(12), pp. 1978-1985, 2000.

Hiroyuki Hirai, "Allegry to PGD2", Folia Pharmacol. Jpn., 123, pp. 15-22, 2004.

RN compounds, SciFinder, pp. 1-3, RN 896524-61-1, RN 896524-52-0 and RN 852678-27-4, May 10, 2006.

English language abstract of JP 3-275678, Dec. 1991.

(56) References Cited

OTHER PUBLICATIONS

English language abstract of JP 3-275679, Dec. 1991.
USPTO English translation of Komo et al. (WO 93/12086), Feb. 2011.
European Search Report issued Dec. 12, 2011 in corresponding European Application No. 11 00 8295, in the English language.
Ciuguranu Constatin et al., "New di-heterocyclic benzofuran and benzimidazole derivatives", Revista De Chimie, Bucharest, RO, vol. 56, No. 8, pp. 817-820 (2005).
Quiroz Andres et al., "Reaction of 7-substituted 4-hydroxyl-1,4-benzoxazin-3-ones in strongly acidic media", Heterocycles, Elsevier Science Publishers B. V. Amsterdam, NL, vol. 32, No. 9, pp. 1681-1685 (1991).

Eckstein Zygmunt et al., "Nitration products of the esters of 2,4- and 2,5-dichloro- and 2,4- and 2,5-dibromophenoxyacetic acids", Przemysl Chemiczny, Wydawnictwo Sigma, PL, vol. 43, No. 4, pp. 216-218 (1964).
G. G. Clarke et al., "Studies on plant growth-regulating substances. XVII. Chloromethylphenoxyacetic acids and chloromethylphenylglycines", Ann. Appl. Biol., pp. 453-458 (1963).
Werner Lowe et al., "Neue Synthese aromatischer Carbonsauren aus Enaminonen", Arch. Pharm., pp. 283-285 (1995).
Satendra Singh et al., "Synthesis and Ligand Binding Studies of 4-Iodobenzoyl Esters of Tropanes and Piperidines at the Dopamine Transporter", J. Med. Chem., pp. 2474-2481 (1997).

\* cited by examiner

SULFONAMIDE DERIVATIVE HAVING PGD2 RECEPTOR ANTAGONISTIC ACTIVITY

TECHNICAL FIELD

This invention relates to a sulfonamide derivative having DP receptor antagonistic activity and a medicinal use thereof.

BACKGROUND ART

Prostaglandin D2 (PGD2) is a metabolic product of arachidonic acid through PGG2 and PGH2, and known to have various potent physiological activities. For example, in non-patent literature 1 it is described that PGD2 is involved in sleeping and secretion of hormones in central nervous system, and in inhibiting activity of platelet aggregation, contraction of bronchial smooth muscle, vasodilation and constriction of a blood vessel etc. in peripheral system. Moreover, PGD2 is considered to be involved in forming pathological condition of an allergic disease such as bronchial asthma since it is a major metabolic product of arachidonic acid produced from a mast cell, and has a potent bronchoconstricting effect, causing an increase of vascular permeability and migration of inflammatory cell such as eosinophils.

A DP receptor (also called DP1 receptor) or CRTH2 receptor (also called DP2 receptor) is known as a receptor of PGD2. A phenylacetic acid derivative having a DP receptor antagonistic activity is disclosed in Patent literature 1, a sulfonamide derivative having a CRTH2 receptor antagonistic activity is disclosed in Patent literature 2 and a phenoxyacetic acid derivative having a CRTH2 receptor antagonistic activity is disclosed in Patent literatures 3-6.

Also, sulfonamide derivatives having an activity other than the PGD2 receptor antagonistic activity are disclosed in Patent literatures 7-12 and Non-patent literatures 2-3.

Patent literature 1: WO 2003/078409 Pamphlet
Patent literature 2: WO 2003/097598 Pamphlet
Patent literature 3: WO 2004/089884 Pamphlet
Patent literature 4: WO 2004/089885 Pamphlet
Patent literature 5: WO 2005/106302 Pamphlet
Patent literature 6: WO 2006/056752 Pamphlet
Patent literature 7: WO 1993/012086 Pamphlet
Patent literature 8: WO 2004/073606 Pamphlet
Patent literature 9: EP 76996A Pamphlet
Patent literature 10: WO 2006/059801 Pamphlet
Patent literature 11: JP 3-275678A Pamphlet
Patent literature 12: JP 3-275679A Pamphlet
Non patent literature 1: Pharmacol. Rev., 1994, Vol. 46, p. 205-22
Non patent literature 2: Chem. & Pharm. Bull., 1994, Vol. 42, p. 521-29
Non patent literature 3: Chem. & Pharm. Bull., 2000, Vol. 48, p. 1978-85

DISCLOSURE OF INVENTION

Problem to be Solved

The present invention provides a sulfonamide derivative having DP receptor antagonistic activity and a pharmaceutical composition comprising the said compound as an active ingredient. The said pharmaceutical composition is useful as a therapeutic agent for treating allergic diseases.

Means for Solving Problem

The present inventors have found that the sulfonamide derivative shown below has a potent DP receptor antagonistic activity and the pharmaceutical composition comprising the said compound as an active ingredient is useful as a therapeutic agent for treating allergic diseases.

The present invention relates to
1) a PGD2 receptor antagonist comprising a compound of the general formula (I):

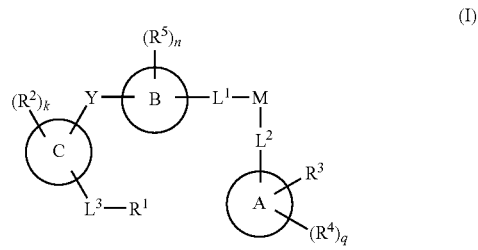

wherein the ring A is an aromatic carbocyclic ring or an aromatic heterocyclic ring;
the ring B is a nitrogen-containing non-aromatic heterocyclic ring or a nitrogen-containing aromatic heterocyclic ring;
the ring C is an aromatic carbocyclic ring or an aromatic heterocyclic ring;
$R^1$ is hydroxyalkyl, carboxy, alkyloxycarbonyl, optionally substituted carbamoyl, cyano or a carboxy equivalent;
$R^2$ is independently a halogen atom, optionally substituted alkyl, optionally substituted alkenyl, optionally substituted alkynyl, optionally substituted cycloalkyl, optionally substituted cycloalkenyl, hydroxy, optionally substituted alkyloxy, optionally substituted alkenyloxy, optionally substituted alkynyloxy, optionally substituted cycloalkyloxy, optionally substituted cycloalkenyloxy, mercapto, optionally substituted alkylthio, optionally substituted alkenylthio, optionally substituted alkynylthio, optionally substituted alkylsulfinyl, optionally substituted alkylsulfonyl, optionally substituted alkylsulfonyloxy, optionally substituted cycloalkylthio, optionally substituted cycloalkylsulfinyl, optionally substituted cycloalkylsulfonyl, optionally substituted cycloalkylsulfonyloxy, optionally substituted cycloalkenylthio, optionally substituted cycloalkenylsulfinyl, optionally substituted cycloalkenylsulfonyl, optionally substituted cycloalkenylsulfonyloxy, optionally substituted amino, acyl, optionally substituted alkyloxycarbonyl, optionally substituted alkenyloxycarbonyl, optionally substituted alkynyloxycarbonyl, optionally substituted aryloxycarbonyl, optionally substituted carbamoyl, optionally substituted sulfamoyl, cyano, nitro, optionally substituted aryl, optionally substituted aryloxy, optionally substituted arylthio, optionally substituted arylsulfinyl, optionally substituted arylsulfonyl, optionally substituted arylsulfonyloxy, optionally substituted heteroaryl, optionally substituted heteroaryloxy, optionally substituted heteroarylthio, optionally substituted heteroarylsulfinyl, optionally substituted heteroarylsulfonyl, optionally substituted heteroarylsulfonyloxy or an optionally substituted non-aromatic heterocyclic group;
$R^3$ is a hydrogen atom, optionally substituted alkyloxy, optionally substituted alkenyloxy, optionally substituted alkynyloxy, optionally substituted cycloalkyloxy, optionally substituted cycloalkenyloxy, optionally substituted aryloxy, optionally substituted heteroaryloxy, optionally substituted alkylthio, optionally substituted alkenylthio, optionally substituted alkynylthio, optionally substituted cycloalkylthio, optionally substituted cycloalkenylthio, optionally substituted arylthio or optionally substituted heteroarylthio;

R⁴ is independently a halogen atom, optionally substituted alkyl, optionally substituted alkenyl, optionally substituted alkynyl, optionally substituted cycloalkyl, optionally substituted cycloalkenyl, hydroxy, optionally substituted alkyloxy, optionally substituted alkenyloxy, optionally substituted alkynyloxy, optionally substituted cycloalkyloxy, optionally substituted cycloalkenyloxy, mercapto, optionally substituted alkylthio, optionally substituted alkenylthio, optionally substituted alkynylthio, optionally substituted alkylsulfinyl, optionally substituted alkylsulfonyl, optionally substituted alkylsulfonyloxy, optionally substituted cycloalkylthio, optionally substituted cycloalkylsulfinyl, optionally substituted cycloalkylsulfonyl, optionally substituted cycloalkylsulfonyloxy, optionally substituted cycloalkenylthio, optionally substituted cycloalkenylsulfinyl, optionally substituted cycloalkenylsulfonyl, optionally substituted cycloalkenylsulfonyloxy, optionally substituted amino, acyl, optionally substituted alkyloxycarbonyl, optionally substituted alkenyloxycarbonyl, optionally substituted alkynyloxycarbonyl, optionally substituted aryloxycarbonyl, optionally substituted carbamoyl, optionally substituted sulfamoyl, cyano, nitro, optionally substituted aryl, optionally substituted aryloxy, optionally substituted arylthio, optionally substituted arylsulfinyl, optionally substituted arylsulfonyl, optionally substituted arylsulfonyloxy, optionally substituted heteroaryl, optionally substituted heteroaryloxy, optionally substituted heteroarylthio, optionally substituted heteroarylsulfinyl, optionally substituted heteroarylsulfonyl, optionally substituted heteroarylsulfonyloxy or an optionally substituted non-aromatic heterocyclic group;

R⁵ is independently a halogen atom, optionally substituted alkyl, optionally substituted alkenyl, optionally substituted alkynyl, optionally substituted cycloalkyl, optionally substituted alkyloxy, oxo, optionally substituted aryl, optionally substituted heteroaryl or an optionally substituted non-aromatic heterocyclic group;

M is carbonyl or sulfonyl;

Y is a single bond, optionally substituted alkylene optionally containing one or two heteroatom(s), an oxygen atom, a sulfur atom or —N(R⁶)—;

L¹, L² and L³ are independently a single bond, optionally substituted alkylene optionally containing one or two heteroatom(s), optionally substituted alkenylene optionally containing one or two heteroatom(s), optionally substituted alkynylene optionally containing one or two heteroatom(s) or —N(R⁷)—;

R⁶ and R⁷ are independently a hydrogen atom, optionally substituted alkyl, optionally substituted alkenyl, optionally substituted alkynyl, optionally substituted cycloalkyl, acyl, optionally substituted alkyloxy, optionally substituted aryl, optionally substituted heteroaryl or an optionally substituted non-aromatic heterocyclic group;

k is 0, 1, 2, 3 or 4;

n is 0, 1 or 2; and q is 0, 1, 2 or 3; provided that a) k is not 0 when the ring B is a 6-membered nitrogen-containing heterocyclic ring containing one or two nitrogen atom(s), and the ring C is a benzene ring, b) the ring C is not an indole ring or an azaindole ring, c) R¹ is not carboxy when the ring C is a benzene ring, -L³- is —(O-alkylene)-, and the substituting position of L³ and Y is an ortho-position each other in the ring C, and d) the substituting position of L³ and Y is not a para-position in the ring C when the ring B is a thiazolidine ring and the ring C is a benzene ring;

a pharmaceutically acceptable salt or solvate thereof as an active ingredient, 2) a PGD2 receptor antagonist of 1) wherein R¹ is carboxy and -L³- is —(O-optionally substituted alkylene)-, 3) a PGD2 receptor antagonist of 1) or 2) wherein the ring C is a benzene ring or a pyridine ring, 4) a PGD2 receptor antagonist of any of 1) to 3) wherein R³ is optionally substituted alkyloxy or optionally substituted alkylthio, 5) a PGD2 receptor antagonist of any of 1) to 4) wherein M is sulfonyl, 6) a PGD2 receptor antagonist of any of 1) to 5) wherein M is sulfonyl, L¹ is a single bond and L² is a single bond, 7) a PGD2 receptor antagonist of any of 1) to 6) wherein Y is a single bond, 8) a PGD2 receptor antagonist of any of 1) to 7) wherein R² is a halogen atom, optionally substituted alkyl, optionally substituted alkyloxy, optionally substituted amino, optionally substituted carbamoyl, optionally substituted aryl, optionally substituted heteroaryl or an optionally substituted non-aromatic heterocyclic group, and k is 1 or 2, 9) a PGD2 receptor antagonist of any of 1) to 7) wherein R² is a halogen atom, optionally substituted amino, optionally substituted carbamoyl, optionally substituted aryl, optionally substituted heteroaryl or an optionally substituted non-aromatic heterocyclic group, and k is 1 or 2, 10) a PGD2 receptor antagonist of any of 1) to 9) wherein R⁴ is a halogen atom, optionally substituted alkyl or optionally substituted alkyloxy, and q is 0 or 1, 11) a PGD2 receptor antagonist of any of 1) to 10) wherein the substituting position of Y and L³ is a meta-position in the ring C, 12) a PGD2 receptor antagonist of any of 1) to 11) which is a therapeutic agent for allegy, 13) a PGD2 receptor antagonist of any of 1) to 11) which is a therapeutic agent for asthma, 14) a compound of the general formula (II):

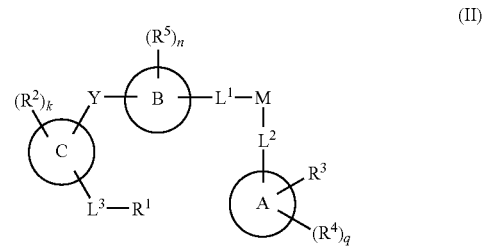

wherein the ring A is an aromatic carbocyclic ring or an aromatic heterocyclic ring;

the ring B is a nitrogen-containing non-aromatic heterocyclic ring or a nitrogen-containing aromatic heterocyclic ring;

the ring C is an aromatic carbocyclic ring or an aromatic heterocyclic ring;

R¹ is hydroxyalkyl, carboxy, alkyloxycarbonyl, optionally substituted carbamoyl, cyano or a carboxy equivalent;

R² is independently a halogen atom, optionally substituted alkyl, optionally substituted alkenyl, optionally substituted alkynyl, optionally substituted cycloalkyl, optionally substituted cycloalkenyl, hydroxy, optionally substituted alkyloxy, optionally substituted alkenyloxy, optionally substituted alkynyloxy, optionally substituted cycloalkyloxy, optionally substituted cycloalkenyloxy, mercapto, optionally substituted alkylthio, optionally substituted alkenylthio, optionally substituted alkynylthio, optionally substituted alkylsulfinyl, optionally substituted alkylsulfonyl, optionally substituted alkylsulfonyloxy, optionally substituted cycloalkylthio, optionally substituted cycloalkylsulfinyl, optionally substituted cycloalkylsulfonyl, optionally substituted cycloalkylsulfonyloxy, optionally substituted cycloalkenylthio, optionally substituted cycloalkenylsulfinyl, optionally substituted cycloalkenylsulfonyl, optionally substituted cycloalkenylsulfonyloxy, optionally substituted amino, acyl, optionally substituted alkyloxycarbonyl, optionally substituted alkenyloxycarbonyl, optionally substituted alkynyloxycarbonyl, optionally substituted aryloxycarbonyl, optionally substituted carbamoyl, optionally substituted sulfamoyl, cyano, nitro, optionally substituted aryl, optionally substituted aryloxy, optionally substituted arylthio, optionally substituted arylsulfinyl, optionally substituted arylsulfonyl, optionally substituted arylsulfonyloxy, optionally substituted heteroaryl, optionally substituted heteroaryloxy, optionally substituted heteroarylthio, optionally substituted heteroarylsulfinyl, optionally substituted heteroarylsulfonyl, optionally substituted heteroarylsulfonyloxy or an optionally substituted non-aromatic heterocyclic group;

$R^3$ is a hydrogen atoms, optionally substituted alkyloxy, optionally substituted alkenyloxy, optionally substituted alkynyloxy, optionally substituted cycloalkyloxy, optionally substituted cycloalkenyloxy, optionally substituted aryloxy, optionally substituted heteroaryloxy, optionally substituted alkylthio, optionally substituted alkenylthio, optionally substituted alkynylthio, optionally substituted cycloalkylthio, optionally substituted cycloalkenylthio, optionally substituted arylthio or optionally substituted heteroarylthio;

$R^4$ is independently a halogen atom, optionally substituted alkyl, optionally substituted alkenyl, optionally substituted alkynyl, optionally substituted cycloalkyl, optionally substituted cycloalkenyl, hydroxy, optionally substituted alkyloxy, optionally substituted alkenyloxy, optionally substituted alkynyloxy, optionally substituted cycloalkyloxy, optionally substituted cycloalkenyloxy, mercapto, optionally substituted alkylthio, optionally substituted alkenylthio, optionally substituted alkynylthio, optionally substituted alkylsulfinyl, optionally substituted alkylsulfonyl, optionally substituted alkylsulfonyloxy, optionally substituted cycloalkylthio, optionally substituted cycloalkylsulfinyl, optionally substituted cycloalkylsulfonyl, optionally substituted cycloalkylsulfonyloxy, optionally substituted cycloalkenylthio, optionally substituted cycloalkenylsulfinyl, optionally substituted cycloalkenylsulfonyl, optionally substituted cycloalkenylsulfonyloxy, optionally substituted amino, acyl, optionally substituted alkyloxycarbonyl, optionally substituted alkenyloxycarbonyl, optionally substituted alkynyloxycarbonyl, optionally substituted aryloxycarbonyl, optionally substituted carbamoyl, optionally substituted sulfamoyl, cyano, nitro, optionally substituted aryl, optionally substituted aryloxy, optionally substituted arylthio, optionally substituted arylsulfinyl, optionally substituted arylsulfonyl, optionally substituted arylsulfonyloxy, optionally substituted heteroaryl, optionally substituted heteroaryloxy, optionally substituted heteroarylthio, optionally substituted heteroarylsulfinyl, optionally substituted heteroarylsulfonyl, optionally substituted heteroarylsulfonyloxy or an optionally substituted non-aromatic heterocyclic group;

$R^5$ is independently a halogen atom, optionally substituted alkyl, optionally substituted alkenyl, optionally substituted alkynyl, optionally substituted cycloalkyl, optionally substituted alkyloxy, oxo, optionally substituted aryl, optionally substituted heteroaryl or optionally substituted non-aromatic heterocyclic group;

M is carbonyl or sulfonyl;

Y is a single bond, optionally substituted alkylene optionally containing one or two heteroatom(s), an oxygen atom, a sulfur atom or —N($R^6$)—;

$L^1$, $L^2$ and $L^3$ are independently a single bond, optionally substituted alkylene optionally containing one or two heteroatom(s), optionally substituted alkenylene optionally containing one or two heteroatom(s), optionally substituted alkynylene optionally containing one or two heteroatom(s) or —N($R^7$)—;

$R^6$ and $R^7$ are independently a hydrogen atom, optionally substituted alkyl, optionally substituted alkenyl, optionally substituted alkynyl, optionally substituted cycloalkyl, acyl, optionally substituted alkyloxy, optionally substituted aryl, optionally substituted heteroaryl or an optionally substituted non-aromatic heterocyclic group;

k is 0, 1, 2, 3 or 4;
n is 0, 1 or 2; and
q is 0, 1, 2 or 3; provided that a) k is not 0 when the ring B is a 6-membered nitrogen-containing heterocyclic ring containing one or two nitrogen atom(s), and the ring C is a benzene ring, b) the ring C is not an indole ring or an azaindole ring, c) Y, $L^1$ and $L^2$ are single bonds, the ring B is piperazine ring and $R^3$ is C2-C4 alkyloxy when the ring C is a benzene ring, -$L^3$- is —(O-alkylene)-, the substituting position of $L^3$ and Y is an ortho-position each other in the ring C and $R^1$ is carboxy, d) the substituting position of $L^3$ and Y is not a para-position in the ring C when the ring B is a thiazolidine ring and the ring C is a benzene ring, and e) the group of the formula of

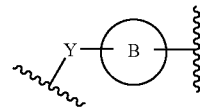

is not a group of the formula of

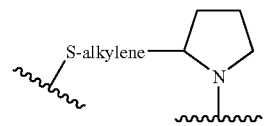

when the ring C is a benzene ring, -$L^3$- is —(O-alkylene)- and the substituting position of $L^3$ and Y is a para-position in the ring C, and f) the ring B is not a diazepindione ring;
a pharmaceutically acceptable salt or solvate thereof,
15) a compound of 14) wherein $R^1$ is carboxy and -$L^3$- is —(O-optionally substituted alkylene)-;
a pharmaceutically acceptable salt or solvate thereof,
16) a compound of 14) or 15) wherein the ring C is a benzene ring or a pyridine ring;
a pharmaceutically acceptable salt or solvate thereof,
17) a compound of any of 14) to 16) wherein $R^3$ is optionally substituted alkyloxy or optionally substituted alkylthio;
a pharmaceutically acceptable salt or solvate thereof,
18) a compound of any of 14) to 17) wherein M is sulfonyl;
a pharmaceutically acceptable salt or solvate thereof,
19) a compound of any of 14) to 17) wherein M is sulfonyl, $L^1$ is a single bond and $L^2$ is a single bond,
a pharmaceutically acceptable salt or solvate thereof,
20) a compound of any of 14) to 19) wherein Y is a single bond;

a pharmaceutically acceptable salt or solvate thereof,
21) a compound of any of 14) to 20) wherein $R^2$ is a halogen atom, optionally substituted alkyl, optionally substituted alkyloxy, optionally substituted amino, optionally substituted carbamoyl, optionally substituted aryl, optionally substituted heteroaryl or an optionally substituted non-aromatic heterocyclic group, and k is 1 or 2;
a pharmaceutically acceptable salt or solvate thereof,
22) a compound of any of 14) to 20) wherein $R^2$ is a halogen atom, optionally substituted amino, optionally substituted carbamoyl, optionally substituted aryl, optionally substituted heteroaryl or an optionally substituted non-aromatic heterocyclic group, and k is 1 or 2;
a pharmaceutically acceptable salt or solvate thereof,
23) a compound of any of 14) to 22) wherein $R^4$ is a halogen atom, optionally substituted alkyl or optionally substituted alkyloxy, and q is 0 or 1,
a pharmaceutically acceptable salt or solvate thereof,
24) a compound of any of 14) to 23) wherein the substituting position of Y and $L^3$ is a meta-position in the ring C,
a pharmaceutically acceptable salt or solvate thereof,
25) a compound of the general formula (III):

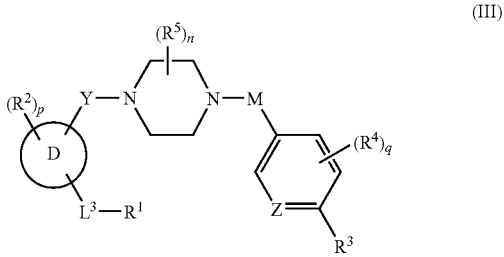

wherein the ring D is a benzene ring, a naphthalene ring, a 2-pyridone ring, a pyridine ring, a benzoxazolone ring, a benzoxadinone ring or a benzimidazole ring;
$R^1$ is hydroxyalkyl, carboxy, alkyloxycarbonyl, optionally substituted carbamoyl, cyano or a carboxy equivalent;
$R^2$ is independently a halogen atom, optionally substituted alkyl, optionally substituted alkenyl, optionally substituted alkynyl, optionally substituted cycloalkyl, optionally substituted cycloalkenyl, hydroxy, optionally substituted alkyloxy, optionally substituted alkenyloxy, optionally substituted alkynyloxy, optionally substituted cycloalkyloxy, optionally substituted cycloalkenyloxy, mercapto, optionally substituted alkylthio, optionally substituted alkenylthio, optionally substituted alkynylthio, optionally substituted alkylsulfinyl, optionally substituted alkylsulfonyl, optionally substituted alkylsulfonyloxy, optionally substituted cycloalkylthio, optionally substituted cycloalkylsulfinyl, optionally substituted cycloalkylsulfonyl, optionally substituted cycloalkylsulfonyloxy, optionally substituted cycloalkenylthio, optionally substituted cycloalkenylsulfinyl, optionally substituted cycloalkenylsulfonyl, optionally substituted cycloalkenylsulfonyloxy, optionally substituted amino, acyl, optionally substituted alkyloxycarbonyl, optionally substituted alkenyloxycarbonyl, optionally substituted alkynyloxycarbonyl, optionally substituted aryloxycarbonyl, optionally substituted carbamoyl, optionally substituted sulfamoyl, cyano, nitro, optionally substituted aryl, optionally substituted aryloxy, optionally substituted arylthio, optionally substituted arylsulfinyl, optionally substituted arylsulfonyl, optionally substituted arylsulfonyloxy, optionally substituted heteroaryl, optionally substituted heteroaryloxy, optionally substituted heteroarylthio, optionally substituted heteroarylsulfinyl, optionally substituted heteroarylsulfonyl, optionally substituted heteroarylsulfonyloxy or an optionally substituted non-aromatic heterocyclic group;
$R^3$ is optionally substituted C1-C6 alkyloxy, optionally substituted C2-C6 alkenyloxy, optionally substituted C2-C6 alkynyloxy, optionally substituted C3-C6 cycloalkyloxy, optionally substituted C3-C6 cycloalkenyloxy, optionally substituted aryloxy, optionally substituted heteroaryloxy, optionally substituted C1-C6 alkylthio, optionally substituted C2-C6 alkenylthio, optionally substituted C2-C6 alkynylthio, optionally substituted 03-C6 cycloalkylthio, optionally substituted C3-C6 cycloalkenylthio, optionally substituted arylthio or optionally substituted heteroarylthio;
$R^4$ is independently a halogen atom, optionally substituted alkyl, optionally substituted alkenyl, optionally substituted alkynyl, optionally substituted cycloalkyl, optionally substituted cycloalkenyl, hydroxy, optionally substituted alkyloxy, optionally substituted alkenyloxy, optionally substituted alkynyloxy, optionally substituted cycloalkyloxy, optionally substituted cycloalkenyloxy, mercapto, optionally substituted alkylthio, optionally substituted alkenylthio, optionally substituted alkynylthio, optionally substituted alkylsulfinyl, optionally substituted alkylsulfonyl, optionally substituted alkylsulfonyloxy, optionally substituted cycloalkylthio, optionally substituted cycloalkylsulfinyl, optionally substituted cycloalkylsulfonyl, optionally substituted cycloalkylsulfonyloxy, optionally substituted cycloalkenylthio, optionally substituted cycloalkenylsulfinyl, optionally substituted cycloalkenylsulfonyl, optionally substituted cycloalkenylsulfonyloxy, optionally substituted amino, acyl, optionally substituted alkyloxycarbonyl, optionally substituted alkenyloxycarbonyl, optionally substituted alkynyloxycarbonyl, optionally substituted aryloxycarbonyl, optionally substituted carbamoyl, optionally substituted sulfamoyl, cyano, nitro, optionally substituted aryl, optionally substituted aryloxy, optionally substituted arylthio, optionally substituted arylsulfinyl, optionally substituted arylsulfonyl, optionally substituted arylsulfonyloxy, optionally substituted heteroaryl, optionally substituted heteroaryloxy, optionally substituted heteroarylthio, optionally substituted heteroarylsulfinyl, optionally substituted heteroarylsulfonyl, optionally substituted heteroarylsulfonyloxy or optionally substituted non-aromatic heterocyclic group;
$R^5$ is independently a halogen atom, optionally substituted alkyl, optionally substituted alkenyl, optionally substituted alkynyl, optionally substituted cycloalkyl, optionally substituted alkyloxy, oxo, optionally substituted aryl, optionally substituted heteroaryl or an optionally substituted non-aromatic heterocyclic group;
M is carbonyl or sulfonyl;
$L^3$ is independently a single bond, optionally substituted alkylene optionally containing one or two heteroatom(s), optionally substituted alkenylene optionally containing one or two heteroatom(s), optionally substituted alkynylene optionally containing one or two heteroatom(s) or —N($R^7$)—;
$R^7$ is hydrogen atom, optionally substituted alkyl, optionally substituted alkenyl, optionally substituted alkynyl, optionally substituted cycloalkyl, acyl, optionally substituted alkyloxy, optionally substituted aryl, optionally substituted heteroaryl or an optionally substituted non-aromatic heterocyclic group;
Y is a single bond or optionally substituted alkylene optionally containing one or two heteroatom(s);
Z is CH, C($R^4$) or N;
n is 0, 1 or 2;

p s 1, 2, 3 or 4; and q is 0, 1, 2 or 3; provided that $R^1$ is not carboxy when the ring D is a benzene ring, -$L^3$- is —(O-alkylene)-, and the substituting position of $L^3$ and Y is an ortho-position in the ring D;

a pharmaceutically acceptable salt or hydrate thereof, 26) a compound of 25) wherein $R^1$ is carboxy and -$L^3$- is —(O-optionally substituted alkylene)-;

a pharmaceutically acceptable salt or solvate thereof, 27) a compound of 25) or 26) wherein the ring D is a benzene ring or a pyridine ring;

a pharmaceutically acceptable salt or solvate thereof, 28) a compound of any of 25) to 27 wherein $R^3$ is optionally substituted C1-C6 alkyloxy, or optionally substituted C1-C6 alkylthio;

a pharmaceutically acceptable salt or solvate thereof, 29) a compound of any of 25) to 28) wherein M is sulfonyl;

a pharmaceutically acceptable salt or solvate thereof, 30) a compound of any of 25) to 29) wherein Y is a single bond;

a pharmaceutically acceptable salt or solvate thereof, 31) a compound of any of 25) to 30) wherein $R^2$ is a halogen atom, optionally substituted alkyl, optionally substituted alkyloxy, optionally substituted amino, optionally substituted carbamoyl, optionally substituted aryl, optionally substituted heteroaryl or an optionally substituted non-aromatic heterocyclic group, and p is 1 or 2;

a pharmaceutically acceptable salt or solvate thereof, 32) a compound of any of 25) to 31) wherein $R^2$ is a halogen atom, optionally substituted amino, optionally substituted carbamoyl, optionally substituted aryl, optionally substituted heteroaryl or an optionally substituted non-aromatic heterocyclic group, and p is 1 or 2;

a pharmaceutically acceptable salt or solvate thereof, 33) a compound of any of 25) to 32) wherein $R^4$ is a halogen atom, optionally substituted alkyl or optionally substituted alkyloxy, and q is 0 or 1, a pharmaceutically acceptable salt or solvate thereof, 34) a compound of any of 25) to 33) wherein the substituting position of Y and $L^3$ is a meta-position in the ring D, a pharmaceutically acceptable salt or solvate thereof, 35) a compound of the general formula (IV):

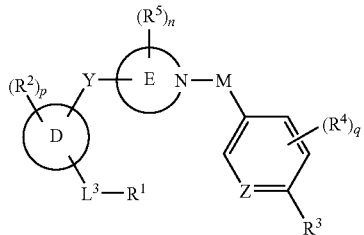

(IV)

wherein the ring D is a benzene ring, a naphthalene ring, a 2-pyridone ring, a pyridine ring, a benzoxazolone ring, a benzoxadinone ring or a benzimidazole ring;

the ring E is a ring of the formula of

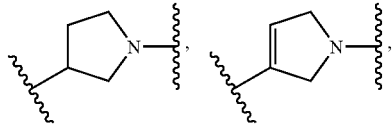

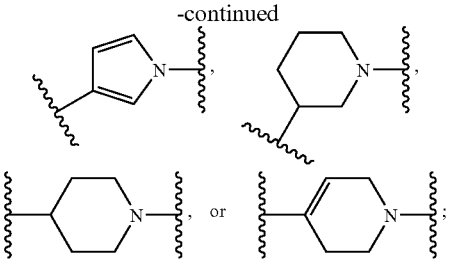

$R^1$ is hydroxyalkyl, carboxy, alkyloxycarbonyl, optionally substituted carbamoyl, cyano or a carboxy equivalent;

$R^2$ is independently a halogen atom, optionally substituted alkyl, optionally substituted alkenyl, optionally substituted alkynyl, optionally substituted cycloalkyl, optionally substituted cycloalkenyl, hydroxy, optionally substituted alkyloxy, optionally substituted alkenyloxy, optionally substituted alkynyloxy, optionally substituted cycloalkyloxy, optionally substituted cycloalkenyloxy, mercapto, optionally substituted alkylthio, optionally substituted alkenylthio, optionally substituted alkynylthio, optionally substituted alkylsulfinyl, optionally substituted alkylsulfonyl, optionally substituted alkylsulfonyloxy, optionally substituted cycloalkylthio, optionally substituted cycloalkylsulfinyl, optionally substituted cycloalkylsulfonyl, optionally substituted cycloalkylsulfonyloxy, optionally substituted cycloalkenylthio, optionally substituted cycloalkenylsulfinyl, optionally substituted cycloalkenylsulfonyl, optionally substituted cycloalkenylsulfonyloxy, optionally substituted amino, acyl, optionally substituted alkyloxycarbonyl, optionally substituted alkenyloxycarbonyl, optionally substituted alkynyloxycarbonyl, optionally substituted aryloxycarbonyl, optionally substituted carbamoyl, optionally substituted sulfamoyl, cyano, nitro, optionally substituted aryl, optionally substituted aryloxy, optionally substituted arylthio, optionally substituted arylsulfinyl, optionally substituted arylsulfonyl, optionally substituted arylsulfonyloxy, optionally substituted heteroaryl, optionally substituted heteroaryloxy, optionally substituted heteroarylthio, optionally substituted heteroarylsulfinyl, optionally substituted heteroarylsulfonyl, optionally substituted heteroarylsulfonyloxy or an optionally substituted non-aromatic heterocyclic group;

$R^3$ is optionally substituted C1-C6 alkyloxy, optionally substituted C2-C6 alkenyloxy, optionally substituted C2-C6 alkynyloxy, optionally substituted C3-C6 cycloalkyloxy, optionally substituted C3-C6 cycloalkenyloxy, optionally substituted aryloxy, optionally substituted heteroaryloxy, optionally substituted C1-C6 alkylthio, optionally substituted C2-C6 alkenylthio, optionally substituted C2-C6 alkynylthio, optionally substituted C3-C6 cycloalkylthio, optionally substituted C3-C6 cycloalkenylthio, optionally substituted arylthio or optionally substituted heteroarylthio;

$R^4$ is independently a halogen atom, optionally substituted alkyl, optionally substituted alkenyl, optionally substituted alkynyl, optionally substituted cycloalkyl, optionally substituted cycloalkenyl, hydroxy, optionally substituted alkyloxy, optionally substituted alkenyloxy, optionally substituted alkynyloxy, optionally substituted cycloalkyloxy, optionally substituted cycloalkenyloxy, mercapto, optionally substituted alkylthio, optionally substituted alkenylthio, optionally substituted alkynylthio, optionally substituted alkylsulfinyl, optionally substituted alkylsulfonyl, optionally substituted alkylsulfonyloxy, optionally substituted cycloalkylthio, optionally substituted cycloalkylsulfinyl, optionally substituted cycloalkylsulfonyl, optionally substituted cycloalkylsulfonyloxy, optionally substituted cycloalkenylthio, optionally substituted cycloalkenylsulfinyl, optionally substituted cycloalkenylsulfonyl, optionally substituted cycloalkenylsulfonyloxy, optionally substituted amino, acyl, optionally substituted alkyloxycarbonyl, optionally substituted alkenyloxycarbonyl, optionally substituted alkynyloxycarbonyl, optionally substituted aryloxycarbonyl, optionally substituted carbamoyl, optionally substituted sulfamoyl, cyano, nitro, optionally substituted aryl, optionally substituted aryloxy, optionally substituted arylthio, optionally substituted arylsulfinyl, optionally substituted arylsulfonyl, optionally substituted arylsulfonyloxy, optionally substituted heteroaryl, optionally substituted heteroaryloxy, optionally substituted heteroarylthio, optionally substituted heteroarylsulfinyl, optionally substituted heteroarylsulfonyl, optionally substituted heteroarylsulfonyloxy or an optionally substituted non-aromatic heterocyclic group;

$R^5$ is independently a halogen atom, optionally substituted alkyl, optionally substituted alkenyl, optionally substituted alkynyl, optionally substituted cycloalkyl, optionally substituted alkyloxy, oxo, optionally substituted aryl, optionally substituted heteroaryl or an optionally substituted non-aromatic heterocyclic group;

M is carbonyl or sulfonyl;

$L^3$ is independently a single bond, optionally substituted alkylene optionally containing one or two heteroatom(s), optionally substituted alkenylene optionally containing one or two heteroatom(s), optionally substituted alkynylene optionally containing one or two heteroatom(s) or —N($R^7$)—;

$R^7$ is hydrogen atom, optionally substituted alkyl, optionally substituted alkenyl, optionally substituted alkynyl, optionally substituted cycloalkyl, acyl, optionally substituted alkyloxy, optionally substituted aryl, optionally substituted heteroaryl or an optionally substituted non-aromatic heterocyclic group, Y is a single bond or optionally substituted alkylene optionally containing one or two heteroatom(s);

Z is CH, C($R^4$) or N;

n is 0, 1 or 2;

p is 1, 2, 3 or 4; and q is 0, 1, 2 or 3; provided that a) $R^1$ is not carboxy when the ring D is a benzene ring, -$L^3$- is —(O-alkylene) and the substituting position of $L^3$ and Y is an ortho-position in the ring D, b) the group of the formula of

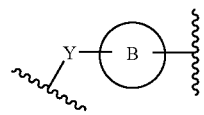

is not a group of the formula of

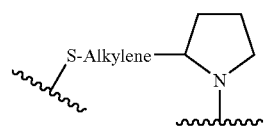

when the ring D is a benzene ring, -$L^3$- is —(O-alkylene)-, and the substituting position of $L^3$ and Y is a para-position in the ring D;

a pharmaceutically acceptable salt or solvate thereof, 36) a compound of 35) wherein $R^1$ is carboxy and -$L^3$- is —(O-optionally substituted alkylene)-;

a pharmaceutically acceptable salt or solvate thereof, 37) a compound of 35) or 36) wherein the ring D is a benzene ring or a pyridine ring;

a pharmaceutically acceptable salt or solvate thereof, 38) a compound of any of 35) to 37) wherein $R^3$ is optionally substituted C1-C6 alkyloxy, or optionally substituted C1-C6 alkylthio;

a pharmaceutically acceptable salt or solvate thereof, 39) a compound of any of 35) to 38) wherein M is sulfonyl;

a pharmaceutically acceptable salt or solvate thereof, 40) a compound of any of 35) to 39) wherein Y is a single bond;

a pharmaceutically acceptable salt or solvate thereof, 41) a compound of any of 35) to 40) wherein $R^2$ is a halogen atom, optionally substituted alkyl, optionally substituted alkyloxy, optionally substituted amino, optionally substituted carbamoyl, optionally substituted aryl, optionally substituted heteroaryl or an optionally substituted non-aromatic heterocyclic group, and p is 1 or 2;

a pharmaceutically acceptable salt or solvate thereof, 42) a compound of any of 35) to 41) wherein $R^2$ is a halogen atom, optionally substituted amino, optionally substituted carbamoyl, optionally substituted aryl, optionally substituted heteroaryl or an optionally substituted non-aromatic heterocyclic group, and p is 1 or 2;

a pharmaceutically acceptable salt or solvate thereof, 43) a compound of any of 35) to 42) wherein $R^4$ is a halogen atom, optionally substituted alkyl or optionally substituted alkyloxy, and q is 0 or 1, a pharmaceutically acceptable salt or solvate thereof, 44) a compound of any of 35) to 43) wherein the substituting position of Y and $L^3$ is a meta-position in the ring D, a pharmaceutically acceptable salt or solvate thereof, 45) a pharmaceutical composition comprising a compound of any of 14) to 44), a pharmaceutically acceptable salt or solvate thereof as an active ingredient, 46) a pharmaceutical composition of 45) which is a DP receptor antagonist, 47) a pharmaceutical composition of 45) which is a therapeutic agent for allergy, 48) a pharmaceutical composition of 45) which is a therapeutic agent for asthma, 49) a method for treating a disease related to DP receptor characterized by administration of the compound of any of 1) to 11) and 14) to 44), pharmaceutically acceptable salt or solvate thereof, 50) a method of 49) wherein the disease related to DP receptor is asthma, 51) use of the compound of any of 1) to 11) and 14) to 44), pharmaceutically acceptable salt or solvate thereof in the manufacturing of a therapeutic agent for treating a disease related to DP receptor, 52) use of the compound of 51), pharmaceutically acceptable salt or solvate thereof wherein the disease related to DP receptor is asthma, 53) a compound of the general formula (V):

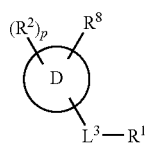

wherein the ring D is a benzene ring, a naphthalene ring, a 2-pyridone ring, a pyridine ring, a benzoxazolone ring, a benzoxadinone ring or a benzimidazole ring;

$R^1$ is hydroxyalkyl, carboxy, alkyloxycarbonyl, optionally substituted carbamoyl, cyano or a carboxy equivalent;

$R^2$ is independently a hydrogen atoms, a halogen atom, optionally substituted alkyl, optionally substituted alkenyl, optionally substituted alkynyl, optionally substituted cycloalkyl, optionally substituted cycloalkenyl, hydroxy, optionally substituted alkyloxy, optionally substituted alkenyloxy, optionally substituted alkynyloxy, optionally substituted cycloalkyloxy, optionally substituted cycloalkenyloxy, mercapto, optionally substituted alkylthio, optionally substituted alkenylthio, optionally substituted alkynylthio, optionally substituted alkylsulfinyl, optionally substituted alkylsulfonyl, optionally substituted alkylsulfonyloxy, optionally substituted cycloalkylthio, optionally substituted cycloalkylsulfinyl, optionally substituted cycloalkylsulfonyl, optionally substituted cycloalkylsulfonyloxy, optionally substituted cycloalkenylthio, optionally substituted cycloalkenylsulfinyl, optionally substituted cycloalkenylsulfonyl, optionally substituted cycloalkenylsulfonyloxy, optionally substituted amino, acyl, optionally substituted alkyloxycarbonyl, optionally substituted alkenyloxycarbonyl, optionally substituted alkynyloxycarbonyl, optionally substituted aryloxycarbonyl, optionally substituted carbamoyl, optionally substituted sulfamoyl, cyano, nitro, optionally substituted aryl, optionally substituted aryloxy, optionally substituted arylthio, optionally substituted arylsulfinyl, optionally substituted arylsulfonyl, optionally substituted arylsulfonyloxy, optionally substituted heteroaryl, optionally substituted heteroaryloxy, optionally substituted heteroarylthio, optionally substituted heteroarylsulfinyl, optionally substituted heteroarylsulfonyl, optionally substituted heteroarylsulfonyloxy or an optionally substituted non-aromatic heterocyclic group;

$L^3$ is independently a single bond, optionally substituted alkylene optionally containing one or two heteroatom(s), optionally substituted alkenylene optionally containing one or two heteroatom(s), optionally substituted alkynylene optionally containing one or two heteroatom(s) or —N($R^7$)—;

$R^7$ is a hydrogen atom, optionally substituted alkyl, optionally substituted alkenyl, optionally substituted alkynyl, optionally substituted cycloalkyl, acyl, optionally substituted alkyloxy, optionally substituted aryl, optionally substituted heteroaryl or an optionally substituted non-aromatic heterocyclic group;

$R^8$ is a halogen atom, trifluoromethanesulfonyloxy or piperazino; and p is 1, 2, 3 or 4; provided that the substituting position of the piperidino group and $L^3$ each other is not an ortho-position in the ring D when the ring D is a benzene ring and -$L^3$- is —(O-alkylene)-;

a pharmaceutically acceptable salt or hydrate thereof, 54) a compound of 53) wherein the ring D is a benzene ring and $R^8$ is a halogen atom;

a pharmaceutically acceptable salt or solvate thereof, 55) a compound of 53) wherein the ring D is a benzene ring and $R^8$ is piperazino;

a pharmaceutically acceptable salt or solvate thereof, 56) a compound of any of 53) to 55) wherein $R^1$ is carboxy or alkyloxycarbonyl and -L3- is —(O-methylene)-;

a pharmaceutically acceptable salt or solvate thereof, 57) a compound of any of 53) to 56) wherein $R^2$ is a halogen atom, optionally substituted amino, optionally substituted carbamoyl, optionally substituted aryl, optionally substituted heteroaryl or an optionally substituted non-aromatic heterocyclic group;

a pharmaceutically acceptable salt or hydrate thereof, and 58) a compound of any of 53) to 57) wherein the substituting position of $R^8$ and $L^3$ each other is a meta-position in the ring D;

a pharmaceutically acceptable salt or solvate thereof.

The present invention also includes the following inventions:

(1) a PGD2 receptor antagonist comprising a compound of the general formula (I-b):

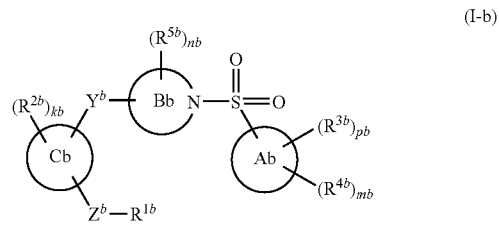

wherein the ring Ab is an aromatic carbocyclic ring or an aromatic heterocyclic ring;

the ring Bb is a 3- to 8-membered nitrogen-containing heterocyclic ring containing one or two nitrogen atom(s);

the ring Cb is a benzene ring, a naphthalene ring, a 2-pyridone ring or a pyridine ring;

$R^{1b}$ is hydroxyalkyl, carboxy, alkyloxycarbonyl, optionally substituted carbamoyl or optionally substituted tetrazolyl;

$R^{2b}$ is independently a halogen atom, optionally substituted alkyl, optionally substituted alkenyl, optionally substituted alkynyl, optionally substituted cycloalkyl, hydroxy, optionally substituted alkyloxy, optionally substituted alkenyloxy, optionally substituted alkynyloxy, optionally substituted alkylthio, optionally substituted alkenylthio, optionally substituted alkynylthio, optionally substituted alkylsulfinyl, optionally substituted alkylsulfonyl, optionally substituted alkylsulfonyloxy, optionally substituted amino, acyl, optionally substituted alkyloxycarbonyl, optionally substituted alkenyloxycarbonyl, optionally substituted alkynyloxycarbonyl, optionally substituted carbamoyl, cyano, nitro, optionally substituted aryl, optionally substituted aryloxy, optionally substituted arylthio, optionally substituted arylsulfinyl, optionally substituted arylsulfonyl, arylsulfonyloxy, optionally substituted heteroaryl, optionally substituted heteroaryloxy, optionally substituted heteroarylthio, optionally substituted heteroarylsulfinyl, optionally substituted heteroarylsulfonyl, optionally substituted heteroarylsulfonyloxy or an optionally substituted non-aromatic heterocyclic group;

$R^{3b}$ is optionally substituted alkyloxy, optionally substituted alkylthio, optionally substituted cycloalkyloxy, optionally substituted cycloalkylthio, optionally substituted aryloxy, optionally substituted arylthio, optionally substituted heteroaryloxy or optionally substituted heteroarylthio;

$R^{4b}$ is independently a halogen atom, optionally substituted alkyl, optionally substituted alkenyl, optionally substituted alkynyl, optionally substituted cycloalkyl, optionally substituted alkyloxy, optionally substituted alkenyloxy, optionally substituted alkynyloxy, optionally substituted alkylthio, optionally substituted alkenylthio, optionally substituted alkynylthio, optionally substituted alkylsulfinyl, optionally substituted alkylsulfonyl, optionally substituted alkylsulfonyloxy, optionally substituted amino, acyl, optionally substituted alkyloxycarbonyl, optionally substituted alkenyloxycarbonyl, optionally substituted alkynyloxycarbonyl, optionally substituted carbamoyl, cyano, nitro, optionally substituted aryl, optionally substituted aryloxy, optionally substituted arylthio, optionally substituted arylsulfinyl, optionally substituted arylsulfonyl, optionally substituted arylsulfonyloxy, optionally substituted heteroaryl, optionally substituted heteroaryloxy, optionally substituted heteroarylthio, optionally substituted heteroarylsulfinyl, optionally substituted heteroarylsulfonyl, optionally substituted heteroarylsulfonyloxy or an optionally substituted non-aromatic heterocyclic group;

$R^{5b}$ is independently optionally substituted alkyl or optionally substituted aryl;

$Y^b$ is a single bond, alkylene, alkenylene, alkynylene, —O—, —S—, —O-alkylene- or —S-alkylene-;

$Z^b$ is a single bond, alkylene, alkenylene, alkynylene, —O-alkylene- or —S-alkylene-;

kb is 0, 1, 2, 3 or 4;

mb is 0, 1 or 2;

nb is 0, 1 or 2; and pb is 0 or 1; provided that k is not 0 when the ring B is a 6-membered nitrogen-containing heterocyclic ring containing one or two nitrogen atom(s) and the ring C is a benzene ring;

a pharmaceutically acceptable salt or hydrate thereof, (2) a PGD2 receptor antagonist of (1) wherein the ring Cb is a benzene ring or a pyridine ring, (3) a PGD2 receptor antagonist of (1) or (2) wherein the ring Bb is a ring of the formula of

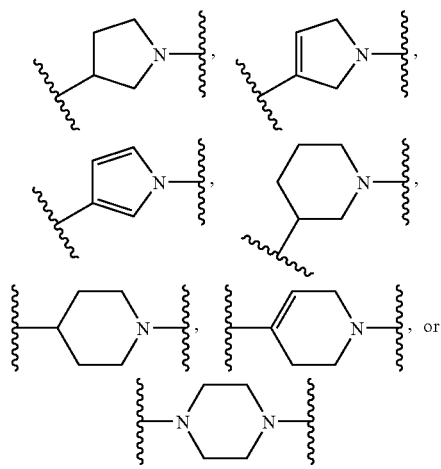

and nb is 0 or 1, (4) a PGD2 receptor antagonist of any of (1) to (3) wherein the ring Ab is a benzene ring or a pyridine ring, (5) a PGD2 receptor antagonist of any of (1) to (4) wherein pb is 1, (6) a PGD2 receptor antagonist of any of (1) to (5) wherein $Y^b$ is a single bond or —O—, (7) a PGD2 receptor antagonist of any of (1) to (6) wherein $R^{1b}$ is carboxy, (8) a PGD2 receptor antagonist of any of (1) to (7) which is a therapeutic agent for allergy, (9) a PGD2 receptor antagonist of any of (1) to (7) which is a therapeutic agent for asthma,

(10) a compound of the general formula (II-b):

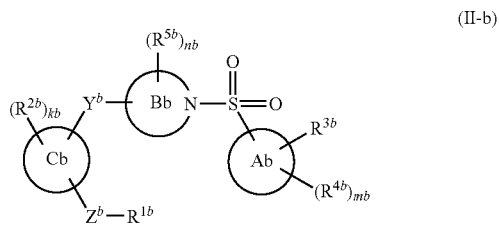

(II-b)

wherein the ring Ab is an aromatic carbocyclic ring or an aromatic heterocyclic ring;

the ring Bb is a 3- to 8-membered nitrogen-containing heterocyclic ring containing one or two nitrogen atom(s);

the ring Cb is a benzene ring, a naphthalene ring, a 2-pyridone ring or a pyridine ring;

$R^{1b}$ is hydroxyalkyl, carboxy, alkyloxycarbonyl, optionally substituted carbamoyl or optionally substituted tetrazolyl;

$R^{2b}$ is independently a halogen atom, optionally substituted alkyl, optionally substituted alkenyl, optionally substituted alkynyl, optionally substituted cycloalkyl, hydroxy, optionally substituted alkyloxy, optionally substituted alkenyloxy, optionally substituted alkynyloxy, optionally substituted alkylthio, optionally substituted alkenylthio, optionally substituted alkynylthio, optionally substituted alkylsulfinyl, optionally substituted alkylsulfonyl, optionally substituted alkylsulfonyloxy, optionally substituted amino, acyl, optionally substituted alkyloxycarbonyl, optionally substituted alkenyloxycarbonyl, optionally substituted alkynyloxycarbonyl, optionally substituted carbamoyl, cyano, nitro, optionally substituted aryl, optionally substituted aryloxy, optionally substituted arylthio, optionally substituted arylsulfinyl, optionally substituted arylsulfonyl, optionally substituted arylsulfonyloxy, optionally substituted heteroaryl, optionally substituted heteroaryloxy, optionally substituted heteroarylthio, optionally substituted heteroarylsulfinyl, optionally substituted heteroarylsulfonyl, optionally substituted heteroarylsulfonyloxy or an optionally substituted non-aromatic heterocyclic group;

$R^{3b}$ is optionally substituted alkyloxy, optionally substituted alkylthio, optionally substituted cycloalkyloxy, optionally substituted cycloalkylthio, optionally substituted aryloxy, optionally substituted arylthio, optionally substituted heteroaryloxy or optionally substituted heteroarylthio;

$R^{4b}$ is independently a halogen atom, optionally substituted alkyl, optionally substituted alkenyl, optionally substituted alkynyl, optionally substituted cycloalkyl, optionally substituted alkyloxy, optionally substituted alkenyloxy, optionally substituted alkynyloxy, optionally substituted alkylthio, optionally substituted alkenylthio, optionally substituted alkynylthio, optionally substituted alkylsulfinyl, optionally substituted alkylsulfonyl, optionally substituted alkylsulfonyloxy, optionally substituted amino, acyl, optionally substituted alkyloxycarbonyl, optionally substituted alkenyloxycarbonyl, optionally substituted alkynyloxycarbonyl, optionally substituted carbamoyl, cyano, nitro, optionally substituted aryl, optionally substituted aryloxy, optionally substituted arylthio, optionally substituted arylsulfinyl, optionally substituted arylsulfonyl, optionally substituted arylsulfonyloxy, optionally substituted heteroaryl, optionally substituted heteroaryloxy, optionally substituted heteroarylthio, optionally substituted heteroarylsulfinyl, optionally substituted heteroarylsulfonyl, optionally substituted heteroarylsulfonyloxy or an optionally substituted non-aromatic heterocyclic group;

$R^{5b}$ is independently optionally substituted alkyl or optionally substituted aryl;

$Y^b$ is a single bond, alkylene, alkenylene, alkynylene, —O—, —S—, —O-alkylene- or —S-alkylene-;

$Z^b$ is is a single bond, alkylene, alkenylene, alkynylene, —O-alkylene- or —S-alkylene-;

kb is 0, 1, 2, 3 or 4;

mb is 0, 1 or 2; and nb is 0, 1 o 2; provided that a) k is not 0 when the ring B is a 6-membered nitrogen-containing heterocyclic ring containing one or two nitrogen atom(s) and the ring C is a benzene ring, b) the group of the formula of is not a group of the formula of when Z is —O-alkylene;

a pharmaceutically acceptable salt or hydrate thereof,

(11) a compound of (10) wherein the ring Bb is a group of the formula of and n is 0 or 1;

a pharmaceutically acceptable salt or hydrate thereof,

(12) a compound of (10) or (11) wherein the ring C is a benzene ring or a pyridine ring;

a pharmaceutically acceptable salt or hydrate thereof,

(13) a compound of any of (10) to (12) wherein $R^{3b}$ is optionally substituted alkyloxy or optionally substituted alkylthio;

a pharmaceutically acceptable salt or hydrate thereof,

(14) a compound of any of (10) to (13) wherein $R^{1b}$ is carboxy;

a pharmaceutically acceptable salt or hydrate thereof,

(15) a compound of the general formula (III-b):

(III-b)

wherein the ring Cb is a benzene ring, a naphthalene ring, a 2-pyridone ring or a pyridine ring;

$R^{1b}$ is hydroxyalkyl, carboxy, alkyloxycarbonyl, optionally substituted carbamoyl or optionally substituted tetrazolyl;

$R^{2b}$ is independently a halogen atom, optionally substituted alkyl, optionally substituted alkenyl, optionally substituted alkynyl, optionally substituted cycloalkyl, hydroxy, optionally substituted alkyloxy, optionally substituted alkenyloxy, optionally substituted alkynyloxy, optionally substituted alkylthio, optionally substituted alkenylthio, optionally substituted alkynylthio, optionally substituted alkylsulfinyl, optionally substituted alkylsulfonyl, optionally substituted alkylsulfonyloxy, optionally substituted amino, acyl, optionally substituted alkyloxycarbonyl, optionally substituted alkenyloxycarbonyl, optionally substituted alkynyloxycarbonyl, optionally substituted carbamoyl, cyano, nitro, optionally substituted aryl, optionally substituted aryloxy, optionally substituted arylthio, optionally substituted arylsulfinyl, optionally substituted arylsulfonyl, optionally substituted arylsulfonyloxy, optionally substituted heteroaryl, optionally substituted heteroaryloxy, optionally substituted heteroarylthio, optionally substituted heteroarylsulfinyl, optionally substituted heteroarylsulfonyl, optionally substituted heteroarylsulfonyloxy or an optionally substituted non-aromatic heterocyclic group;

$R^{3b}$ is optionally substituted alkyloxy, optionally substituted alkylthio, optionally substituted cycloalkyloxy, optionally substituted cycloalkylthio, optionally substituted aryloxy, optionally substituted arylthio, optionally substituted heteroaryloxy or optionally substituted heteroarylthio, $R^{4b}$ is independently a halogen atom, optionally substituted alkyl, optionally substituted alkenyl, optionally substituted alkynyl, optionally substituted cycloalkyl, optionally substituted alkyloxy, optionally substituted alkenyloxy, optionally substituted alkynyloxy, optionally substituted alkylthio, optionally substituted alkenylthio, optionally substituted alkynylthio, optionally substituted alkylsulfinyl, optionally substituted alkylsulfonyl, optionally substituted alkylsulfonyloxy, optionally substituted amino, acyl, optionally substituted alkyloxycarbonyl, optionally substituted alkenyloxycarbonyl, optionally substituted alkynyloxycarbonyl, optionally substituted carbamoyl, cyano, nitro, optionally substituted aryl, optionally substituted aryloxy, optionally substituted arylthio, optionally substituted arylsulfinyl, optionally substituted arylsulfonyl, optionally substituted arylsulfonyloxy, optionally substituted heteroaryl, optionally substituted heteroaryloxy, optionally substituted heteroarylthio, optionally substituted heteroarylsulfinyl, optionally substituted heteroarylsulfonyl, optionally substituted heteroarylsulfonyloxy or an optionally substituted non-aromatic heterocyclic group;

$R^{5b}$ is independently optionally substituted alkyl and optionally substituted aryl;

$X^b$ is CH or N;

$Y^b$ is a single bond, alkylene, alkenylene, alkynylene, —O—, —S—, —O-alkylene- or —S-alkylene-;

$Z^b$ is a single bond, alkylene, alkenylene, alkynylene, —O-alkylene- or —S-alkylene-;

mb is 0, 1 or 2;

nb is 0, 1 or 2; and qb is 1, 2, 3 or 4;

a pharmaceutically acceptable salt or hydrate thereof,

(16) a compound of 15) wherein the ring Cb is a benzene ring or a pyridine ring;

a pharmaceutically acceptable salt or hydrate thereof,

(17) a compound of (15) or (16) wherein $R^{3b}$ is optionally substituted alkyloxy (the substituent is a halogen atom, alkyloxy, aryl or heteroaryl), optionally substituted alkylthio (the substituent is a halogen atom, alkyloxy, aryl or heteroaryl), optionally substituted cycloalkyloxy (the substituent is a halogen atom, alkyl, aryl or heteroaryl), optionally substituted cycloalkylthio (the substituent is a halogen atom, alkyloxy, aryl or heteroaryl), optionally substituted aryloxy (the substituent is a halogen atom, alkyl or alkyloxy), optionally substituted arylthio (the substituent is a halogen atom, alkyl or alkyloxy), optionally substituted heteroaryloxy (the substituent is a halogen atom, alkyl or haloalkyl), or optionally substituted heteroarylthio (the substituent is a halogen atom, alkyl or haloalkyl);

a pharmaceutically acceptable salt or hydrate thereof,

(18) a compound of (15) or (16) wherein $R^{3b}$ is optionally substituted alkyloxy (the substituent is a halogen atom, alkyloxy, aryl or heteroaryl) or alkylthio (the substituent is a halogen atom, alkyloxy, aryl or heteroaryl);

a pharmaceutically acceptable salt or hydrate thereof,

(19) a compound of any of (15) to (18) wherein $R^{2b}$ is a halogen atom, cyano, nitro or optionally substituted heteroaryl;

a pharmaceutically acceptable salt or hydrate thereof,

(20) a compound of any of (15) to (19) wherein $R^{2b}$ is optionally substituted 5-membered heteroaryl;

a pharmaceutically acceptable salt or hydrate thereof,

(21) a compound of any of (15) to (20) wherein $R^{1b}$ is carboxy;

a pharmaceutically acceptable salt or hydrate thereof,

(22) a compound of the general formula (IV-b):

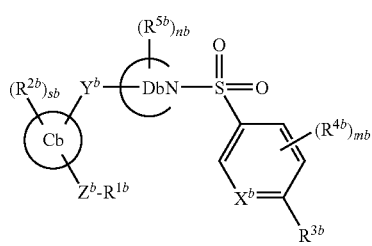

(IV-b)

wherein the ring Cb is a benzene ring, a naphthalene ring, a 2-pyridone ring or a pyridine ring;

the ring Db is a ring of the formula of

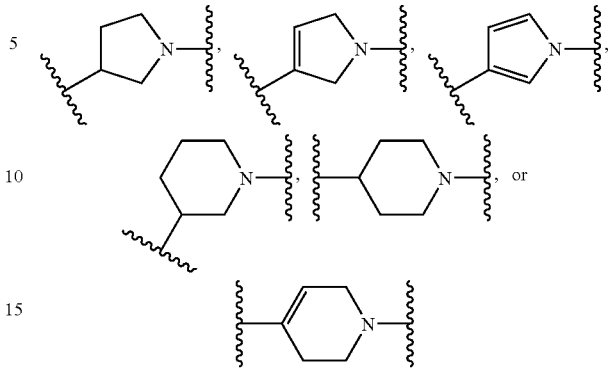

$R^{1b}$ is hydroxyalkyl, carboxy, alkyloxycarbonyl, optionally substituted carbamoyl or optionally substituted tetrazolyl;

$R^{2b}$ is independently a halogen atom, optionally substituted alkyl, optionally substituted alkenyl, optionally substituted alkynyl, optionally substituted cycloalkyl, hydroxy, optionally substituted alkyloxy, optionally substituted alkenyloxy, optionally substituted alkynyloxy, optionally substituted alkylthio, optionally substituted alkenylthio, optionally substituted alkynylthio, optionally substituted alkylsulfinyl, optionally substituted alkylsulfonyl, optionally substituted alkylsulfonyloxy, optionally substituted amino, acyl, optionally substituted alkyloxycarbonyl, optionally substituted alkenyloxycarbonyl, optionally substituted alkynyloxycarbonyl, optionally substituted carbamoyl, cyano, nitro, optionally substituted aryl, optionally substituted aryloxy, optionally substituted arylthio, optionally substituted arylsulfinyl, optionally substituted arylsulfonyl, optionally substituted arylsulfonyloxy, optionally substituted heteroaryl, optionally substituted heteroaryloxy, optionally substituted heteroarylthio, optionally substituted heteroarylsulfinyl, optionally substituted heteroarylsulfonyl, optionally substituted heteroarylsulfonyloxy or an optionally substituted non-aromatic heterocyclic group;

$R^{3b}$ is optionally substituted alkyloxy, optionally substituted alkylthio, optionally substituted cycloalkyloxy, optionally substituted cycloalkylthio, optionally substituted aryloxy, optionally substituted arylthio, optionally substituted heteroaryloxy or optionally substituted heteroarylthio;

$R^{4b}$ is independently a halogen atom, optionally substituted alkyl, optionally substituted alkenyl, optionally substituted alkynyl, optionally substituted cycloalkyl, optionally substituted alkyloxy, optionally substituted alkenyloxy, optionally substituted alkynyloxy, optionally substituted alkylthio, optionally substituted alkenylthio, optionally substituted alkynylthio, optionally substituted alkylsulfinyl, optionally substituted alkylsulfonyl, optionally substituted alkylsulfonyloxy, optionally substituted amino, acyl, optionally substituted alkyloxycarbonyl, optionally substituted alkenyloxycarbonyl, optionally substituted alkynyloxycarbonyl, optionally substituted carbamoyl, cyano, nitro, optionally substituted aryl, optionally substituted aryloxy, optionally substituted arylthio, optionally substituted arylsulfinyl, optionally substituted arylsulfonyl, optionally substituted arylsulfonyloxy, optionally substituted heteroaryl, optionally substituted heteroaryloxy, optionally substituted heteroarylthio, optionally substituted heteroarylsulfinyl, optionally substituted heteroarylsulfonyl, optionally substituted heteroarylsulfonyloxy or an optionally substituted non-aromatic heterocyclic group;

$R^{5b}$ is independently optionally substituted alkyl or optionally substituted aryl;

$X^b$ is CH or N;

$Y^b$ is a single bond, alkylene, alkenylene, alkynylene, —O—, —S—, —O-alkylene- or —S-alkylene-;

$Z^b$ is a single bond, alkylene, alkenylene, alkynylene, —O-alkylene- or —S-alkylene-;

mb is 0, 1 or 2 nb is 0, 1 or 2; and sb is 1, 2, 3 or 4;

a pharmaceutically acceptable salt or hydrate thereof,

(23) a compound of 22) wherein the ring Cb is a benzene ring or a pyridine ring;

a pharmaceutically acceptable salt or hydrate thereof,

(24) a compound of (22) or (23) wherein $R^{3b}$ is optionally substituted alkyloxy (the substituent is a halogen atom, alkyloxy, aryl or heteroaryl), optionally substituted alkylthio (the substituent is a halogen atom, alkyloxy, aryl or heteroaryl), optionally substituted cycloalkyloxy (the substituent is a halogen atom, alkyl, aryl or heteroaryl), optionally substituted cycloalkylthio (the substituent is a halogen atom, alkyloxy, aryl or heteroaryl), optionally substituted aryloxy (the substituent is a halogen atom, alkyl or alkyloxy), optionally substituted arylthio (the substituent is a halogen atom, alkyl or alkyloxy), optionally substituted heteroaryloxy (the substituent is a halogen atom, alkyl or haloalkyl), or optionally substituted heteroarylthio (the substituent is a halogen atom, alkyl or haloalkyl);

a pharmaceutically acceptable salt or hydrate thereof,

(25) a compound of (22) or (23) wherein $R^{3b}$ is optionally substituted alkyloxy (the substituent is a halogen atom, alkyloxy, aryl or heteroaryl), optionally substituted alkylthio (the substituent is a halogen atom, alkyloxy, aryl or heteroaryl);

a pharmaceutically acceptable salt or hydrate thereof,

(26) a compound of any of (22) to (25) wherein $R^{1b}$ is carboxy;

a pharmaceutically acceptable salt or hydrate thereof,

(27) a compound of the general formula (V-b)

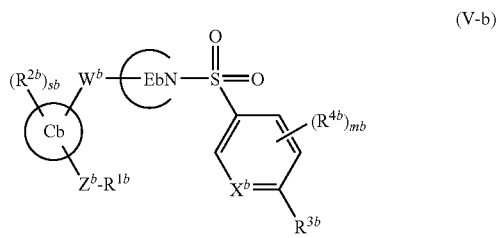

(V-b)

wherein the ring Cb is a benzene ring, a naphthalene ring or a pyridine ring;

the ring Eb is a ring of the formula of

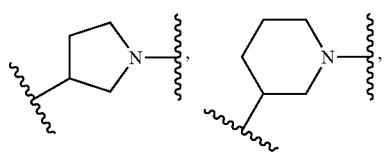

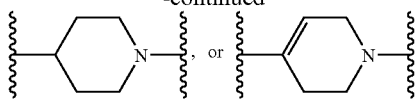

$R^{1b}$ is hydroxyalkyl, carboxy, alkyloxycarbonyl, optionally substituted carbamoyl or optionally substituted tetrazolyl;

$R^{2b}$ is independently a halogen atom, optionally substituted alkyl, optionally substituted alkenyl, optionally substituted alkynyl, optionally substituted cycloalkyl, hydroxy, optionally substituted alkyloxy, optionally substituted alkenyloxy, optionally substituted alkynyloxy, optionally substituted alkylthio, optionally substituted alkenylthio, optionally substituted alkynylthio, optionally substituted alkylsulfinyl, optionally substituted alkylsulfonyl, optionally substituted alkylsulfonyloxy, optionally substituted amino, acyl, optionally substituted alkyloxycarbonyl, optionally substituted alkenyloxycarbonyl, optionally substituted alkynyloxycarbonyl, optionally substituted carbamoyl, cyano, nitro, optionally substituted aryl, optionally substituted aryloxy, optionally substituted arylthio, optionally substituted arylsulfinyl, optionally substituted arylsulfonyl, optionally substituted arylsulfonyloxy, optionally substituted heteroaryl, optionally substituted heteroaryloxy, optionally substituted heteroarylthio, optionally substituted heteroarylsulfinyl, optionally substituted heteroarylsulfonyl, optionally substituted heteroarylsulfonyloxy or an optionally substituted non-aromatic heterocyclic group;

$R^{3b}$ is optionally substituted alkyloxy, optionally substituted alkylthio, optionally substituted cycloalkyloxy, optionally substituted cycloalkylthio, optionally substituted aryloxy, optionally substituted arylthio, optionally substituted heteroaryloxy or optionally substituted heteroarylthio;

$R^{4b}$ is independently a halogen atom, optionally substituted alkyl, optionally substituted alkenyl, optionally substituted alkynyl, optionally substituted cycloalkyl, optionally substituted alkyloxy, optionally substituted alkenyloxy, optionally substituted alkynyloxy, optionally substituted alkylthio, optionally substituted alkenylthio, optionally substituted alkynylthio, optionally substituted alkylsulfinyl, optionally substituted alkylsulfonyl, optionally substituted alkylsulfonyloxy, optionally substituted amino, acyl, optionally substituted alkyloxycarbonyl, optionally substituted alkenyloxycarbonyl, optionally substituted alkynyloxycarbonyl, optionally substituted carbamoyl, cyano, nitro, optionally substituted aryl, optionally substituted aryloxy, optionally substituted arylthio, optionally substituted arylsulfinyl, optionally substituted arylsulfonyl, optionally substituted arylsulfonyloxy, optionally substituted heteroaryl, optionally substituted heteroaryloxy, optionally substituted heteroarylthio, optionally substituted heteroarylsulfinyl, optionally substituted heteroarylsulfonyl, optionally substituted heteroarylsulfonyloxy or an optionally substituted non-aromatic heterocyclic group;

$X^b$ is CH or N;

$W^b$ is a single bond, alkylene or —O—;

$Z^b$ is a single bond, alkylene, alkenylene, alkynylene, —O-alkylene- or —S-alkylene-;

mb is 0, 1 or 2; and sb is 1, 2, 3 or 4;

a pharmaceutically acceptable salt or hydrate thereof,

(28) a compound of (27) wherein the ring Cb is a benzene ring or a pyridine ring; a pharmaceutically acceptable salt or hydrate thereof,

(29) a compound of (27) or (28) wherein $R^{3b}$ is optionally substituted alkyloxy (the substituent is a halogen atom, alkyloxy, aryl or heteroaryl), optionally substituted alkylthio (the substituent is a halogen atom, alkyloxy, aryl or heteroaryl), optionally substituted cycloalkyloxy (the substituent is a halogen atom, alkyl, aryl or heteroaryl), optionally substituted cycloalkylthio (the substituent is a halogen atom, alkyloxy, aryl or heteroaryl), optionally substituted aryloxy (the substituent is a halogen atom, alkyl or alkyloxy), optionally substituted arylthio (the substituent is a halogen atom, alkyl or alkyloxy), optionally substituted heteroaryloxy (the substituent is a halogen atom, alkyl or haloalkyl), or optionally substituted heteroarylthio (the substituent is a halogen atom, alkyl or haloalkyl);
a pharmaceutically acceptable salt or hydrate thereof,

(30) a compound of (27) or (28) wherein $R^{3b}$ is optionally substituted alkyloxy (the substituent is a halogen atom, alkyloxy, aryl or heteroaryl), optionally substituted alkylthio (the substituent is a halogen atom, alkyloxy, aryl or heteroaryl);
a pharmaceutically acceptable salt or hydrate thereof,

(31) a compound of any of (27) to (30) wherein $R^{1b}$ is carboxy;
a pharmaceutically acceptable salt or hydrate thereof,

(32) a pharmaceutical composition comprising a compound of any of (10) to (31), a pharmaceutically acceptable salt or hydrate thereof as an active ingredient,

(33) a pharmaceutical composition of (32) which is a DP receptor antagonist,

(34) a pharmaceutical composition of (32) which is a therapeutic agent for allergy,

(35) a pharmaceutical composition of (32) which is a therapeutic agent for asthma,

(36) a method for treating a disease related to DP receptor characterized by administration of the compound of any of (1) to (7) and (10) to (31), pharmaceutically acceptable salt or hydrate thereof,

(37) a method of (36) wherein the disease related to DP receptor is asthma,

(38) use of the compound of any of (1) to (7) and (10) to (31), pharmaceutically acceptable salt or hydrate thereof in the manufacturing of a therapeutic agent for treating a disease related to DP receptor, and

(39) use of the compound of (38), pharmaceutically acceptable salt or hydrate thereof wherein the disease related to DP receptor is asthma.

The present invention also includes the following inventions:

[1] a PDG2 antagonist comprising a compound of the general formula (I-a):

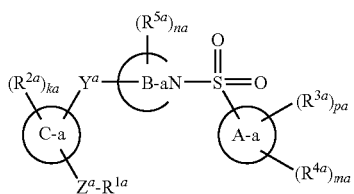

(I-a)

wherein the ring A-a is an aromatic carbocyclic ring or an aromatic heterocyclic ring;
the ring B-a is a 4- to 8-membered nitrogen-containing heterocyclic ring containing one or two nitrogen atom(s);
the ring C-a is a benzene ring, a naphthalene ring or a pyridine ring;

$R^{1a}$ is hydroxyalkyl, carboxy, alkyloxycarbonyl, optionally substituted carbamoyl or optionally substituted tetrazolyl;

$R^{2a}$ is independently a halogen atom, optionally substituted alkyl, optionally substituted alkenyl, optionally substituted alkynyl, optionally substituted cycloalkyl, optionally substituted alkyloxy, optionally substituted alkenyloxy, optionally substituted alkynyloxy, optionally substituted alkylthio, optionally substituted alkenylthio, optionally substituted alkynylthio, optionally substituted alkylsulfinyl, optionally substituted alkylsulfonyl, optionally substituted alkylsulfonyloxy, optionally substituted amino, acyl, optionally substituted alkyloxycarbonyl, optionally substituted alkenyloxycarbonyl, optionally substituted alkynyloxycarbonyl, optionally substituted carbamoyl, cyano, nitro, optionally substituted aryl, optionally substituted aryloxy, optionally substituted arylthio, optionally substituted arylsulfinyl, optionally substituted arylsulfonyl, optionally substituted arylsulfonyloxy, optionally substituted heteroaryl, optionally substituted heteroaryloxy, optionally substituted heteroarylthio, optionally substituted heteroarylsulfinyl, optionally substituted heteroarylsulfonyl, optionally substituted heteroarylsulfonyloxy or an optionally substituted non-aromatic heterocyclic group;

$R^{3a}$ is optionally substituted alkyloxy, optionally substituted alkylthio, optionally substituted cycloalkyloxy, optionally substituted cycloalkylthio, optionally substituted aryloxy, optionally substituted arylthio, optionally substituted heteroaryloxy or optionally substituted heteroarylthio;

$R^{4a}$ is independently a halogen atom, optionally substituted alkyl, optionally substituted alkenyl, optionally substituted alkynyl, optionally substituted cycloalkyl, optionally substituted alkyloxy, optionally substituted alkenyloxy, optionally substituted alkynyloxy, optionally substituted alkylthio, optionally substituted alkenylthio, optionally substituted alkynylthio, optionally substituted alkylsulfinyl, optionally substituted alkylsulfonyl, optionally substituted alkylsulfonyloxy, optionally substituted amino, acyl, optionally substituted alkyloxycarbonyl, optionally substituted alkenyloxycarbonyl, optionally substituted alkynyloxycarbonyl, optionally substituted carbamoyl, cyano, nitro, optionally substituted aryl, optionally substituted aryloxy, optionally substituted arylthio, optionally substituted arylsulfinyl, optionally substituted arylsulfonyl, optionally substituted arylsulfonyloxy, optionally substituted heteroaryl, optionally substituted heteroaryloxy, optionally substituted heteroarylthio, optionally substituted heteroarylsulfinyl, optionally substituted heteroarylsulfonyl, optionally substituted heteroarylsulfonyloxy or an optionally substituted non-aromatic heterocyclic group;

$R^{5a}$ is independently optionally substituted alkyl or optionally substituted aryl;

$Y^a$ is a single bond, alkylene, alkenylene, alkynylene, —O—, —S—, —O-alkylene- or —S-alkylene-;

$Z^a$ is a single bond, alkylene, alkenylene, alkynylene, —O-alkylene- or —S-alkylene-;

ka is 0, 1, 2, 3 or 4;
ma is 0, 1 or 2;
na is 0, 1 or 2; and
pa is 0 or 1; provided that ka is not 0 when the ring B-a is a 6-membered nitrogen-containing heterocyclic ring containing one or two nitrogen atom(s) and the ring C-a is a benzene ring;
a pharmaceutically acceptable salt or hydrate thereof as an active ingredient,

[2] a PGD2 antagonist of [1] wherein the ring C-a is a benzene ring or a pyridine ring,
[3] a PGD2 antagonist of [1] or [2] wherein the ring B-a is a ring of the formula of

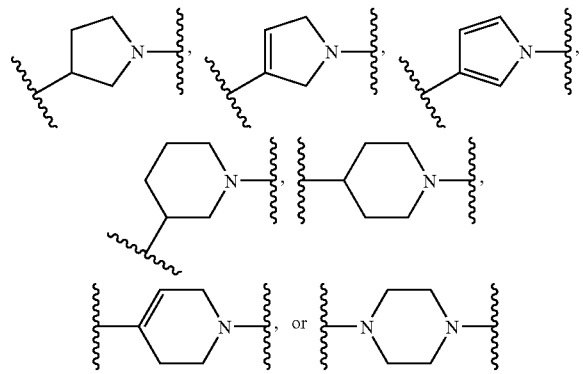

and n is 0,
[4] a PGD2 antagonist of any of [1] to [3] wherein the ring A-a is a benzene ring or a pyridine ring,
[5] a PGD2 antagonist of any of [1] to [4] wherein pa is 1,
[6] a PGD2 antagonist of any of [1] to [5] wherein $Y^a$ is a single bond or —O—,
[7] a PGD2 antagonist of any of [1] to [6] wherein $R^{1a}$ is carboxy,
[8] a PGD2 antagonist of any of [1] to [7] which is a therapeutic agent for allergy,
[9] a PGD2 antagonist of any of [1] to [7] which is a therapeutic agent for asthma,
[10] a compound of the general formula (II-a)

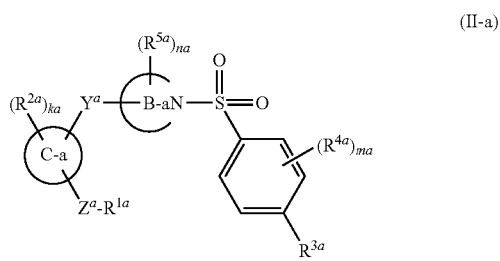

(II-a)

wherein the ring B-a is a 4- to 8-membered nitrogen-containing heterocyclic ring containing one or two nitrogen atom(s);
the ring C-a is a benzene ring, a naphthalene ring or a pyridine ring;
$R^{1a}$ is hydroxyalkyl, carboxy, alkyloxycarbonyl, optionally substituted carbamoyl or optionally substituted tetrazolyl;
$R^{2a}$ is independently a halogen atom, optionally substituted alkyl, optionally substituted alkenyl, optionally substituted alkynyl, optionally substituted cycloalkyl, optionally substituted alkyloxy, optionally substituted alkenyloxy, optionally substituted alkynyloxy, optionally substituted alkylthio, optionally substituted alkenylthio, optionally substituted alkynylthio, optionally substituted alkylsulfinyl, optionally substituted alkylsulfonyl, optionally substituted alkylsulfonyloxy, optionally substituted amino, acyl, optionally substituted alkyloxycarbonyl, optionally substituted alkenyloxycarbonyl, optionally substituted alkynyloxycarbonyl, optionally substituted carbamoyl, cyano, nitro, optionally substituted aryl, optionally substituted aryloxy, optionally substituted arylthio, optionally substituted arylsulfinyl, optionally substituted arylsulfonyl, optionally substituted arylsulfonyloxy, optionally substituted heteroaryl, optionally substituted heteroaryloxy, optionally substituted heteroarylthio, optionally substituted heteroarylsulfinyl, optionally substituted heteroarylsulfonyl, optionally substituted heteroarylsulfonyloxy or an optionally substituted non-aromatic heterocyclic group;
$R^{3a}$ is optionally substituted alkyloxy, optionally substituted alkylthio, optionally substituted cycloalkyloxy, optionally substituted cycloalkylthio, optionally substituted aryloxy, optionally substituted arylthio, optionally substituted heteroaryloxy or optionally substituted heteroarylthio;
$R^{4a}$ is independently a halogen atom, optionally substituted alkyl, optionally substituted alkenyl, optionally substituted alkynyl, optionally substituted cycloalkyl, optionally substituted alkyloxy, optionally substituted alkenyloxy, optionally substituted alkynyloxy, optionally substituted alkylthio, optionally substituted alkenylthio, optionally substituted alkynylthio, optionally substituted alkylsulfinyl, optionally substituted alkylsulfonyl, optionally substituted alkylsulfonyloxy, optionally substituted amino, acyl, optionally substituted alkyloxycarbonyl, optionally substituted alkenyloxycarbonyl, optionally substituted alkynyloxycarbonyl, optionally substituted carbamoyl, cyano, nitro, optionally substituted aryl, optionally substituted aryloxy, optionally substituted arylthio, optionally substituted arylsulfinyl, optionally substituted arylsulfonyl, optionally substituted arylsulfonyloxy, optionally substituted heteroaryl, optionally substituted heteroaryloxy, optionally substituted heteroarylthio, optionally substituted heteroarylsulfinyl, optionally substituted heteroarylsulfonyl, optionally substituted heteroarylsulfonyloxy or an optionally substituted non-aromatic heterocyclic group;
$R^{5a}$ is independently optionally substituted alkyl or optionally substituted aryl;
$Y^a$ is a single bond, alkylene, alkenylene, alkynylene, —O—, —S—, —O-alkylene- or —S-alkylene-;
$Z^a$ is a single bond, alkylene, alkenylene, alkynylene, —O-alkylene- or —S-alkylene-;
ka is 0, 1, 2, 3 or 4;
ma is 0, 1 or 2; and
na is 0, 1 or 2; provided that a) ka is not 0 when the ring B-a is a 6-membered nitrogen-containing heterocyclic ring containing one or two nitrogen atom(s) and the ring C-a is a benzene ring and b) the group of the formula of

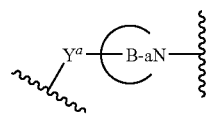

is not a group of the formula of

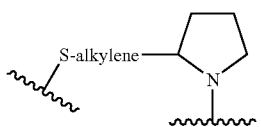

when $Z^a$ is —O-alkylene;
a pharmaceutically acceptable salt or hydrate thereof,

[11] a compound of [11] wherein the ring B-a is a ring of the formula of

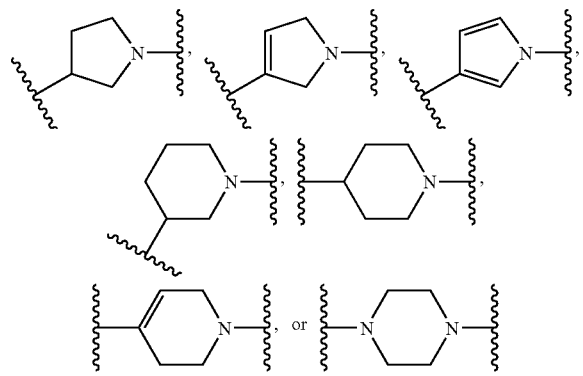

and na is 0;
a pharmaceutically acceptable salt or hydrate thereof,

[12] a compound of [10] or [11] wherein the ring C-a is a benzene ring or a pyridine ring;
a pharmaceutically acceptable salt or hydrate thereof,

[13] a compound of any of [10] to [12] wherein $R^{3a}$ is optionally substituted alkyloxy or optionally substituted alkylthio;
a pharmaceutically acceptable salt or hydrate thereof,

[14] a compound of any of [10] to [13] wherein $R^{1a}$ is carboxy;
a pharmaceutically acceptable salt or hydrate thereof,

[15] a compound of the general formula (III-a):

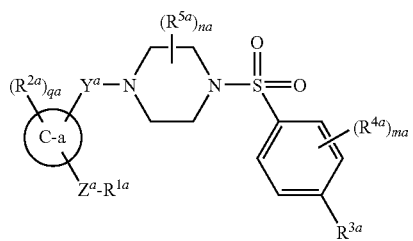

(III-a)

wherein the ring C-a is a benzene ring, a naphthalene ring or a pyridine ring;

$R^{1a}$ is hydroxyalkyl, carboxy, alkyloxycarbonyl, optionally substituted carbamoyl or optionally substituted tetrazolyl;

$R^{2a}$ is independently a halogen atom, optionally substituted alkyl, optionally substituted alkenyl, optionally substituted alkynyl, optionally substituted cycloalkyl, optionally substituted alkyloxy, optionally substituted alkenyloxy, optionally substituted alkynyloxy, optionally substituted alkylthio, optionally substituted alkenylthio, optionally substituted alkynylthio, optionally substituted alkylsulfinyl, optionally substituted alkylsulfonyl, optionally substituted alkylsulfonyloxy, optionally substituted amino, acyl, optionally substituted alkyloxycarbonyl, optionally substituted alkenyloxycarbonyl, optionally substituted alkynyloxycarbonyl, optionally substituted carbamoyl, cyano, nitro, optionally substituted aryl, optionally substituted aryloxy, optionally substituted arylthio, optionally substituted arylsulfinyl, optionally substituted arylsulfonyl, optionally substituted arylsulfonyloxy, optionally substituted heteroaryl, optionally substituted heteroaryloxy, optionally substituted heteroarylthio, optionally substituted heteroarylsulfinyl, optionally substituted heteroarylsulfonyl, optionally substituted heteroarylsulfonyloxy or an optionally substituted non-aromatic heterocyclic group;

$R^{3a}$, is optionally substituted alkyloxy, optionally substituted alkylthio, optionally substituted cycloalkyloxy, optionally substituted cycloalkylthio, optionally substituted aryloxy, optionally substituted arylthio, optionally substituted heteroaryloxy or optionally substituted heteroarylthio;

$R^{4a}$ is independently a halogen atom, optionally substituted alkyl, optionally substituted alkenyl, optionally substituted alkynyl, optionally substituted cycloalkyl, optionally substituted alkyloxy, optionally substituted alkenyloxy, optionally substituted alkynyloxy, optionally substituted alkylthio, optionally substituted alkenylthio, optionally substituted alkynylthio, optionally substituted alkylsulfinyl, optionally substituted alkylsulfonyl, optionally substituted alkylsulfonyloxy, optionally substituted amino, acyl, optionally substituted alkyloxycarbonyl, optionally substituted alkenyloxycarbonyl, optionally substituted alkynyloxycarbonyl, optionally substituted carbamoyl, cyano, nitro, optionally substituted aryl, optionally substituted aryloxy, optionally substituted arylthio, optionally substituted arylsulfinyl, optionally substituted arylsulfonyl, optionally substituted arylsulfonyloxy, optionally substituted heteroaryl, optionally substituted heteroaryloxy, optionally substituted heteroarylthio, optionally substituted heteroarylsulfinyl, optionally substituted heteroarylsulfonyl, optionally substituted heteroarylsulfonyloxy or an optionally substituted non-aromatic heterocyclic group;

$R^{5a}$ is independently optionally substituted alkyl or optionally substituted aryl;

$Y^a$ is a single bond, alkylene, alkenylene, alkynylene, —O—, —S—, —O-alkylene- or —S-alkylene-;

$Z^a$ is a single bond, alkylene, alkenylene, alkynylene, —O-alkylene- or —S-alkylene-;

ma is 0, 1 or 2;
na is 0, 1 or 2; and
qa is 1, 2, 3 or 4;
a pharmaceutically acceptable salt or hydrate thereof,

[16] a compound of [15] wherein the ring C-a is a benzene ring or a pyridine ring; a pharmaceutically acceptable salt or hydrate thereof,

[17] a compound of [15] or [16] wherein $R^{3a}$ is alkyloxy which may be substituted with one to three substituent(s) selected from the substituent group Q-a comprising a halogen atom, alkyloxy, aryl and heteroaryl or optionally substituted alkylthio;
a pharmaceutically acceptable salt or hydrate thereof,

[18] a compound of any of [15] to [17] wherein $R^{1a}$ is carboxy;
a pharmaceutically acceptable salt or hydrate thereof,

[19] a compound of the general formula (IV-a):

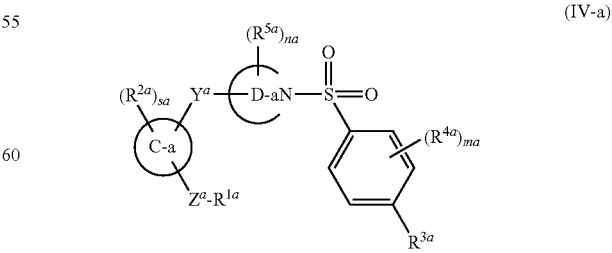

(IV-a)

wherein the ring C-a is a benzene ring, a naphthalene ring or a pyridine ring;

the ring D-a is a ring of the formula of

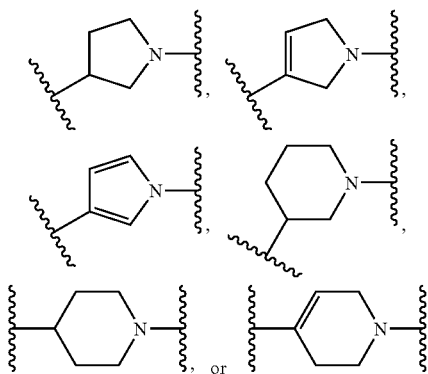

R$^{1a}$ is hydroxyalkyl, carboxy, alkyloxycarbonyl, optionally substituted carbamoyl or optionally substituted tetrazolyl;

R$^{2a}$ is independently a halogen atom, optionally substituted alkyl, optionally substituted alkenyl, optionally substituted alkynyl, optionally substituted cycloalkyl, optionally substituted alkyloxy, optionally substituted alkenyloxy, optionally substituted alkynyloxy, optionally substituted alkylthio, optionally substituted alkenylthio, optionally substituted alkynylthio, optionally substituted alkylsulfinyl, optionally substituted alkylsulfonyl, optionally substituted alkylsulfonyloxy, optionally substituted amino, acyl, optionally substituted alkyloxycarbonyl, optionally substituted alkenyloxycarbonyl, optionally substituted alkynyloxycarbonyl, optionally substituted carbamoyl, cyano, nitro, optionally substituted aryl, optionally substituted aryloxy, optionally substituted arylthio, optionally substituted arylsulfinyl, optionally substituted arylsulfonyl, optionally substituted arylsulfonyloxy, optionally substituted heteroaryl, optionally substituted heteroaryloxy, optionally substituted heteroarylthio, optionally substituted heteroarylsulfinyl, optionally substituted heteroarylsulfonyl, optionally substituted heteroarylsulfonyloxy or an optionally substituted non-aromatic heterocyclic group;

R$^{3a}$ is optionally substituted alkyloxy, optionally substituted alkylthio, optionally substituted cycloalkyloxy, optionally substituted cycloalkylthio, optionally substituted aryloxy, optionally substituted arylthio, optionally substituted heteroaryloxy or optionally substituted heteroarylthio;

R$^{4a}$ is independently a halogen atom, optionally substituted alkyl, optionally substituted alkenyl, optionally substituted alkynyl, optionally substituted cycloalkyl, optionally substituted alkyloxy, optionally substituted alkenyloxy, optionally substituted alkynyloxy, optionally substituted alkylthio, optionally substituted alkenylthio, optionally substituted alkynylthio, optionally substituted alkylsulfinyl, optionally substituted alkylsulfonyl, optionally substituted alkylsulfonyloxy, optionally substituted amino, acyl, optionally substituted alkyloxycarbonyl, optionally substituted alkenyloxycarbonyl, optionally substituted alkynyloxycarbonyl, optionally substituted carbamoyl, cyano, nitro, optionally substituted aryl, optionally substituted aryloxy, optionally substituted arylthio, optionally substituted arylsulfinyl, optionally substituted arylsulfonyl, optionally substituted arylsulfonyloxy, optionally substituted heteroaryl, optionally substituted heteroaryloxy, optionally substituted heteroarylthio, optionally substituted heteroarylsulfinyl, optionally substituted heteroarylsulfonyl, optionally substituted heteroarylsulfonyloxy or an optionally substituted non-aromatic heterocyclic group;

R$^{5a}$ is independently optionally substituted alkyl or optionally substituted aryl;

Y$^a$ is a single bond, alkylene, alkenylene, alkynylene, —O—, —S—, —O-alkylene- or —S-alkylene-;

Z$^a$ is a single bond, alkylene, alkenylene, alkynylene, —O-alkylene- or —S-alkylene-;

ma is 0, 1 or 2;
na is 0, 1 or 2;
sa is 1, 2, 3 or 4
a pharmaceutically acceptable salt or hydrate thereof,

[20] a compound of [19] wherein the ring C-a is a benzene ring or a pyridine ring; a pharmaceutically acceptable salt or hydrate thereof,

[21] a compound of [19] or [20] wherein R$^{3a}$ is alkyloxy which may be substituted with one to three substituent(s) selected from the substituent group Q-a comprising a halogen atom, alkyloxy, aryl and heteroaryl or optionally substituted alkylthio;
a pharmaceutically acceptable salt or hydrate thereof,

[22] a compound of any of [19] to [21] wherein R$^{1a}$ is carboxy;
a pharmaceutically acceptable salt or hydrate thereof,

[23] a compound of the general formula (V-a)

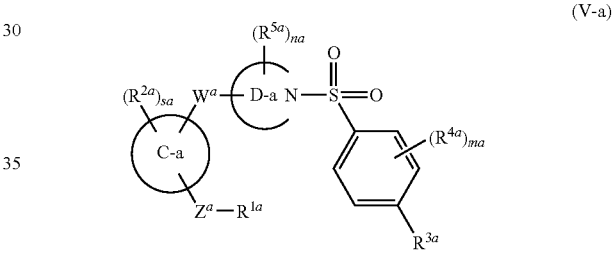

wherein the ring C-a is a benzene ring, a naphthalene ring or a pyridine ring;
the ring D-a is a ring of the formula of

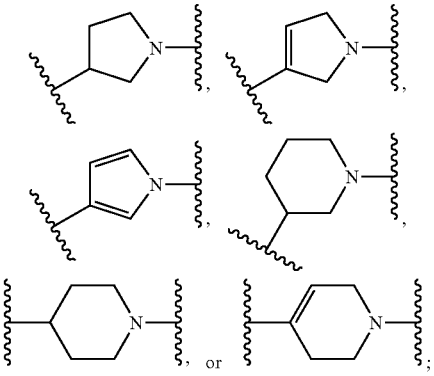

R$^{1a}$ is hydroxyalkyl, carboxy, alkyloxycarbonyl, optionally substituted carbamoyl or optionally substituted tetrazolyl;

R$^{2a}$ is independently a halogen atom, optionally substituted alkyl, optionally substituted alkenyl, optionally substituted alkynyl, optionally substituted cycloalkyl, optionally substituted alkyloxy, optionally substituted alkenyloxy, optionally substituted alkynyloxy, optionally substituted alkylthio, optionally substituted alkenylthio, optionally substituted alkynylthio, optionally substituted alkylsulfinyl, optionally substituted alkylsulfonyl, optionally substituted alkylsulfonyloxy, optionally substituted amino, acyl, optionally substituted alkyloxycarbonyl, optionally substituted alkenyloxycarbonyl, optionally substituted alkynyloxycarbonyl, optionally substituted carbamoyl, cyano, nitro, optionally substituted aryl, optionally substituted aryloxy, optionally substituted arylthio, optionally substituted arylsulfinyl, optionally substituted arylsulfonyl, optionally substituted arylsulfonyloxy, optionally substituted heteroaryl, optionally substituted heteroaryloxy, optionally substituted heteroarylthio, optionally substituted heteroarylsulfinyl, optionally substituted heteroarylsulfonyl, optionally substituted heteroarylsulfonyloxy or an optionally substituted non-aromatic heterocyclic group;

$R^{3a}$ is optionally substituted alkyloxy, optionally substituted alkylthio, optionally substituted cycloalkyloxy, optionally substituted cycloalkylthio, optionally substituted aryloxy, optionally substituted arylthio, optionally substituted heteroaryloxy or optionally substituted heteroarylthio;

$R^{4a}$ is independently a halogen atom, optionally substituted alkyl, optionally substituted alkenyl, optionally substituted alkynyl, optionally substituted cycloalkyl, optionally substituted alkyloxy, optionally substituted alkenyloxy, optionally substituted alkynyloxy, optionally substituted alkylthio, optionally substituted alkenylthio, optionally substituted alkynylthio, optionally substituted alkylsulfinyl, optionally substituted alkylsulfonyl, optionally substituted alkylsulfonyloxy, optionally substituted amino, acyl, optionally substituted alkyloxycarbonyl, optionally substituted alkenyloxycarbonyl, optionally substituted alkynyloxycarbonyl, optionally substituted carbamoyl, cyano, nitro, optionally substituted aryl, optionally substituted aryloxy, optionally substituted arylthio, optionally substituted arylsulfinyl, optionally substituted arylsulfonyl, optionally substituted arylsulfonyloxy, optionally substituted heteroaryl, optionally substituted heteroaryloxy, optionally substituted heteroarylthio, optionally substituted heteroarylsulfinyl, optionally substituted heteroarylsulfonyl, optionally substituted heteroarylsulfonyloxy or an optionally substituted non-aromatic heterocyclic group;

$R^{5a}$ is independently optionally substituted alkyl or optionally substituted aryl;

$W^a$ is a single bond, alkylene, alkenylene, alkynylene, —O— or —S—;

$Z^a$ is a single bond, alkylene, alkenylene, alkynylene, —O-alkylene- or —S-alkylene-;

ma is 0, 1 or 2;

na is 0, 1 or 2;

sa is 1, 2, 3 or 4;

a pharmaceutically acceptable salt or hydrate thereof,

[24] a compound of [23] wherein the ring C-a is a benzene ring or a pyridine ring; a pharmaceutically acceptable salt or hydrate thereof,

[25] a compound of [23] or [24] wherein $R^{3a}$ is alkyloxy which may be substituted with one to three substituent(s) selected from the substituent group Q-a comprising a halogen atom, alkyloxy, aryl and heteroaryl or optionally substituted alkylthio;

a pharmaceutically acceptable salt or hydrate thereof,

[26] a compound of any of [23] to [25] wherein $R^{1a}$ is carboxy;

a pharmaceutically acceptable salt or hydrate thereof,

[27] a pharmaceutical composition comprising a compound of any of [10] to

[26] a pharmaceutically acceptable salt or hydrate thereof as an active ingredient,

[28] a pharmaceutical composition of [27] which is a DP receptor antagonist,

[29] a pharmaceutical composition of [27] which is a therapeutic agent for allergy,

[30] a pharmaceutical composition of [27] which is a therapeutic agent for asthma,

[31] a method for treating a disease related to DP receptor characterized by administration of the compound of any of [1] to [7] and [10] to [26], pharmaceutically acceptable salt or hydrate thereof,

[32] a method of [31] wherein the disease related to DP receptor is asthma,

[33] use of the compound of any of [1] to [7] and [10] to [26], pharmaceutically acceptable salt or hydrate thereof in the manufacturing of a therapeutic agent for treating a disease related to DP receptor,

[34] use of the compound of [33], pharmaceutically acceptable salt or hydrate thereof wherein the disease related to DP receptor is asthma, Terms herein used are explained below. In the present specification each term is used under the unified definition and has the same meaning when used alone or in combination with other terms.

In the present specification, a term of "halogen atom" means a fluorine atom, a chlorine atom, a bromine atom and an iodine atom. A fluorine atom, a chlorine atom and a bromine atom are preferable.

In the present specification, a term of "hetero atom" means an oxygen atom, a sulfur atom and a nitrogen atom.

In the present specification, a term of "alkyl" includes a monovalent straight or branched hydrocarbon group having one to eight carbon atom(s). For example, methyl, ethyl, n-propyl, isopropyl, n-butyl, isobutyl, sec-butyl, tert-butyl, n-pentyl, isopentyl, neo-pentyl, n-hexyl, isohexyl, n-heptyl, n-octyl and the like are exemplified. C1-C6 alkyl is preferred. C1-C4 alkyl is further preferred. When a number of carbon is specified, it means "alkyl" having the carbon number within the range.

In the present specification, a term of "hydroxyalkyl" includes a "alkyl" above, a hydrogen atom of which is substituted with a hydroxy group. For example, hydroxymethyl, 1-hydroxyethyl, 2-hydroxyethyl, 1-hydroxypropyl, 2-hydroxypropyl and the like are exemplified. Hydroxymethyl is preferred.

In the present specification, a term of "alkenyl" includes a monovalent straight or branched hydrocarbon group having two to eight carbon atoms and one or more double bond(s). For example, vinyl, allyl, 1-propenyl, 2-butenyl, 2-pentenyl, 2-hexenyl, 2-heptenyl, 2-octenyl and the like are exemplified. C2-C6 alkenyl is preferred. Moreover, C2-C4 alkenyl is further preferred.

In the present specification, a term of "alkynyl" includes a monovalent straight or branched hydrocarbon group having two to eight carbon atoms and one or more triple bond(s). For example, ethynyl, 1-propynyl, 2-propynyl, 2-butynyl, 2-pentynyl, 2-hexynyl, 2-heptynyl, 2-octynyl and the like are exemplified. C2-C6 alkynyl is preferred. Moreover, C2-C4 alkynyl is further preferred.

In the present specification, a term of "cycloalkyl" includes a cycloalkyl having three to eight carbon atoms and for example, cyclopropyl, ctclobutyl, cyclopentyl, cyclohexyl, cycloheptyl, cyclooctyl and the like are exemplified. C3-C6 cycloalkyl is preferred.

In the present specification, a term of "cycloalkenyl" includes a cycloalkenyl having three to eight carbon atoms and for example, cyclopropenyl, cyclobutenyl, cyclopentenyl, cyclohexenyl, cycloheptenyl, cyclooctenyl and the like are exemplified. C3-C6 cycloalkenyl is preferred.

In the present specification, a term of "alkyloxy" includes a group wherein an oxygen atom is substituted with one "alkyl" above and for example, methyloxy, ethyloxy, n-propyloxy, isopropyloxy, n-butyloxy, isobutyloxy, sec-butyloxy, tert-butyloxy, n-pentyloxy, isopentyloxy, 2-pentyloxy, 3-pentyloxy, n-hexyloxy, isohexyloxy, 2-hexyloxy, 3-hexyloxy, n-heptyloxy, n-octyloxy, and the like are exemplified. C1-C6 alkyloxy is preferred. Moreover, C1-C4 alkyloxy is further preferred. When a number of carbon is specified, it means "alkyloxy" having the carbon number within the range.

In the present specification, a term of "alkenyloxy" includes a group wherein an oxygen atom is substituted with one "alkenyl" above and for example, vinyloxy, allyloxy, 1-propenyloxy, 2-butenyloxy, 2-pentenyloxy, 2-hexenyloxy, 2-heptenyloxy, 2-octenyloxy and the like are exemplified. C2-C6 alkenyloxy is preferred. Moreover, C2-C4 alkenyloxy is further preferred. When a number of carbon is specified, it means "alkenyloxy" having the carbon number within the range.

In the present specification, a term of "alkynyloxy" includes a group wherein an oxygen atom is substituted with one "alkynyl" above and for example, ethynyloxy, 1-propynyloxy, 2-propynyloxy, 2-butynyloxy, 2-pentynyloxy, 2-hexynyloxy, 2-heptynyloxy, 2-octynyloxy and the like are exemplified. C2-C6 alkynyloxy is preferred. Moreover, C2-C4 alkynyloxy is further preferred. When a number of carbon is specified, it means "alkynyloxy" having the carbon number within the range.

In the present specification, a term of "cycloalkyloxy" includes a group wherein an oxygen atom is substituted with one "cycloalkyl" above and for example, cyclopropyloxy, cyclobutyloxy, cyclopentyloxy, cyclohexyloxy, cycloheptyloxy and cyclooctyloxy are exemplified. C3-C6 cycloalkyloxy is preferred. When a number of carbon is specified, it means "cycloalkyloxy" having the carbon number within the range.

In the present specification, a term of "cycloalkenyloxy" includes a group wherein an oxygen atom is substituted with one "cycloalkenyl" above and for example, cyclopropenyloxy, cyclobutenyloxy, cyclopentenyloxy, cyclohexenyloxy, cycloheptenyloxy and cyclooctenyloxy are exemplified. C3-C6 cycloalkenyloxy is preferred. When a number of carbon is specified, it means "cycloalkenyloxy" having the carbon number within the range.

In the present specification, a term of "alkylthio" includes a group wherein a sulfur atom is substituted with one "alkyl" above, and for example, methylthio, ethylthio, n-propylthio, isopropylthio, n-butylthio, isobutylthio, sec-butylthio, tert-butylthio, n-pentylthio, isopentylthio, 2-pentylthio, 3-pentylthio, n-hexylthio, isohexylthio, 2-hexylthio, 3-hexylthio, n-heptylthio, n-octylthio, and the like are exemplified. C1-C6 Alkylthio is preferred. Moreover, C1-C4 alkylthio is further preferred. When a number of carbon is specified, it means "alkylthio" having the carbon number within the range.

In the present specification, a term of "alkenylthio" includes a group wherein a sulfur atom is substituted with one "alkenyl" above, and for example, vinylthio, allylthio, 1-propenylthio, 2-butenylthio, 2-pentenylthio, 2-hexenylthio, 2-heptenylthio, 2-octenylthio and the like are exemplified. C2-C6 Alkenylthio is preferred. Moreover, C2-C4 alkylthio is further preferred. When a number of carbon is specified, it means "alkenylthio" having the carbon number within the range.

In the present specification, a term of "alkynylthio" includes a group wherein a sulfur atom is substituted with one "alkynyl" above and for example, ethynylthio, 1-propynylthio, 2-propynylthio, 2-butynylthio, 2-pentynylthio, 2-hexynylthio, 2-heptynylthio, 2-octynylthio and the like are exemplified. C2-C6 alkynylthio is preferred. Moreover, C2-C4 alkynylthio is further preferred. When a number of carbon is specified, it means "alkynylthio" having the carbon number within the range.

In the present specification, a term of "alkylsulfinyl" includes a group wherein sulfinyl is substituted with one "alkyl" above and for example, methylsulfinyl, ethylsulfinyl, n-propylsulfinyl, isopropylsulfinyl, n-butylsulfinyl, isobutylsulfinyl, sec-butylsulfinyl, tert-butylsulfinyl, n-pentylsulfinyl, isopentylsulfinyl, 2-pentylsulfinyl, 3-pentylsulfinyl, n-hexylsulfinyl, isohexylsulfinyl, 2-hexylsulfinyl, 3-hexylsulfinyl, n-heptylsulfinyl, n-octylsulfinyl and the like are exemplified. C1-C6 alkylsulfinyl is preferred. Moreover, C1-C4 alkylsulfinyl is further preferred.

In the present specification, a term of "alkylsulfonyl" includes a group wherein sulfonyl is substituted with one "alkyl" above and for example, methylsulfonyl, ethylsulfonyl, n-propylsulfonyl, isopropylsulfonyl, n-butylsulfonyl, isobutylsulfonyl, sec-butylsulfonyl, tert-butylsulfonyl, n-pentylsulfonyl, isopentylsulfonyl, 2-pentylsulfonyl, 3-pentylsulfonyl, n-hexylsulfonyl, isohexylsulfonyl, 2-hexylsulfonyl, 3-hexylsulfonyl, n-heptylsulfonyl, n-octylsulfonyl and the like are exemplified. C1-C6 alkylsulfonyl is preferred. Moreover, C1-C4 alkylsulfonyl is further preferred.

In the present specification, a term of "alkylsulfonyloxy" includes a group wherein an oxygen atom is substituted with one "alkylsulfonyl" above and for example, methylsulfonyloxy, ethylsulfonyloxy, n-propylsulfonyloxy, isopropylsulfonyloxy, n-butylsulfonyloxy, isobutylsulfonyloxy, sec-butylsulfonyloxy, tert-butylsulfonyloxy, n-pentylsulfonyloxy, isopentylsulfonyloxy, 2-pentylsulfonyloxy, 3-pentylsulfonyloxy, n-hexylsulfonyloxy, isohexylsulfonyloxy, 2-hexylsulfonyloxy, 3-hexylsulfonyloxy, n-heptylsulfonyloxy, n-octylsulfonyloxy and the like are exemplified. C1-C6 alkylsulfonyl is preferred. Moreover, C1-C4 alkylsulfonyl is further preferred.

In the present specification, a term of "cycloalkylthio" includes a group wherein a sulfur atom is substituted with one "cycloalkyl" above and for example, cyclopropylthio, cyclobutylthio, cyclopentylthio, cyclohexylthio, cycloheptylthio, cyclooctylthio and the like are exemplified. C3-C6 cycloalkylthio is preferred. When a number of carbon is specified, it means "cycloalkylthio" having the carbon number within the range.

In the present specification, a term of "cycloalkylsulfinyl" includes a group in which sulfinyl is substituted with one "cycloalkyl" above. For example, cyclopropylsulfinyl, cyclobutylsulfinyl, cyclopentylsulfinyl, cyclohexylsulfinyl, cycloheptylsulfinyl, and cyclooctylsulfinyl are exemplified. Preferably C3-C6 cycloalkylsulfinyl is exemplified.

In the present specification, a term of "cycloalkylsulfonyl" includes a group in which sulfonyl is substituted with one "cycloalkyl" above. For example, cyclopropylsulfonyl, cyclobutylsulfonyl, cyclopentylsulfonyl, cyclohexylsulfonyl, cycloheptylsulfonyl, and cyclooctylsulfonyl are exemplified. Preferably C3-C6 cycloalkylsulfonyl is exemplified.

In the present specification, a term of "cycloalkylsulfonyloxy" includes a group in which an oxygen atom is substituted with one "cycloalkylsulfonyl" above. For example, cyclopropylsulfonyloxy, cyclobutylsulfonyloxy, cyclopentylsulfonyloxy, cyclohexylsulfonyloxy, cycloheptylsulfonyloxy, and cyclooctylsulfonyloxy are exemplified. Preferably C3-C6 cycloalkylsulfonyloxy is exemplified.

In the present specification, a term of "cycloalkenylthio" includes a group in which a sulfur atom is substituted with one "cycloalkenyl" above. For example, cyclopropenylthio, cyclobutenylthio, cyclopentenylthio, cyclohexenylthio, cycloheptenylthio, and cyclooctenylthio are exemplified. Preferably C3-C6 cycloalkenylthio is exemplified. When a number of carbon is specified, it means "cycloalkenylthio" having the carbon number within the range.

In the present specification, a term of "cycloalkenylsulfinyl" includes a group in which sulfinyl is substituted with one "cycloalkenyl" above. For example, cyclopropenylsulfinyl, cyclobutenylsulfinyl, cyclopentenylsulfinyl, cyclohexenylsulfinyl, cycloheptenylsulfinyl, and cyclooctenylsulfinyl are exemplified. Preferably C3-C6 cycloalkenylsulfinyl is exemplified.

In the present specification, a term of "cycloalkenylsulfonyl" includes a group in which sulfonyl is substituted with one "cycloalkenyl" above. For example, cyclopropenylsulfonyl, cyclobutenylsulfonyl, cyclopentenylsulfonyl, cyclohexenylsulfonyl, cycloheptenylsulfonyl, and cyclooctenylsulfonyl are exemplified. Preferably C3-C6 cycloalkenylsulfonyl is exemplified.

In the present specification, a term of "cycloalkenylsulfonyloxy" includes a group in which an oxygen atom is substituted with one "cycloalkenylsulfonyl" described above. For example, cyclopropenylsulfonyloxy, cyclobutenylsulfonyloxy, cyclopentenylsulfonyloxy, cyclohexenylsulfonyloxy, cycloheptenylsulfonyloxy, and cyclooctenylsulfonyloxy are exemplified. Preferably C3-C6 cycloalkenylsulfonyloxy is exemplified.

In the present specification, a term of "alkyloxycarbonyl" includes a group in which carbonyl is substituted with one "alkyloxy" above. For example, methyloxycarbonyl, ethyloxycarbonyl, n-propyloxycarbonyl, isopropyloxycarbonyl, n-butyloxycarbonyl, tert-butyloxycarbonyl and n-pentyloxycarbonyl are exemplified. Preferably C1-C4 alkyloxycarbonyl is exemplified. Moreover, C1-C2 alkyloxycarbonyl is further preferable.

In the present specification, a term of "alkenyloxycarbonyl" includes a group in which carbonyl is substituted with one "alkenyloxy" above. For example, vinyloxycarbonyl, allyloxycarbonyl, 1-propenyloxycarbonyl, 2-butenyloxycarbonyl and 2-pentenyloxyarbonyl are exemplified. Preferably C2-C4 alkyloxycarbonyl is exemplified.

In the present specification, a term of "alkynyloxycarbonyl" includes a group in which carbonyl is substituted with one "alkynyloxy" above. For example, ethynyloxycarbonyl, 1-propynyloxycarbonyl, 2-propynyloxycarbonyl, 2-butynyloxyarbonyl and 2-pentynyloxycarbonyl are exemplified. Preferably C2-C4 alkynyloxycarbonyl is exemplified.

In the present specification, a term of "acyl" includes alkylcarbonyl wherein the part of alkyl is "alkyl" before, alkenylcarbonyl wherein the part of alkenyl is "alkenyl" before, alkynylcarbonyl wherein the part of alkynyl is "alkynyl" before, cycloalkylcarbonyl wherein the part of cycloalkyl is "cycloalkyl" before, arylcarbonyl wherein the part of aryl is "aryl" below, heteroarylcarbonyl wherein the part of heteroaryl is "heteroaryl" below and non-aromatic heterocyclic-carbonyl wherein the part of non-aromatic heterocyclic group is "non-aromatic heterocyclic group" below. "Alkyl", "alkenyl", "alkynyl", "cycloalkyl", "aryl", "heteroaryl" and "non-aromatic heterocyclic group" may be substituted respectively with substituent groups exemplified in "optionally substituted alkyl", "optionally substituted alkenyl", "optionally substituted alkynyl", "optionally substituted cycloalkyl", "optionally substituted aryl", "optionally substituted heteroaryl" and "optionally substituted non-aromatic heterocyclic group" below. Examples of the acyl group include acetyl, propionyl, butyroyl, cyclohexylcarbonyl, benzoyl, pyridinecarbonyl and the like.

In the present specification, a term of "optionally substituted amino" includes an amino group which may be substituted with one or two group(s) of "alkyl" before, "alkenyl" before, "alkynyl" before, "cycloalkyl" before, "cycloalkynyl" before, "aryl" below, "heteroaryl" below, "acyl" before, "alkyloxycarbonyl" before, "alkenyloxycarbonyl" before, "alkynyloxycarbonyl" before, "alkylsulfonyl", "alkenylsulfonyl", "alkynylsulfonyl", "arylsulfonyl" and/or "heteroarylsulfonyl" before. Examples of the optionally substituted amino group include amino, methylamino, dimethylamino, ethylamino, diethylamino, ethylmethylamino, benzylamino, acetylamino, benzoylamino, methyloxycarbonylamino and methanesulfonylamino. Preferably, amino, methylamino, dimethylamino, ethylmethylamino, diethylamino, acetylamino and methanesulfonylamino are exemplified.

In the present specification, a term of "optionally substituted carbamoyl" includes an aminocarbonyl group wherein the part of optionally substituted amino is "optionally substituted amino" before and examples of the optionally substituted carbamoyl group includes carbamoyl, N-methylcarbamoyl, N,N-dimethylcarbamoyl, N-ethyl-N-methylcarbamoyl, N,N-diethylcarbamoyl, N-phenylcarbamoyl, N-benzylcarbamoyl, N-acetylcarbamoyl and N-methylsulfonylcarbamoyl etc. Preferably, carbamoyl, N-methylcarbamoyl, N,N-dimethylcarbamoyl and N-methylsulfonylcarbamoyl etc. are exemplified.

In the present specification, a term of "optionally substituted sulfamoyl" includes an aminosulfonyl group wherein the part of optionally substituted amino is "optionally substituted amino" before and examples of the optionally substituted sulfamoyl group include sulfamoyl, N-methylsulfamoyl, N,N-dimethylsulfamoyl, N-ethyl-N-methylsulfamoyl, N,N-diethylsulfamoyl, N-phenylsulfamoyl, N-benzylsulfamoyl, N-acetylsulfamoyl and N-methylsulfonylsulfamoyl etc. Preferably, sulfamoyl, N-methylsulfamoyl, N,N-dimethylsulfamoyl and N-methylsulfonylsulfamoyl etc. are exemplified.

In the present specification, a term of "alkylene" means a straight or branched alkylene group having one to ten carbon atom(s) and for example, methylene, 1-methylmethylene, 1,1-dimethylmethylene, ethylene, 1-methylethylene, 1-ethylethylene, 1,1-dimethylethylene, 1,2-dimethylethylene, 1,1-diethylethylene, 1,2-diethylethylene, 1-ethyl-2-methylethylene, trimethylene, 1-methyltrimethylene, 2-methyltrimethylene, 1,1-dimethyltrimethylene, 1,2-dimethyltrimethylene, 2,2-dimethyltrimethylene, 1-ethyltrimethylene, 2-ethyltrimethylene, 1,1-diethyltrimethylene, 1,2-diethyltrimethylene, 2,2-diethyltrimethylene, 2-ethyl-2-methyltrimethylene, tetramethylene, 1-methyltetramethylene, 2-methyltetramethylene, 1,1-dimethyltetramethylene, 1,2-dimethyltetramethylene, 2,2-dimethyltetramethylene, 2,2-di-n-propyltrimethylene etc. are exemplified. Especially, a straight or branched alkylene groups having two to six carbon atom(s) are preferred.

In the present specification, a term of "alkenylene" means a straight or branched alkenylene group having two to ten carbon atom(s) and for example, ethenylene, 1-methylethenylene, 1-ethylethenylene, 1,2-dimethylethenylene, 1,2-diethylethenylene, 1-etnyl-2-methylethenylene, propenylene, 1-methyl-2-propenylene, 2-methyl-2-propenylene, 1,1-dimethyl-2-propenylene, 1,2-dimethyl-2-propenylene, 1-ethyl-2-propenylene, 2-ethyl-2-propenylene, 1,1-dietnyl-2-propenylene, 1,2-diethyl-2-propenylene, 1-butenylene,2-butenylene, 1-methyl-2-butenylene, 2-methyl-2-butenylene, 1,1-dimethyl-2-butenylene, 1,2-dimethyl-2-butenylene etc, are exemplified. Especially, a straight or branched alkenylene groups having two to six carbon atom(s) are preferred.

In the present specification, a term of "alkynylene" means a straight or branched alkynylene group having two to ten carbon atom(s) and for example, ethynylene, propynylene, 1-methyl-2-propynylene, 1-ethyl-2-propynylene, butynylene, 1-methyl-2-butynylene, 2-methyl-3-butynylene, 1,1-dimethyl-2-butynylene, 1,2-dimethyl-3-butynylene, 2,2-dimethyl-3-butynylene etc, are are exemplified. Especially, a straight or branched alkynylene groups having two to six carbon atom(s) are preferred.

In the present specification, a term of "—O-alkylene" in Y includes a group of "alkylene" above, a terminal of which is linked to —O— and for example, —O-methylene- , —O-1-methylethylene-, —O-1,1-dimethylmethylene-, —O-ethylene-, —O-1-methylethylene-, —O-trimethylene etc are exemplified. Preferably, O-methylene-, —O-1-methylethylene- and —O-1,1-dimethylmethylene- are exemplified. In addition, the ring C and the ring B are linked in a manner of "the ring C—O-alkylene-the ring B".

In the present specification, a term of "—O-alkylene" of "—O-alkylene-R1" in —Z—$R^1$ includes a group of "alkylene" above, a terminal of which is linked to —O— and for example, —O-methylene-, —O-1-methylethylene-, —O-1,1-dimethylmethylene-, —O-ethylene-, —O-1-methylethylene-, —O-trimethylene etc are exemplified. —O-Methylene-, —O-1-methylethylene- and —O-1,1-dimethylmethylene- are preferred.

In the present specification, a term of "—S-alkylene" in Y includes a group of "alkylene" above, a terminal of which is linked to —S— and for example, —S-methylene-, —S-1-methylethylene-, —S-1,1-dimethylmethylene-, —S-ethylene-, —S-1-methylethylene-, —S-trimethylene etc are exemplified. Preferably, —S-methylene-, —S-1-methylethylene-, —S-1,1-dimethylmethylene- are exemplified. In addition, the ring C and the ring B are linked in a manner of "the ring C—S-alkylene- the ring B".

In the present specification, a term of "—S-alkylene" of "—S-alkylene-$R^1$" in —Z—$R^1$ includes a group of "alkylene" above, a terminal of which is linked to —S— and for example, —S-methylene-, —S-1-methylethylene-, —S-1,1-dimethylmethylene-, —S-ethylene-, —S-1-methylethylene-, —S-trimethylene etc are exemplified. —S-Methylene-, —S-1-methylethylene- and —S-1,1-dimethylmethylene- are preferred.

In the present specification, a term of "aryl" includes an aromatic monocyclic or aromatic fused cyclic hydrocarbons and it may be fused with "cycloalkyl" before, "cycloalkenyl" before or "non-aromatic heterocyclic group" below at any possible position. Both of monocyclic ring and fused ring may be substituted at any position and for example, phenyl, 1-naphthyl, 2-naphthyl, anthryl, tetrahydronaphthyl, 1,3-benzodioxolyl, 1,4-benzodioxanyl etc. are exemplified. Phenyl, 1-naphthyl and 2-naphthyl are preferred. Moreover, phenyl is further preferred.

In the present specification, a term of "non-aromatic heterocyclic group" includes a 5- to 7-membered non-aromatic heterocyclic ring containing one or more of heteroatom(s) selected independently from oxygen, sulfur and nitrogen atoms or a multicyclic ring formed by fusing the two or more rings thereof. For example, pyrrolidinyl (e.g., 1-pyrrolidinyl, 2-pyrrolidinyl), pyrrolinyl (e.g., 3-pyrrolinyl), imidazolidinyl (e.g., 2-imidazolidinyl), imidazolinyl (e.g., imidazolinyl), pyrazolidinyl (e.g., 1-pyrazolidinyl, 2-pyrazolidinyl), pyrazolinyl (e.g., pyrazolinyl), piperidyl (e.g., piperidino, 2-piperidyl), piperazinyl (e.g., 1-piperazinyl), indolinyl (e.g., 1-indolinyl), isoindolinyl (e.g., isoindolinyl), morpholinyl (e.g., morpholino, 3-morpholinyl) etc. are exemplified.

In the present specification, a term of "heteroaryl" in $R^2$, $R^{2a}$ and $R^{2b}$ includes a 5- to 6-membered aromatic ring containing one or more of heteroatom(s) selected independently from oxygen, sulfur and nitrogen atoms and it may be fused with "cycloalkyl" before, "aryl" before, "non-aromatic heterocyclic group" or other heteroaryl at any possible position. The heteroaryl group may be substituted at any position whenever it is a monocyclic ring or a fused ring. For example, pyrrolyl (e.g., 1-pyrrolyl, 2-pyrrolyl, 3-pyrrolyl), furyl (e.g., 2-furyl, 3-furyl), thienyl (e.g., 2-thienyl, 3-thienyl), imidazolyl (e.g., 2-imidazolyl, 4-imidazolyl), pyrazolyl (e.g., 1-pyrazolyl, 3-pyrazolyl), isothiazolyl (e.g., 3-isothiazolyl), isoxazolyl (e.g., 3-isoxazolyl), oxazolyl (e.g., 2-oxazolyl), thiazolyl (e.g., 2-thiazolyl), pyridyl (e.g., 2-pyridyl, 3-pyridyl, 4-pyridyl), pyrazinyl (e.g., 2-pyrazinyl), pyrimidinyl (e.g., 2-pyrimidinyl, 4-pyrimidinyl), pyridazinyl (e.g., 3-pyridazinyl), tetrazolyl (e.g., 1 H-tetrazolyl), oxadiazolyl (e.g., 1,3,4-oxadiazolyl), thiadiazolyl (e.g., 1,3,4-thiadiazolyl), indolidinyl (e.g., 2-indolidinyl, 6-indolidinyl), isoindolynyl (e.g., 2-isoindolynyl), indolyl (e.g., 1-indolyl, 2-indolyl, 3-indolyl), indazolyl (e.g., 3-indazolyl), purinyl (e.g., 8-purinyl), quinolidinyl (e.g., 2-quinolidinyl), isoquinolyl (e.g., 3-isoquinolyl), quinolyl (e.g., 2-quinolyl, 5-quinolyl), phtharazinyl (e.g., 1-phtharazinyl), naphthylidinyl (e.g., 2-naphthylidinyl), quinolanyl (e.g., 2-quinolanyl), quinazolinyl (e.g., 2-quinazolinyl), cinnolinyl (e.g., 3-cinnolinyl), pteridinyl (e.g., 2-pteridinyl), carbazolyl (e.g., 2-carbazolyl, 4-carbazolyl), phenanthridinyl (e.g., 2-phenanthridinyl, 3-phenanthridinyl), acridinyl (e.g.,1-acridinyl, 2-acridinyl), dibenzofuranyl (e.g., 1-dibenzofuranyl, 2-dibenzofuranyl), benzoimidazolyl (e.g., 2-benzoimidazolyl), benzoisoxazolyl (e.g., 3-benzoisoxazolyl), benzooxazolyl (e.g., 2-benzooxazolyl), benzooxadiazolyl (e.g., 4-benzooxadiazolyl), benzoisothiazolyl (e.g., 3-benzoisothiazolyl), benzothiazolyl (e.g., 2-benzothiazolyl), benzofuryl (e.g., 3-benzofuryl), benzothienyl (e.g., 2-benzothienyl), dibenzothienyl (e.g., 2-dibenzothienyl) and benzodioxolyl (e.g., 1,3-benzodioxolyl) etc. are exemplified.

In the present specification, a term of "heteroaryl" in $R^3$, $R^{3a}$, $R^{3b}$, $R^4$, $R^{4a}$, $R^{4b}$, $R^5$, $R^{5a}$, $R^{5b}$, $R^6$ and $R^7$ includes a 5- to 6-membered aromatic ring containing one or more of heteroatom(s) selected independently from oxygen, sulfur and nitrogen atoms and it may be fused with "cycloalkyl" before, "aryl" before, "non-aromatic heterocyclic group" or other heteroaryl at any possible position. The heteroaryl group may be substituted at any position whenever it is a monocyclic ring or a fused ring. For example, furyl (e.g., 2-furyl, 3-furyl), thienyl (e.g., 2-thienyl, 3-thienyl), imidazolyl (e.g., 2-imidazolyl, 4-imidazolyl), pyrazolyl (e.g., 1-pyrazolyl, 3-pyrazolyl), isothiazolyl (e.g., 3-isothiazolyl), isoxazolyl (e.g., 3-isoxazolyl), oxazolyl (e.g., 2-oxazolyl), thiazolyl (e.g., 2-thiazolyl), pyridyl (e.g., 2-pyridyl, 3-pyridyl, 4-pyridyl), pyrazinyl (e.g., 2-pyrazinyl), pyrimidinyl (e.g., 2-pyrimidinyl, 4-pyrimidinyl), pyridazinyl (e.g., 3-pyridazinyl), oxadiazolyl (e.g., 1,3,4-oxadiazolyl), thiadiazolyl (e.g., 1,3,4-thiadiazolyl), benzoimidazolyl (e.g., 2-benzoimidazolyl), benzoisoxazolyl (e.g., 3-benzoisoxazolyl), benzooxazolyl (e.g., 2-benzooxazolyl), benzofuryl (e.g., 3-benzofuryl), benzothienyl (e.g., 2-benzothienyl) etc. are exemplified.

In the present specification, "2-pyridone" means pyridine-2-one.

In the present specification, a term of "aryloxy" includes a group in which an oxygen atom is substituted with one "aryl" before and for example, phenyloxy and naphthyloxy etc. are exemplified.

In the present specification, a term of "arylthio" includes a group in which a sulfur atom is substituted with one "aryl" before and for example, phenylthio and naphthylthio etc. are exemplified.

In the present specification, a term of "arylsulfinyl" includes a group in which sulfinyl is substituted with one "aryl" before and for example, phenylsulfinyl and naphthylsulfinyl etc. are exemplified.

In the present specification, a term of "arylsulfonyl" includes a group in which sulfonyl is substituted with one "aryl" before and for example, phenylsulfonyl and naphthylsulfoinyl etc. are exemplified.

In the present specification, examples of "arylsulfonyloxy include phenylsulfonyloxy and naphthylsulfonyloxy etc.

In the present specification, a term of "aryloxycarbonyl" includes a group in which carbonyl is substituted with one "aryloxy" before and for example, phenyloxycarbonyl, 1-naphthyloxycarbonyl and 1-naphthyloxycarbonyl etc. are exemplified.

In the present specification, a term of "heteroaryloxy" includes a group in which an oxygen atom is substituted with one "heteroaryl" before. For example, pyrrolyloxy, furyloxy, thienyloxy, imidazolyloxy, pyrazolyloxy, isothiazolyloxy, isoxazolyloxy, oxazolyloxy, thiazolyloxy, pyridyloxy, pyrazinyloxy, pyrimidinyloxy, pyridazinyloxy, tetrazolyloxy, oxadiazolyloxy, thiadiazolyloxy, indolidinyloxy, isoindolynyloxy, indolyloxy, indazolyloxy, purinyloxy, quinolidinyloxy, isoquinolyloxy, quinolyloxy, phtharazinyloxy, naphthylidinyloxy, quinolanyloxy, quinazolinyloxy, cinnolinyloxy, pteridinyloxy, carbazolyloxy, phenanthridinyloxy, acridinyloxy, dibenzofuranyloxy, benzoimidazolyloxy, benzoisoxazolyloxy, benzooxazolyloxy, benzooxadiazolyloxy, benzoisothiazolyloxy, benzothiazolyloxy, benzofuryloxy, benzothienyloxy, dibenzothienyloxy and benzodioxolyloxy are exemplified. Preferably furyloxy, thienyloxy, imidazolyloxy, pyrazolyloxy, isothiazolyloxy, isoxazolyloxy, oxazolyloxy, thiazolyloxy, pyridyloxy, pyrazinyloxy, pyrimidinyloxy and pyridazinyloxy are exemplified In the present specification, a term of "heteroarylthio" includes a group in which a sulfur atom is substituted with one "heteroaryl" before. For example, pyrrolylthio, furylthio, thienylthio, imidazolylthio, pyrazolylthio, isothiazolylthio, isoxazolylthio, oxazolylthio, thiazolylthio, pyridylthio, pyrazinylthio, pyrimidinylthio, pyridazinylthio, tetrazolylthio, oxadiazolylthio, thiadiazolylthio, indolidinylthio, isoindolynylthio, indolylthio, indazolylthio, purinylthio, quinolidinylthio, isoquinolylthio, quinolylthio, phtharazinylthio, naphthylidinylthio, quinolanylthio, quinazolinylthio, cinnolinylthio, pteridinylthio, carbazolylthio, phenanthridinylthio, acridinylthio, dibenzofuranylthio, benzoimidazolylthio, benzoisoxazolylthio, benzooxazolylthio, benzooxadiazolylthio, benzoisothiazolylthio, benzothiazolylthio, benzofurylthio, benzothienylthio, dibenzothienylthio and benzodioxolylthio etc. are exemplified. Preferably furylthio, thienylthio, imidazolylthio, pyrazolylthio, isothiazolylthio, isoxazolylthio, oxazolylthio, thiazolylthio, pyridylthio, pyrazinylthio, pyrimidinylthio, and pyridazinylthio etc. are exemplified.

In the present specification, a term of "heteroarylsulfinyl" includes a group in which sulfinyl is substituted with one "heteroaryl" before. For example, pyrrolylsulfinyl, furylsulfinyl, thienylsulfinyl, imidazolylsulfinyl, pyrazolylsulfinyl, isothiazolylsulfinyl, isoxazolylsulfinyl, oxazolylsulfinyl, thiazolylsulfinyl, pyridylsulfinyl, pyrazinylsulfinyl, pyrimidinylsulfinyl, pyridazinylsulfinyl, tetrazolylsulfinyl, oxadiazolylsulfinyl, thiadiazolylsulfinyl, indolidinylsulfinyl, isoindolylsulfinyl, indolylsulfinyl, indazolylsulfinyl, purinylsulfinyl, quinolidinylsulfinyl, isoquinolylsulfinyl, quinolylsulfinyl, phtharazinylsulfinyl, naphthylidinylsulfinyl, quinolanylsulfinyl, quinazolinylsulfinyl, cinnolinylsulfinyl, pteridinylsulfinyl, carbazolylsulfinyl, phenanthridinylsulfinyl, acridinylsulfinyl, dibenzofuranylsulfinyl, benzoimidazolylsulfinyl, benzoisoxazolylsulfinyl, benzooxazolylsulfinyl, benzooxadiazolylsulfinyl, benzoisothiazolylsulfinyl, benzothiazolylsulfinyl, benzofurylsulfinyl, benzothienylsulfinyl, dibenzothienylsulfinyl and benzodioxolylsulfinyl etc. are exemplified. Preferably furylsulfinyl, thienylsulfinyl, imidazolylsulfinyl, pyrazolylsulfinyl, isothiazolylsulfinyl, isoxazolylsulfinyl, oxazolylsulfinyl, thiazolylsulfinyl, pyridylsulfinyl, pyrazinylsulfinyl, pyrimidinylsulfinyl and pyridazinylsulfinyl etc. are exemplified.

In the present specification, a term of "heteroarylsulfonyl" includes a group in which sulfonyl is substituted with one "heteroaryl" before. For example, pyrrolylsulfonyl, furylsulfonyl, thienylsulfonyl, imidazolylsulfonyl, pyrazolylsulfonyl, isothiazolylsulfonyl, isoxazolylsulfonyl, oxazolylsulfonyl, thiazolylsulfonyl, pyridylsulfonyl, pyrazinylsulfonyl, pyrimidinylsulfonyl, pyridazinylsulfonyl, tetrazolylsulfonyl, oxadiazolylsulfonyl, thiadiazolylsulfonyl, indolizinylsulfonyl, isoindolylsulfonyl, indolylsulfonyl, indazolylsulfonyl, purinylsulfonyl, quinolidinylsulfonyl, isoquinolylsulfonyl, quinolylsulfonyl, phtharazinylsulfonyl, naphthilidinylsulfonyl, quinolanyl sulfonyl, quinazolinylsulfonyl, cinnolinylsulfonyl, pteridinylsulfonyl, carbazolylsulfonyl, phenanthridinylsulfonyl, acridinylsulfonyl, dibenzofuranylsulfonyl, benzoimidazolylsulfonyl, benzoisoxazolylsulfonyl, benzooxazolylsulfonyl, benzooxadiazolylsulfonyl, benzoisothiazolylsulfonyl, benzothiazolylsulfonyl, benzofurylsulfonyl, benzothienylsulfonyl, dibenzothienylsulfonyl and benzodioxolylsulfonyl are exemplified. Preferably furylsulfonyl, thienylsulfonyl, imidazolylsulfonyl, pyrazolylsulfonyl, isothiazolylsulfonyl, isoxazolylsulfonyl, oxazolylsulfonyl, thiazolylsulfonyl, pyridylsulfonyl, pyrazinylsulfonyl, pyrimidinylsulfonyl and pyridazinylsulfonyl are exemplified.

In the present specification, a term of "heteroarylsulfonyloxy" includes a group in which an oxygen atom is substituted with one "heteroarylsulfonyl" before. For example, pyrrolylsulfonyloxy, furylsulfonyloxy, thienylsulfonyloxy, imidazolylsulfonyloxy, pyrazolylsulfonyloxy, isothiazolylsulfonyloxy, isoxazolylsulfonyloxy, oxazolylsulfonyloxy, thiazolylsulfonyloxy, pyridylsulfonyloxy, pyrazinylsulfonyloxy, pyrimidinylsulfonyloxy, pyridazinylsulfonyloxy, tetrazolylsulfonyloxy, oxadiazolylsulfonyloxy, thiadiazolylsulfonyloxy, indolizinylsulfonyloxy, isoindolylsulfonyloxy, indolylsulfonyloxy, indazolylsulfonyloxy, purinylsulfonyloxy, quinolidinylsulfonyloxy, isoquinolylsulfonyloxy, quinolylsulfonyloxy, phtharazinylsulfonyloxy, naphthilidinylsulfonyloxy, quinolanylsulfonyloxy, quinazolinylsulfonyloxy, cinnolinylsulfonyloxy, pteridinylsulfonyloxy, carbazolylsulfonyloxy, phenanthridinylsulfonyloxy, acridinylsulfonyloxy, dibenzofuranylsulfonyloxy, benzoimidazolylsulfonyloxy, benzoisoxazolylsulfonyloxy, benzooxazolylsulfonyloxy, benzooxadiazolylsulfonyloxy, benzoisothiazolylsulfonyloxy, benzothiazolylsulfonyloxy, benzofurylsulfonyloxy, benzothienylsulfonyloxy, dibenzothienylsulfonyloxy and benzodioxolylsulfonyloxy etc. are exemplified. Preferably, furylsulfonyloxy, thienylsulfonyloxy, imidazolylsulfonyloxy, pyrazolylsulfonyloxy, isothiazolylsulfonyloxy, isoxazolylsulfonyloxy, oxazolylsulfonyloxy, thiazolylsulfonyloxy, pyridylsulfonyloxy, pyrazinylsulfonyloxy, pyrimidinylsulfonyloxy and pyridazinylsulfonyloxy etc. are exemplified.

In the present specification, a term of "aromatic carbocyclic ring" includes an aromatic monocyclic or aromatic fused carbocyclic ring and for example, a benzene ring, a naphthalene ring and an anthracene ring are exemplified. A benzene ring is preferred.

In the present specification, a term of "aromatic heterocyclic ring" includes an aromatic monocyclic or aromatic fused heterocyclic ring. For example, a pyrrole ring, a furan ring, a thiophen ring, a pyrazole ring, an imidazole ring, an isothiazole ring, an isoxazole ring, an oxazole ring, a thiazole ring, a pyrazine ring, a pyrimidine ring, a pyridazine ring, a tetrazole ring, an oxadiazole ring, a thiadiazole ring, an indolizine ring, an isoindole ring, an indole ring, an indazole ring, a purine ring, a quinolidine ring, an isoquinoline ring, a quinoline ring, a phtharazine ring, a naphthyridine ring, a quinolane ring, a quinazoline ring, a cinnoline ring, a pteridine ring, a carbazole ring, a phenanthridine ring, an acridine ring, a dibenzofuran ring, a benzoxazolon ring, a benzoxadinone ring, a benzoimidazole ring, a benzoisoxazole ring, a benzooxazole ring, a benzooxadiazole ring, a benzoisothiazole ring, a benzothiazole ring, a benzofuran ring, a benzothiophen ring, a dibenzothiophen ring and a benzodixolane ring are exemplified. Preferably a pyridine ring, a furan ring and a thiophen ring are exemplified.

In the present specification, a term of "azaindole" includes 4-azaindole, 5-azaindole, 6-azaindole, 7-azaindole, 4,5-diazaindole-, 4,6-diazaindole, 4,7-diazaindole, 5,6-diazaindole, 5,7-diazaindole, 6,7-diazaindole, 4,5,6-triazaindole, 4,5,7-triazaindole and 5,6,7-triazaindole.

In the present specification, a term of "C1-C6 alkylene" includes a straight or branched alkylene group having one to six carbon atom(s), and for example, —CH$_2$—, —CH(CH$_3$)—, —C(CH$_3$)$_2$—, —CH$_2$CH$_2$—, —CH(CH$_3$)CH$_2$—, —C(CH$_3$)$_2$CH$_2$—, —CH$_2$CH$_2$CH$_2$—, —CH$_2$CH$_2$CH$_2$CH$_2$—, —CH$_2$CH$_2$CH$_2$CH$_2$CH$_2$— and —CH$_2$CH$_2$CH$_2$CH$_2$CH$_2$CH$_2$— are exemplified. Preferably, —CH$_2$—, —CH$_2$CH$_2$—, —CH$_2$CH$_2$CH$_2$— and —CH$_2$CH$_2$CH$_2$CH$_2$— are exemplified.

In the present specification, a term of "alkylene optionally containing one or two heteroatom(s)" of "optionally sunstituted alkylene optionally containing one or two heteroatom(s)" includes a straight or branched alkylene group having one to six carbon atoms, optionally containing one or two heteroatom(s) which may be substituted with "alkyl" above, and for example, —CH$_2$—, —CH$_2$CH$_2$—, —CH$_2$CH$_2$CH$_2$—, —CH$_2$CH$_2$CH$_2$CH$_2$—, —CH$_2$CH$_2$CH$_2$CH$_2$—, —CH$_2$CH$_2$CH$_2$CH$_2$CH$_2$CH$_2$—, —CH$_2$O—, —OCH$_2$—, —CH$_2$CH$_2$O—, —OCH$_2$CH$_2$—, —CH$_2$S—, —S CH$_2$—, —CH$_2$CH$_2$S—, —SCH$_2$CH$_2$—, —CH$_2$CH$_2$OCH$_2$CH$_2$—, —OCH$_2$CH$_2$O—, —OCH$_2$O—, —NHCH$_2$—, —N(CH$_3$)CH$_2$—, —N$^+$(CH$_3$)$_2$CH$_2$—, —NHCH$_2$CH$_2$CH$_2$— and —N(CH$_3$)CH$_2$CH$_2$CH$_2$— etc. are exemplified. Preferably, —CH$_2$—, —CH$_2$CH$_2$—, —CH$_2$CH$_2$CH$_2$—, —CH$_2$CH$_2$CH$_2$CH$_2$—, —OCH$_2$CH$_2$O—, —OCH$_2$O— and —N(CH$_3$)CH$_2$CH$_2$CH$_2$— are exemplified.

In the present specification, a term of "alkenylene optionally containing one or two heteroatom(s)" of "optionally sunstituted alkylene optionally containing one or two heteroatom(s)" includes a straight or branched alkenylene group having two to six carbon atoms, optionally containing one or two heteroatom(s) which may be substituted with "alkyl" above, and for example, —CH═CHCH═CH—, —CH═CHO—, —OCH═CH—, —CH═CHS—, —SCH═CH—, —CH═CHNH—, —NHCH═CH—, —CH═CH—CH═N— and —N═CH—CH═CH— are exemplified. Preferably, —CH═CHCH═CH—, —CH═CHCH═N— and —N═CHCH═CH— are exemplified.

In the present specification, a term of "alkynylene optionally containing one or two heteroatom(s)" includes a straight or branched alkynylene group having two to six carbon atoms, optionally containing one or two heteroatom(s) which may be substituted with "alkyl" above, and for example, —CH$_2$C≡CCH$_2$—, —CH$_2$C≡CCH$_2$O—, —OCH$_2$C≡CH—, —CH$_2$C≡CCH$_2$S—, —SCH$_2$C≡CH—, —CH$_2$C≡CCH$_2$NH—, —NHCH$_2$C≡CH—, —CH$_2$C≡CCH$_2$N(CH$_3$)— and —N(CH$_3$)CH$_2$C≡CH— are exemplified. Especially, —CH$_2$C≡CCH$_2$— and —OCH$_2$C≡CH— are preferred.

In the present specification, a term of "nitrogen-containing non-aromatic heterocyclic ring" includes a 3- to 12-membered non-aromatic heterocyclic ring containing one or more of nitrogen atom(s), and further optionally containing an oxygen atom and/or a sulfur atom, and a formula of

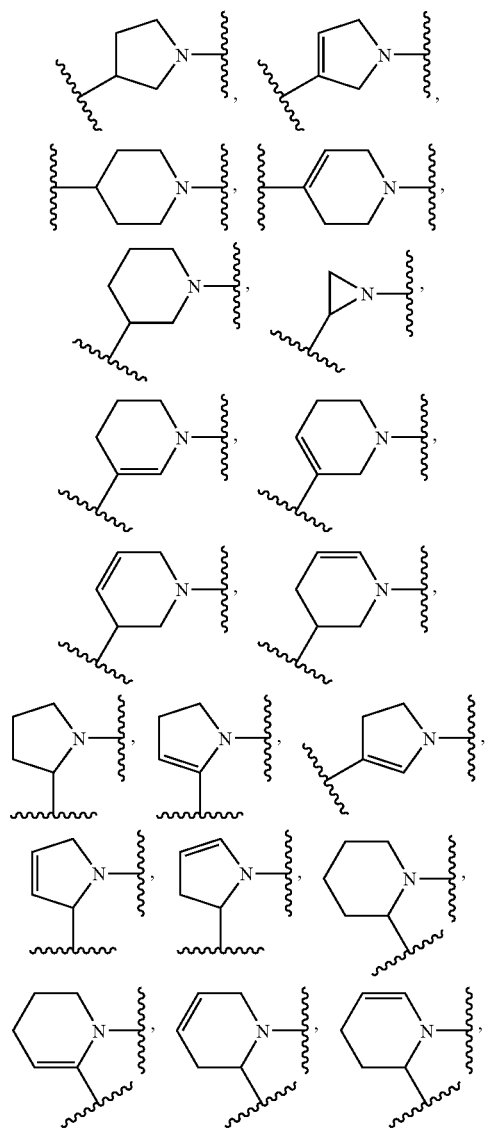

-continued
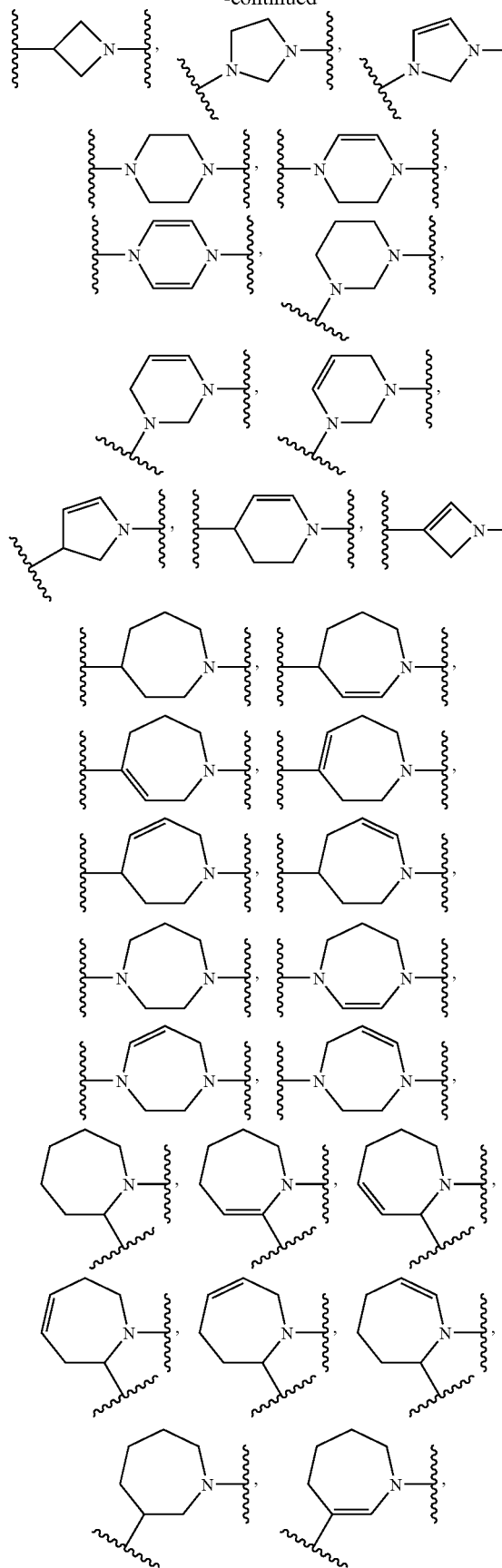
-continued
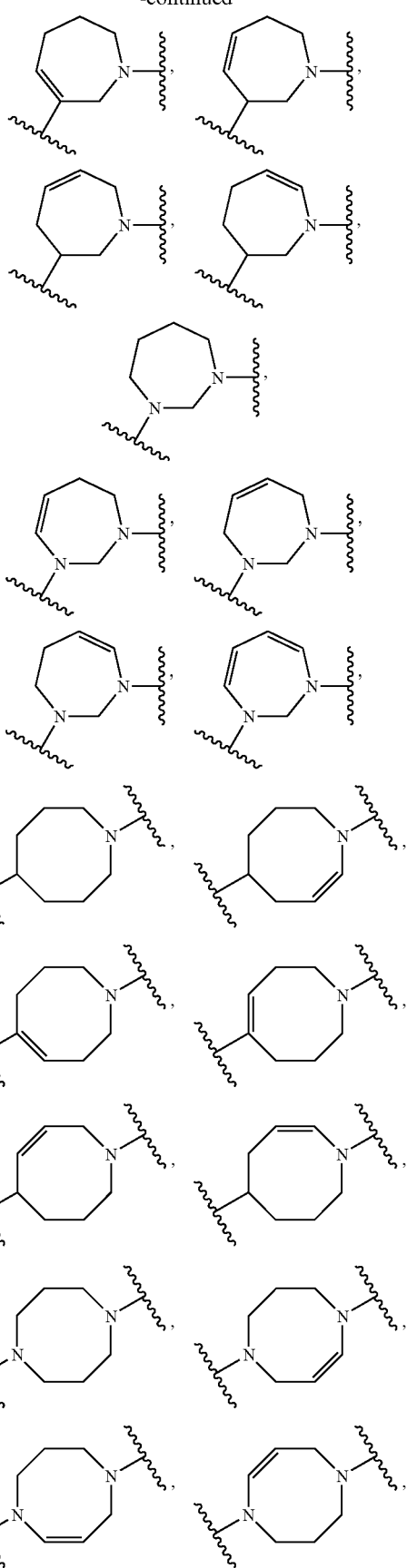

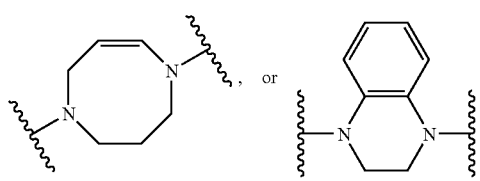

exemplified.

In the present specification, a term of "nitrogen-containing aromatic heterocyclic ring" includes a 3- to 12-membered aromatic heterocyclic ring containing one or more of nitrogen atom(s), and further optionally an oxygen atom and/or sulfur atom in the ring. For example, pyrrolyl (e.g., 1-pyrrolyl, 2-pyrrolyl, 3-pyrrolyl), imidazolyl (e.g., 2-imidazolyl, 4-imidazolyl), pyrazolyl (e.g., 1-pyrazolyl, 3-pyrazolyl), isothiazolyl (e.g., 3-isothiazolyl), isoxazolyl (e.g., 3-isoxazolyl), oxazolyl (e.g., 2-oxazolyl), thiazolyl (e.g., 2-thiazolyl), pyridyl (e.g., 2-pyridyl, 3-pyridyl, 4-pyridyl), pyrazinyl (e.g., 2-pyrazinyl), pyrimidinyl (e.g., 2-pyrimidinyl, 4-pyrimidinyl), pyridazinyl (e.g., 3-pyridazinyl), tetrazolyl (e.g., 1 H-tetrazolyl), oxadiazolyl (e.g., 1,3,4-oxadiazolyl) and thiadiazolyl (e.g., 1,3,4-thiadiazolyl) are exemplified.

In the present specification, examples of "3- to 8-membered nitrogen-containing aromatic heterocyclic ring containing one or two nitrogen atom(s)" includes a ring shown in the formula of

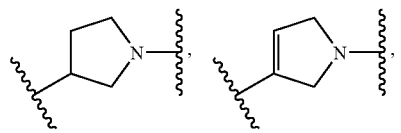

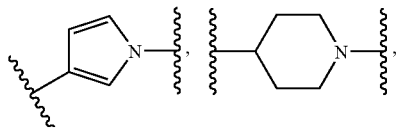

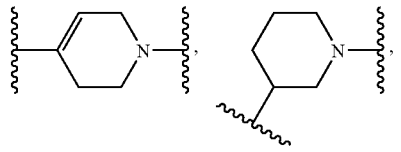

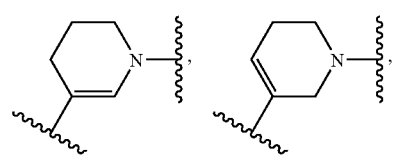

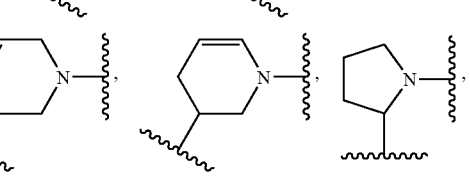

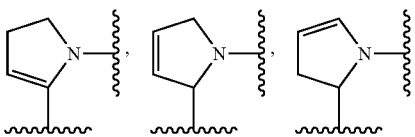

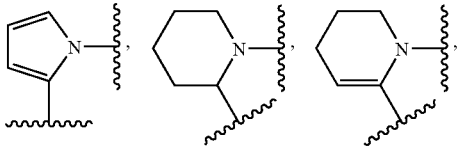

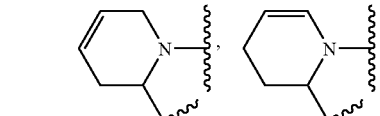

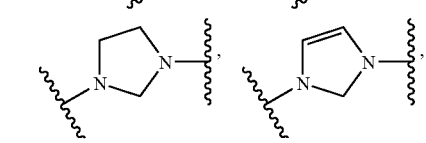

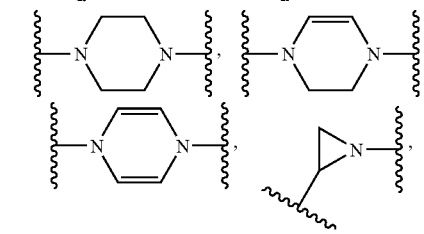

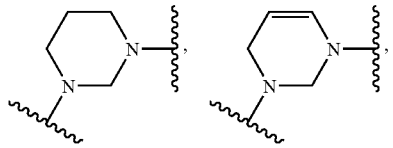

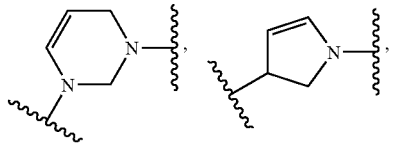

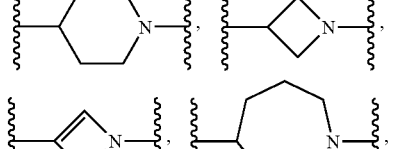

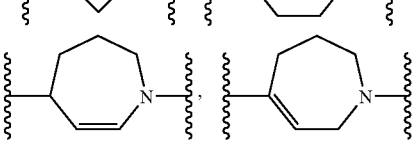

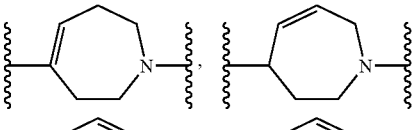

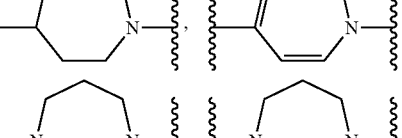

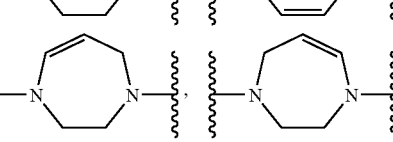

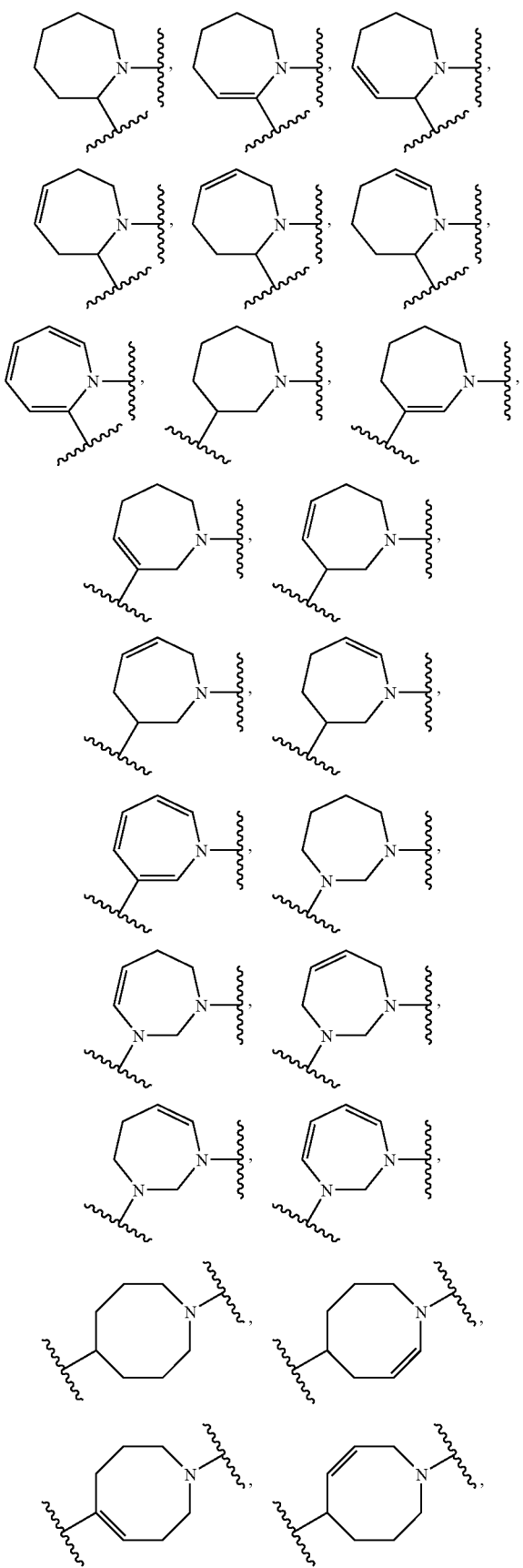
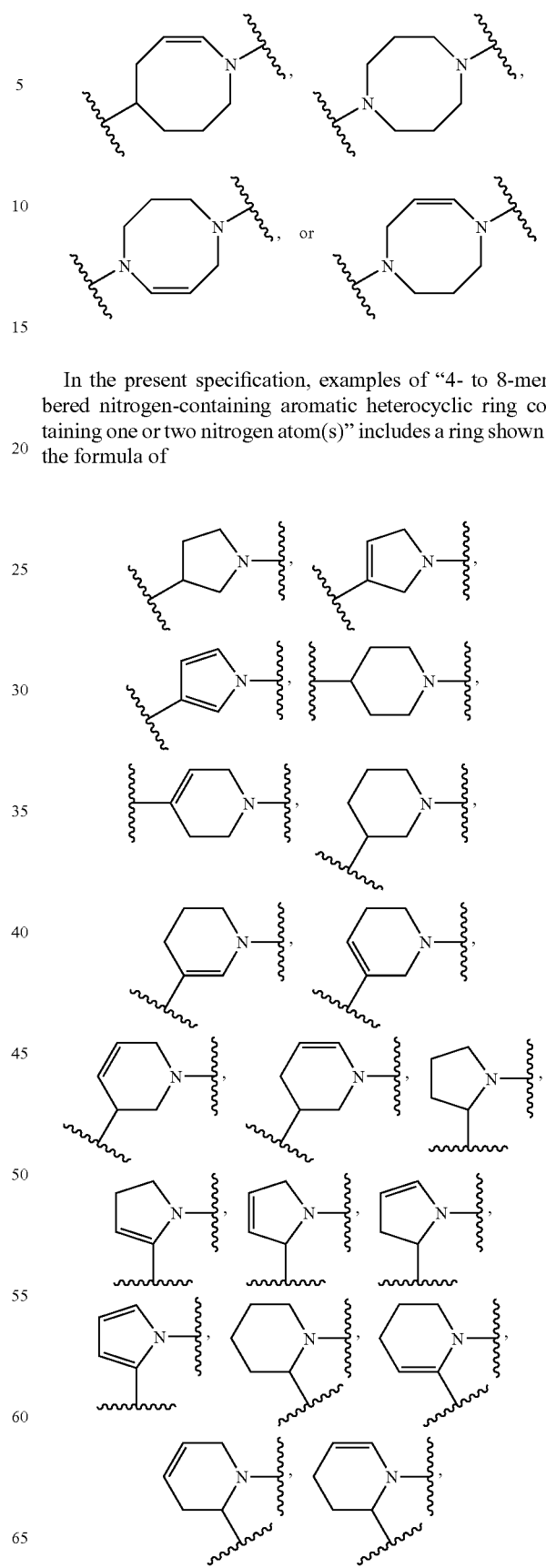
In the present specification, examples of "4- to 8-membered nitrogen-containing aromatic heterocyclic ring containing one or two nitrogen atom(s)" includes a ring shown in the formula of

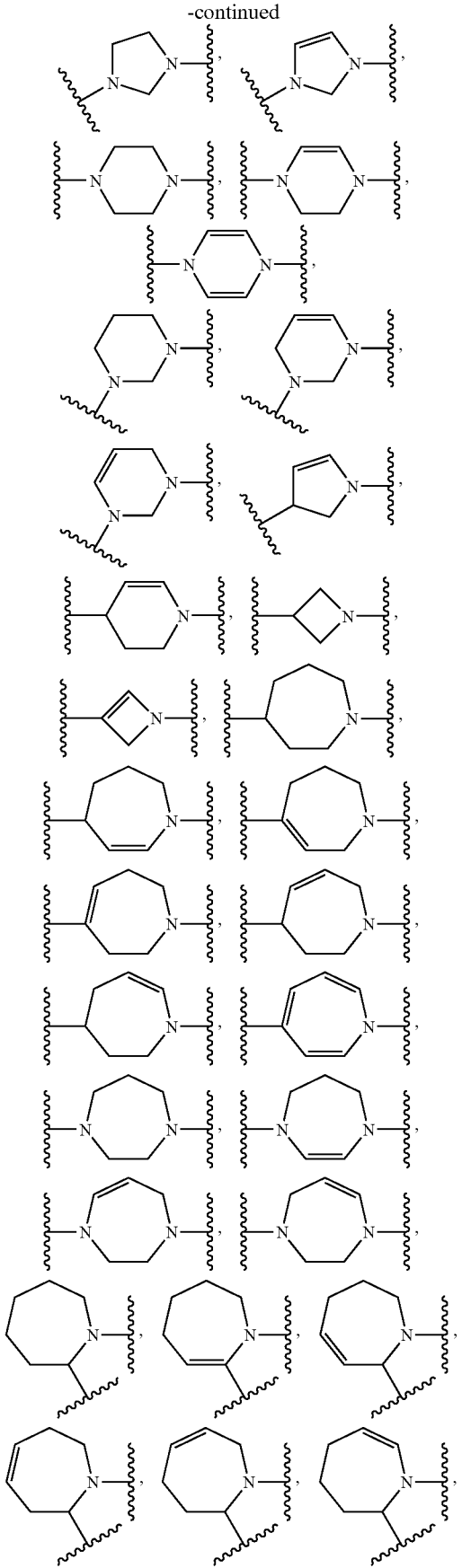
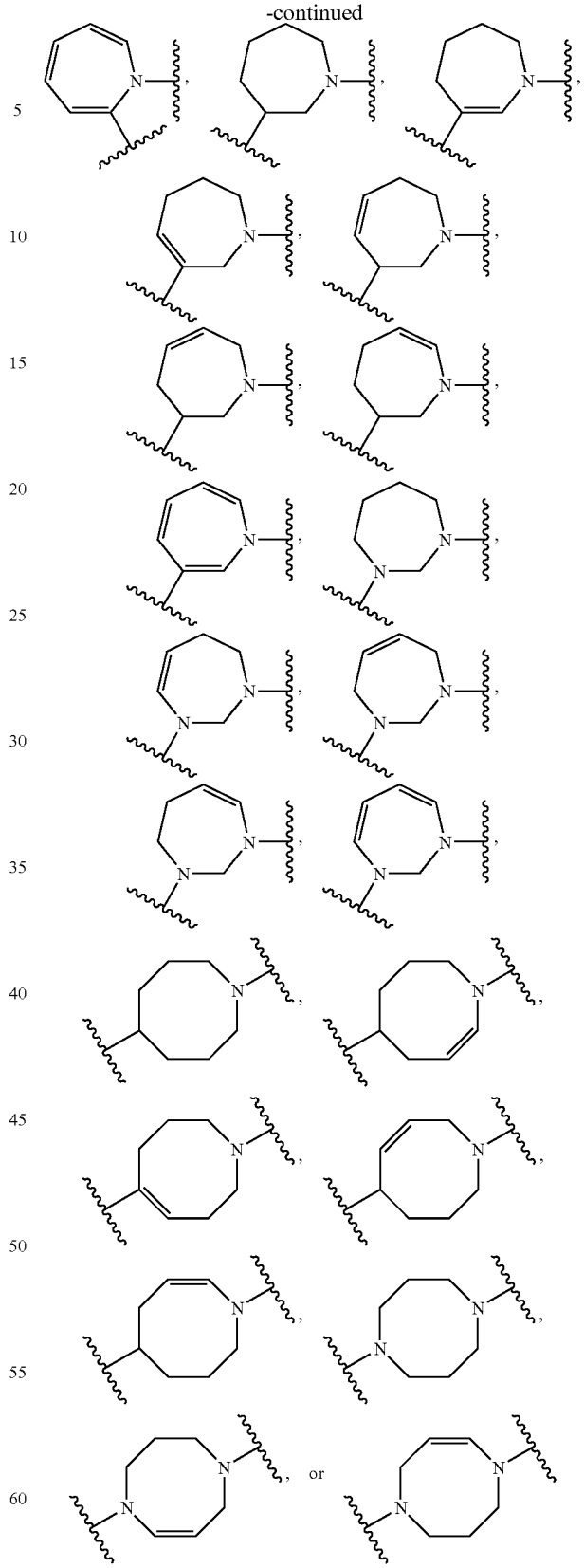
In the present specification, ortho-, meta- and para-substituting position of $L^3$ and Y mean the relationship of the formula:

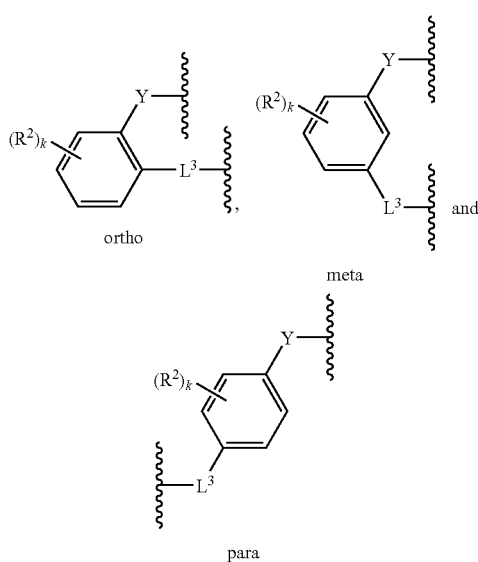

when the ring C is a benzene ring.

In the present specification, examples of substituents in "optionally substituted alkyl", "optionally substituted alkyloxy", "optionally substituted alkylthio", "optionally substituted alkylsulfinyl", "optionally substituted alkylsulfonyl", "optionally substituted alkylsulfonyloxy" and "the optionally substituted alkyloxycarbonyl" include cycloalkyl, alkylene optionally containing one or two heteroatom(s), hydroxy, oxo, alkyloxy optionally substituted with a substituent group A at one to three position(s), mercapto, alkylthio, a halogen atom, nitro, cyano, carboxy, alkyloxycarbonyl, optionally substituted amino, optionally substituted carbamoyl, acyl, aryl optionally substituted with a substituent group B at one to three position(s) (e.g., phenyl), heteroaryl optionally substituted with a substituent group C at one to three position(s) (e.g., pyridyl, furyl, thienyl, imidazolyl, oxazolyl, thiazolyl, pyrazolyl), an optionally substituted non-aromatic heterocyclic ring group which may be substituted with a substituent group C at one to three position(s) (e.g., morpholinyl, pyrrolidinyl, piperazinyl), aryloxy optionally substituted with a substituent group B at one to three position(s) (e.g., phenyloxy), alkylsulfonyl and the like. These can be substituted with one to three substituent(s) at any possible position.

In the present specification, examples of substituents in "optionally substituted alkenyl", "optionally substituted alkynyl", "optionally substituted alkenyloxy", "optionally substituted alkynyloxy", "optionally substituted alkenylthio", "optionally substituted alkynylthio", "optionally substituted alkenyloxycarbonyl", "optionally substituted alkynyloxycarbonyl", "optionally substituted cycloalkyl", "optionally substituted cycloalkenyl", "optionally substituted cycloalkyloxy, "optionally substituted cycloalkenyloxy", "optionally substituted cycloalkylthio", "optionally substituted cycloalkenylthio", "optionally substituted cycloalkylsulfinyl", "optionally substituted cycloalkenylsulfinyl", "optionally substituted cycloalkylsulfonyl", "optionally substituted cycloalkenylsulfonyl", "optionally substituted cycloalkylsulfonyloxy", "optionally substituted cycloalkenylsulfonyloxy", "optionally substituted alkenyloxycarbonyl", "optionally substituted C1-C6 alkylene", "optionally substituted alkylene", "optionally substituted alkenylene" and "the optionally substituted alkynylene" include alkyl optionally substituted with a substituent group D at one to three position(s), cycloalkyl, alkylene optionally containing one or two heteroatom(s), hydroxy, oxo, alkyoxyl optionally substituted with a substituent group A at one to three position(s), mercapto, alkylthio, a halogen atom, nitro, cyano, carboxy, alkyloxycarbonyl, optionally substituted amino, optionally substituted carbamoyl, acyl acyloxy, aryl optionally substituted with a substituent group B at one to three position(s) (e.g., phenyl), heteroaryl optionally substituted with a substituent group C at one to three position(s) (e.g., pyridyl, furyl, thienyl, imidazolyl, oxazolyl, thiazolyl, pyrazolyl), non-aromatic heterocyclic group optionally substituted with a substituent group C at one to three position(s) (e.g., morpholinyl, pyrrolidinyl, piperazinyl), aryloxy optionally substituted with a substituent group C at one to three position(s) (e.g., phenyloxy), alkylsulfonyl and the like. These can be substituted with one or more substituent(s) at any possible position.

In the present specification, examples of substituents in "optionally substituted aryl", "optionally substituted phenoxy", "optionally substituted aryloxy", "optionally substituted phenylthio", "optionally substituted arylthio", "optionally substituted arylsulfinyl", "optionally substituted arylsulfonyl", "optionally substituted arylsulfonyloxy", "optionally substituted heteroaryl", "optionally substituted heteroaryloxy", "optionally substituted heteroarylthio", "optionally substituted heteroarylsulfinyl", "optionally substituted heteroarylsulfonyl", "optionally substituted heteroarylsulfonyloxy" and "optionally substituted non-aromatic heterocyclic group" include alkyl optionally substituted with a substituent group D at one to three position(s), cycloalkyl, alkenyl, alkynyl, hydroxy, alkyloxy optionally substituted with a substituent group A at one to three position(s), aryloxy optionally substituted with a substituent group B at one to three position(s) (e.g., phenoxy),mercapto, alkylthio, a halogen atom, nitro, cyano, carboxy, alkyloxycarbonyl, acyl, alkylsulfonyl, optionally substituted amino, optionally substituted carbamoyl, aryl optionally substituted with a substituent group B at one to three position(s) (e.g., phenyl), heteroaryl optionally substituted with a substituent group C at one to three position(s) (e.g., pyridyl, furyl, thienyl, imidazolyl, oxazolyl, thiazolyl, pyrazolyl), non-aromatic heterocyclic group optionally substituted with a substituent group C at one to three position(s) (e.g., morpholinyl, pyrrolidinyl, piperazinyl) and the like. These can be substituted with one or more substituent(s) at any possible position.

Substituent group A is comprised of a halogen atom and phenyl optionally substituted with one to three substituent(s) selected from the Substituent group B.

Substituent group B is comprised of a halogen atom, alkyl, alkyloxy, cyano and nitro.

Substituent group C is comprised of a halogen atom and alkyl.

Substituent group D is comprised of a halogen atom and alkyloxy.

In the specification a term of "carboxy equivalent" means a biological equivalent and includes substituents having the same polar effect as a carboxy group. For example, —CONHCN, —CONHOH, —CONHOMe, —CONHOt-Bu, —CONHOCH$_2$Ph, —SO$_3$H, —SO$_2$NH$_2$, —SO$_2$NHMe, —NHCONH$_2$, —NHCONMe$_2$, —P(=O)(OH)$_2$, —P(=O)(OH)(OEt), —P(=O)(OH)NH$_2$, —P(=O)(OH)NHMe, —CONHSO$_2$Ph, —SO$_2$NHCOMe, —SO$_2$NHCOPh, and the formulae of;

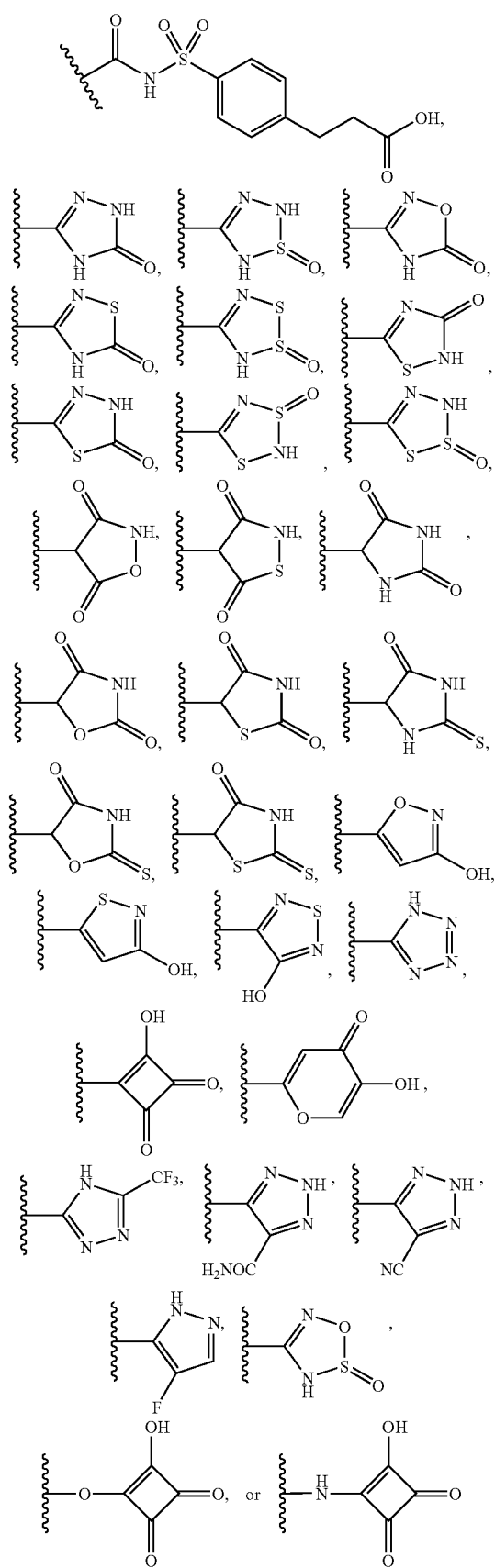
are exemplified.
Preferably, —CONHOt-Bu, —CONHOCH$_2$Ph, —SO$_3$H, —CONHSO$_2$Ph, —SO$_2$NHCOMe, —SO$_2$NHCOPh, and the formulae of;
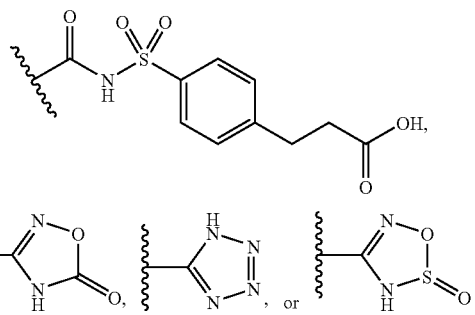
are exemplified.
A compound of the general formula (I) includes a compound of the general formula of
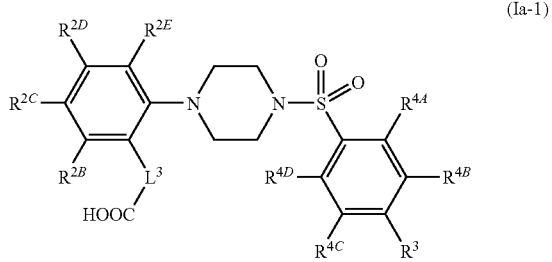
(Ia-1)
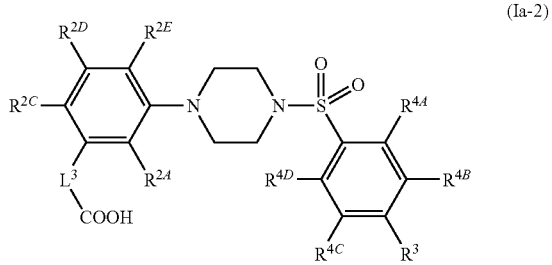
(Ia-2)
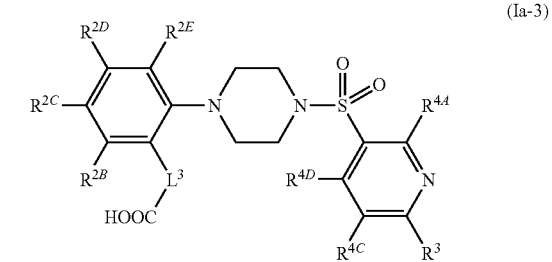
(Ia-3)
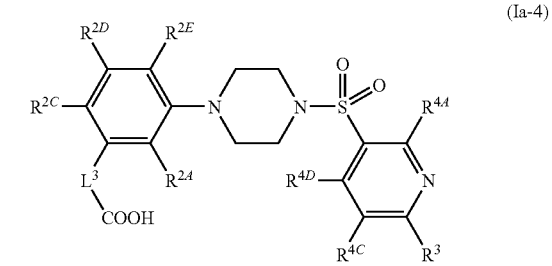
(Ia-4)

-continued

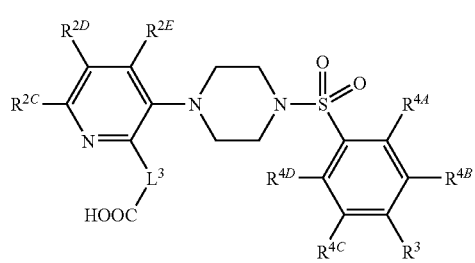
(Ia-5)

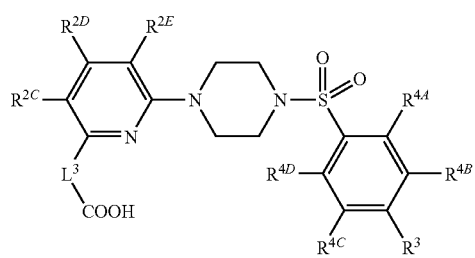
(Ia-6)

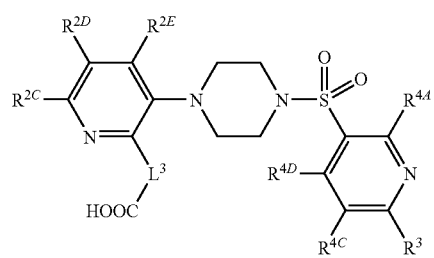
(Ia-7)

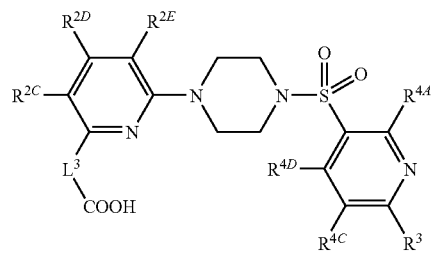
(Ia-8)

wherein $R^{2A}$, $R^{2B}$, $R^{2C}$, $R^{2D}$ and $R^{2E}$ are independently a hydrogen atom, a halogen atom, optionally substituted alkyl, optionally substituted alkenyl, optionally substituted alkynyl, optionally substituted cycloalkyl, optionally substituted cycloalkenyl, hydroxy, optionally substituted alkyloxy, optionally substituted alkenyloxy, optionally substituted alkynyloxy, optionally substituted cycloalkyloxy, optionally substituted cycloalkenyloxy, mercapto, optionally substituted alkylthio, optionally substituted alkenylthio, optionally substituted alkynylthio, optionally substituted alkylsulfinyl, optionally substituted alkylsulfonyl, optionally substituted alkylsulfonyloxy, optionally substituted cycloalkylthio, optionally substituted cycloalkylsulfinyl, optionally substituted cycloalkylsulfonyl, optionally substituted cycloalkylsulfonyloxy, optionally substituted cycloalkenylthio, optionally substituted cycloalkenylsulfinyl, optionally substituted cycloalkenylsulfonyl, optionally substituted cycloalkenylsulfonyloxy, optionally substituted amino, acyl, optionally substituted alkyloxycarbonyl, optionally substituted alkenyloxycarbonyl, optionally substituted alkynyloxycarbonyl, optionally substituted aryloxycarbonyl, optionally substituted carbamoyl, optionally substituted sulfamoyl, cyano, nitro, optionally substituted aryl, optionally substituted aryloxy, optionally substituted arylthio, optionally substituted arylsulfinyl, optionally substituted arylsulfonyl, optionally substituted arylsulfonyloxy, optionally substituted heteroaryl, optionally substituted heteroaryloxy, optionally substituted heteroarylthio, optionally substituted heteroarylsulfinyl, optionally substituted heteroarylsulfonyl, optionally substituted heteroarylsulfonyloxy or an optionally substituted non-aromatic heterocyclic group; $L^3$ is the same meaning as 1) before;

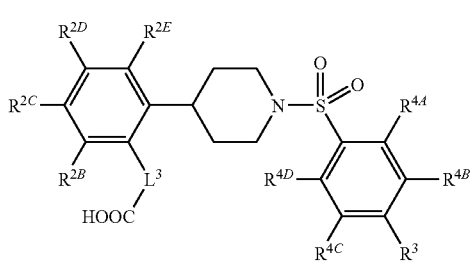
(Ib-1)

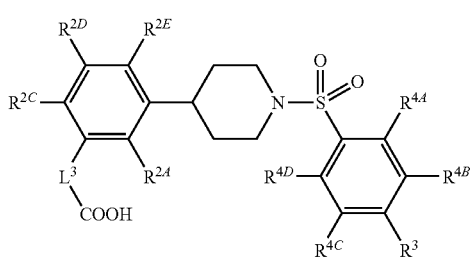
(Ib-2)

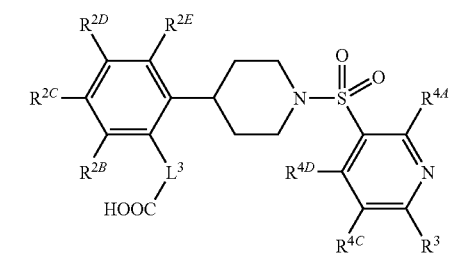
(Ib-3)

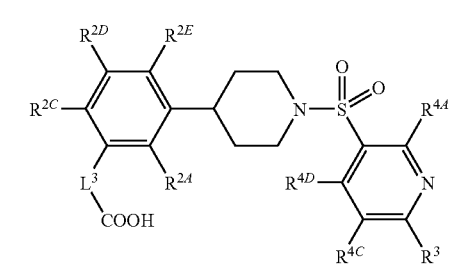
(Ib-4)

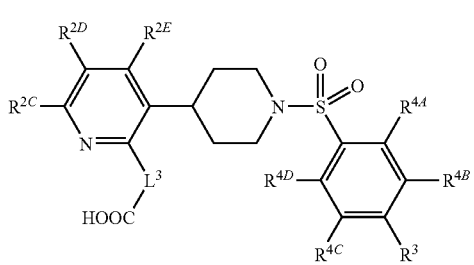
(Ib-5)

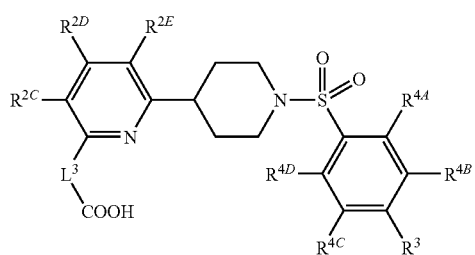
(Ib-6)
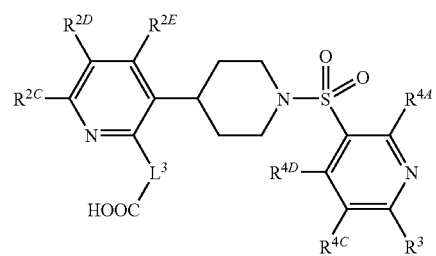
(Ib-7)
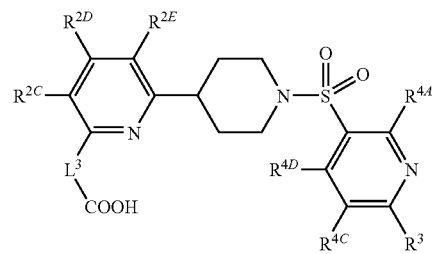
(Ib-8)
wherein $R^{2A}$, $R^{2B}$, $R^{2C}$, $R^{2D}$ and $R^{2E}$ are the same as before; $R^3$ is the same as 1) before; $R^{4A}$, $R^{4B}$, $R^{4C}$ and $R^{4D}$ are the same as before; $L^3$ is the same as 1) before;
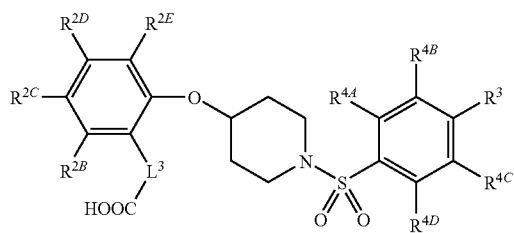
(Ic-1)
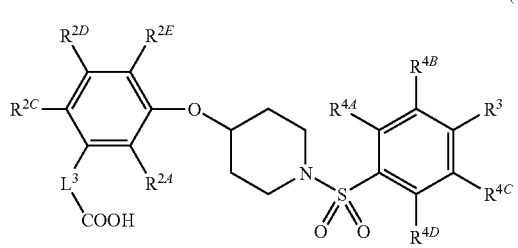
(Ic-2)
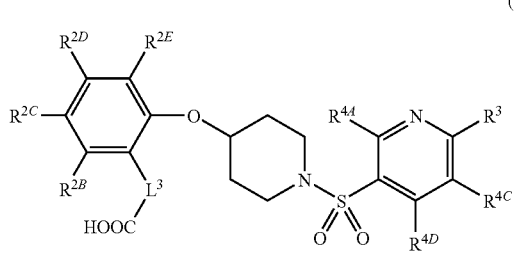
(Ic-3)
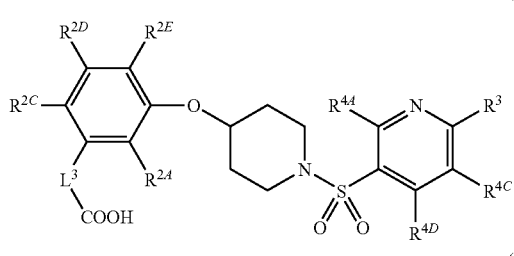
(Ic-4)
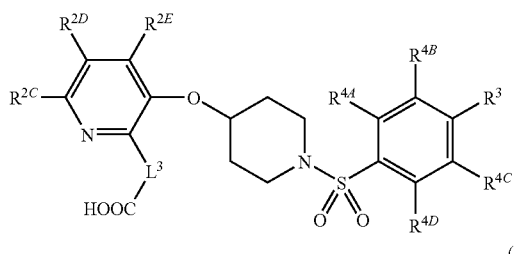
(Ic-5)
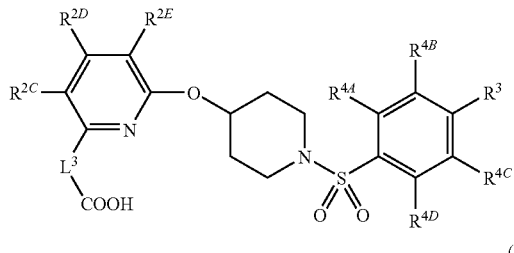
(Ic-6)
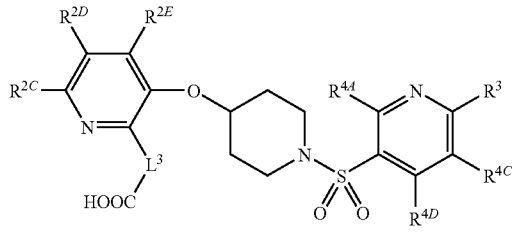
(Ic-7)
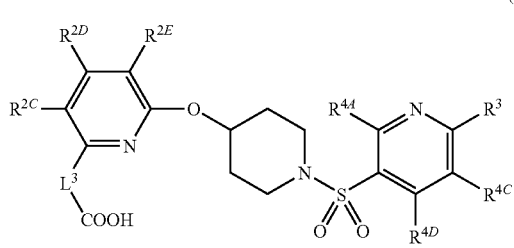
(Ic-8)
wherein $R^{2A}$, $R^{2B}$, $R^{2C}$, $R^{2D}$ and $R^{2E}$ are the same as before; $R^3$ is the same as 1) before; $R^{4A}$, $R^{4B}$, $R^{4C}$ and $R^{4D}$ are the same as before; $L^3$ is the same as 1) before;

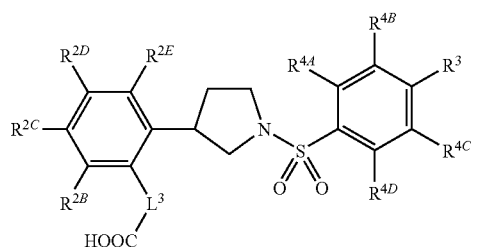 (Id-1)
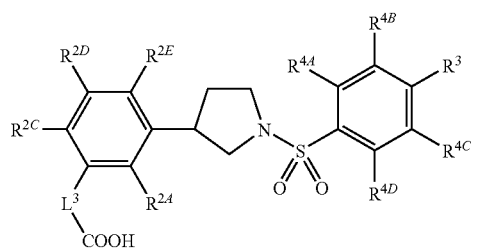 (Id-2)
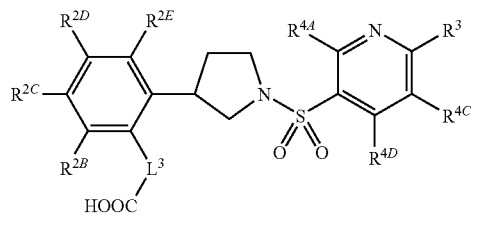 (Id-3)
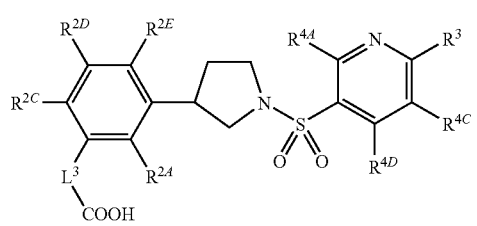 (Id-4)
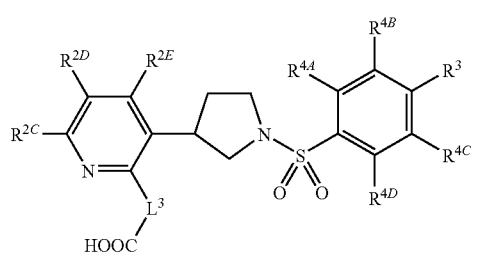 (Id-5)
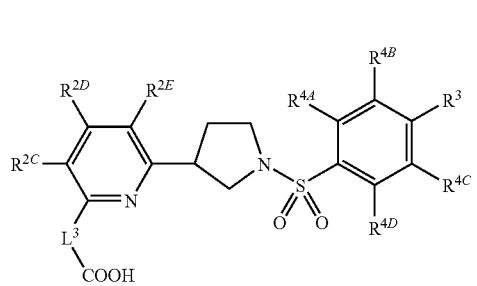 (Id-6)
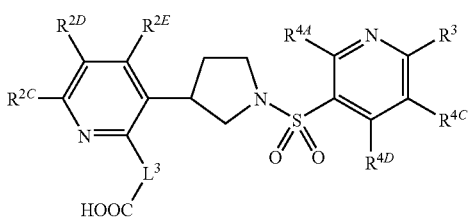 (Id-7)
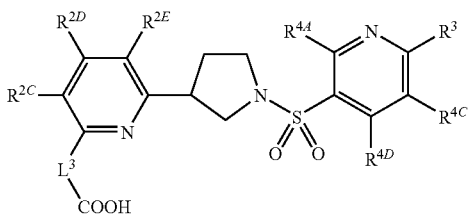 (Id-8)
wherein $R^{2A}$, $R^{2B}$, $R^{2C}$, $R^{2D}$ and $R^{2E}$ are the same as before; $R^3$ is the same as 1) before; $R^{4A}$, $R^{4B}$, $R^{4C}$ and $R^{4D}$ are the same as before; $L^3$ is the same as 1) before;
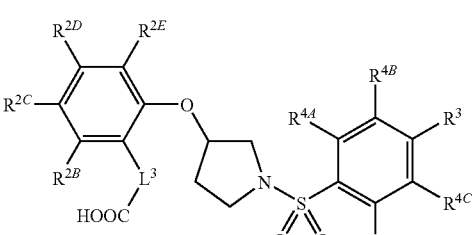 (Ie-1)
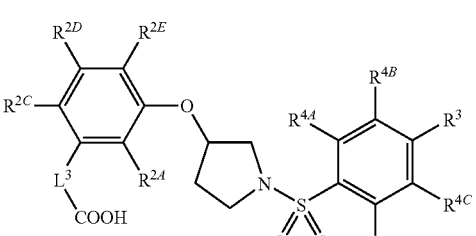 (Ie-2)
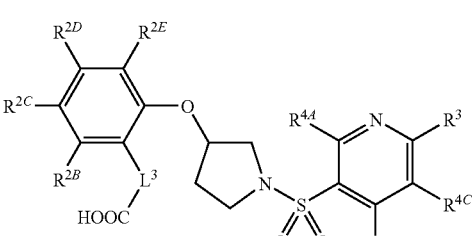 (Ie-3)
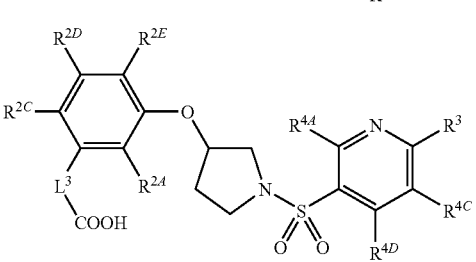 (Ie-4)

-continued
(Ie-5)
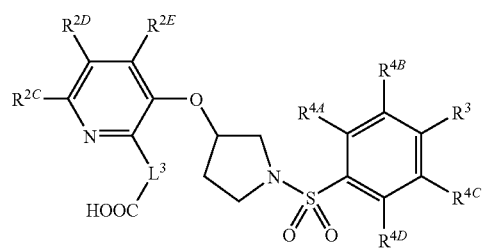
(Ie-6)
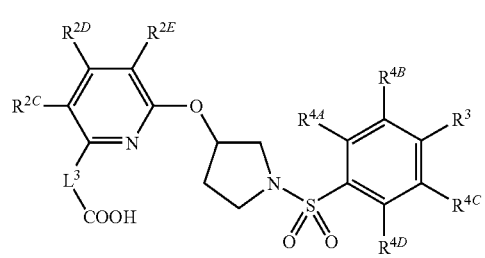
(Ie-7)
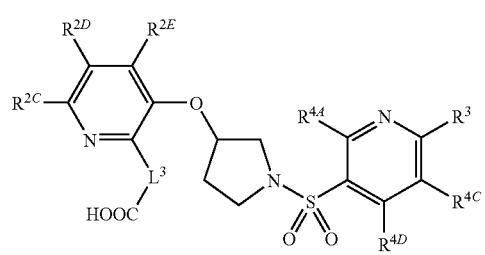
(Ie-8)
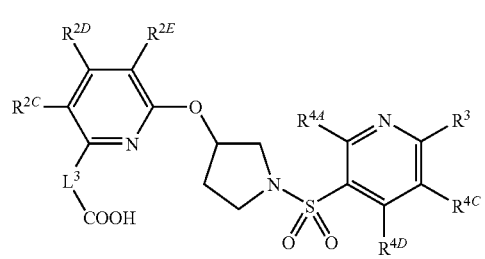
wherein $R^{2A}$, $R^{2B}$, $R^{2C}$, $R^{2D}$ and $R^{2E}$ are the same as before; $R^3$ is the same as 1) before; $R^{4A}$, $R^{4B}$, $R^{4C}$ and $R^{4D}$ are the same as before; $L^3$ is the same as 1) before;
(If-1)
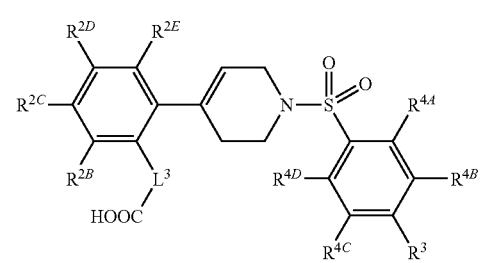
-continued
(If-2)
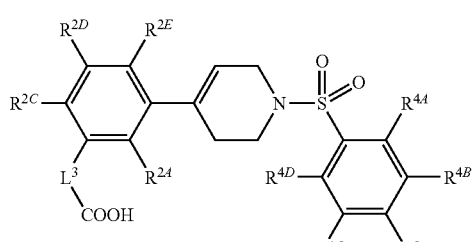
(If-3)
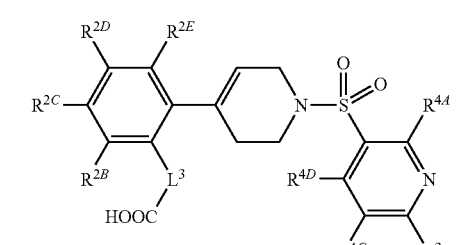
(If-4)
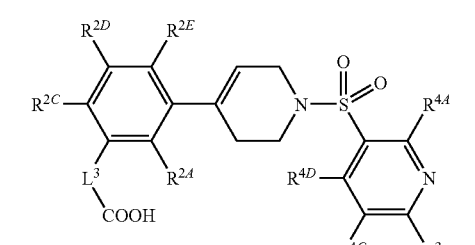
(If-5)
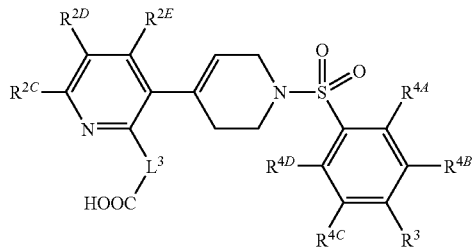
(If-6)
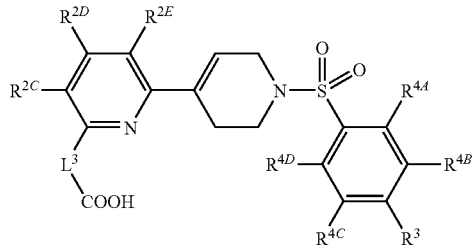
(If-7)
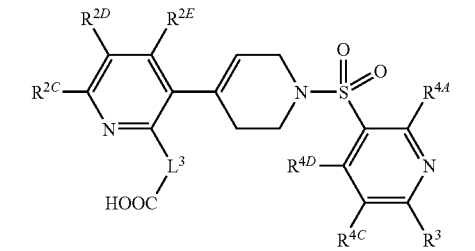

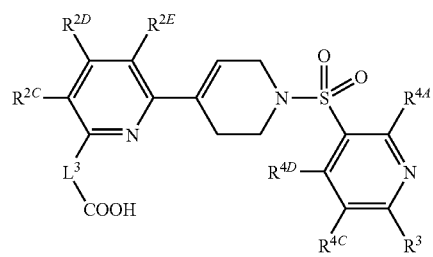
wherein $R^{2A}$, $R^{2B}$, $R^{2C}$, $R^{2D}$ and $R^{2E}$ are the same as before; $R^3$ is the same as 1) before; $R^{4A}$, $R^{4B}$, $R^{4C}$ and $R^{4D}$ are the same as before; $L^3$ is the same as 1) before.
Among the compounds of the general formulae above, compounds of the general formulae of
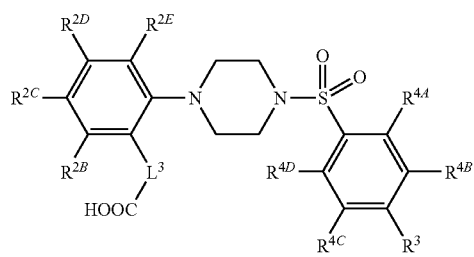
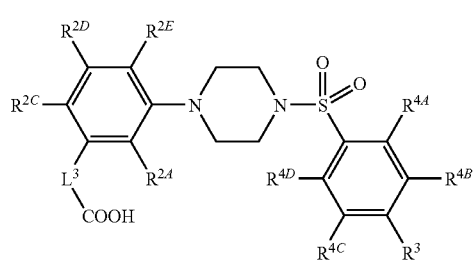
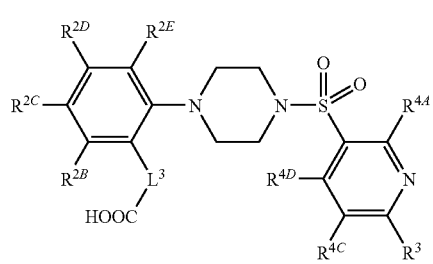
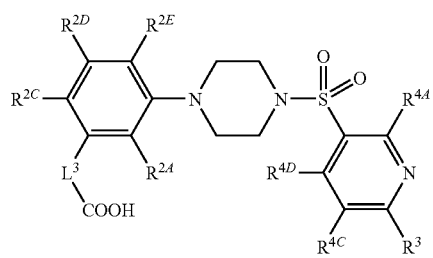
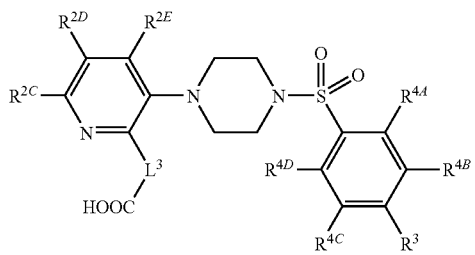
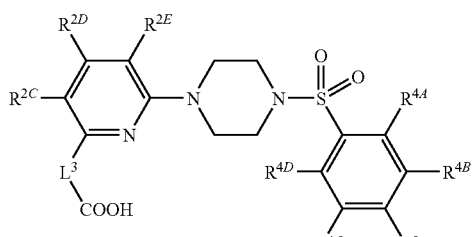
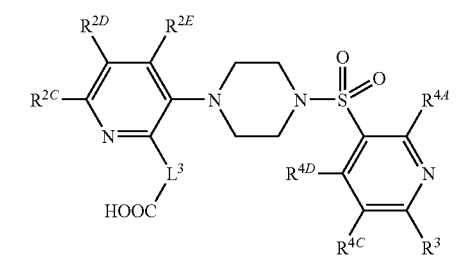
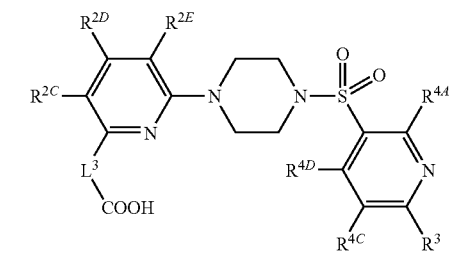
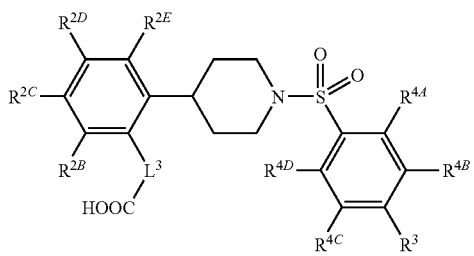
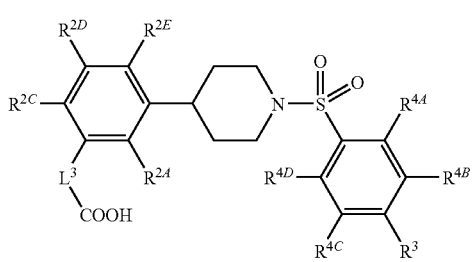

(Ic-1)
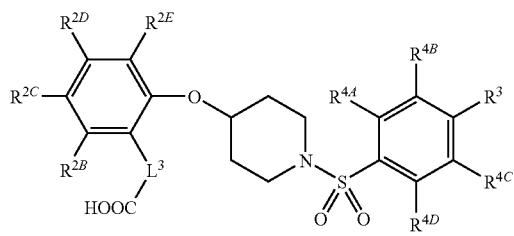
(Ic-2)
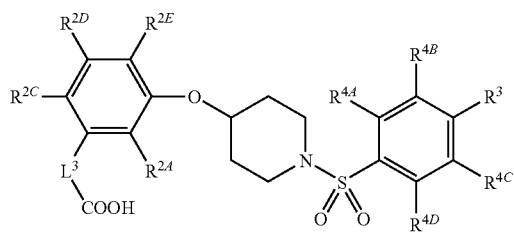
(Id-1)
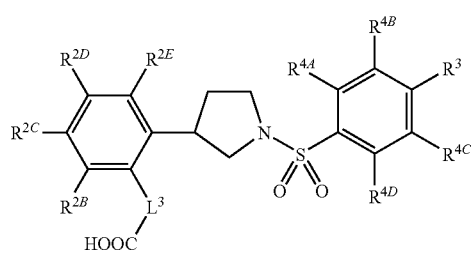
(Id-2)
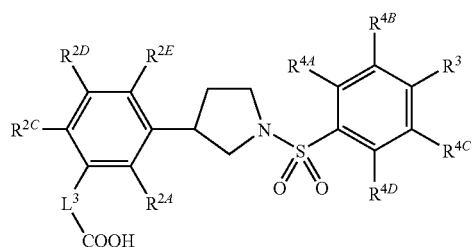
(Ie-1)
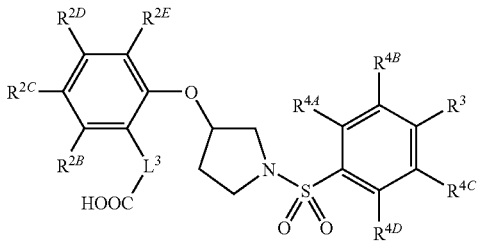
(Ie-2)
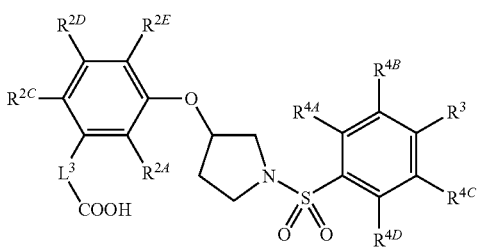
(If-1)
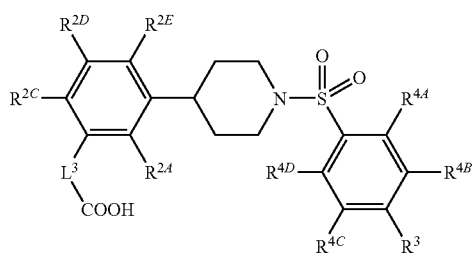
(If-2)
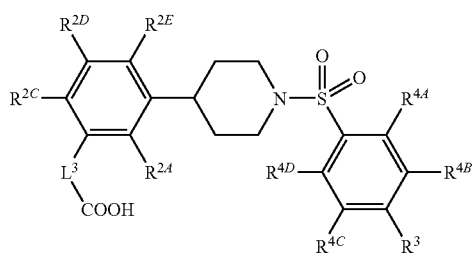
wherein $R^{2A}$, $R^{2B}$, $R^{2C}$, $R^{2D}$ and $R^{2E}$ are the same as before; $R^3$ is the same as 1) before; $R^{4A}$, $R^{4B}$, $R^{4C}$ and $R^{4D}$ are the same as before; $L^3$ is the same as 1) before; are preferred, and compounds of the general formulae of
(Ia-1)
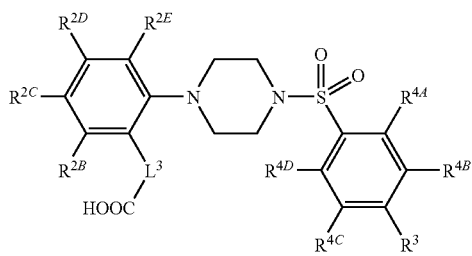
(Ia-2)
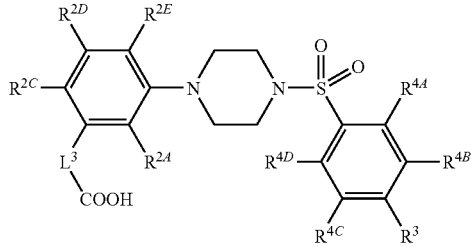
(Ia-5)
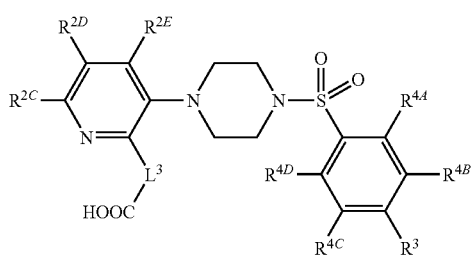

(Ia-6) 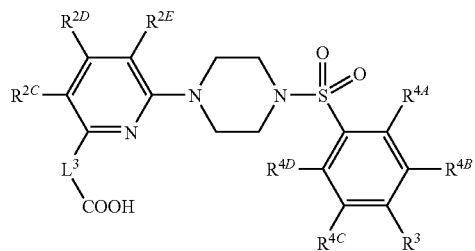
(Ib-1) 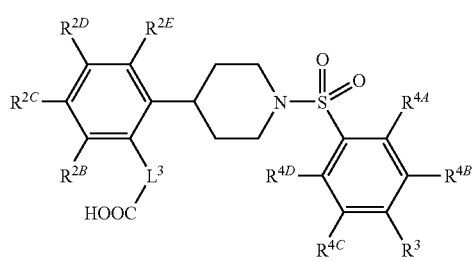
(Ib-2) 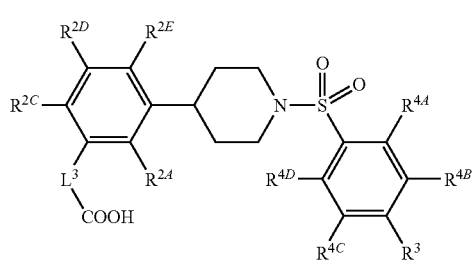
(Ic-1) 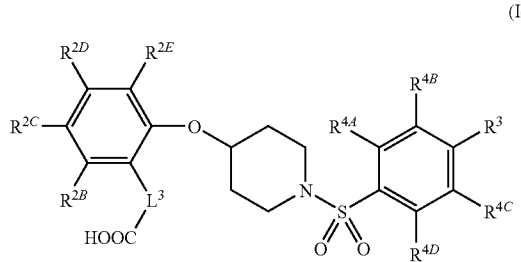
(Ic-2) 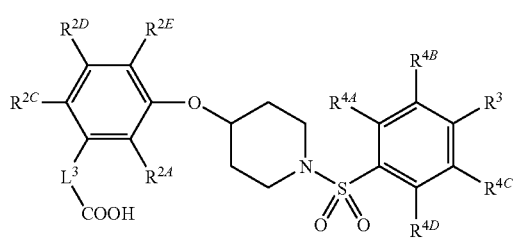
(Id-1) 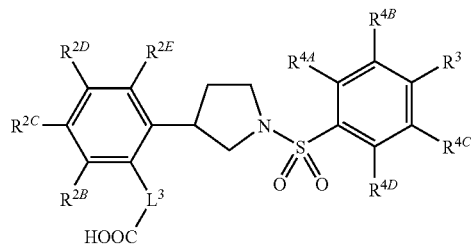
(Id-2) 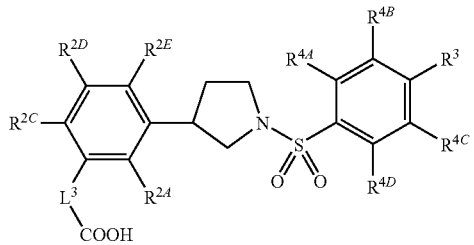
(If-1) 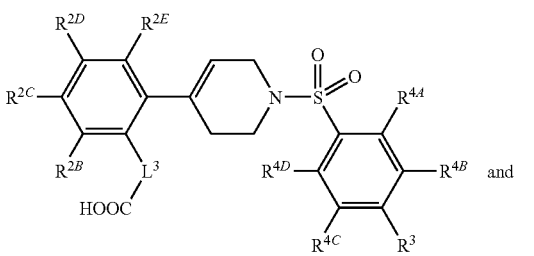
(If-2) 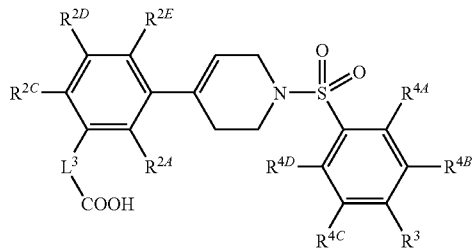
wherein $R^{2A}$, $R^{2B}$, $R^{2C}$, $R^{2D}$ and $R^{2E}$ are the same as before; $R^3$ is the same as 1) before; $R^{4A}$, $R^{4a}$, $R^{4C}$ and $R^{4D}$ are the same as before; $L^3$ is the same as 1) before; are most preferred.
In the general formula (I), examples of the group of the formula:
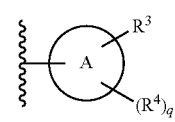
include groups of the formulae of
(A-1) 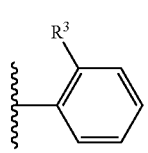
(A-2) 
(A-3) 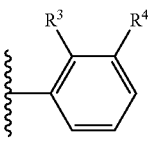

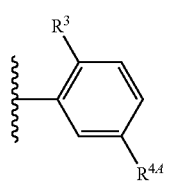 (A-4)
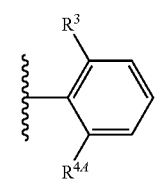 (A-5)
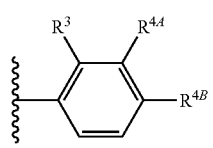 (A-6)
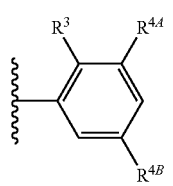 (A-7)
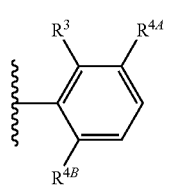 (A-8)
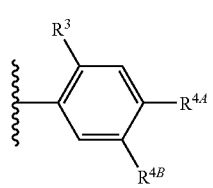 (A-9)
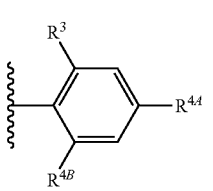 (A-10)
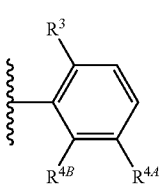 (A-11)
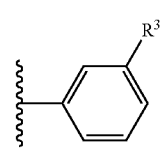 (B-1)
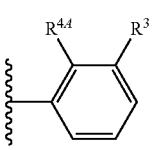 (B-2)
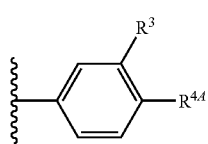 (B-3)
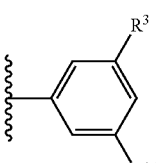 (B-4)
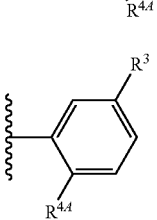 (B-5)
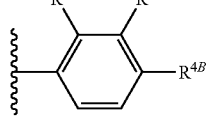 (B-6)
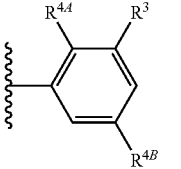 (B-7)
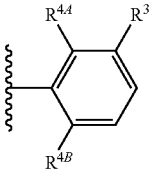 (B-8)
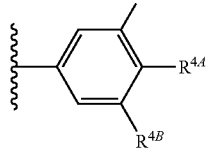 (B-9)
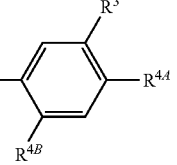 (B-10)

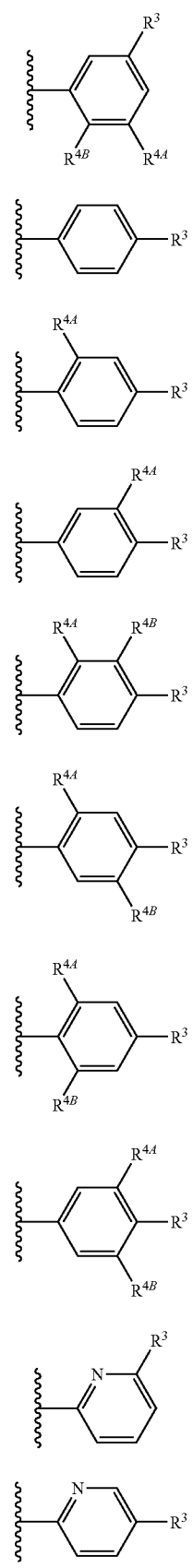
(B-11)
(C-1)
(C-2)
(C-3)
(C-4)
(C-5)
(C-6)
(C-7)
(D-1)
(D-2)
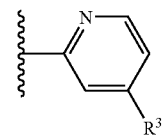
(D-3)
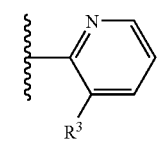
(D-4)
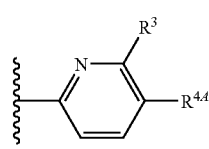
(D-5)
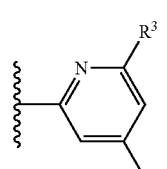
(D-6)
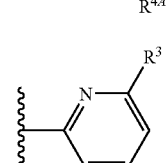
(D-7)
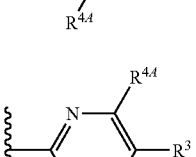
(D-8)
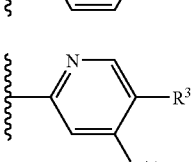
(D-9)
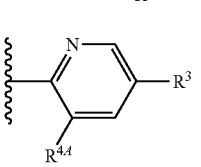
(D-10)
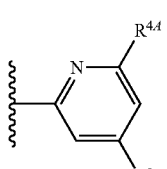
(D-11)
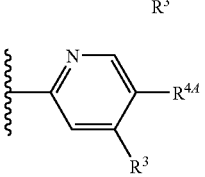
(D-12)

-continued
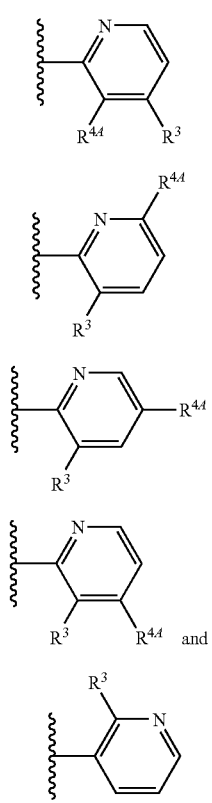
(D-13)
(D-14)
(D-15)
(D-16) and
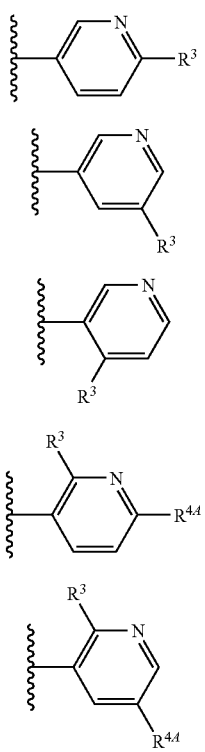
(E-1)
wherein $R^3$ is the same as 1) before; $R^{4A}$ and $R^{4B}$ are the same as before; and groups of the formulae of
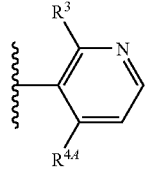 (E-2)
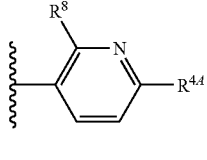 (E-3)
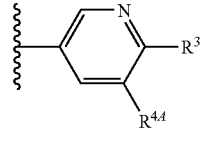 (E-4)
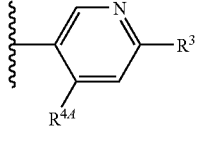 (E-5)
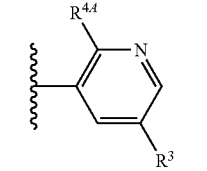 (E-6)
-continued
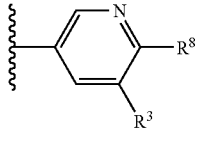 (E-7)
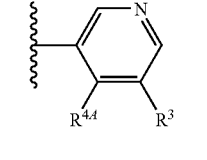 (E-8)
(E-9)
(E-10)
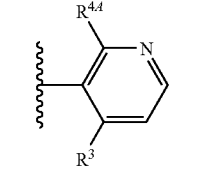 (E-11)
(E-12)
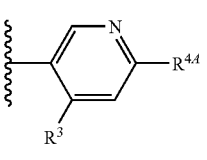 (E-13)
(E-14)
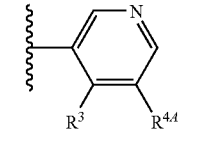 (E-15)
(E-16)

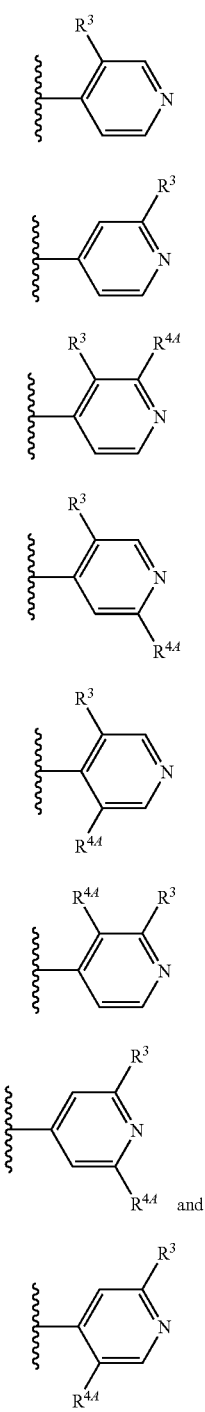
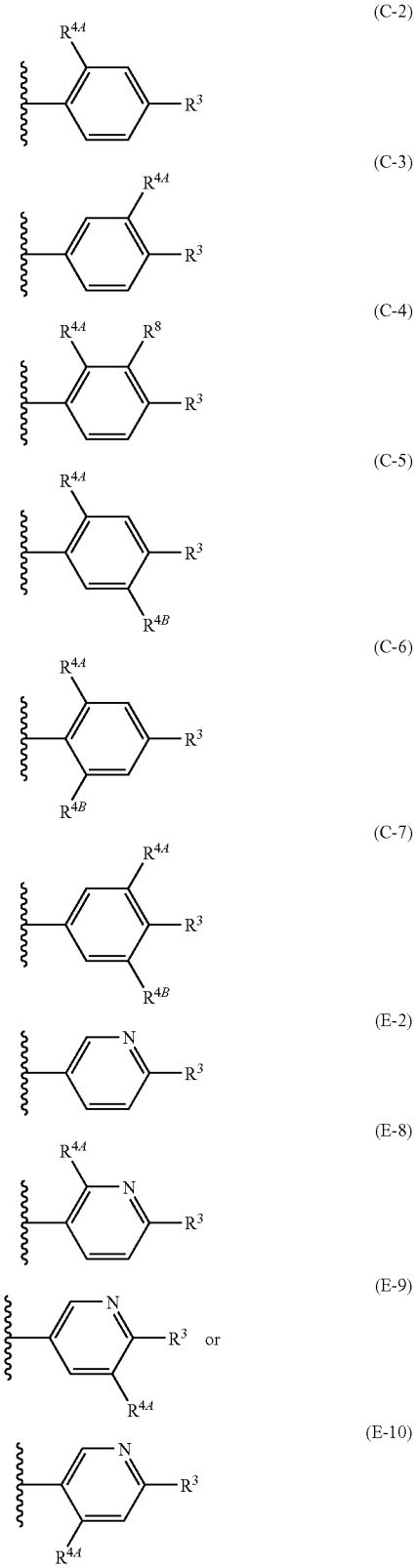
wherein $R^3$ is the same as 1) before; $R^{4A}$ is the same as before.
Among the groups above, a group of the formula of
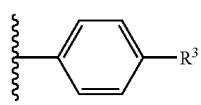
wherein $R^3$ is the same as 1) before; $R^{4A}$ and $R^{4B}$ are the same as before; is preferred.
Groups of preferred substituents in the ring A, ring B, ring C, $R^1$ to $R^5$, M, Y, $L_1$, $L^2$, $L^3$, k, n and q of the compound of general formula (I) are shown with (Ia) to (III). Compounds having possible combination of them are preferable.

In the ring A, (Ia) a benzen ring, a furan ring, a thiophen ring or a pyridine ring is preferable, and further (Ib) a benzene ring or a pyridine ring is more preferable.

In the ring B, (Ic) a group of the formula of

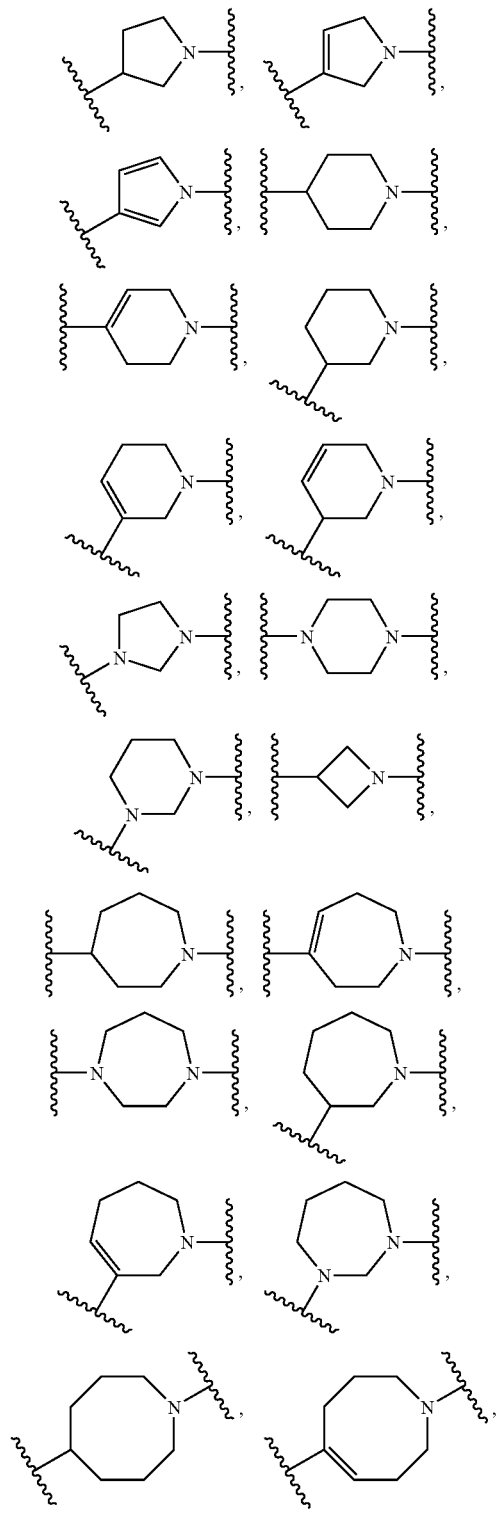

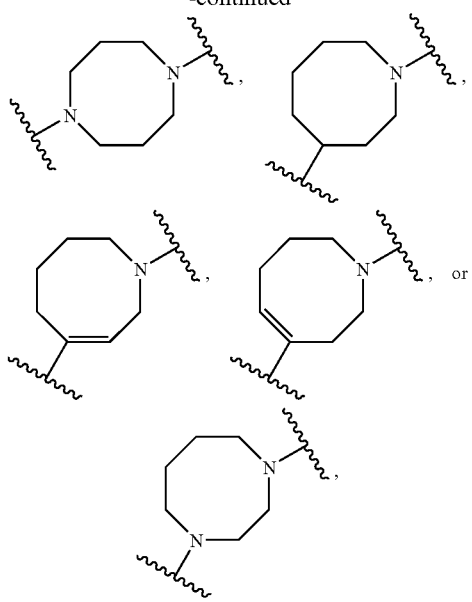

is preferable, (Id) a group of the formula of

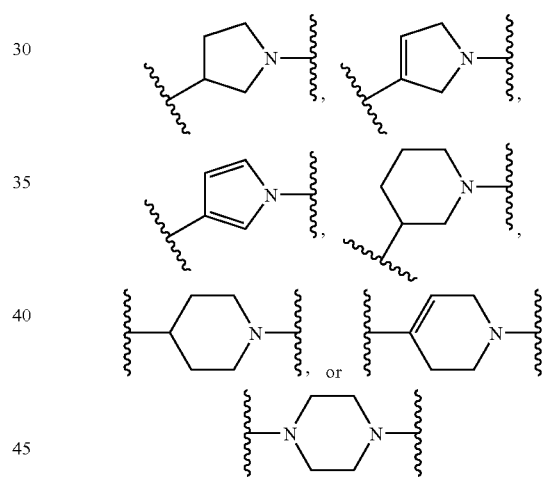

is more preferable, and (Ie) a group of the formula of

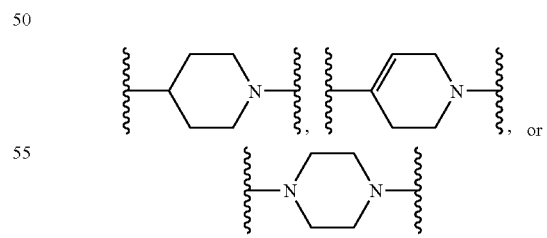

is most preferable.

In the ring C, (If) a benzene ring, a naphthalene ring, a pyridine ring or a benzimidazole ring is preferable, and further (Ig) a benzene ring is more preferable.

In $R^1$, (Ih) carboxy, alkoxycarbonyl, optionally substituted carbamoyl or a carboxy equivalent is preferable, and (Ii) carboxy is more preferable.

In $R^2$, (Ij) a halogen atom, optionally substituted alkyl, optionally substituted alkyloxy, optionally substituted amino, optionally substituted carbamoyl, cyano, nitro, optionally substituted aryl, optionally substituted heteroaryl or an optionally substituted non-aromatic heterocyclic ring is preferable, further (Ik) a halogen atom, optionally substituted alkyl, optionally substituted alkyloxy, optionally substituted amino, optionally substituted carbamoyl, optionally substituted aryl, optionally substituted heteroaryl or an optionally substituted non-aromatic heterocyclic ring is more preferable, and (Il) a halogen atom, optionally substituted alkyl, optionally substituted alkyloxy, optionally substituted aryl or optionally substituted heteroaryl is most preferable.

In $R^3$, (Im) optionally substituted alkyloxy, optionally substituted alkylthio, optionally substituted cycloalkyloxy or optionally substituted aryloxy is preferable, further (In) optionally substituted C1-C6 alkyloxy or optionally substituted C1-C6 alkylthio is more preferable, and (Io) optionally substituted C2-C4 alkyloxy or optionally substituted C2-C4 alkylthio is most preferable.

In $R^4$, (Ip) a halogen atom, optionally substituted alkyl, optionally substituted alkyloxy, cyano, nitro, optionally substituted aryl or optionally substituted heteroaryl is preferable, further (Iq) a halogen atom, optionally substituted alkyl or optionally substituted alkyloxy is more preferable, and (Ir) a halogen atom or optionally substituted alkyl is most preferable.

In $R^5$, (Is) optionally substituted alkyl or oxo is preferable, and further (It) alkyl is more preferable.

In M, (Iu) sulfonyl or carbonyl is preferable, and further (Iv) sulfonyl is more preferable.

In Y, (Iw) a single bond or optionally substituted alkylene optionally containing one or two heteroatom(s) is preferable, and further (Ix) a single bond is more preferable.

In $L^1$, (Iy) a single bond or optionally substituted alkylene optionally containing one or two heteroatom(s) or —NH— is preferable, and further (Iz) a single bond is more preferable.

In $L^2$, (IIa) a single bond or optionally substituted alkylene optionally containing one or two heteroatom(s) or —NH— is preferable, and further (IIb) a single bond is more preferable.

In $L^3$, (IIc) a single bond, methylene, —O-methylene or —NH-methylene is preferable, further (IId) —O-methylene or —NH-methylene is more preferable, and (IIe) —O-methylene is most preferable.

In k, (IIf) 0, 1 or 2 is preferable, and further (IIg) 1 or 2 is more preferable.

In n, (IIh) 0, 1 or 2 is preferable, and further (IIi) 0 is more preferable.

In q, (IIj) 0 or 1 is preferable, and further (IIk) 1 or (Ill) 0 is more preferable.

Groups of preferred substituents in the ring A, ring B, ring C, $R^1$ to $R^5$, Y, $L^1$, $L^2$, $L^3$, k, n and q of the compound of general formula (II) are shown with (Ia) to (Ill). Compounds having possible combination of them are preferable.

In the ring A, (Ia) above is preferable, and further (Ib) above is more preferable.

In the ring B, a ring of the formula (Ic) above is preferable, further a ring of the formula (Id) above is more preferable, and a ring of the formula (Ie) above is most preferable.

In the ring C, (If) above is preferable, and further (Ig) above is more preferable.

In $R^1$, (Ih) above is preferable, and further (Ii) above is more preferable.

In $R^2$, (Ij) above is preferable, further (Ik) above is more preferable and (Il) above is most preferable.

In $R^3$, (Im) above is preferable, further (In) above is more preferable and (Io) above is most preferable.

In $R^4$, (Ip) above is preferable, further (Iq) above is more preferable and (Ir) above is most preferable.

In $R^5$, (Is) above is preferable, and further (It) above is more preferable.

In M, (Iu) above is preferable, and further (Iv) above is more preferable.

In Y, (Iw) above is preferable, and further (Ix) above is more preferable.

In $L^1$, (Iy) above is preferable, and further (Iz) above is more preferable.

In $L^2$, (IIa) above is preferable, and further (IIb) above is more preferable.

In $L^3$, (IIc) above is preferable, further (IId) above is more preferable and (IIe) above is most preferable.

In k, (IIf) above is preferable, and further (IIg) above is more preferable.

in n, (IIh) above is preferable, and further (IIi) above is more preferable.

in q, (IIj) above is preferable, and further (IIk) above or (Ill) above is more preferable.

Groups of preferred substituents in the ring D, $R^1$ to $R^5$, M, Y, Z, $L^3$, p, n and q of the compound of general formula (III) are shown with (If) to (Ix), (IIc) to (IIe) and (IIg) to (IIn). Compounds having possible combination of them are preferable.

In the ring D, (If) above is preferable, and further (Ig) above is more preferable.

In $R^1$, (Ih) above is preferable, and further (Ii) above is more preferable.

In $R^2$, (Ij) above is preferable, further (Ik) above is more preferable and (Il) above is most preferable.

In $R^3$, (Im) above is preferable, further (In) above is more preferable and (Io) above is most preferable.

In $R^4$, (Ip) above is preferable, further (Iq) above is more preferable and (Ir) above is most preferable.

In $R^5$, (Is) above is preferable, and further (It) above is more preferable.

In M, (Iu) above is preferable, and further (Iv) above is more preferable.

In Y, (Iw) above is preferable, and further (Ix) above is more preferable.

In Z, (IIm) CH, C—$R^4$ or N is preferable, and further (IIn) CH above is more preferable.

In $L^3$, (IIc) above is preferable, further (IId) above is more preferable and (IIe) above is most preferable.

In n, (IIh) above is preferable, and further (IIi) above is more preferable.

In q, (IIj) above is preferable, and further (IIk) above or (Ill) above is more preferable.

In p, (IIg) above is preferable.

Groups of preferred substituents in the ring D, the ring E, $R^1$ to $R^5$, M, Y, Z, $L^3$, p, n and q of the compound of general formula (IV) are shown with (If) to (Ix), (IIc) to (IIe) and (IIg) to (IIp). Compounds having possible combination of them are preferable.

In the ring D, (If) above is preferable, and further (Ig) above is more preferable.

In $R^1$, (Ih) above is preferable, and further (Ii) above is more preferable.

In $R^2$, (Ij) above is preferable, further (Ik) above is more preferable and (Il) above is most preferable.

In $R^3$, (Im) above is preferable, further (In) above is more preferable and (Io) above is most preferable.

In $R^4$, (Ip) above is preferable, further (Iq) above is more preferable and (Ir) above is most preferable.

In R⁵, (Is) above is preferable, and further (It) above is more preferable.

In M, (Iu) above is preferable, and further (Iv) above is more preferable.

In Y, (Iw) above is preferable, and further (Ix) above is more preferable.

In Z, (IIm) CH, C—R⁴ or N is preferable, and further (IIn) CH above is more preferable.

In L³, (IIc) above is preferable, further (IId) above is more preferable and (IIe) above is most preferable.

In n, (IIh) above is preferable, and further (IIi) above is more preferable.

In q, (IIj) above is preferable, and further (IIk) above or (III) above is more preferable.

In p, (IIg) above is preferable.

In the ring E, (IIo) a ring of the formula of

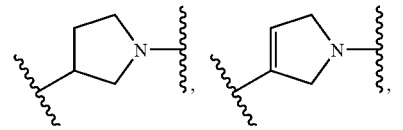

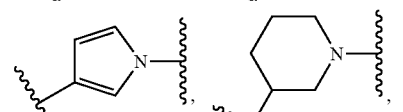

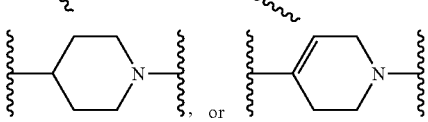

is preferable, and further (IIp) a ring of the formula of

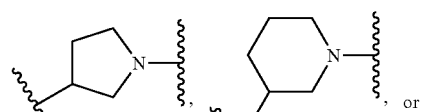

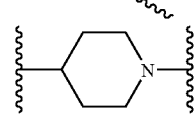

is more preferable.

Groups of preferred substituents in the ring Ab, the ring Bb, the ring Cb, R¹ᵇ to R⁵ᵇ, Yᵇ, Zᵇ, kb, mb, nb and p of the compound of general formula (I-b) are shown with (IIIa) to (IVc). Compounds having possible combination of them are preferable.

In the ring Ab, (IIIa) a benzene ring, a furan ring, a thiophen ring or a pyridine ring is preferable, and further (IIIb) a benzene ring or a pyridine ring is more preferable.

In the ring Bb, (IIIc) a ring of the formula of

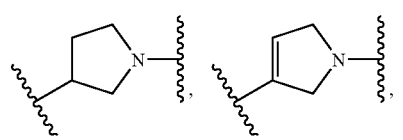

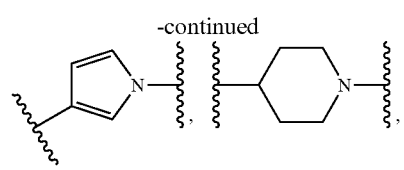

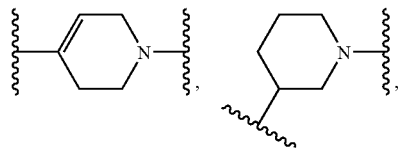

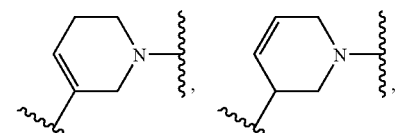

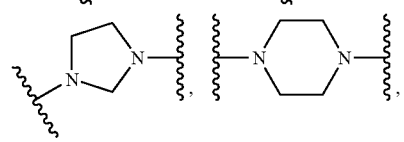

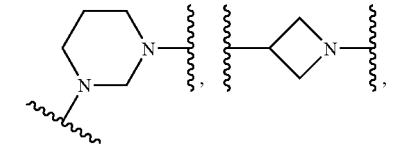

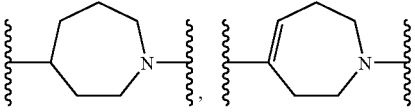

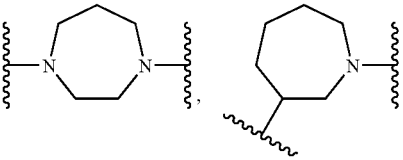

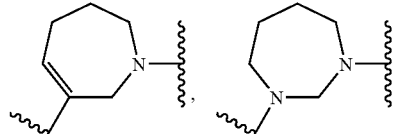

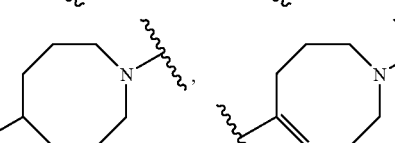

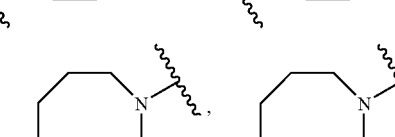

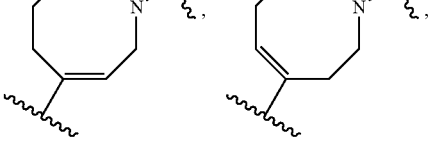

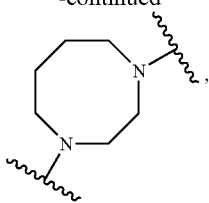

is preferable, further (IIId) a ring of the formula of

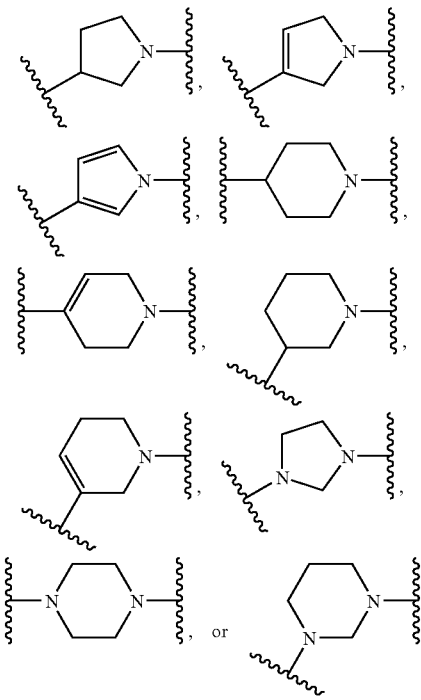

is more preferable and (IIIe) a ring of the formula of

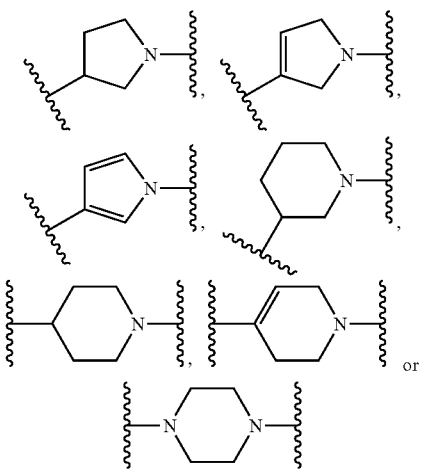

is most preferable.

In the ring Cb, (IIIf) a benzene ring, a naphthalene ring or a pyridine ring is preferable, and further (IIIg) a benzene ring is more preferable.

In $R^{1b}$, (IIIh) hydroxyalkyl, carboxy or alkoxycarbonyl is preferable, and further (IIIi) carboxy is more preferable.

In $R^{2b}$, (IIIj) a halogen atom, optionally substituted alkyl, optionally substituted alkyloxy, optionally substituted amino, cyano, nitro, optionally substituted aryl or optionally substituted heteroaryl is preferable, and further (IIIk) a halogen atom, optionally substituted alkyl, optionally substituted alkyloxy, optionally substituted aryl or optionally substituted heteroaryl is more preferable.

In $R^{3b}$, (IIIl), optionally substituted alkyloxy, optionally substituted alkylthio, optionally substituted cycloalkyloxy or optionally substituted aryloxy is preferable, and further (IIIm) optionally substituted C2-C4 alkyloxy or optionally substituted C2-C4 alkylthio is more preferable.

In $R^{4b}$, (IIIn) a halogen atom, optionally substituted alkyl, cyano, nitro, optionally substituted aryl or optionally substituted heteroaryl is preferable, and further (IIIo) a halogen atom or optionally substituted alkyl is more preferable.

In $R^{5b}$, (IIIp) optionally substituted alkyl is preferable, and further (IIIq) alkyl is more preferable.

In $Y^b$, (IIIr) a single bond, alkylene or —O— is preferable, and further (IIIs) a single bond or —O— is preferable.

In $Z^b$, (IIIt) alkylene, alkenylene or —O-alkylene is preferable, and further (IIIu) methylene or —O-alkylene is more preferable.

In kb, (IIIv) 1, 2 or 3 is preferable, and further (IIIw) 1 or 2 is more preferable.

In mb, (IIIx) 0, 1 or 2 is preferable, and further (IIIy) 0 or 1 is more preferable.

In nb, (IIIz) 0, 1 or 2 is preferable, and further (IVa) 0 is more preferable.

In pb, (IVb) 0 or 1 is preferable, and further (IVc) 1 is more preferable.

Groups of preferred substituents in the ring Ab, the ring Bb, the ring Cb, $R^{1b}$ to $R^{5b}$, $Y^b$, $Z^b$, kb, mb and nb of the compound of general formula (II-b) are shown with (IIIa) to (IVa). Compounds having possible combination of them are preferable.

In the ring Ab, (IIIa) above is preferable, and further (IIIb) above is more preferable.

In the ring Bb, a ring of the formula (IIIc) above is preferable, further a ring of the formula (IIId) above is more preferable, and a ring of the formula (IIIe) is most preferable.

In the ring Cb, (IIIf) above is preferable, and further (IIIg) above is more preferable.

In $R^{1b}$, (IIIh) above is preferable, and further (IIIi) above is more preferable.

In $R^{2b}$, (IIIj) above is preferable, and further (IIIk) above is more preferable.

In $R^{3b}$, (IIIl) above is preferable, and further (IIIm) above is more preferable.

In $R^{4b}$, (IIIn) above is preferable, and further (IIIo) above is more preferable.

In $R^{5b}$, (IIIp) above is preferable, and further (IIIq) above is more preferable.

In $Y^b$, (IIIr) above is preferable, and further (IIIs) above is more preferable.

In $Z^b$, (IIIt) above is preferable, and further (IIIu) above is more preferable.

In kb, (IIIv) above is preferable, and further (IIIw) above is more preferable.

In mb, (IIIx) above is preferable, and further (IIIy) above is more preferable.

In nb, (IIIz) above is preferable, and further (IVa) above is more preferable.

Groups of preferred substituents in the ring Cb, $R^{1b}$ to $R^{5b}$, $X^b$, $Y^b$, $Z^b$, mb, nb and qb of the compound of general formula (III-b) are shown with (IIIf) to (IIIu), (IIIx) to (IVa) and (IVd) to (IVg). Compounds having possible combination of them are preferable.

In the ring Cb, (IIIf) above is preferable, and further (IIIg) above is more preferable.

In $R^{1b}$, (IIIh) above is preferable, and further (IIIi) above is more preferable.

In $R^{2b}$, (IIIj) above is preferable, and further (IIIk) above is more preferable.

In $R^{3b}$, (IIIl) above is preferable, and further (IIIm) above is more preferable.

In $R^{4b}$, (IIIn) above is preferable, and further (IIIo) above is more preferable.

In $R^{5b}$, (IIIp) above is preferable, and further (IIIq) above is more preferable.

In $Y^b$, (IIIr) above is preferable, and further (IIIs) above is more preferable.

In $Z^b$, (IIIt) above is preferable, and further (IIIu) above is more preferable.

In mb, (IIIx) above is preferable, and further (IIIy) above is more preferable.

In nb, (IIIz) above is preferable, and further (IVa) above is more preferable.

In qb, (IVd) above 1, 2 or 3 is preferable, and further (IVe) 1 or 2 is more preferable.

In $X^b$, (IVf) CH or (IVg) N is preferable.

Groups of preferred substituents in the ring Cb, the ring Db, $R^{1b}$ to $R^{5b}$, $X^b$, $Y^b$, $Z^b$, mb, nb and sb of the compound of general formula (IV-b) are shown with (IIIf) to (IIIu), (IIIx) to (IVa) and (IVf) to (IVk). Compounds having possible combination of them are preferable.

In the ring Cb, (IIIf) above is preferable, and further (IIIg) above is more preferable.

In $R^{1b}$, (IIIh) above is preferable, and further (IIIi) above is more preferable.

In $R^{2b}$, (IIIj) above is preferable, and further (IIIk) above is more preferable.

In $R^{3b}$, (IIIl) above is preferable, and further (IIIm) above is more preferable.

In $R^{4b}$, (IIIn) above is preferable, and further (IIIo) above is more preferable.

In $R^{5b}$, (IIIp) above is preferable, and further (IIIq) above is more

In $Y^b$, (IIIr) above is preferable, and further (IIIs) above is more preferable.

In $Z^b$, (IIIt) above is preferable, and further (IIIu) above is more preferable.

In mb, (IIIx) above is preferable, and further (IIIy) above is more preferable.

In nb, (IIIz) above is preferable, and further (IVa) above is more preferable.

In $X^b$, (IVf) above or (IVg) above is preferable.

In the ring Db, (IVh) a ring of the formula of

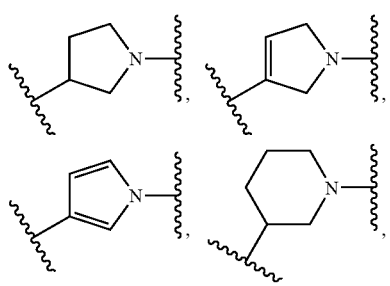

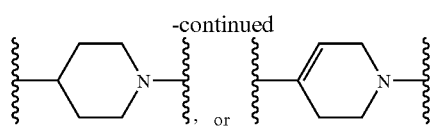

is preferable, and further (IVi) a ring of the formula of

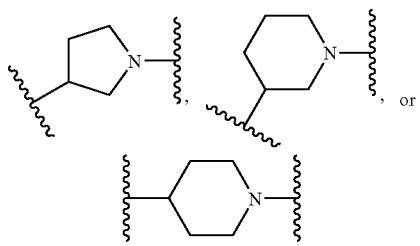

is more preferable.

In sb, (IVj) 1, 2 or 3 is preferable, and further (IVk) 1 or 2 is more preferable.

Groups of preferred substituents in the ring Cb, the ring Eb, $R^{1b}$ to $R^{4b}$, $X^b$, $W^b$, $Z^b$, mb, nb and sb of the compound of general formula (V-b) are shown with (IIIf) to (IIIo), (IIIt) to (IIIu), (IIIx) to (IVa), (IVf) to (IVg) and (IVj) to (IVo). Compounds having possible combination of them are preferable.

In the ring Cb, (IIIf) above is preferable, and further (IIIg) above is more preferable.

In $R^{1b}$, (IIIh) above is preferable, and further (IIIi) above is more preferable.

In $R^{2b}$, (IIIj) above is preferable, and further (IIIk) above is more preferable.

In $R^{3b}$, (IIIl) above is preferable, and further (IIIm) above is more preferable.

In $R^{4b}$, (IIIn) above is preferable, and further (IIIo) above is more preferable.

In $Z^b$, (IIIt) above is preferable, and further (IIIu) above is more preferable.

In mb, (IIIx) above is preferable, and further (IIIy) above is more preferable.

In nb, (IIIz) above is preferable, and further (IVa) above is more preferable.

In $X^b$, (IVf) above or (IVg) above is preferable.

In sb, (IVj) above is preferable, and further (IVk) above is more preferable.

In the ring Eb, (IVl) a ring of the formula of

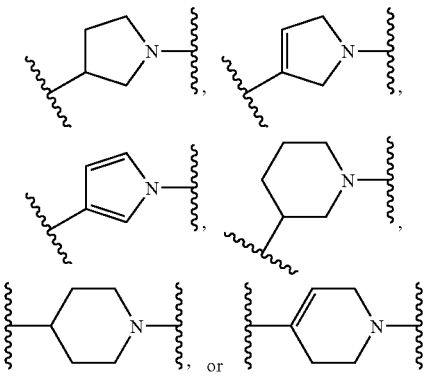

is preferable, and further (IVm) a ring of the formula of

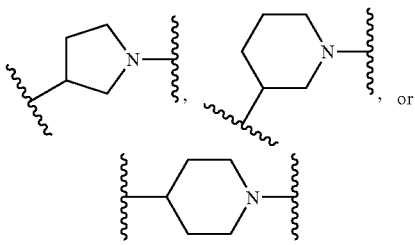

is more preferable.

In $W^b$, (IVn) a single bond, alkylene or —O— is preferable, and further (IVo) a single bond or —O— is more preferable.

EFFECT OF INVENTION

The compounds of the present invention are useful as a therapeutic agent, especially for treating allergic diseases, since they have an excellent DP receptor antagonistic activity and high safety.

BEST MODE FOR CARRYING OUT THE INVENTION

The compounds of the present invention can be prepared by the method A, B or C set forth below. In addition, a racemate or an optical isomer is included in structural formulae of (IV) to (XV), (XVII), (XVIII), (XIX) and (XX).

Method A is set forth below,

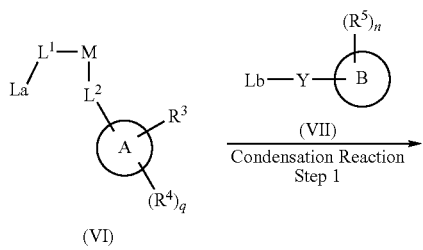

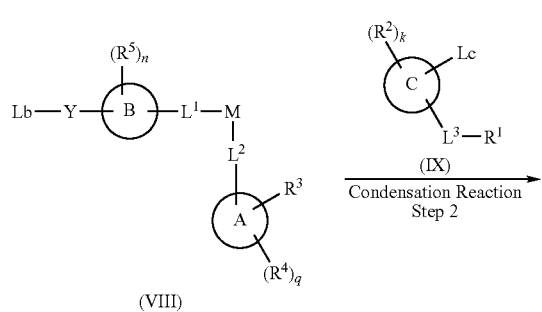

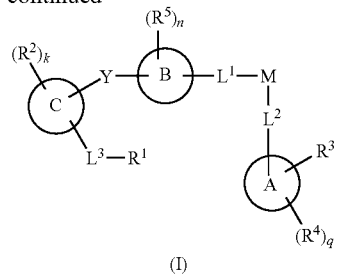

(I)

wherein the ring A, the ring B, the ring C, $R^1$, $R^2$, $R^3$, $R^4$, $R^5$, M, Y, $L^1$, $L^2$, $L^3$, k, n and q are the same as 1) above; La is a halogen atom or a hydroxy group; Lb is a hydrogen atom, a halogen atom, a hydroxy group, methylsulfonyloxy, p-toluenesulfonyloxy or tert-butyloxycarbonyl.

A starting compound of the formula (VI) is available from commercial products or by chemical modification of the substituent on the compound of the formula (VI) such as general alkylation, esterification, amidation, hydrolysis, reductive reaction, oxidative reaction, Suzuki-coupling reaction, protection and de-protection reaction and the like.

Step 1 is a process in which a compound of the formula (VI) is reacted with a compound of the formula (VII) to give a compound of the formula (VIII).

The reaction can be carried out by reacting 0.5 to 5 equivalents of the compound (VII) compared to the compound (VI) in a solvent at 0° C. to 150° C. for 5 minutes to 48 hours.

The reaction may be conducted under the presence of 1 to 5 equivalents of a base. Examples of the preferable base include sodium hydride, potassium carbonate, sodium carbonate, potassium bicarbonate, sodium bicarbonate, triethylamine and the like.

Examples of the preferable solvent include tetrahydrofuran, N,N-dimethylformamide, dimethylsulfoxide, water and the like, which can be used alone or as a mixed solvent.

When Lb is tert-butyloxycarbonyl, the compound can be de-protected in a solvent such as ethyl acetate etc. at 0° C. to 150° C. for 5 minutes to 48 hours using hydrochloric acid.

Step 2 is a process in which a compound of the formula (VIII) is condensed with a compound of the formula (IX), and the product is hydrolyzed under basic condition if necessary, to give a compound of the formula (I).

The reaction can be carried out by reacting 0.5 to 5 equivalents of the compound (IX) compared to the compound (VIII) in a solvent at 0° C. to 150° C. for 5 minutes to 48 hours.

Examples of the preferable solvent include ethyl acetate, methylene chloride, tetrahydrofuran, toluene, N,N-dimethylformamide, methanol, dioxane, water and the like, which can be used alone or as a mixed solvent.

If necessary, 0.05 to 5 equivalents of a) 1,1'-(azodicarbonyl)dipiperidine and tributylphosphine or b) tris(dibenzylideneacetone)-dipalladium(0), xantphos and sodium tert-butoxide respectively compared to the compound of the formula (VIII) can be used as a condensing agent.

Hydrolysis can be conducted by reacting 1 to 5 equivalent(s) of a base compared to the the compound of the formula (VII) at 0° C. to 150° C. for 5 minutes to 48 hours.

Examples of the preferable solvent include tetrahydrofuran, methanol, N,N-dimethylformamide, water and the like, which can be used alone or as a mixed solvent.

Examples of the preferable base include sodium hydroxide, potassium hydroxide, potassium carbonate, sodium carbonate, potassium bicarbonate, sodium bicarbonate and the like.

In addition, each substituent may be converted to the other substituent using a general reaction such as alkylation, esterification, amidation, hydrolysis, reductive reaction, oxidative reaction, Suzuki-coupling reaction, protection and de-protection reaction and the like. A product (VIII) and (I) of each step may be purified by a usual method such as column chromatography or re-crystalization.

Method B is set forth below,

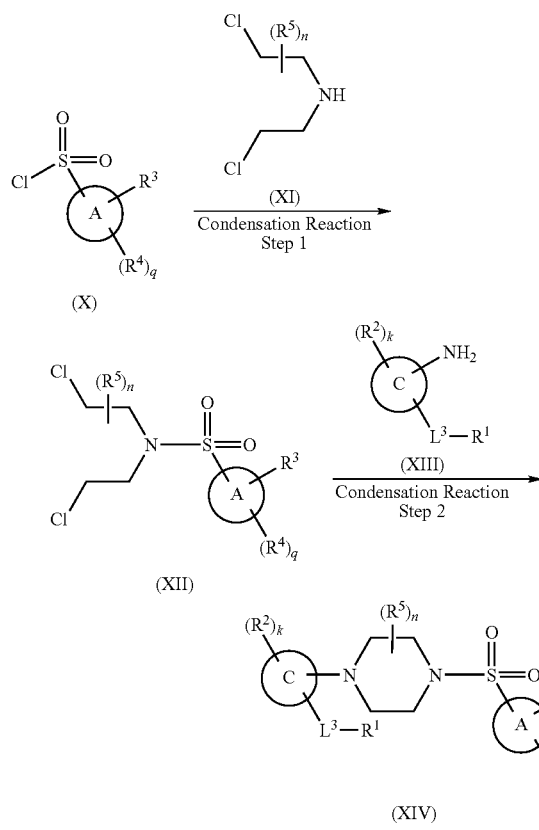

wherein the ring A, the ring C, $R^1$, $R^2$, $R^3$, $R^4$, $R^5$, $L^3$, k, n and q are the same as 1) above.

Step 1 is a process in which a compound of the formula (X) is reacted with a compound of the formula (XI) to give a compound of the formula (XII).

The reaction can be carried out by reacting 0.5 to 5 equivalents of the compound (XI) compared to the compound (X) in a solvent at 0° C. to 150° C. for 5 minutes to 48 hours.

The reaction may be conducted under the presence of 1 to 5 equivalent(s) of a base. Examples of the preferable base include sodium hydride, potassium carbonate, sodium carbonate, potassium bicarbonate, sodium bicarbonate, triethylamine and the like.

Examples of the preferable solvent include tetrahydrofuran, N,N-dimethylformamide, dimethylsulfoxide, water and the like, which can be used alone or as a mixed solvent.

Step 2 is a process in which a compound of the formula (XII) is reacted with a compound of the formula (XIII), and the product is hydrolyzed under basic condition if necessary, to give a compound of the formula (XIV).

The reaction can be carried out by reacting 0.5 to 5 equivalents of the compound (XIII) compared to the compound (XII) in a solvent at 0° C. to 150° C. for 5 minutes to 48 hours.

Examples of the preferable solvent include ethyl acetate, methylene chloride, tetrahydrofuran, N,N-dimethylformamide, methanol, dioxane, water and the like, which can be used alone or as a mixed solvent.

If necessary, the reaction may be carried out under the presence of 1 to 5 equivalent(s) of a base. Examples of the preferable base include sodium hydride, potassium carbonate, sodium carbonate, potassium bicarbonate, sodium bicarbonate, triethylamine and the like.

Further, 0.2 to 4 equivalents of potassium iodide can be used compared to the compound of the formula (XIII).

Hydrolysis can be conducted by reacting 1 to 5 equivalent(s) of a base compared to the the compound of the formula (XII) at 0° C. to 150° C. for 5 minutes to 48 hours.

Examples of the preferable solvent include tetrahydrofuran, methanol, N,N-dimethylformamide, water and the like, which can be used alone or as a mixed solvent.

Examples of the preferable base include sodium hydroxide, potassium hydroxide, potassium carbonate, sodium carbonate, potassium bicarbonate, sodium bicarbonate and the like.

In addition, each substituent may be converted to the other substituent using a general reaction such as alkylation, esterification, amidation, hydrolysis, reductive reaction, oxidative reaction, Suzuki-coupling reaction, protection and de-protection reaction and the like. A product (XII) and (XIV) of each step may be purified by a usual method such as column chromatography or re-crystalization.

Method C is set forth below,

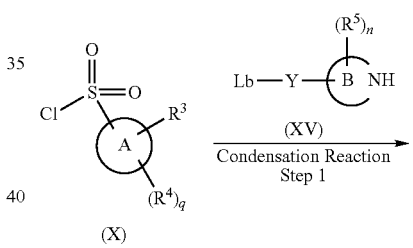

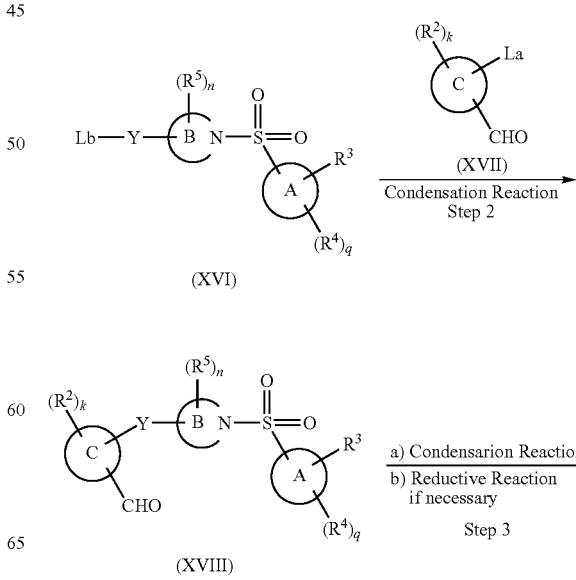

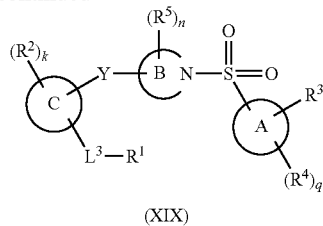

(XIX)

wherein the ring A, the ring B, the ring C, $R^1$, $R^2$, $R^3$, $R^4$, $R^5$, Y, $L^3$, k, n and q are the same as 1) above; and Lb is a hydrogen atom, a halogen atom, a hydroxyl group, methylsulfonyloxy, p-toluenesulfonyloxy or tert-butyloxycarbonyl.

Step 1 is a process in which a compound of the formula (X) is reacted with a compound of the formula (XV) to give a compound of the formula (XVI).

The reaction can be carried out by reacting 0.5 to 5 equivalents of the compound (XV) compared to the compound (X) in a solvent at 0° C. to 150° C. for 5 minutes to 48 hours.

The reaction may be conducted under the presence of 1 to 5 equivalent(s) of a base. Examples of the preferable base include sodium hydride, potassium carbonate, sodium carbonate, potassium bicarbonate, sodium bicarbonate, triethylamine and the like.

Examples of the preferable solvent include tetrahydrofuran, N,N-dimethylformamide, dimethylsulfoxide, water and the like, which can be used alone or as a mixed solvent.

When Lb is tert-butyloxycarbonyl, the compound can be de-protected in a solvent such as ethyl acetate etc. at 0° C. to 150° C. for 5 minutes to 48 hours using hydrochloric acid.

Step 2 is a process in which a compound of the formula (XVI) is condensed with a compound of the formula (XVII) to give a compound of the formula (XVIII).

The reaction can be carried out by reacting 0.5 to 5 equivalents of the compound (XVII) compared to the compound (XVI) in a solvent at 0° C. to 150° C. for 5 minutes to 48 hours.

Examples of the preferable solvent include ethyl acetate, methylene chloride, tetrahydrofuran, N,N-dimethylformamide, methanol, dioxane, water and the like, which can be used alone or as a mixed solvent.

If necessary, 0.5 to 5 equivalents of 1,1'-(azodicarbonyl)dipiperidine and tributylphosphine compared to the compound of the formula (XVI) can be used as a condensing agent.

Step 3 is a process in which a compound of the formula (XVIII) is condensed, and if necessary further reduced and/or hydrolyzed under a basic condition to give a compound of the formula (XIX).

The condensation reaction can be carried out by reacting 0.5 to 5 equivalents of a condensing agent compared to the compound (XVIII) in a solvent at 0° C. to 150° C. for 5 minutes to 48 hours.

Examples of the preferable solvent include ethyl acetate, methylene chloride, tetrahydrofuran, N,N-dimethylformamide, dimethylsulfoxide, water and the like, which can be used alone or as a mixed solvent.

As a condensing agent, carboethoxymethylenetriphenylphosphorane and the like can be used. A double bond or triple bond formed by the condensation reaction can be reduced to a saturated bond by a usual reductive reaction.

Hydrolysis can be conducted by reacting 1 to 5 equivalent(s) of a base compared to the compound of the formula (XVIII) in a solvent at 0° C. to 150° C. for 5 minutes to 48 hours.

Examples of the preferable solvent include tetrahydrofuran, methanol, N,N-dimethylformamide, water and the like, which can be used alone or as a mixed solvent.

Examples of the preferable base include sodium hydroxide, potassium hydroxide, potassium carbonate, sodium carbonate, potassium bicarbonate, sodium bicarbonate and the like.

In addition, each substituent may be converted to the other substituent using a general reaction such as alkylation, esterification, amidation, hydrolysis, reductive reaction, oxidative reaction, Suzuki-coupling reaction and the like.

The product (XVI), (XVIII) or (XIX) of each step can be purified if necessary by usual methods such as column chromatography and re-crystallization etc.

In addition, a compound of the general formula (X) can be prepared by the next method;

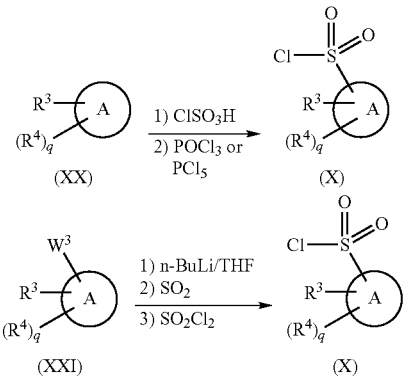

wherein the ring A, $R^3$, $R^4$ and q are the same as 1) before, and $W^3$ is a halogen atom.

In a method for preparing the compound of the formula (X) from the compound of the formula (XX), the compound of the formula (XX) is 1) converted to a $SO_3H$ derivative by treating with $ClSO_3Cl$, and 2) followed by chlorination of the hydroxy group by the reaction with $POCl_3$ or $PCl_5$ to give the compound of the formula (X).

In a method for preparing the compound of the formula (X) from the compound of the formula (XXI), the compound of the formula (XIX) is 1) lithiated by n-BuLi, and 2) followed by conversion to a $SO_2Li$ derivative by the reaction with $SO_2$, and finally 3) reacted with $SO_2Cl_2$ to give the compound of the formula (XX). A bromine atom or an iodine atom is preferable as $W^3$.

In addition, each substituent may be converted to the other substituent in each step using a general reaction such as alkylation, esterification, amidation, hydrolysis, reductive reaction, oxidative reaction, Suzuki-coupling reaction and the like.

In this specification, a term of "solvate" includes, for example, a solvate with an organic solvent, a hydrate and the like. In a case of forming the solvate with an organic solvent, any number of molecules of the organic solvent may be coordinated. In a case of forming the hydrate, any number of water molecules may be coordinated. A hydrate is usually preferred.

A term of "compound of the present invention" includes a pharmaceutically acceptable salt and a solvate thereof. Examples of the salt include salts with alkaline metal(lithium, sodium and potassium etc.), alkaline earth metal(magnesium and calcium etc.), ammonium, organic bases and amino acids and salts with inorganic acids (hydrochloric acid, hydrobromic acid, phosphoric acid and sulfuric acid, etc.) and organic acids (acetic acid, citric acid, maleic acid, fumaric acid, benzenesulfonic acid and p-toluenesulfonic acid etc.). These salts can be formed by the usual method.

A compound of the present invention is not limited to the specified isomer but includes all possible isomers and racemates.

A compound of the present invention shows an excellent DP receptor antagonistic activity as described in the following examples. Accordingly, a pharmaceutical composition of the present invention can be used as a therapeutic agent for preventing and/or treating allergic diseases such as asthma, allergic rhinitis, allergic dermatitis, allergic conjunctivitis, food allergy and the like; systemic mastocytosis; systemic disorder of mastcell-activation; lung emphysema; chronic bronchitis; chronic obstructive lung disease; skin disorder characterized by pruritus such as atopic dermatitis and hives; diseases occuring secondarily due to behavior accompanied by pruritus such as cataract and retinal detachment; brain damages such as cerebrovascular disorder, degenerative brain disorder and demyelinating disease; sleep-waking disorder; Churg-Strauss syndrome; papular dermatitis such as filariasis; vasculitis; polyarteritis; cutaneous eosoiophilic granuloma; autoimmune diseases such as multiple sclerosis and transplant rejection; eosoiophilic pneumonopathy; histiocytosis; pneumonia; aspergillosis; pleurisy; sarcoidosis; pulmonary fibrosis; eosinophilia; skin flush such as face flush by nicotinic acid; filariasis; schistosomiasis; trichinelliasis; coccidioidomycosis; tuberculosis; bronchial cancer; lymphoma; Hodgkin's disease and the like.

When a compound of the present invention is administered to a human in order to treat the diseases above, oral administration through a powder, granule, tablet, capsule, pill, liquid formulation and the like, or parenteral administration through an injection, suppository, transdermal formulation, inhalant and the like is possible.

A pharmaceutical composition can be obtained by mixing a therapeutically effective amount of a compound of the present invention with a pharmaceutical additives such as an excipient, binder, wetting agent, disintegrating agent, lubricant and the like, which is suitable to the selected formulation. An injection can be formulated by sterilization together with a suitable carrier.

In the treatment of the diseases related to PGD2 receptor above, it is possible to use the compound of the present invention combined with or in a coupled formulation with the other therapeutic agent. In the case of treating inflammatory diseases including allergy, the compound can be used combined with or in a coupled formulation with leukotriene receptor antagonist (e.g., montelukast sodium, zafirlukast, pranlukast hydrate, leukotriene B4 receptor antagonist); leukotriene synthesis inhibitor such as zileuton, PDE IV inhibitor (e.g., theophylline, cilomilast, roflumilast), corticosteroid (e.g., prednisolone, fluticasone, budesonide, ciclesonide), β2-agonist (e.g., salbutamol, salmeterol, formoterol), anti IgE antibody (e.g., omalizumab), histamine H1 receptor antagonist (e.g., chlorpheniramine, loratadine, cetirizine), immunosuppressant (tacrolimus, cyclosporin), thromboxane A2 receptor antagonist (e.g., ramatroban), chemokine receptor (especially CCR-1, CCR-2, CCR-3) antagonist, other prostanoid receptor antagonist (e.g., CRTH2 antagonist), adhesion molecule antagonist (e.g., VLA-4 antagonist), cytokine antagonist (e.g., antibody, anti-IL-3 antibody), Non-steroidal anti-inflammatory agent (e.g., propionic acid derivative such as ibuprofen, ketoprofen, and naproxen etc.; acetic acid derivative such as indomethacin, and diclofenac etc.; salicylic acid such as acetyl salicylic acid; cyclooxigenase-2 inhibitor such as celecoxib and etoricoxib).

Further, uses combined with or in a coupled formulation with antitussive agent (e.g., codein, hydrocodein), cholesterol lowering agent (lovastatin, simvastatin, fluvastatin. rosuvastatin), anticholinergic drug (e.g., tiotropium, ipratropium, flutropium, oxitropium) are also possible.

Dose of the compounds of the present invention depends on condition of diseases, route of administration, age and body weight of a patient. In the case of oral administration to an adult, the dose range is usually 0.1 to 100 mg/kg/day, preferably 1 to 20 mg/kg/day.

EXAMPLE

The present invention is illustrated more in detail below by examples and test examples, but not limited to these examples.

In examples, the following abbreviations are used;
Me: methyl
Et: ethyl
n-Pr: n-propyl
i-Pr: isopropyl
Ac: acetyl
Ph: phenyl
Bn: benzyl
Boc: tert-butyloxycarbonyl
MOM: methyloxymethyl
THF: tetrahydrofuran
DMF: N,N-dimethylformamide
MeOH: methanol
HOBt: 1-hydroxybenzotriazole
WSCD HCl: 1-ethyl-3-(3-dimethylaminopropyl)carbodiimide hydrochloride Example 1

Preparation of the Compound I-1

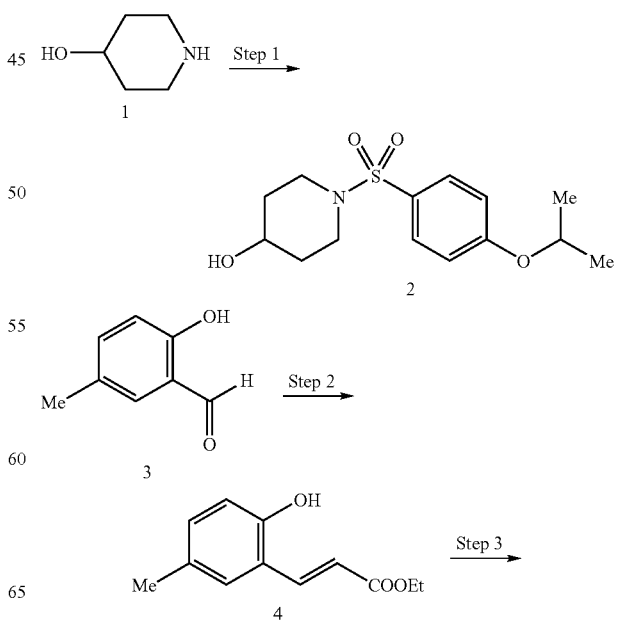

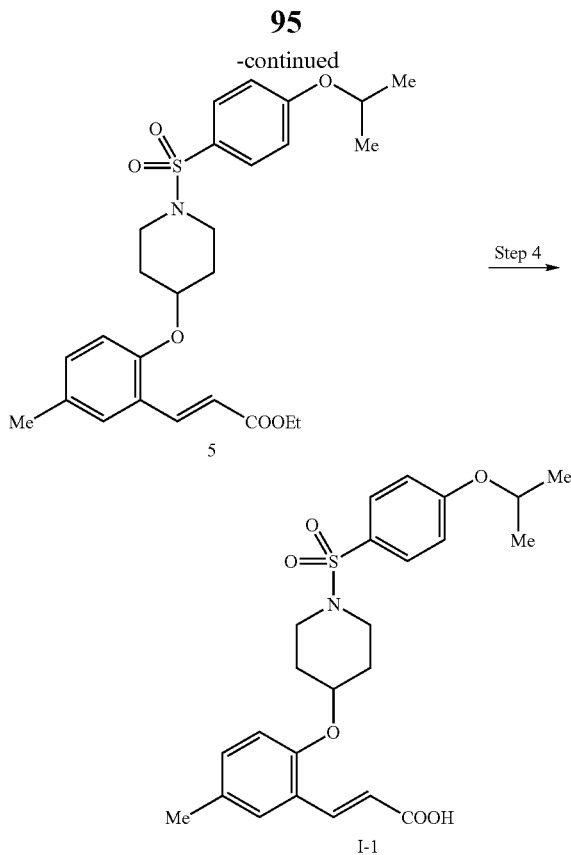

Step 1

4-Isopropoxybenzenesulfonyl chloride (2.34 g, 10.0 mmol) and triethylamine (4.2 mL, 30.0 mmol) were added at 0° C. to a solution of 4-hydroxypiperidine(1.01 g, 10.0 mmol) in THF (20 mL) and the mixture was stirred for an hour. Diluted hydrochloric acid (60 mL) and ethyl acetate (60 mL) were added to the reaction solution, the mixture was extracted and the organic layer was washed with a saturated aqueous solution of sodium bicarbonate and saturated brine successively, dried and concentrated. n-Hexane was added to the residue and the resulting crystalline was filtered to give the compound (2) (2.8 g, 94% yield).

$^1$H-NMR (CDCl$_3$) δ ppm: 1.36 (d, J=6.0 Hz, 6H), 1.71 (m, 2H), 1.93 (m, 2H), 2.84 (m, 2H), 3.23 (m, 2H), 3.77 (m, 1H), 4.06 (m, 1H), 6.95 (d, J=8.7 Hz, 2H), 7.66 (d, J=8.7 Hz, 2H).

Step 2

Carboethoxymethylenetriphenylphosphorane (920 mg, 2.6 mmol) was added to a solution of 2-hydroxy-4-methylbenzaldehyde(3) (300 mg, 2.2 mmol) in THF (5 mL) and the mixture was heated under reflux for an hour. After the reaction mixture was cooled down, the solvent was evaporated. The resulting residue was purified by a silica gel column chromatography (hexane:ethyl acetate=5:1) and concentrated to give the compound (4) (320 mg, 70% yield).

$^1$H-NMR (CDCl$_3$) δ ppm: 1.34 (t, J=7.2 Hz, 3H), 2.28 (s, 3H), 4.27 (m, 2H), 6.09 (s, 1H), 6.60 (d, J=16.2 Hz, 1H), 6.74 (d, J=8.1 Hz, 1H), 7.04 (dd, J=2.1, 8.1 Hz, 1H), 7.27 (d, J=2.1 Hz, 1H), 8.00 (d, J=16.2 Hz, 1H).

Step 3

The compound (2) (218 mg, 0.7 mmol) obtained in step 1,1,1'-(azodicarbonyl) dipiperidine (238 mg, 0.9 mmol) and tributylphosphine (0.57 mL, 2.2 mmol) were added to a solution of the compound (4) (150 mg, 0.7 mmol) in THF (10 mL), and the mixture was stirred at room temperature for 4 hours. Water was added to the reaction solution, the mixture was extracted with ethyl acetate and the organic layer was washed with a saturated aqueous solution of sodium bicarbonate and saturated brine successively, dried and concentrated. The resulting residue was purified by a silica gel column chromatography (hexane:ethyl acetate=3:1) to give the compound (5) (130 mg, 37% yield).

Step 4

A 2M aqueous solution of sodium hydroxide (0.4 mL, 0.8 mmol) was added to a solution of the compound (5) (40 mg, 0.08 mmol) in THF (6 mL) and MeOH(2 mL) and the mixture was stirred at room temperature for 18 hours. After the reaction solution was acidified by adding diluted hydrochloric acid, the mixture was extracted with ethyl aetate, and the extract was washed with water, dried and concentrated. The residue was crystallized from hexane-ethyl acetate to give the compound I-1 (15 mg, 40% yield).

$^1$H-NMR (CDCl$_3$) δ ppm: 1.35 (d, 6H, J=9.0 Hz), 2.01 (m, 4H), 2.28 (s, 3H), 3.15 (m, 4H), 4.62 (m, 1H), 6.38 (d, J=16.2 Hz, 1H), 6.74 (d, J=8.4 Hz, 1H), 6.96 (d, J=9.0 Hz, 2H), 7.11 (dd, J=1.8, 8.4 Hz, 1H), 7.31 (d, J=1.8 Hz, 1H), 7.68 (d, J=9.0 Hz, 2H), 7.89 (d, J=16.2 Hz, 1H).

Example 2

Preparation of the Compound II-9 and III-1

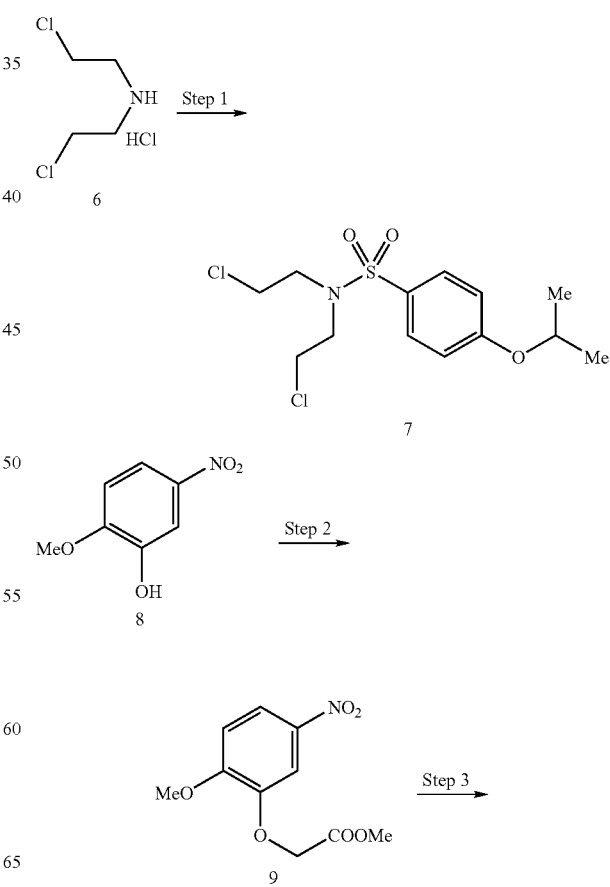

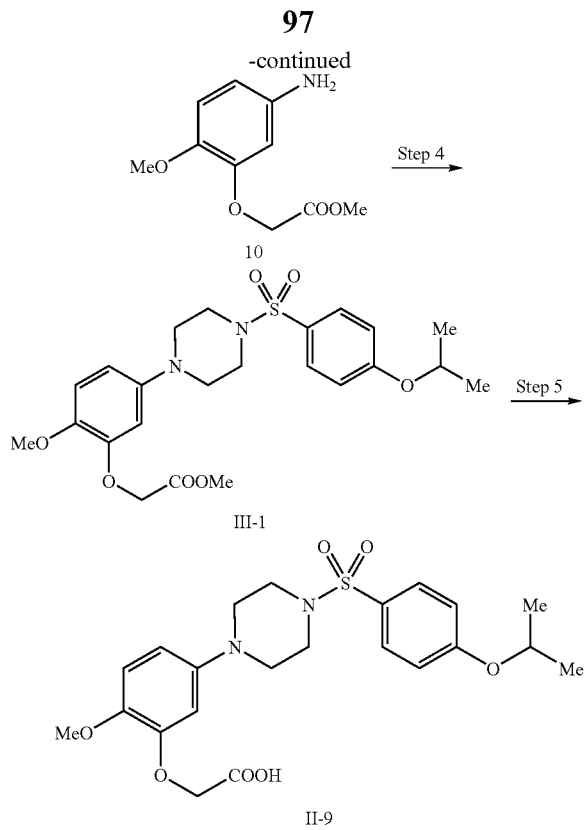

Step 1

4-Isopropoxybenzenesulfonyl chloride (2.35 g, 10.0 mmol) and triethylamine (3.7 mL, 22.0 mmol) were added to a solution of bis(2-chloroethyl)amine hydrochloride(6) (1.78 g, 10.0 mmol) in DMF (20 mL) and the mixture was stirred at room temperature for 2 hours. Diluted hydrochloric acid (200 mL) was added to the reaction solution, the mixture was extracted with ethyl acetate (200 mL) and the organic layer was washed with a saturated aqueous solution of sodium bicarbonate and saturated brine successively, dried and concentrated. The resulting residue was purified by a silica gel column chromatography (hexane:ethyl acetate=8:1) to give the compound (7) (1.79 g, 53% yield).

$^1$H-NMR (CDCl$_3$) δ ppm: 1.37 (d, J=6.3 Hz, 6H), 2.98 (m, 4H), 3.74 (m, 4H), 4.64 (m, 1H), 6.97 (d, J=9.0 Hz, 2H), 7.66 (d, J=9.0 Hz, 2H).

Step 2

Methyl bromoacetate (7.1 mL, 75.0 mmol), potassium carbonate (13.8 g, 100.0 mmol) and potassium iodide (0.83 g, 5.0 mmol) were added to a solution of 2-methoxy-5-nitrophenol (8) (8.46 g, 50.0 mmol) in DMF (80 mL) and the mixture was stirred at 30° C. for 2 hours. Water was added to the reaction mixture and the precipitated crystalline was washed with water and dried to give the compound (9) (11.9 g, 99.9% yield).

$^1$H-NMR (CDCl$_3$) δ ppm: 3.83 (s, 3H), 3.99 (s, 3H), 4.78 (s, 2H), 6.96 (d, J=9.0 Hz, 1H), 7.69 (d, J=2.4 Hz, 1H), 7.98 (dd, J=2.4, 9.0 Hz, 1H).

Step 3

To a solution of the compound (9) (5.95 g, 25.0 mmol) in a mixture of THF (60 mL) and MeOH (60 mL) was added 10% palladium carbon (1.2 g) and the mixture was stirred under hydrogen atmosphere at room temperature for 5 hours. The reaction mixture was filtered through Celite and the filtrate was concentrated to give the compound (10) (5.28 g, 99.9% yield).

$^1$H-NMR (CDCl$_3$) δ ppm: 3.20 (brs, 2H), 3.79 (s, 3H), 3.81 (s, 3H), 4.65 (s, 3H), 6.28-6.34 (m, 2H), 6.73 (d, J=8.4 Hz, 1H).

Step 4

The compound (7) (749 mg, 2.2 mmol), potassium carbonate (1.11 g, 8.0 mmol) and potassium iodide (66.4 mg, 0.4 mmol) were added to a solution of the compound (10) (422 mg, 2.0 mmol) in DMF (5 mL) and the mixture was stirred at room temperature for 18 hours. Diluted hydrochloric acid (50 mL) was added to the reaction solution and the mixture was extracted with ethyl acetate (50 mL), and the organic layer was washed with a saturated aqueous solution of sodium bicarbonate and saturated brine, dried and concentrated. The resulting residue was purified by a silica gel column chromatography (hexane:ethyl acetate=2:1) to give the compound III-1 (43 mg, 5% yield)

$^1$H-NMR (CDCl$_3$) δ ppm: 1.37 (d, J=6.0 Hz, 6H), 3.15 (brs, 8H), 3.78 (s, 3H), 3.83 (s, 3H), 4.60 (m, 1H), 4.65 (s, 2H), 6.60-6.63 (m, 2H), 6.81 (d, J=7.8 Hz, 1H), 6.96 (d, J=9.0 Hz, 2H), 7.69 (d, J=9.0 Hz, 2H).

Step 5

The compound III-1 (40 mg, 0.084 mmol) was dissolved in MeOH (1.0 mL) and THF (1.0 mL). A 2M aqueous solution of sodium hydroxide (0.12 mL, 0.25 mmol) was added and the mixture was stirred at room temperature for 2 hours. After the reaction solution was diluted with water and acidified by adding diluted hydrochloric acid, the mixture was extracted with ethyl acetate and the extract was washed with water, dried and concentrated. The residue was crystallized from hexane-ethyl acetate to give the compound II-9 (35 mg, 91% yield).

$^1$H-NMR (CDCl$_3$) δ ppm: 1.38 (d, J=6.0 Hz, 6H), 1.95 (brs, 1H), 3.16 (brs, 8H), 3.86 (s, 3H), 4.60-4.69 (m, 3H), 6.60-6.63 (m, 2H), 6.85 (d, J=9.0 Hz, 1H), 6.98 (d, J=9.0 Hz, 2H), 7.70 (d, J=9.0 Hz, 2H).

Example 3

Preparation of the Compound II-6 and III-2

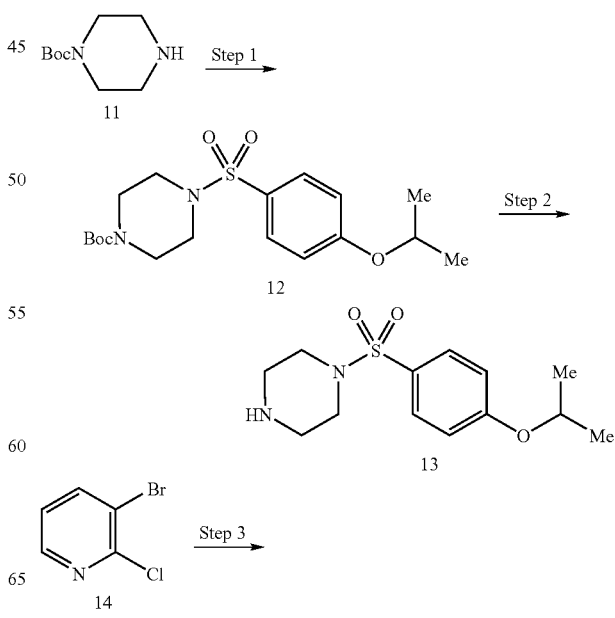

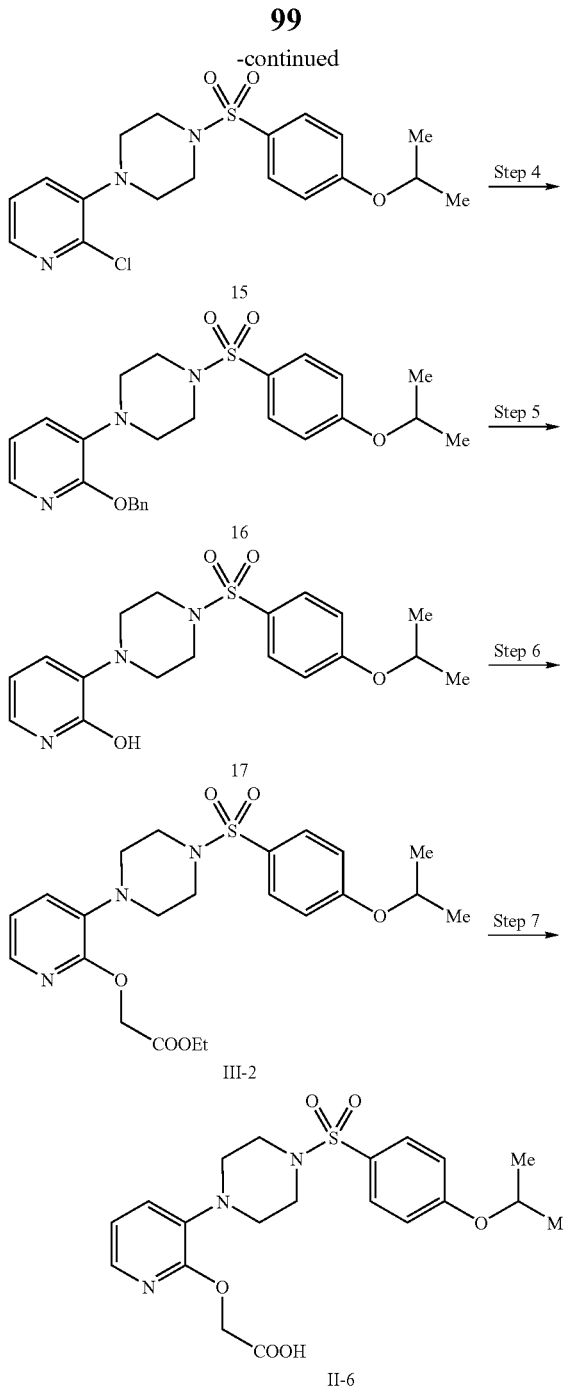

Step 1

4-Isopropoxybenzenesulfonyl chloride (4.46 g, 19.0 mmol) and triethylamine (5.6 mL, 40.0 mmol) were added to a solution of 1-(tert-butoxycarbonyl)piperazine(11) 3.73 g, 20.0 mmol) in THF (40 mL) and the mixture was stirred at room temperature for 2 hours. Diluted hydrochloric acid (200 mL) was added to the reaction solution and the mixture was extracted with ethyl acetate (200 mL), and the organic layer was washed with a saturated aqueous solution of sodium bicarbonate and saturated brine succesively, dried and concentrated. The residue was crystallized from hexane-ethyl acetate to give the compound (12) (6.78 g, 88% yield)

$^1$H-NMR (CDCl$_3$) δ ppm: 1.37 (d, J=6.0 Hz, 6H), 1.41 (s, 9H), 2.95 (m, 4H), 3.51 (m, 4H), 4.63 (m, 1H), 6.96 (d, J=8.7 Hz, 2H), 7.65 (d, J=8.7 Hz, 2H).

Step 2

A 4M solution of hydrochloric acid in ethyl acetate was added to a solution of the compound (12) (6.78 g, 17.6 mmol) in ethyl acetate (30 mL) and the mixture was stirred at room temperature for 2 hours and the stirring was further continued at 50° C. for 1 hour. Water (200 mL) was added to the reaction solution and extracted with ethyl acetate (200 mL). After the aqueous layer was adjusted to pH=11 by adding a 2M aqueous solution of sodium hydroxide, the mixture was extracted with ethyl acetate (400 mL). The organic layer was washed with water and saturated brine successively, dried and concentrated. The residue was crystallized from hexane-ethyl acetate to give the compound (13) (4.58 g, 92% yield).

$^1$H-NMR (CDCl$_3$) δ ppm: 1.37 (d, J=6.0 Hz, 6H), 2.95 (m, 8H), 4.63 (m, 1H), 6.94 (d, J=8.7 Hz, 2H), 7.65 (d, J=8.7 Hz, 2H).

Step 3

Tris(dibenzylideneacetone)-dipalladium(0) (71 mg, 0.08 mmol), xanthophos (134 mg, 0.23 mmol) and sodium tert-butoxide (288 mg, 3.0 mmol) were added to a solution of 3-bromo-2-chloropyridine(14) (192.4 mg, 1.0 mmol) and the compound (3) (219 mg, 0.77 mmol) in toluene (10 mL) and the mixture was heated under reflux under nitrogen atmosphere for 3 hours. After being cooled, water (40 mL) was poured to the reaction solution and extracted with ethyl acetate (100 mL). The organic layer was washed with diluted hydrochloric acid, a saturated aqueous solution of sodium bicarbonate and saturated brine successively, dried and concentrated. The resulting residue was purified by a silica gel column chromatography (hexane:ethyl acetate=3:1) to give the compound (15) (189 mg, 62% yield).

$^1$H-NMR (CDCl$_3$) δ ppm: 1.39 (d, J=6.0 Hz, 6H), 3.17 (m, 8H), 4.65 (m, 1H), 6.98 (d, J=8.7 Hz, 2H), 7.19-7.34 (m, 2H), 7.65 (d, J=8.7 Hz, 2H), 8.08 (dd, J=1.5, 4.5 Hz, 1H).

Step 4

60% Sodium hydride (150 mg, 3.7 mmol) was added to a solution of benzyl alcohol (0.35 mL, 3.4 mmol) in DMF (10 mL) at 0° C., and the mixture was stirred for 30 minutes. To the reaction solution was added dropwise a solution of the compound (15) (673 mg, 3.4 mmol) in DMF (5 mL) at 0° C. and the mixture was stirred at 90° C. After being cooled, water (100 mL) was poured to the reaction solution and extracted with ethyl acetate (100 mL). The organic layer was washed with diluted hydrochloric acid, a saturated aqueous solution of sodium bicarbonate and saturated brine successively, dried and concentrated. The resulting residue was purified by a silica gel column chromatography (hexane:ethyl acetate=3:1) and concentrated to give the residue, which was used in the next step without further purification.

$^1$H-NMR(CDCl$_3$) δ ppm: 1.37 (d, J=6.0 Hz, 6H), 3.17 (brs, 8H), 4.63 (m, 1H), 4.70 (s, 2H), 6.87 (dd, J=2.4, 7.8 Hz, 1H), 6.96 (d, J=9.0 Hz, 2H), 7.09 (m, 1H), 7.28-7.34 (m, 5H), 7.68 (d, J=9.0 Hz, 2H), 8.08 (dd, J=1.5, 4.8 Hz, 1H).

Step 5

To the residue obtained in the step 4 were added THF (2 mL) and MeOH (2 mL), and further 10% palladium carbon (150 mg), and the mixture was stirred under hydrogen atmosphere at room temperature for 1.5 hours. The reaction solution was filtered through Celite and the filtrate was concentrated. The residue was crystallized from hexane-ethyl acetate to give the compound (17) (365 mg, 57% yield/two steps).

$^1$H-NMR (CDCl$_3$) δ ppm: 1.37 (d, J=6.0 Hz, 6H), 3.25 (m, 8H), 4.63 (m, 1H), 6.26 (m, 1H), 6.94-7.04 (m, 4H), 7.67 (d, J=8.7 Hz, 2H).

Step 6

Ethyl iodoacetate (0.95 mL, 0.8 mmol) and silver carbonate (166 mg, 0.6 mmol) were added to a solution of the compound (17) (151 mg, 0.4 mmol) in toluene (20 mL) and the mixture was heated under reflux for 3 hours under nitrogen atmosphere. After being cooled, the reaction solution was filtered through a glass filter. The filtrate was concentrated and the resulting residue was purified by a silica gel column chromatography (hexane:ethyl acetate=5:1) to give the compound III-2 (83 mg, 45% yield).

$^1$H-NMR (CDCl$_3$) δ ppm: 1.25 (t, J=7.2 Hz, 3H), 1.38 (d, J=6.0 Hz, 6H), 3.23 (brs, 8H), 4.20 (m, 2H), 4.63 (m, 1H), 4.93 (s, 2H), 6.85-6.98 (m, 3H), 7.18 (m, 1H), 7.68-7.76 (m, 3H).

Step 7

The compound III-2 (80 mg, 0.17 mmol) was dissolved in MeOH (1.0 mL) and THF (1.0 mL). A 2M aqueous solution of sodium hydroxide (0.34 mL, 0.69 mmol) was added thereto and the mixture was stirred at room temperature for 2 hours. The reaction solution was diluted with water and acidified by adding diluted hydrochloric acid. The mixture was extracted with ethyl acetate and the extract was washed with water, dried and concentrated. The residue was crystallized from hexane-ethyl acetate to give the compound II-6 (53 mg, 70% yield).

$^1$H-NMR (DMSO-d$_6$) δ ppm: 1.31 (d, J=6.0 Hz, 6H), 2.99 (brs, 4H), 3.13 (brs, 4H), 4.72-4.79 (m, 3H), 6.92 (dd, J=5.1, 7.5 Hz, 1H), 7.15 (d, J=8.7 Hz, 2H), 7.23 (d, J=7.8 Hz, 1H), 7.67-7.70 (m, 3H), 12.75 (brs, 1H).

Example 4

Preparation of the Compound I-3, I-4, III-3 and III-4

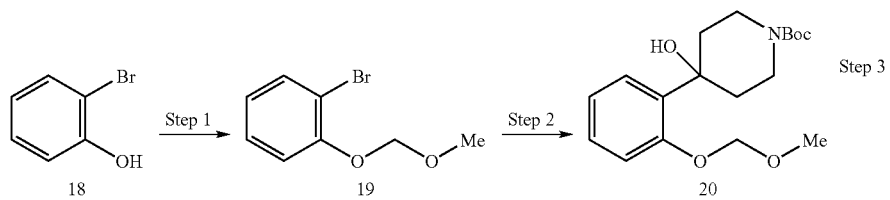

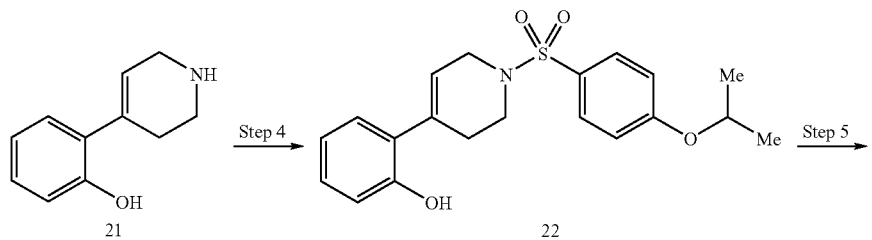

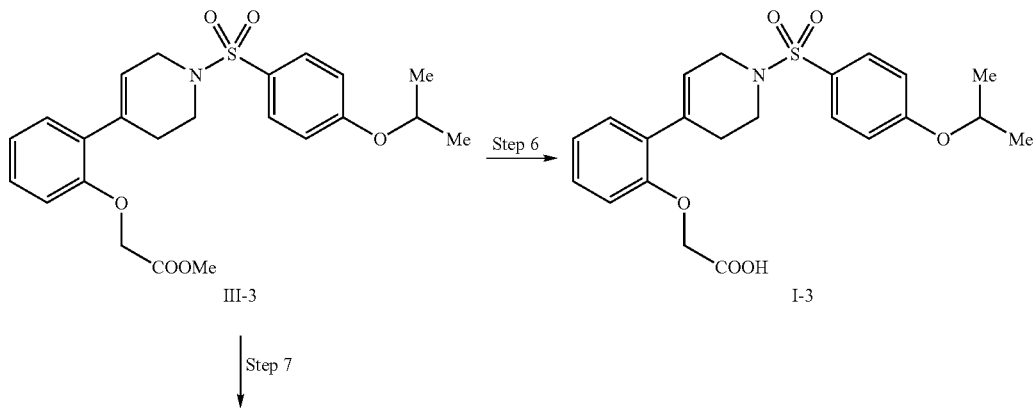

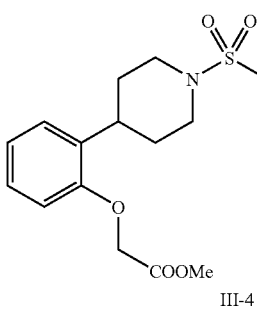

III-4

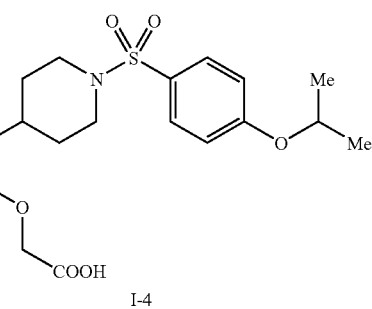

I-4

Step 1

Sodium hydride (5.6 mL, 40.0 mmol) was added to a solution of 2-bromophenol(18) (5.19 g, 30.0 mmol) in DMF (50 mL) at 0° C. and the mixture was stirred for 0.5 hours. Thereto was added chloromethyl methyl ether (3.4 mL, 45.0 mmol) dropwise at 0° C. and the mixture was stirred at room temperature for an hour. Water (300 mL) was added to the reaction solution and extracted with diethyl ether (300 mL). The extract was washed with water and saturated brine successively, dried and concentrated to give the compound (19) (6.6 g, 99% yield)

$^1$H-NMR (CDCl$_3$) δ ppm: 3.52 (s, 3H), 5.25 (s, 2H), 6.89 (m, 1H), 7.13-7.28 (m, 2H), 7.55 (m, 1H).

Step 2

A solution of the compound (19) (2.17 g, 10.0 mmol) in THF (125 mL) was cooled to −78° C., thereto was added a hexane solution of n-butyl lithium (7.5 mL, 12.0 mmol) dropwise during 10 minutes and the mixture was stirred at the same temperature for 30 minutes. The solution was warmed up to −50° C., a solution of 1-(tert-butoxycarbonyl)piperidone (3.79 g, 19.0 mmol) in THF (100 mL) was added dropwise at −50° C. and then the mixture was stirred at −20° C. for 30 minutes. A saturated aqueous solution of NH$_4$Cl (300 mL) was poured to the reaction solution and the mixture was extracted with diethyl ether (300 mL). The extract was washed with water and saturated brine successively, dried and concentrated. The resulting residue was purified by a silica gel column chromatography (hexane:ethyl acetate=2:1) to give the compound (20) (650 mg, 19% yield).

$^1$H-NMR (CDCl$_3$) δ ppm: 1.48 (s, 9H), 2.00 (m, 4H), 3.28 (m, 2H), 3.51 (s, 3H), 4.01 (m, 2H), 5.30 (s, 2H), 7.01 (m, 1H), 7.14-7.30 (m, 3H).

Step 3

Trifluoroacetic acid (3.0 mL) was added to a solution of the compound (20) (650 mg, 10.0 mmol) in dichloromethane (10 mL) cooled to 0° C., and the mixture was stirred at room temperature for 18 hours. The reaction solution was cooled to 0° C., adjusted to pH=7 by adding a saturated aqueous solution of sodium bicarbonate and extracted with ethyl acetate (100 mL). The extract was washed with water and saturated brine successively, dried and concentrated. The resulting residue[the compound (21)] was directly used in the next step.

Step 4

THF (7 mL) was added to the residue obtained in step 3, and 4-isopropoxybenzenesulfonyl chloride (435 mg, 1.85 mmol) and triethylamine (1.03 mL, 7.4 mmol) were added and stirred at room temperature for 2 hours. Diluted hydrochloric acid (200 mL) was added to the reaction solution and extracted with ethyl acetate (200 mL). The organic layer was washed with a saturated aqueous solution of sodium bicarbonate and saturated brine successively, dried and concentrated. The resulting residue was purified by a silica gel column chromatography (hexane:ethyl acetate=5:1) to give the compound (22) (150 mg, 21% yield/two steps).

$^1$H-NMR (CDCl$_3$) δ ppm: 1.37 (d, J=6.3 Hz, 6H), 2.33 (m, 2H), 3.35 (t, J=5.7 Hz, 2H), 3.77 (m, 2H), 4.64 (m, 1H), 5.79 (m, 1H), 6.83-7.00 (m, 5H), 7.14 (m, 1H), 7.73 (d, J=9.0 Hz, 2H).

Step 5

Methyl bromoacetate (29 μL, 0.31 mmol), potassium carbonate (70 mg, 0.51 mmol) and potassium iodide (4.2 mg, 0.025 mmol) were added to a solution of the compound (22) (95 mg, 0.25 mmol) in DMF (1 mL) and the mixture was stirred at room temperature for 2 hours. Water (200 mL) was added to the reaction solution and extracted with ethyl acetate (20 mL). The organic layer was washed with saturate brine, dried and concentrated. The residue was crystallized from hexane-ethyl acetate to give the compound III-3 (90.7 mg, 80% yield).

Step 6

The compound I-3 (25 mg, 0.06 mmol) was dissolved in MeOH (1.0 mL)-THF(1.0 mL). An 2M aqueous solution of sodium hydroxide (84 μL) was added and the solution was stirred at room temperature for 2 hours. The reaction solution was diluted with water, acidified by adding diluted hydrochloric acid and extracted with ethyl acetate. The extract was washed with water, dried and concentrated. The residue was crystallized from hexane-ethyl acetate to give the compound I-XX (15 mg, 62% yield).

$^1$H-NMR(DMSO-d6) δ ppm: 1.30 (d, J=4.5 Hz, 6H), 2.50 (brs, 2H), 3.14 (brs, 2H), 3.61 (brs, 2H), 4.63 (s, 2H), 4.74 (brs, 1H), 5.72 (s, 1H), 6.82-6.92 (m, 2H), 7.02-7.19 (m, 4H), 7.71 (d, J=7.5 Hz, 2H), 13.01 (brs, 1H).

Step 7

THF (1 mL) and MeOH (1 mL) were added to the compound III-3 (61.6 mg, 0.138 mmol) and then 10% palladium carbon (18 mg) was added, and the mixture was stirred under hydrogen atmosphere at room temperature for 1.5 hours. The reaction mixture was filtered through Celite and the filtrate was concentrated The residue was crystallized from hexane-ethyl acetate to give the compound III-4 (62 mg, 99% yield).

Step 8

The compound III-4 (62 mg, 0.138 mmol) was dissolved in MeOH (1.0 mL) and THF (1.0 mL). A 2M aqueous solution of sodium hydroxide (207 μL) was added and the solution was stirred at room temperature for 2 hours. The reaction solution was diluted with water, acidified by adding diluted hydrochloric acid and extracted with ethyl acetate. The extract was washed with water, dried and concentrated. The residue was crystallized from hexane-ethyl acetate to give the compound I-4 (20 mg, 33% yield).

$^1$H-NMR (DMSO-d6) δ ppm: 1.32 (d, J=6.0 Hz, 6H), 1.60-1.71 (m, 2H), 1.82 (d, J=11.7 Hz, 2H), 2.26 (t, J=10.5 Hz, 2H), 2.84 (t, J=11.7 Hz, 1H), 3.75 (d, J=11.4 Hz, 2H), 4.64 (s, 2H), 4.72-4.80 (m, 1H), 6.80 (d, J=8.4 Hz, 1H), 6.90 (t, J=7.2 Hz, 1H), 7.11-7.15 (m, 4H), 7.67 (d, J=8.7 Hz, 2H), 13.00 (brs, 1H).

Example 5

Preparation of the Compound II-13, III-13 and (26)

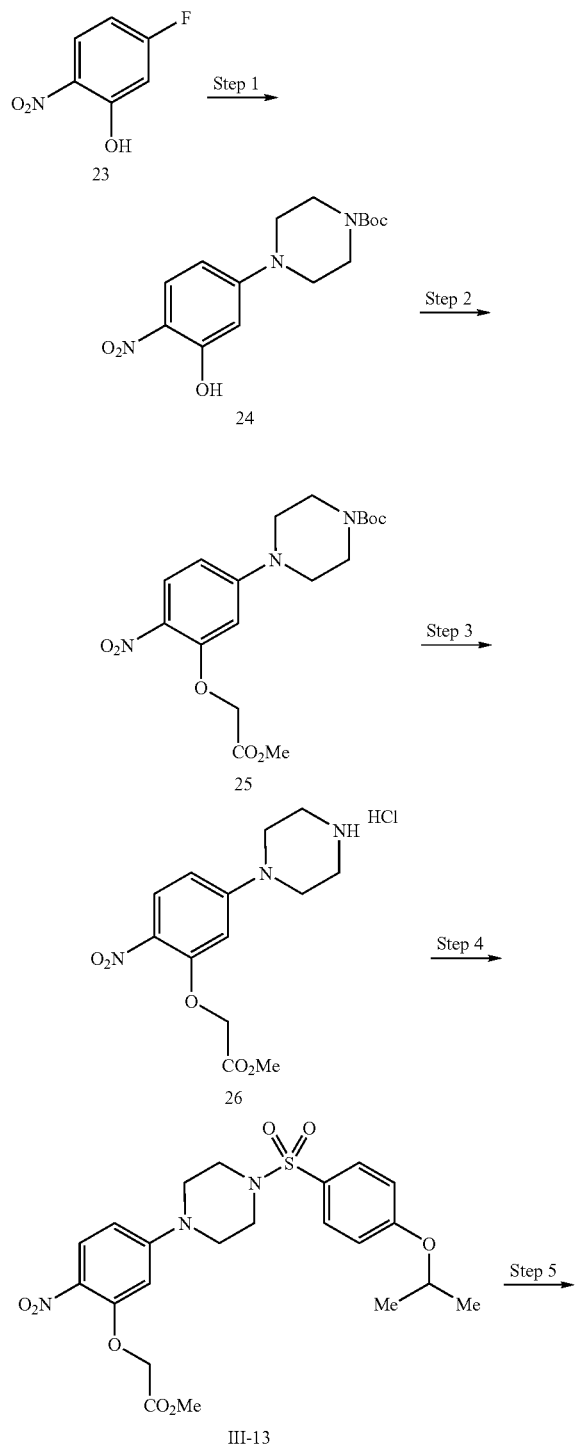

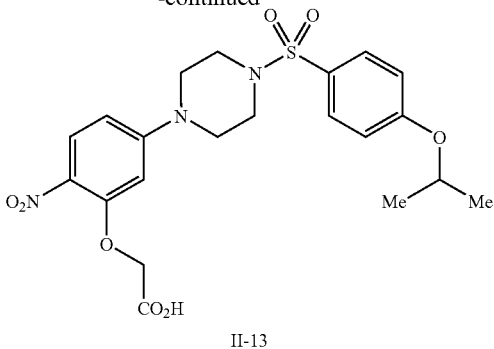

Step 1

1-(t-Butylcarbonyl)piperadine (46.6 g, 250 mmol) was added to the compound (23) (15.7 g, 100 mmol) and stirred at 80° C. for an hour. The reaction solution was poured into water and extracted with ethyl acetate. The organic layer was washed with 2N hydrochloric acid and water, and dried over anhydrous magnesium sulfate. The solvent was evaporated to give the product (24) (28.4 g, 88% yield) as a yellow powder.

Step 2

Potassium carbonate (5.53 g, 40.0 mmol), potassium iodide (0.33 g, 2.0 mmol) and methyl bromoacetate (2.8 mL, 30.0 mmol) were added to a solution of the compound (24) (6.47 g, 20.0 mmol) obtained in step 1 in DMF (60.0 mL) and stirred at room temperature for an hour. The reaction solution was poured into water and the precipitated crystalline was collected by filtration and washed with water. The obtained crude crystalline was washed with hexane to give the product (25) (9.9 g) as a yellow powder.

Step 3

4N Hydrochloric acid/dioxane (40.0 mL) was added to a solution of the compound (25) (9.9 g) obtained in step 2 in ethyl acetate (50.0 mL) and stirred at 50° C. for 0.5 hour. The reaction solution was filtered and the crude crystalline was washed with hexane and ethyl acetate to give the product (26) (6.38 g, 96% yield) as a yellow powder.

Step 4

A solution of the compound (26) (3.32 g, 10.0 mmol) obtained in step 3 in THF (10.0 mL) was cooled to 0° C., and triethylamine (4.2 mL, 30.0 mmol) and 4-isopropoxybenzenesulfonyl chloride (2.58 g, 11.0 mmol) were added thereto. After stirring at room temperature for 15 hours, the reaction solution was poured into water and extracted with ethyl acetate. The organic layer was washed with 2N hydrochloric acid, water and saturated brine successively, and dried over anhydrous magnesium sulfate. The solvent was evaporated in vacuo to give the product III-13 (4.17 g, 85% yield) as a yellow powder.

Step 5

A 2M aqueous solution of sodium hydroxide (0.60 mL, 1.2 mmol) was added to a solution of the compound III-13 (197 mg, 0.40 mmol) obtained in step 4 in MeOH (2.0 mL)-THF (2.0 mL) and stirred at room temperature for 2 hours. The reaction solution was poured into water and washed with ether. The aqueous layer was acidified by adding 2N hydrochloric acid, an extracted with ethyl acetate. The organic layer was washed with water, dried over anhydrous magnesium sulfate and concentrated in vacuo. The crude crystalline was re-crystallized from hexane-ethyl acetate to give the product II-13 (166 mg, 87% yield) as a yellow powder.

$^1$H-NMR (CDCl$_3$) δ ppm: 1.37 (d, 6H, J=6.3 Hz), 3.15 (brt, 4H, J=4.8 Hz), 3.50 (brt, 4H, J=4.2 Hz), 4.60-4.70 (m, 1H), 4.75 (s, 2H), 6.24, (s, 1H), 6.49 (dd, 1H, J=2.1, 9.3 Hz), 6.98 (d, 2H, J=9.0 Hz), 7.69 (d, 2H, J=8.7 Hz), 8.06 (d, 2H, J =9.6 Hz).

Example 6

Preparation of the Compound II-24 and III-24

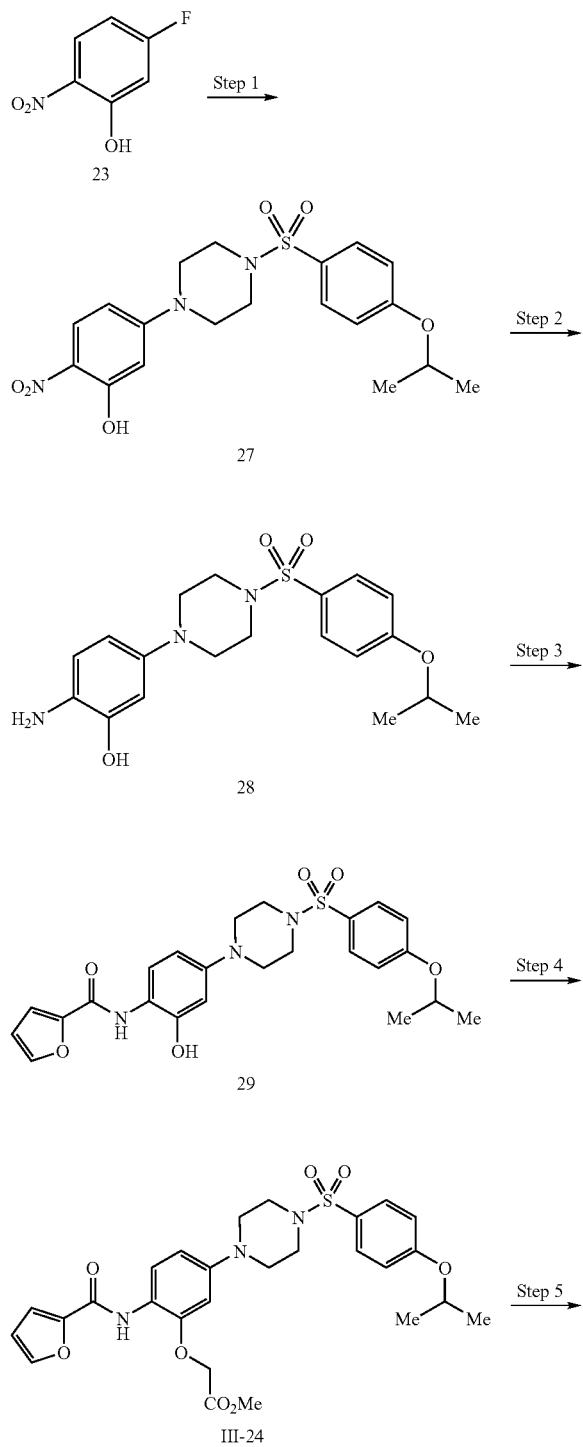

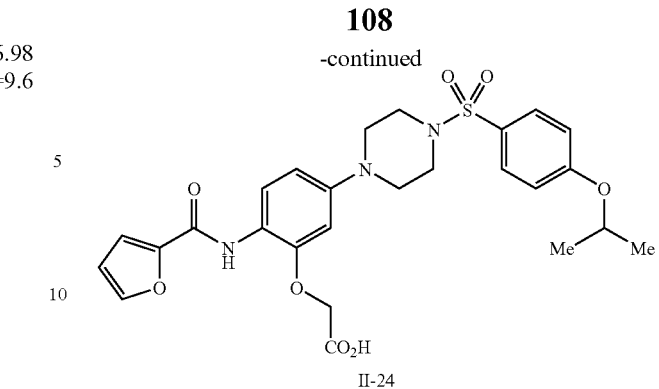

Step 1

Triethylamine (5.6 mL, 40.0 mmol) and p-isopropoxybenzenesulfonyl piperazine (8.53 g, 30.0 mmol) were added to a solution of the compound (23) (3.14 g, 20.0 mmol) in DMF (150 mL) and stirred at 80° C. for 4 hours. 2N Hydrochloric acid was added to the reaction solution at room temperature. The precipitated crystalline was collected by filtration and washed with water. The crude crystalline was washed with hexane to give the product (27) (9.06 g) as a yellow powder.

Step 2

10% Palladium-carbon (1.35 g) was added to a solution of the compound (27) (9.0 g) obtained in step 1 in MeOH (90.0 mL)-THF (90.0 mL) and hydrogenated at room temperature for 2 hours. The catalyst was filtered through Celite and the filtrate was concentrated in vacuo. The resulting crude crystalline was washed with ether to give the product (28) (5.00 g, 77% yield) as a purple powder.

Step 3

A solution of the compound (28) (1.17 g, 3.0 mmol) obtained in step 2 in pyridine (5.0 mL) was cooled to 0° C. and 2-furilic acid chloride (0.28 mL, 2.85 mmol) was added thereto. After stirring at room temperature for 18 hours, the reaction solution was poured into water and extracted with ethyl acetate. The organic layer was washed with a 0.5M citric acid solution and water, and dried over anhydrous magnesium sulfate. The solvent was evaporated in vacuo to give the product (29) (660 mg, 45% yield) as a purple powder.

Step 4

Potassium carbonate (370 mg, 2.68 mmol) and methyl bromoacetate (0.19 mL, 2.01 mmol) were added to a solution of the compound (29) (650 mg, 1.34 mmol) obtained in step 3 in DMF (5.0 mL) and stirred at room temperature for 2 hours. The reaction solution was poured into water and extracted with ethyl acetate. The organic layer was washed with a 0.5M citric acid solution and water, dried over anhydrous magnesium sulfate and concentrated in vacuo. The residue was purified by a silica gel column chromatography (chloroform:methanol=500:1) and the crude crystalline obtained was re-crystallized to give the compound III-24 (360 mg, 48% yield) as a pale purple powder.

Step 5

A 2M solution of sodium hydroxide (2.39 mL, 4.77 mmol) was added to a solution of the compound III-24 (350 mg, 1.59 mmol) obtained in step 4 in MeOH (3.5 mL)-THF (3.5 mL) and stirred at room temperature for 2 hours. The reaction solution was poured into water and washed with ether. 2N Hydrochloric acid was added to the aqueous layer and the precipitated crystalline was collected by filtration. The obtained crude crystalline was re-crystallized from MeOH and further re-crystallized from ethyl acetate to give the product II-24 (120 mg, 14% yield) as a pale green powder.

$^1$H-NMR (DMSO-d$_6$) δ ppm: 1.30 (d, J=6.0 Hz, 6H), 2.97 (brs, 4H), 3.20 (brs, 4H), 4.71-4.79 (m, 3H), 6.55 (dd, J=2.4, 8.7 Hz, 1H), 6.68-6.70 (m, 2H), 7.15 (d, J=8.7 Hz, 2H), 7.23 (dd, J=0.6, 2.2 Hz, 1H), 7.68 (d, J=9.0 Hz, 2H), 7.81 (d, J=8.7 Hz, 1H), 7.89-7.90 (m, 1H), 9.30 (s, 1H).

Example 7

Preparation of the Compound II-33 and III-33

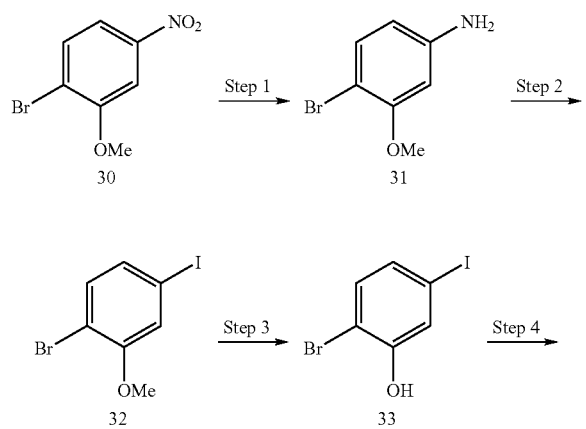

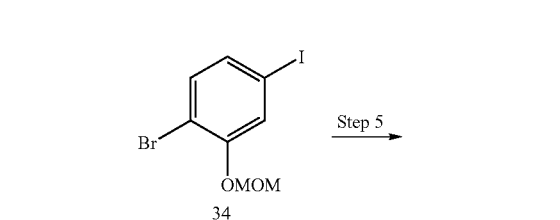

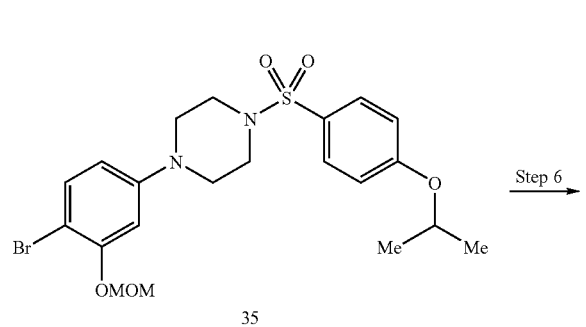

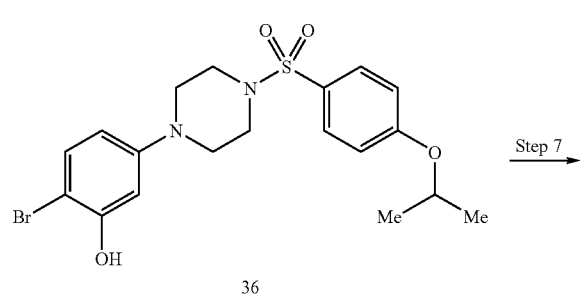

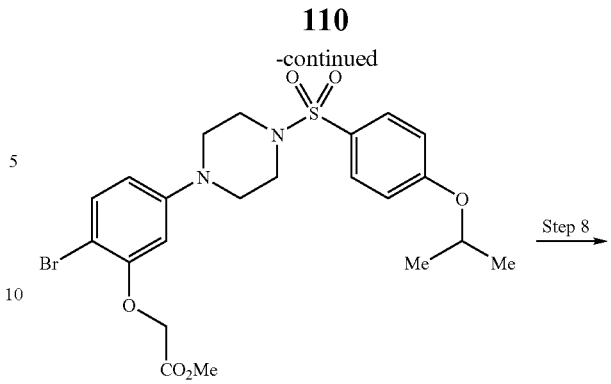

Step 1

Iron (5.59 g, 100 mmol), ammonium chloride (5.35 g, 100 mmol) and water (75.0 mL) were added to a solution of the compound (30) (11.6 g, 50.0 mmol) in MeOH (150 mL) and stirred at 100° C. for 6 hours. The reaction solution was filtered through Celite to remove iron and the filtrate was poured into water. The reaction solution was acidified by adding 2N hydrochloric acid and washed with ether. The reaction solution was made alkaline by adding a 2M solution of sodium hydroxide and extracted with ethyl acetate. The organic layer was dried over anhydrous magnesium sulfate and the solvent was evaporated in vacuo to give the product (31) (4.20 g, 42% yield) as a brown powder.

Step 2

Concentrated hydrochloric acid (32.0 mL) was added to the compound (31) (4.12 g, 20.4 mmol) obtained in step 1 and stirred at room temperature for 18 hours. The reaction solution was cooled to 0° C. and an aqueous solution (10.0 mL) of sodium nitrate (3.37 g, 48.8 mmol) was added dropwise during 20 minutes. Then, an aqueous solution (10.0 mL) of potassium iodide (9.96 g, 61.0 mmol) was added dropwise during 20 minutes. After stirring at 0° C. for an hour, the reaction solution was extracted with ether. The organic layer was washed with a saturated aqueous solution of sodium thiosulfate and water and dried over anhydrous magnesium sulfate. The solvent was evaporated in vacuo to give the product (32) (5.00 g, 65% yield).

Step 3

A solution of the compound (32) (5.00 g, 16.0 mmol) obtained in step 2 in dichloromethylane (10.0 mL) was cooled to 0° C. and a 1M solution of boron tribromide in dichloromethylane (32.0 mL) was added dropwise during 30 minutes. After stirring at 0° C. for an hour, it was stirred at room temperature for 3 hours. The reaction solution was poured into ice-water, concentrated hydrochloric acid was added and the mixture was stirred at room temperature for an hour. The mixture was extracted with ether and the organic layer was extracted with a 2M aqueous solution of sodium hydroxide.

The aqueous layer was acidified by adding 2N hydrochloric acid and extracted with ethyl acetate. The organic layer was washed with water and dried over anhydrous magnesium sulfate. The solvent was evaporated in vacuo to give the product (33) (4.30 g, 90% yield)

Step 4

Potassium carbonate (3.98, 28.8 mmol) and chloromethyl methyl ether (2.2 mL, 28.8 mmol) were added to a solution of the compound (33) (4.30 g, 14.4 mmol) obtained in step 3 in DMF (40.0 mL) and stirred at room temperature for 18 hours. The reaction solution was poured into water and extracted with ether. The organic layer was washed with water, dried over anhydrous magnesium sulfate and concentrated in vacuo. The residue was purified by a silica gel column chromatography (hexane) to give the product (34) (5.42 g, 99% yield).

Step 5 p-Isopropyloxybenzenesulfonyl piperazine (683 mg, 2.4 mmol), tris(dibenzylideneacetone)dipalladium (91.8 mg, 0.1 mmol), rac-2,2'-bis(diphenylphosphino)-1,1'-binaphthyl (249 mg, 0.4 mmol) and sodium t-butoxide (384 mg, 4.0 mmol) were added to a solution of the compound (34) (686 mg, 2.0 mmol) obtained in step 4 in toluene (3.4 mL) and stirred at 50° C. for 4 hours. The reaction solution was poured into water and extracted with ethyl acetate. The organic layer was washed with water, dried over anhydrous magnesium sulfate and concentrated in vacuo. The residue was purified by a silica gel column chromatography (ethyl acetate:hexane=2:1) and the crude crystalline was re-crystallized to give the product (35) (412 mg, 41% yield).

Step 6

2N Hydrochloric acid was added to a solution of the compound (35) (300 mg, 0.60 mmol) obtained in step 5 in MeOH (2.0 mL)-THF (2.0 mL) and stirred at room temperature for 18 hours. The reaction solution was poured into water and extracted with ethyl acetate. The organic layer was washed with water, and concentrated in vacuo. The resulting residue was dissolved in ether and extracted with a 2M aqueous solution of sodium hydroxide. The aqueous layer was acidified by adding 2N hydrochloric acid and extracted with ethyl acetate. The organic layer was dried over anhydrous magnesium sulfate, and the solvent was evaporated in vacuo to give the product (36) (179 mg, 66% yield) as a colorless powder.

Step 7

Potassium carbonate (103 mg, 0.75 mmol) and methyl bromoacetate (0.042 mL, 0.45 mmol) were added to a solution of the compound (36) (170 mg, 0.37 mmol) obtained in step 6 in DMF (2.0 mL) and stirred at room temperature for 18 hours. The reaction solution was poured into water and extracted with ethyl acetate. The organic layer was washed with 2N hydrochloric acid and water, and dried over anhydrous magnesium sulfate. The solvent was evaporated in vacuo to give the product III-33 (150 mg, 76% yield) as a colorless powder.

Step 8

A 2M aqueous solution of sodium hydroxide (0.43 mL, 0.85 mmol) was added to a solution of the compound III-33 (150 mg, 0.28 mmol) obtained in step 7 in MeOH (2.0 mL)-THF (2.0 mL) and stirred at room temperature for 3 hours. The reaction solution was poured into water and extracted with ether. The aqueous layer was acidified by adding 2N hydrochloric acid and extracted with ethyl acetate. The organic layer was washed with water, dried over anhydrous magnesium sulfate and concentrated in vacuo. The obtained crude crystalline was re-crystallized from ethyl acetate/hexane to give the product II-33 (142 mg, 97% yield) as a colorless powder.

$^1$H-NMR (DMSO-$d_6$) δ ppm: 1.30 (d, J=6.0 Hz, 6H), 2.95 (brs, 4H), 3.02 (brs, 4H), 4.71-4.79 (m, 3H), 6.42 (dd, J=2.4, 9.0 Hz, 1H), 6.54 (d, J=2.4 Hz, 1H), 7.13 (d, J=9.0 Hz, 2H), 7.32 (d, J=8.7 Hz, 1H), 7.66 (d, J=8.7 Hz, 2H).

Example 8

Preparation of the Compound II-54 and III-54

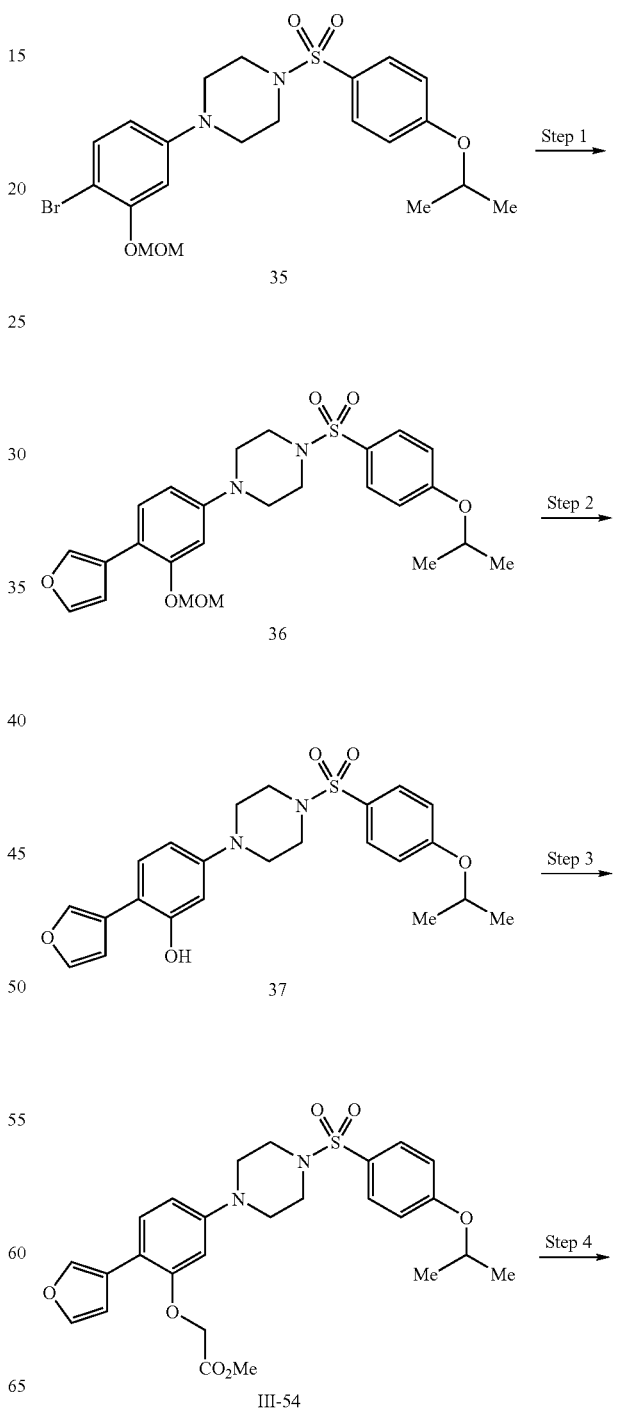

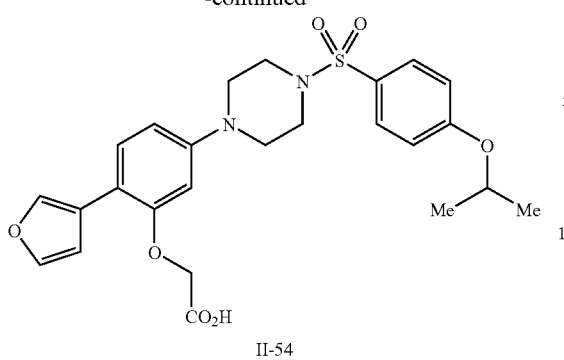

II-54

Step 1

A solution of the compound (35) (350 mg, 0.70 mmol), 3-furyl boric acid (94.1 mg, 0.84 mmol), palladium acetate (7.9 mg, 0.035 mmol), triphenylphosphine (36.8 mg, 0.14 mmol) and a 2M aqueous solution of potassium carbonate (2.1 mL) in DMF (6.3 mL) were stirred at 80° C. for 4 hours. The reaction solution was poured into water and extracted with ethyl acetate. The aqueous layer was washed with a 0.5M aqueous solution of citric acid and water, dried over anhydrous magnesium sulfate and concentrated in vacuo. The residue was purified by a silica gel column chromatography (ethyl acetate:hexane=3:1) to give the product (37) (266 mg, 78% yield) as a yellow powder.

Step 2

6N Hydrochloric acid (0.35 mL) was added to a solution of the compound (37) (200 mg, 0.41 mmol) obtained in step 1 in MeOH(3.0 mL)-THF(3.0 mL) and stirred at room temperature for 6 hours. The reaction solution was poured into water and extracted with ethyl acetate. The organic layer was washed with water and dried over anhydrous magnesium sulfate. The solvent was evaporated in vacuo to give the product (38) (151 mg, 67% yield) as a gray powder.

Step 3

Potassium carbonate (87.3 g, 0.63 mmol) and methyl bromoacetate (0.036 mL, 0.38 mmol) were added to a solution of the compound (38) (140 mg, 0.32 mmol) obtained in step 2 in DMF (2.0 mL) and stirred at room temperature for 18 hours. The reaction solution was poured into water and extracted with ethyl acetate. The organic layer was washed with 2N hydrochloric acid and water, and dried over anhydrous magnesium sulfate. The solvent was evaporated in vacuo to give the product III-54 (110 mg, 68% yield) as a colorless powder.

Step 4

A 2M solution of sodium hydroxide (0.29 mL, 0.58 mmol) was added to a solution of the compound III-54 (100 mg, 0.19 mmol) obtained in step 3 in MeOH (2.0 mL)-THF (2.0 mL) and stirred at room temperature for 2 hours. The reaction solution was poured into water and extracted with ether. The aqueous layer was acidified by adding 2N hydrochloric acid and extracted with ethyl acetate. The organic layer was washed with water, dried over anhydrous magnesium sulfate and concentrated in vacuo. The obtained crude crystalline was re-crystallized from ethyl acetate/hexane to give the compound II-54 (85 mg, 88% yield) as a colorless powder.

$^1$H-NMR (DMSO-$d_6$) δ ppm: 1.29 (d, J=6.0 Hz, 6H), 2.97 (brs, 4H), 3.26 (brs, 4H), 4.79-4.70 (m, 3H), 6.52 (d, J=9.0 Hz, 1H), 6.55 (s, 1H), 6.97 (s, 1H), 7.14 (d, J=9.0 Hz, 2H), 7.44 (d, J=9.0 Hz, 1H), 7.66 (s, 1H), 7.67 (d, J=9.0 Hz, 2H), 8.36 (s, 1H).

Example 9

Preparation of the Compound II-63 and III-63

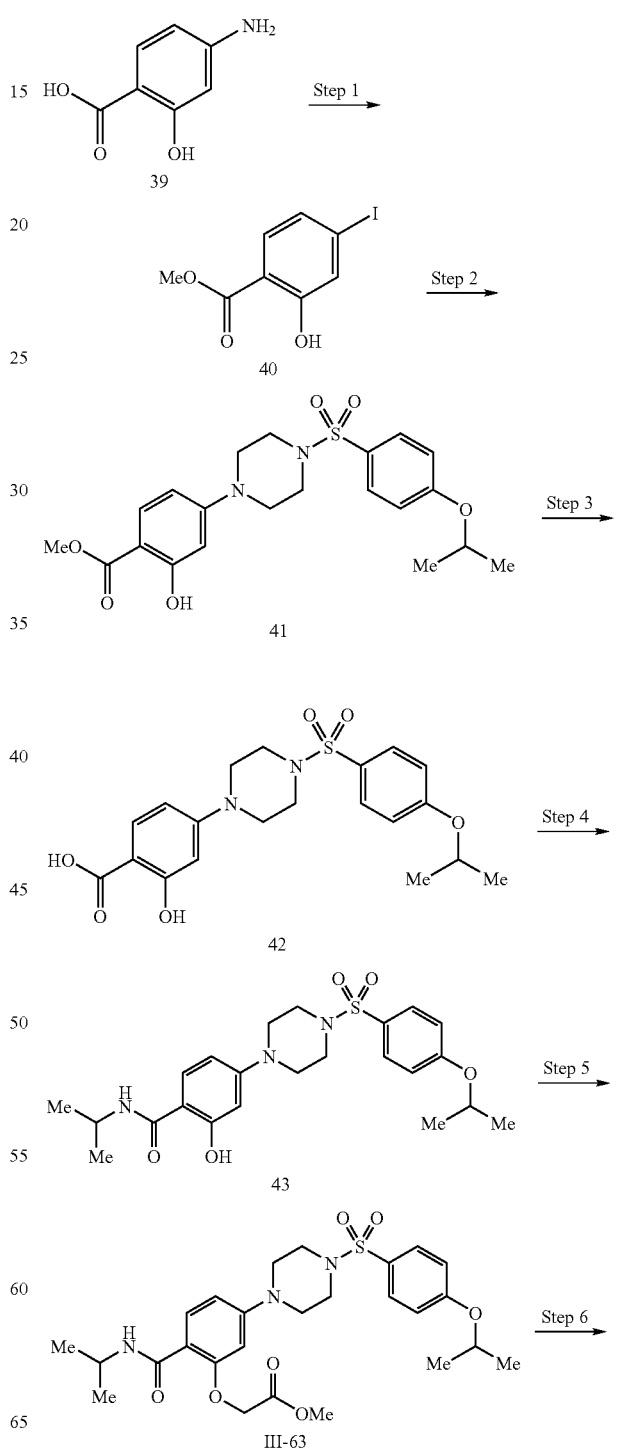

-continued

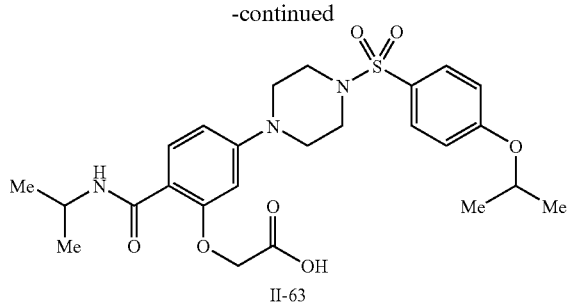

II-63

Step 1

A solution of the compound (39) (5.0 g, 32.6 mmol) in 15% sulfuric acid (45 mL) was stirred at 5° C. A solution of sodium nitrate (2.25 g, 32.6 mmol) in water (10 mL) and a solution of potassium iodide (8.13 g) in 1N sulfuric acid (20 mL) were added to the reaction solution. After stirring at 5° C. for 10 minutes, the reaction solution was further stirred at 90° C. for 30 minutes. After being cooled to room temperature, the precipitated solid was collected by filtration and dried. The obtained solid was dissolved in THF (20 mL)-MeOH (20 mL) and thereto was added a 2M solution of TMSCH$_2$N$_2$ in hexane (40 mL) and stirred for 2 hours. The reaction solution was concentrated in vacuo, the resulting residue was purified by a silica gel column chromatography (ethyl acetate/hexane=1/10), and the obtained crude product was re-crystallized from hexane to give the product (40) (3.95 g, 44% yield) as a white powder.

Step 2

A solution of the compound (40) (1.8 g, 6.48 mmol) obtained in step 1, the compound (13) (2.03 g, 7.12 mmol) obtained in step 2 of Example 3, palladium acetate (58 mg, 0.26 mmol), rac-2,2'-bis(diphenylphosohino)-1,1'-binaphthyl(242 mg, 0.39 mmol) and cesium carbonate (2.95 g, 9.07 mmol) in toluene (20 mL) was stirred at 100° C. under nitrogen atmosphere for 12 hours. After being cooled to room temperature, the reaction solution was extracted with chloroform. The organic layer was washed with water and 2N hydrochloric acid, and concentrated in vacuo. The residue was crystallized from ethanol-chloroform to give the product (41) (1.35 g, 48% yield).

Step 3

A solution of the compound (41) (380 mg, 0.875 mmol) obtained in step 2, potassium t-butoxide (980 mg, 8.75 mmol) and water (63 μL, 3.5 mmol) in THF (5 mL) was stirred at room temperature for 1.5 hours. The reaction solution was extracted with ethyl acetate and the organic layer was washed with water, 2N hydrochloric acid and saturated brine. The solvent was evaporated in vacuo and the residue was crystallized from ethyl acetate-hexane to give the product (42) (353 mg, 96% yield).

Step 4

A solution of the compound (42) (250 mg, 0.59 mmol) obtained in step 3, WSCD HCl (137 mg, 0.71 mmol), HOBt (97 mg, mmol), isopropylamine (61 μL, 0.71 mmol) in DMF (2 mL) was stirred at room temperature for 2 hours. The reaction solution was extracted with ethyl acetate and the organic layer was washed with water and 2N hydrochloric acid. The solvent was evaporated in vacuo and the residue was purified by a silica gel column chromatography (ethyl acetate/hexane=1/4) to give the product (43) (177 mg, 64% yield).

Step 5

A solution of the compound (43) (170 mg, 0.37 mmol) obtained in step 4, cesium carbonate (180 mg, 0.55 mmol) and methyl bromoacetate (0.052 mL, 0.55 mmol) in DMF (2 mL) was stirred at room temperature for 3 hours. The reaction solution was extracted with ethyl acetate and the organic layer was washed with water, 2N hydrochloric acid and saturated brine. The solvent was evaporated in vacuo and the residue was purified by a silica gel column chromatography (ethyl acetate/hexane=1/1) to give the product III-63 (195 mg, quant.)

Step 6

A solution of the compound III-63 (190 mg, 0.36 mmol) obtained in step 5 and a 4N aqueous solution of sodium hydroxide (220 μL, 0.89 mmol) in THF (1 mL)-MeOH (1 mL) was stirred overnight. 2N Hydrochloric acid was added to the reaction solution and extracted with ethyl acetate. The organic layer was washed with water and saturated brine. The solvent was evaporated in vacuo to give the product III-63 (165 mg, 89% yield).

$^1$H-NMR (CDCl$_3$) δ ppm: 1.24 (d, 6H, J=6.3 Hz), 1.37 (d, 6H, J=6.0 Hz), 3.14 (t, 4H), 3.35 (t, 4H), 4.65 (m, 1H), 4.71 (s, 2H), 6.29 (d, 1H, J=2.4 Hz), 6.53 (dd, 1H, J=8.7 Hz, 2.1 Hz), 6.97 (d, 2H, J=3.0 Hz)), 7.66-7.72 (m, 3H), 7.84 (d, 1H, J=8.7 Hz).

Example 10

Preparation of the Compound II-74 and III-74

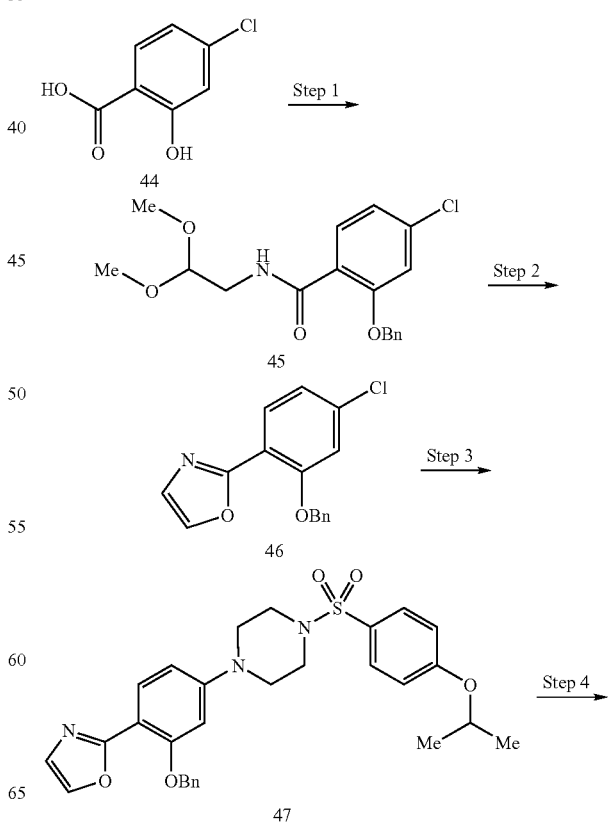

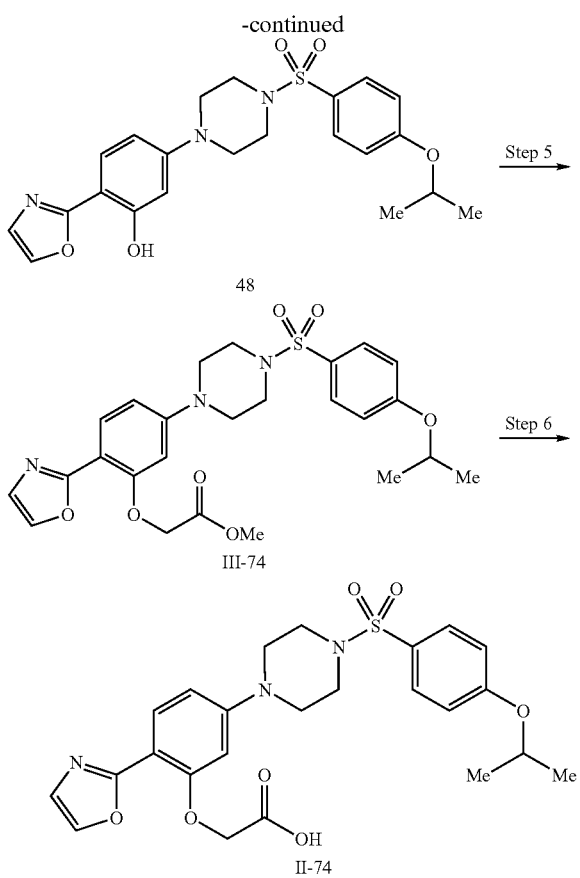

Step 1

A solution of the compound (44) (15.0 g, 86.92 mmol), WSCD HCl (20.0 g, 104.32 mmol), HOBt (11.70 g, 86.57 mmol), 2,2'-dimethyloxyethylamine (13.70 g, 130.30 mmol) in THF (75 mL) was stirred for 2 hours. Water was added to the reaction solution and the reaction solution was extracted with ethyl acetate. The organic layer was washed with saturated brine and the solvent was evaporated in vacuo. A solution of the resulting solid, potassium carbonate (18.0 g, 130.23 mmol) and benzyl bromide (19.20 g, 112.25 mmol) in DMF (50 mL)-ethyl acetate (50 mL) was stirred at 60° C. for 2 hours. Water was added to the reaction solution and the reaction solution was extracted with ethyl acetate. The organic layer was washed with saturated brine and the solvent was evaporated in vacuo. The obtained crystalline was washed with 10% ethyl acetate-hexane to give the product (45) (23.40 g, 76% yiled).

Step 2

2N Hydrochloric acid (15 mL) was added to a solution of the compound (45) (5.0 g, 14.29 mmol) obtained in step 1 in TH (20 mL) and stirred at 70° C. for 2 hours. After being cooled to room temperature, the reaction mixture was extracted with ethyl acetate, the organic layer was washed with saturated brine and the solvent was evaporated in vacuo. Acetonitrile (15 mL) was added to the resulting residue and the solution was used in the next step.

A solution of triphenylphosphine (7.45 g, 28.40 mmol) and hexachloroethane (6.72 g, 28.40 mmol) in acetonitrile was stirred for 30 minutes, the solution of the obtained residue in acetonitrile (15 mL) and pyridine (4.6 mL, 56.80 mmol) were added thereto and the mixture was stirred at room temperature for 30 minutes. Further, it was stirred at 60° C. for a hour. Water was added to the reaction solution and the reaction solution was extracted with ethyl acetate. The organic layer was washed with water and 10% aqueous solution of citric acid, and the solvent was evaporated in vacuo. The residue was purified by a silica gel column chromatography (ethyl acetate/hexane=1/4) to give the product (46) (3.35 g, 83% yield).

Step 3

A solution of the compound (46) (200 mg, 0.70 mmol) obtained in step 2, the compound (13) (239 mg, 0.84 mmol) obtained in step 2 of Example 3, lead tetraacetate (3.1 mg, 0.014 mmol), butyldiadamantylphosphine (10.0 mg, 0.028 mmol) and sodium t-butoxide (94.2 mg, 0.98 mmol) in toluene (2 mL) was stirred at 110° C. under nitrogen atmosphere for 15 hours. After being cooled to room temperature, the reaction solution was extracted with chloroform, citric acid (147 mg, 0.70 mmol) was added to the organic layer and the organic layer was washed with water and saturated brine. The solvent was evaporated in vacuo and crystallized from ethyl acetate-hexane to give the product (47) (331 mg, 89% yield).

Step 4

A solution of the compound (47) (100 mg, 0.187 mmol) obtained in step 3 and 10% palladium carbon (30 mg) in THF (15 mL)-MeOH (15 mL) was stirred under hydrogen atmosphere for 2 hours. After filtration, the filtrate was concentrated in vacuo to give the product (48) (81.3 mg, 98% yield) as a white solid.

Step 5

A solution of the compound (48) (200 mg, 0.45 mmol) obtained in step 4, potassium carbonate (93 mg, 0.67 mmol), potassium iodide (15 mmol) and methyl bromoacetate (0.064 mL, 0.68 mmol) in DMF (1.6 mL) was stirred at 90° C. for an hour. After being cooled to 0° C., 2N hydrochloric acid (0.23 mL), MeOH (5.0 mL) and water (5.0 mL) were added. The obtained crystalline was collected by filtration to give the product III-74 (212 mg, 91% yield) as a white crystalline.

Step 6

A solution of the compound III-74 (65 mg, 0.126 mmol) obtained in step 5 and 4N aqueous solution of sodium hydroxide (80 μL, 0.315 mmol) in DMF (1 mL) was stirred overnight. After 2N hydrochloric acid (315 μL) was added to the reaction solution and stirred, water (20. mL) was added to the reaction mixture and stirred at 0° C. for 30 minutes. The precipitated crystalline was collected by filtration to give the product II-74 (50.6 mg, 80% yield) as a white crystalline.

$^1$H-NMR (CDCl$_3$) δ ppm: 1.37 (d, 6H, J=6.0 Hz), 3.16 (t, 4H), 3.42 (t, 4H), 4.63 (m, 1H), 4.77 (s, 2H), 6.40 (d, 1H, J=2.7 Hz), 6.62 (dd, 1H, J=9.0 Hz, 2.4 Hz), 6.98 (d, 2H, J=3.0 Hz), 7.27 (d, 1H), 7.67-7.72 (m, 3H), 7.79 (d, 1H, J=3.0 Hz).

Example 11

Preparation of the Compound II-96 and III-96

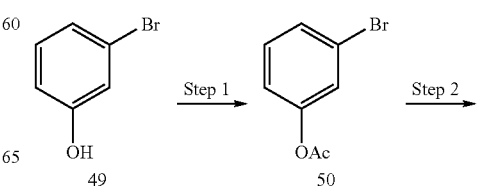

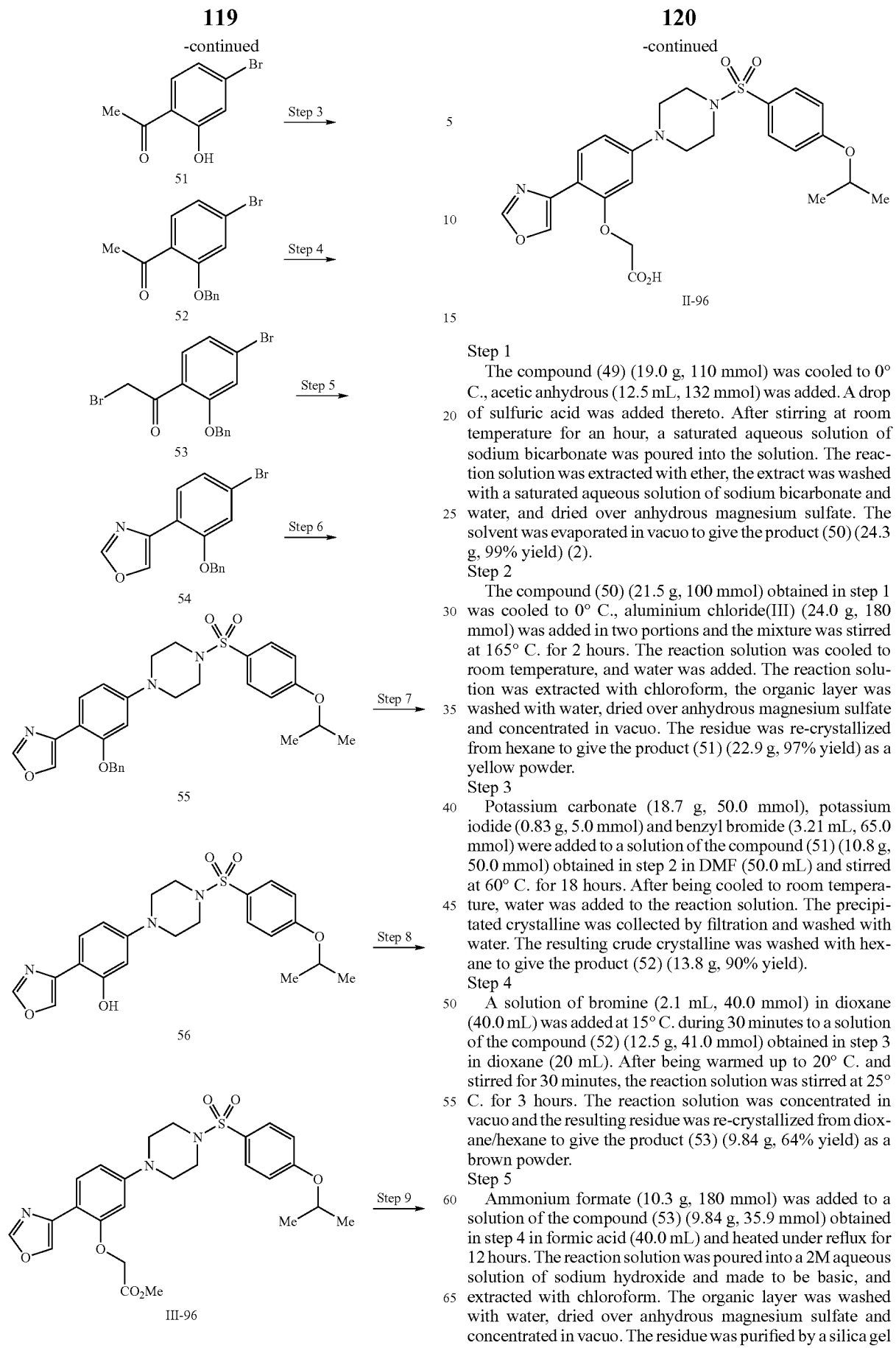

Step 1

The compound (49) (19.0 g, 110 mmol) was cooled to 0° C., acetic anhydrous (12.5 mL, 132 mmol) was added. A drop of sulfuric acid was added thereto. After stirring at room temperature for an hour, a saturated aqueous solution of sodium bicarbonate was poured into the solution. The reaction solution was extracted with ether, the extract was washed with a saturated aqueous solution of sodium bicarbonate and water, and dried over anhydrous magnesium sulfate. The solvent was evaporated in vacuo to give the product (50) (24.3 g, 99% yield) (2).

Step 2

The compound (50) (21.5 g, 100 mmol) obtained in step 1 was cooled to 0° C., aluminium chloride(III) (24.0 g, 180 mmol) was added in two portions and the mixture was stirred at 165° C. for 2 hours. The reaction solution was cooled to room temperature, and water was added. The reaction solution was extracted with chloroform, the organic layer was washed with water, dried over anhydrous magnesium sulfate and concentrated in vacuo. The residue was re-crystallized from hexane to give the product (51) (22.9 g, 97% yield) as a yellow powder.

Step 3

Potassium carbonate (18.7 g, 50.0 mmol), potassium iodide (0.83 g, 5.0 mmol) and benzyl bromide (3.21 mL, 65.0 mmol) were added to a solution of the compound (51) (10.8 g, 50.0 mmol) obtained in step 2 in DMF (50.0 mL) and stirred at 60° C. for 18 hours. After being cooled to room temperature, water was added to the reaction solution. The precipitated crystalline was collected by filtration and washed with water. The resulting crude crystalline was washed with hexane to give the product (52) (13.8 g, 90% yield).

Step 4

A solution of bromine (2.1 mL, 40.0 mmol) in dioxane (40.0 mL) was added at 15° C. during 30 minutes to a solution of the compound (52) (12.5 g, 41.0 mmol) obtained in step 3 in dioxane (20 mL). After being warmed up to 20° C. and stirred for 30 minutes, the reaction solution was stirred at 25° C. for 3 hours. The reaction solution was concentrated in vacuo and the resulting residue was re-crystallized from dioxane/hexane to give the product (53) (9.84 g, 64% yield) as a brown powder.

Step 5

Ammonium formate (10.3 g, 180 mmol) was added to a solution of the compound (53) (9.84 g, 35.9 mmol) obtained in step 4 in formic acid (40.0 mL) and heated under reflux for 12 hours. The reaction solution was poured into a 2M aqueous solution of sodium hydroxide and made to be basic, and extracted with chloroform. The organic layer was washed with water, dried over anhydrous magnesium sulfate and concentrated in vacuo. The residue was purified by a silica gel column chromatography (ethyl acetate/hexane=10/1) to give the product (54) (1.19 g, 10% yield) as a yellow powder.

Step 6 p-Isopropyloxybenzenesulfonylpiperazine (1.23 g, 4.33 mmol), tris(dibenzylideneacetone)dipalladium (152 mg, 0.17 mmol), rac-2,2'-bis(diphenylphosohino)-1,1'-binaphthyl (414 mg, 0.67 mmol) and sodium t-butoxide (640 mg, 6.66 mmol) were added to a solution of the compound (54) (1.10 g, 3.33 mmol) obtained in step 5 in toluene (3.4 mL) and stirred at 100° C. for 12 hours. Water was added to the reaction solution and extracted with ethyl acetate. The organic layer was filtered through Celite, washed with 2N hydrochloric acid and water, dried over anhydrous magnesium sulfate and concentrated in vacuo. The residue was purified by a silica gel column chromatography (ethyl acetate/hexane=2/1) to give the product (55) (450 mg, 25% yield) as a yellow powder.

Step 7

10% Palladium carbon (20 mg) was added to a solution of the compound (55) (200 mg, 0.38 mmol) obtained in step 6 in THF (2.0 mL) and hydrogenated. After stirring at room temperature for 2 hours, the mixture was filtered through Celite and the filtrate was concentrated in vacuo. The residue was dissolved in MeOH (2.0 mL), 20% palladium hydroxide carbon (20 mg) was added and the mixture was hydrogenated. After stirring at room temperature for 3 hours, 2N hydrochloric acid (0.20 mL) was added and further hydrogenated. After stirring at room temperature for 9 hours, the reaction solution was filtered through Celite. The solvent of the filtrate was evaporated in vacuo to give the product (56) (135 mg, 81% yield) as a yellow powder.

Step 8

Potassium carbonate (81.0 g, 0.59 mmol) and methyl bromoacetate (0.097 mL, 0.35 mmol) were added to a solution of the compound (56) (130 mg, 0.29 mmol) obtained in step 7 in DMF (2.0 mL) and stirred at room temperature for 2 hours. The reaction solution was poured into water, the precipitated crystalline was collected by filtration and washed with water. The obtained crude product was washed with hexane to give the product III-96 (75% yield) as a colorless powder.

Step 9

A 2M aqueous solution of sodium hydroxide (0.33 mL, 0.66 mmol) was added to a solution of the compound (9), III-96 (114 mg, 0.22 mmol) obtained in step 8 in MeOH (2.0 mL)-THF (2.0 mL) and stirred at room temperature for 2 hours. The reaction solution was poured into water and extracted with ether. The organic layer was washed with water, dried over anhydrous magnesium sulfate and concentrated in vacuo. The resulting crude crystalline was re-crystallized from ethyl acetate-hexane to give the product III-96 (15 mg, 14%) as a colorless powder.

$^1$H-NMR(DMSO-d6) δ ppm:1.29 (d, J=6.0 Hz, 6H), 2.96 (brs, 4H), 3.26 (brs, 4H), 4.30 (s, 2H), 4.69-4.77 (m, 1H), 6.50 (s, 1H), 6.53 (d, J=9.0 Hz 1H), 7.12 (d, J=8.7 Hz, 2H), 7.65 (d, J=9.0 Hz, 2H), 7.78 (d, J=8.7 Hz, 1H), 8.31 (s, 1H), 9.13 (s, 1H).

The compounds I-2, I-5 to I-31, II-1 to II-5, II-7 to II-8, II-10 to II-12, II-14 to II-23, II-25 to II-32, II-34 to II-53, II-55 to II-62, II-64 to II-73, II-75 to II-95, II-99 to II-103, II-105 to II-106, II-108 to II-118, II-122 to II-123, II-127 to II-131, II-133 to II-135, and II-140 to II-143 were prepared in the same manner as set forth above. The structures and physical properties thereof were shown in Tables 1-41.

TABLE 1

| Comd. No. | $R^{2A}$ | $R^{2B}$ | $R^{2C}$ | $R^{2D}$ | $R^{2E}$ |
|---|---|---|---|---|---|
| I-1 | CH=CH-COOH | H | Me | H | H |
| I-2 | CH2-CH2-COOH | H | Me | H | H |
| I-5 | CH=CH-COOH | H | OMe | H | H |
| I-6 | CH=CH-COOH | H | Cl | H | H |
| I-7 | CH=CH-COOH | H | H | H | H |
| I-8 | CH=CH-COOH | OMe | H | H | H |
| I-9 | CH2-CH2-COOH | H | OMe | H | H |
| I-10 | CH2-CH2-COOH | H | Cl | H | H |
| I-11 | CH2-CH2-COOH | H | H | H | H |
| I-12 | CH2-CH2-COOH | OMe | H | H | H |

TABLE 1-continued

[Structure: piperidine N-sulfonyl-(4-isopropoxyphenyl), piperidine 4-O-linked to phenyl ring with substituents R2A, R2B, R2C, R2D, R2E]

| Comd. No. | R2A | R2B | R2C | R2D | R2E |
|---|---|---|---|---|---|
| I-17 | -CH=CH-COOH (trans) | H | F | H | H |
| I-18 | -CH2CH2CH2-COOH | H | F | H | H |

TABLE 2

[Structure: piperidine N-sulfonyl-(4-isopropoxyphenyl), piperidine 4-O-linked to phenyl ring with substituents R2A, R2B, R2C, R2D, R2E]

| Comd. No. | R2A | R2B | R2C | R2D | R2E |
|---|---|---|---|---|---|
| I-19 | -CH=CH-COOH (trans) | H | H | OMe | H |
| I-20 | -CH2CH2CH2-COOH | H | H | OMe | H |
| I-21 | -CH=CH-COOH (trans) | H | H | H | OMe |
| I-22 | -CH2CH2CH2-COOH | H | H | H | OMe |
| I-25 | H | -CH=CH-COOH (trans) | H | H | H |

TABLE 2-continued

[Structure: piperidine N-sulfonyl-(4-isopropoxyphenyl), with 4-O-aryl bearing R2A-R2E substituents]

| Comd. No. | R2A | R2B | R2C | R2D | R2E |
|---|---|---|---|---|---|
| I-26 | H | ⁓(CH2)2COOH | H | H | H |
| I-27 | ⁓CH=CHCOOH | H | Cl | H | Cl |
| I-28 | ⁓(CH2)2COOH | H | Cl | H | Cl |

TABLE 3

[Structure: 4-aryl-4-hydroxypiperidine N-sulfonyl-(4-isopropoxyphenyl)]

| Comd. No. | R2A | R2B | R2C | R2D | R2E |
|---|---|---|---|---|---|
| I-29 | H | ⁓OCH2COOH | Cl | H | H |

TABLE 4
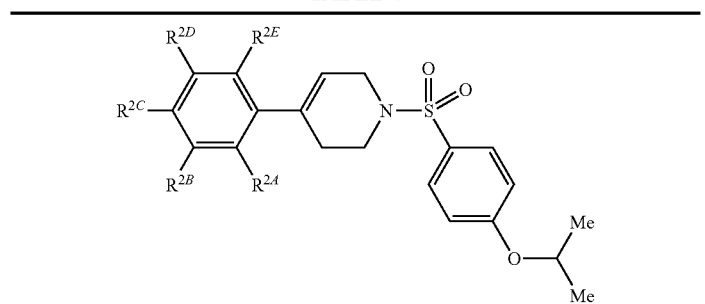
| Comd. No. | $R^{2A}$ | $R^{2B}$ | $R^{2C}$ | $R^{2D}$ | $R^{2E}$ |
|---|---|---|---|---|---|
| I-3 | ⸺O–CH₂–COOH | H | H | H | H |
| I-30 | H | ⸺O–CH₂–COOH | Cl | H | H |
TABLE 5
| Comd. No. | $R^{2A}$ | $R^{2B}$ | $R^{2C}$ | $R^{2D}$ | $R^{2E}$ |
|---|---|---|---|---|---|
| I-4 | ⸺O–CH₂–COOH | H | H | H | H |
| I-31 | H | ⸺O–CH₂–COOH | Cl | H | H |

TABLE 6
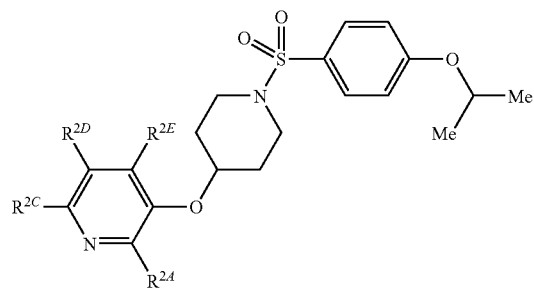
| Comd. No. | R²ᴬ | R²ᶜ | R²ᴰ | R²ᴱ |
|---|---|---|---|---|
| I-13 | 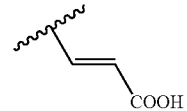 [SMILES: */C=C/C(=O)O] | H | H | H |
| I-14 | 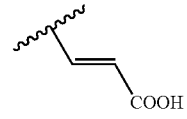 [SMILES: */C=C/C(=O)O] | Me | H | H |
| I-15 | 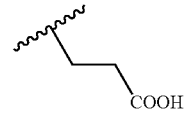 | H | H | H |
| I-16 | 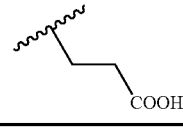 | Me | H | H |
TABLE 7
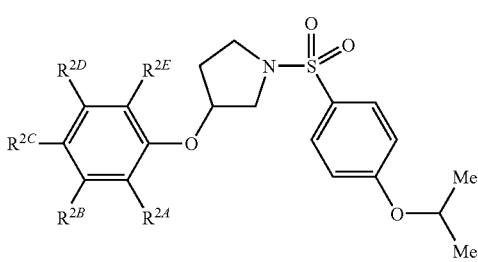
| Comd. No. | R²ᴬ | R²ᴮ | R²ᶜ | R²ᴰ | R²ᴱ |
|---|---|---|---|---|---|
| I-23 | 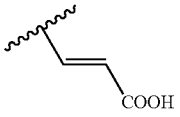 [SMILES: */C=C/C(=O)O] | H | H | H | H |
| I-24 | 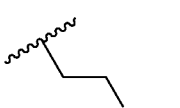 | H | H | H | H |
TABLE 8
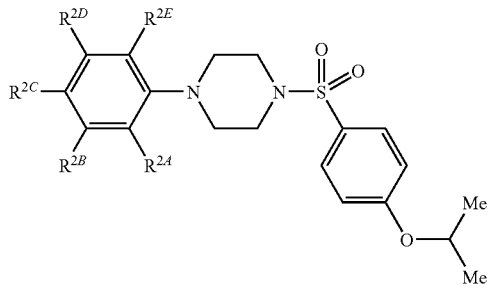
| Comd. No. | R²ᴬ | R²ᴮ | R²ᶜ | R²ᴰ | R²ᴱ |
|---|---|---|---|---|---|
| II-1 | 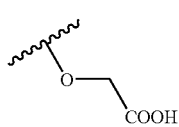 [SMILES: *OCC(=O)O] | H | H | H | H |
| II-3 | H | 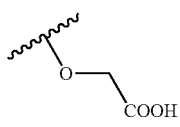 [SMILES: *OCC(=O)O] | H | H | H |

TABLE 8-continued
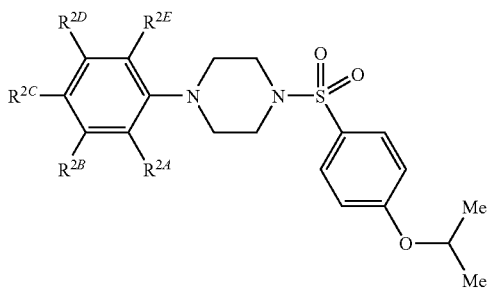
| Comd. No. | $R^{2A}$ | $R^{2B}$ | $R^{2C}$ | $R^{2D}$ | $R^{2E}$ |
|---|---|---|---|---|---|
| II-4 | H | H | —O—CH$_2$—COOH | H | H |
| II-7 | —O—CH$_2$—COOH | H | F | H | H |
| II-8 | H | —O—CH$_2$—COOH | Me | H | H |
| II-9 | H | —O—CH$_2$—COOH | OMe | H | H |
| II-10 | H | —O—CH$_2$—COOH | Cl | H | H |
| II-13 | H | —O—CH$_2$—COOH | NO$_2$ | H | H |
| II-15 | H | —CH(COOH)— | Cl | H | H |
| II-16 | H | —O—CH$_2$—COOH | F | F | H |
| II-17 | H | —O—CH$_2$—COOH | H | Br | H |
| II-18 | H | —CH=CH—COOH | Cl | H | H |

TABLE 8-continued
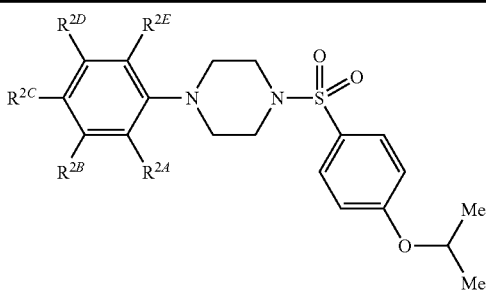
| Comd. No. | $R^{2A}$ | $R^{2B}$ | $R^{2C}$ | $R^{2D}$ | $R^{2E}$ |
|---|---|---|---|---|---|
| II-19 | H | ⁓O-CH₂-COOH | H | CF₃ | H |
TABLE 9
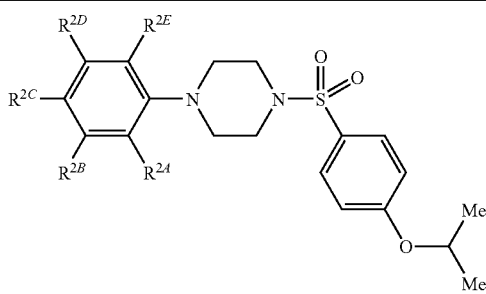
| Comd. No. | $R^{2A}$ | $R^{2B}$ | $R^{2C}$ | $R^{2D}$ | $R^{2E}$ |
|---|---|---|---|---|---|
| II-20 | H | ⁓CH₂-COOH | Cl | H | H |
| II-21 | H | ⁓CH₂CH₂-COOH | Cl | H | H |
| II-22 | H | ⁓CH₂CH₂-COOH | H | H | H |
| II-23 | H | ⁓O-CH(COOH)-CH₂-NH-C(O)Me | H | H | H |
| II-24 | H | ⁓O-CH(COOH)-CH₂-NH-C(O)-(2-furyl) | H | H | H |

TABLE 9-continued
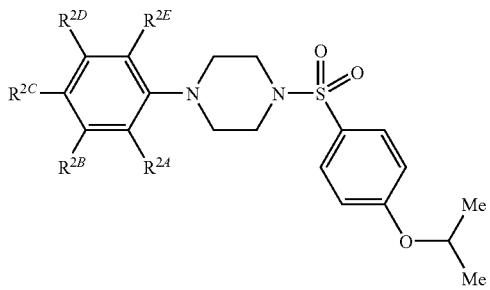
| Comd. No. | $R^{2A}$ | $R^{2B}$ | $R^{2C}$ | $R^{2D}$ | $R^{2E}$ |
|---|---|---|---|---|---|
| II-25 | H | 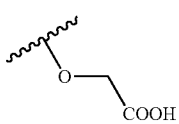 [SMILES: *OCC(=O)O] | H | F | H |
| II-26 | H | 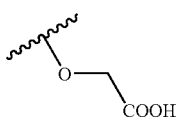 | H | Cl | H |
| II-28 | H | 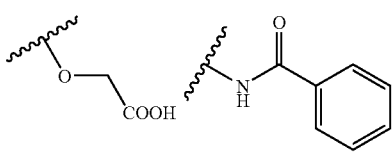 |  | H | H |
| II-32 | H | 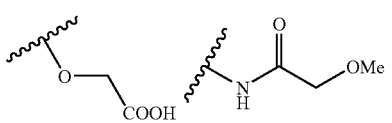 |  | H | H |
| II-33 | H | 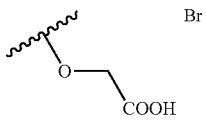 | Br | H | H |
| II-37 | H |  | H |  | H |
| II-38 | H |  | H |  | H |

TABLE 10
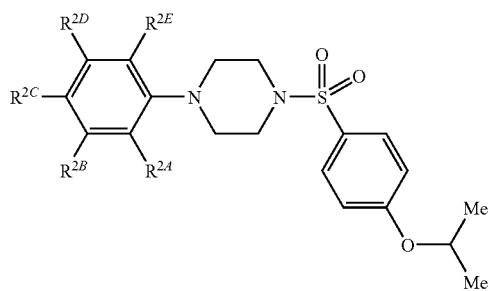
| Comd. No. | R²ᴬ | R²ᴮ | R²ᶜ | R²ᴰ | R²ᴱ |
|---|---|---|---|---|---|
| II-39 | H | ~O-CH₂-COOH | H | 4-pyridyl | H |
| II-40 | H | ~O-CH₂-COOH | H | 3-pyridyl | H |
| II-41 | H | ~O-CH₂-COOH | H | Me | H |
| II-45 | ~O-CH₂-COOH | H | H | Cl | H |
| II-46 | H | ~O-CH₂-COOH | 1,3,4-oxadiazol-2-yl | H | H |
| II-47 | H | ~O-CH₂-COOH | ~NHC(O)-(pyridin-2-yl) | H | H |
| II-48 | H | ~O-CH₂-COOH | ~NHC(O)-(pyridin-3-yl) | H | H |
| II-49 | H | ~O-CH₂-COOH | ~NHC(O)-(pyridin-4-yl) | H | H |

TABLE 10-continued

[Structure: R2A-R2E substituted phenyl-piperazine-sulfonyl-phenyl-O-CH(Me)2]

| Comd. No. | R2A | R2B | R2C | R2D | R2E |
|---|---|---|---|---|---|
| II-50 | H | ⁓(CH2)3-OH | Cl | H | H |
| II-51 | H | ⁓O-CH2-COOH | H | ⁓(2-thienyl) | H |

TABLE 11

[Structure: R2A-R2E substituted phenyl-piperazine-sulfonyl-phenyl-O-CH(Me)2]

| Comd. No. | R2A | R2B | R2C | R2D | R2E |
|---|---|---|---|---|---|
| II-52 | H | ⁓O-CH2-COOH | Cl | H | H |
| II-53 | H | ⁓O-CH2-COOH | ⁓phenyl | H | H |
| II-54 | H | ⁓O-CH2-COOH | ⁓(3-furyl) | H | H |
| II-56 | H | ⁓(CH2)2-OH | Cl | H | H |

TABLE 11-continued
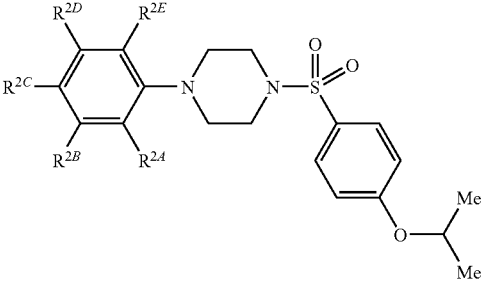
| Comd. No. | $R^{2A}$ | $R^{2B}$ | $R^{2C}$ | $R^{2D}$ | $R^{2E}$ |
|---|---|---|---|---|---|
| II-57 | H | 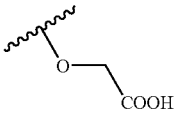 | H | 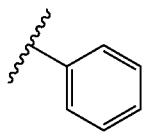 | H |
| II-58 | H | 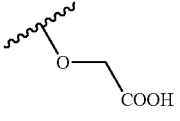 [SMILES: *OCC(=O)O] | 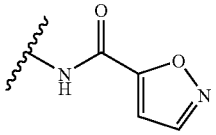 [SMILES: *NC(=O)c1ccno1] | H | H |
| II-59 | H | 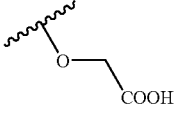 [SMILES: *OCC(=O)O] | 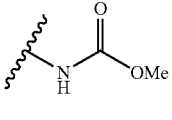 | H | H |
| II-60 | H | 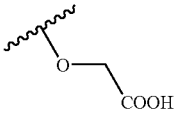 | 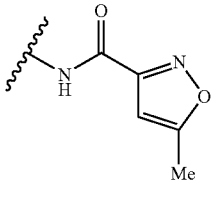 [SMILES: *NC(=O)c1cc(C)on1] | H | H |
| II-61 | H | 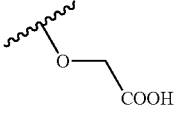 | 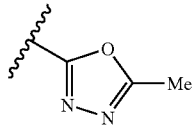 [SMILES: *c1nnc(C)o1] | H | H |
| II-62 | H | 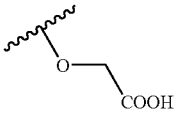 [SMILES: *OCC(=O)O] | 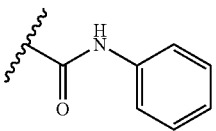 [SMILES: *C(=O)Nc1ccccc1] | H | H |
| II-63 | H | 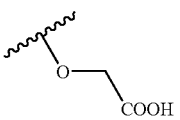 | 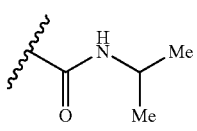 [SMILES: *C(=O)NC(C)C] | H | H |

TABLE 12

[Core structure: 4-substituted phenyl-piperazine-sulfonyl-(4-isopropoxyphenyl), with substituents $R^{2A}$, $R^{2B}$, $R^{2C}$, $R^{2D}$, $R^{2E}$ on the left phenyl ring]

| Comd. No. | $R^{2A}$ | $R^{2B}$ | $R^{2C}$ | $R^{2D}$ | $R^{2E}$ |
|---|---|---|---|---|---|
| II-64 | H | -OCH₂COOH | H | -C(O)NH-CH(Me)₂ | H |
| II-65 | H | -OCH₂COOH | furan-2-yl | H | H |
| II-66 | H | -OCH₂COOH | H | 1,3,4-oxadiazol-2-yl | H |
| II-67 | H | -OCH₂COOH | -NHC(O)O-CH(Me)₂ | H | H |
| II-68 | H | -OCH₂COOH | -NHC(O)NH-CH(Me)₂ | H | H |
| II-69 | H | -OCH₂COOH | H | H | Cl |
| II-70 | H | -OCH₂COOH | -O-CH(Me)₂ | H | H |
| II-71 | H | -OCH₂COOH | -O-CH₂-Ph | H | H |
| II-72 | H | -OCH₂COOH | -N(Me)C(O)-(furan-2-yl) | H | H |

TABLE 12-continued

[Structure: R²D, R²E, R²C, R²B, R²A substituted phenyl-piperazine-sulfonyl-phenyl-O-CH(Me)₂]

| Comd. No. | R²ᴬ | R²ᴮ | R²ᶜ | R²ᴰ | R²ᴱ |
|---|---|---|---|---|---|
| II-73 | H | ⁓O-CH₂-COOH | 5-methyl-oxazol-2-yl | | |
| II-74 | H | ⁓O-CH₂-COOH | oxazol-2-yl | | |
| II-75 | H | ⁓O-CH₂-COOH | 5-methyl-1,3,4-thiadiazol-2-yl | | |

TABLE 13

[Structure: R²D, R²E, R²C, R²B, R²A substituted phenyl-piperazine-sulfonyl-phenyl-O-CH(Me)₂]

| Comd. No. | R²ᴬ | R²ᴮ | R²ᶜ | R²ᴰ | R²ᴱ |
|---|---|---|---|---|---|
| II-76 | H | ⁓O-CH₂-COOH | OH | H | H |
| II-77 | H | ⁓O-CH₂-COOH | ⁓O-CH₂-(furan-3-yl) | H | H |

TABLE 13-continued
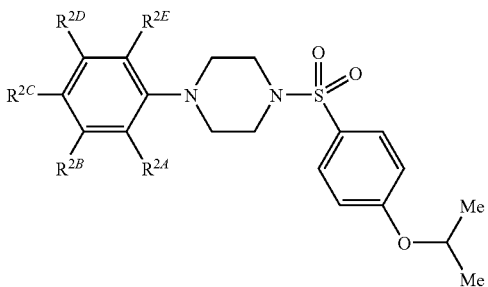
| Comd. No. | R2A | R2B | R2C | R2D | R2E |
|---|---|---|---|---|---|
| II-78 | H | ⟿O-CH2-COOH | ⟿O-CH2-CH(Me)-Me (isobutoxy) | H | H |
| II-79 | H | ⟿O-CH2-COOH | ⟿O-phenyl | H | H |
| II-80 | H | ⟿O-CH2-COOH | CN | H | H |
| II-81 | H | ⟿O-CH2-COOH | ⟿C(=O)NH2 | H | H |
| II-82 | H | ⟿O-CH2-COOH | ⟿C(=O)NHMe | H | H |
| II-83 | H | ⟿O-CH2-COOH | ⟿C(=O)NH-CH2-CH2-Me | H | H |
| II-84 | H | ⟿O-CH2-COOH | ⟿-oxazole | H | H |
| II-86 | H | ⟿CH=CH-COOH | OH | H | H |
| II-87 | H | ⟿CH=CH-COOH | ⟿O-CH2-phenyl | H | H |

TABLE 13-continued
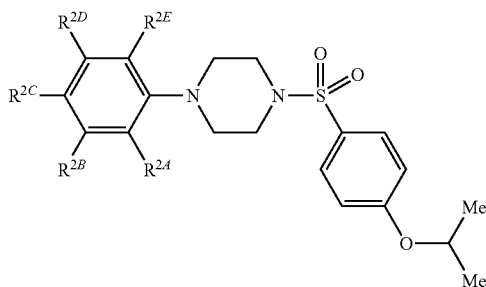
| Comd. No. | R²ᴬ | R²ᴮ | R²ᶜ | R²ᴰ | R²ᴱ |
|---|---|---|---|---|---|
| II-88 | H | ⁓O-CH₂-COOH | ⁓(1,3,4-thiadiazol-2-yl) | H | H |
TABLE 14
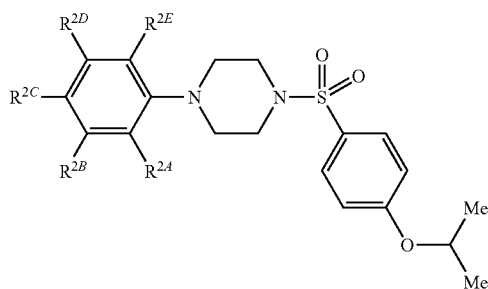
| Comd. No. | R²ᴬ | R²ᴮ | R²ᶜ | R²ᴰ | R²ᴱ |
|---|---|---|---|---|---|
| II-89 | H | ⁓O-CH₂-COOH | ⁓C(O)NH-cyclopropyl | H | H |
| II-91 | H | ⁓O-CH₂-COOH | ⁓C(O)Me | H | H |
| II-92 | H | ⁓O-CH₂-COOH | ⁓(thiazol-2-yl) | H | H |
| II-93 | H | ⁓O-CH₂-COOH | ⁓S(O)₂Me | H | H |
| II-95 | H | ⁓O-CH₂-COOH | ⁓(1H-pyrazol-1-yl) | H | H |

TABLE 14-continued

| Comd. No. | R²ᴬ | R²ᴮ | R²ᶜ | R²ᴰ | R²ᴱ |
|---|---|---|---|---|---|
| II-96 | H | —O—CH₂—COOH | oxazol-4-yl | H | H |
| II-99 | H | —O—CH₂—COOH | —C(O)NH—CH₂-(thiophen-2-yl) | H | H |
| II-100 | H | —O—CH₂—COOH | —C(O)NH—CH₂-(pyridin-2-yl) | H | H |
| II-101 | H | —O—CH₂—COOH | —C(O)NH-(1H-benzimidazol-2-yl) | H | H |

TABLE 15

| Comd. No. | R²ᴬ | R²ᴮ | R²ᶜ | R²ᴰ | R²ᴱ |
|---|---|---|---|---|---|
| II-102 | —O—CH₂—COOH | H | oxazol-2-yl | H | H |

TABLE 15-continued
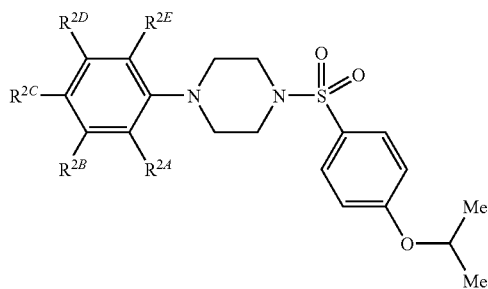
| Comd. No. | R2A | R2B | R2C | R2D | R2E |
|---|---|---|---|---|---|
| II-105 | H | 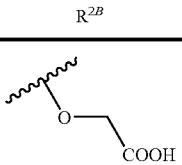 | 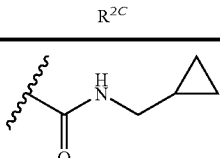 | H | H |
| II-106 | H | 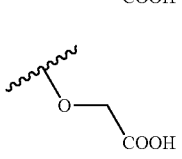 | 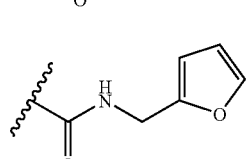 | H | H |
| II-108 | H | 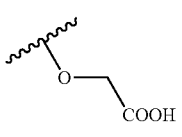 | 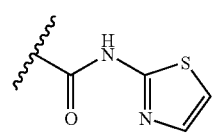 [SMILES: *C(=O)Nc1nccs1] | H | H |
| II-109 | H | 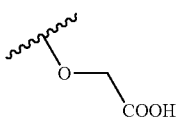 | 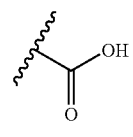 [SMILES: *C(=O)O] | H | H |
| II-110 | H | 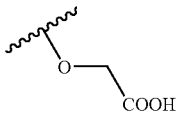 | 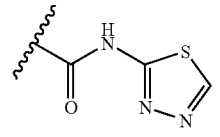 [SMILES: *C(=O)Nc1nncs1] | H | H |
| II-111 | H | 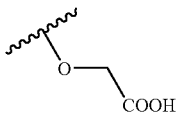 | 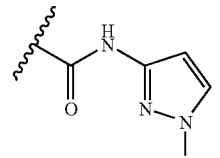 | H | H |
| II-112 | H | 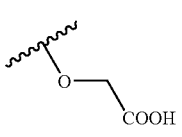 | 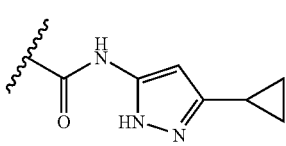 [SMILES: *C(=O)Nc1cc(C2CC2)n[nH]1] | H | H |
| II-113 | H | 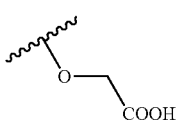 [SMILES: *OCC(=O)O] | 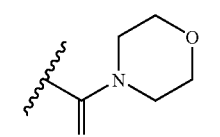 | H | H |

TABLE 16

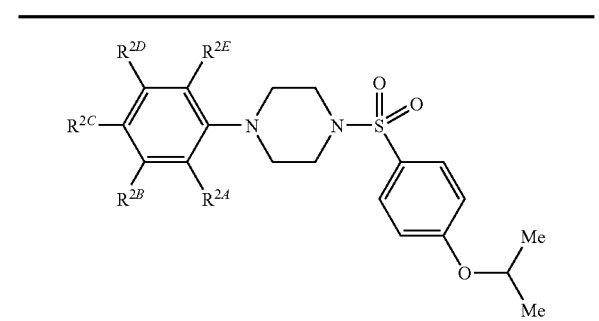

| Comd. No. | R2A | R2B | R2C | R2D | R2E |
|---|---|---|---|---|---|
| II-114 | H | ⁓O-CH2-COOH | ⁓C(=O)-N(pyrrolidine) | H | H |
| II-115 | H | ⁓O-CH2-COOH | ⁓C(=O)-NMe2 | H | H |
| II-118 | H | ⁓O-CH2-COOH | ⁓C(=O)-Ph | H | H |
| II-122 | H | ⁓O-CH2-COOH | ⁓CH2-Ph | H | H |
| II-123 | H | ⁓O-CH2-COOH | ⁓C(=O)-(2-thienyl) | H | H |
| II-127 | H | ⁓O-CH2-COOH | ⁓NHSO2Ph | H | H |
| II-129 | H | ⁓O-CH2-COOH | ⁓C(=O)-(2-furyl) | H | H |

TABLE 17

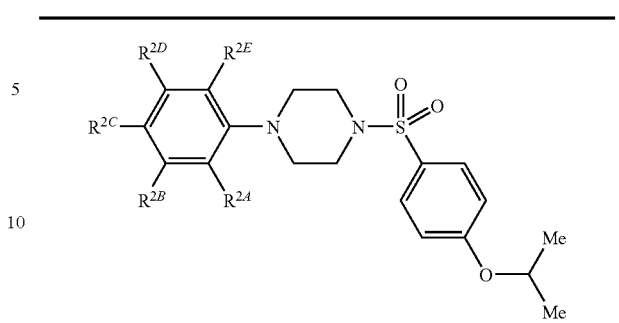

| Comd. No. | R2A | R2B | R2C | R2D | R2E |
|---|---|---|---|---|---|
| II-133 | H | ⁓O-CH2-COOH | ⁓NHSO2Me | H | H |
| II-135 | H | ⁓NH-CH2-COOH | ⁓NO2 | H | H |
| II-140 | H | ⁓NH-CH2-COOH | ⁓(2-oxazolyl) | H | H |
| II-141 | H | ⁓O-CH2-COOH | ⁓SO2-N(morpholine) | H | H |
| II-143 | H | ⁓O-CH2-COOH | ⁓CH2NMe2 | H | H |

TABLE 18
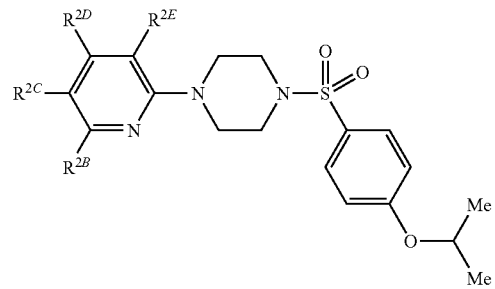
| Comd. No. | R²ᴮ | R²ᶜ | R²ᴰ | R²ᴱ |
|---|---|---|---|---|
| II-11 | ~O-CH₂-COOH | H | H | H |
| II-12 | H | H | ~O-CH₂-COOH | H |
| II-90 | ~O-CH₂-COOH | Br | H | H |
TABLE 19
(structure as shown with R²ᴬ, R²ᶜ, R²ᴰ, R²ᴱ on pyridine)
| Comd. No. | R²ᴬ | R²ᶜ | R²ᴰ | R²ᴱ |
|---|---|---|---|---|
| II-6 | ~O-CH₂-COOH | H | H | H |
| II-42 | H | H | ~O-CH₂-COOH | H |
TABLE 20
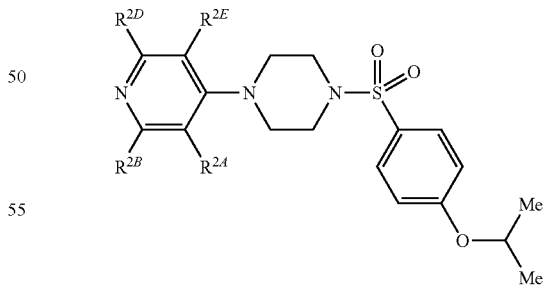
| Comd. No. | R²ᴬ | R²ᴮ | R²ᴰ | R²ᴱ |
|---|---|---|---|---|
| II-14 | H | ~O-CH₂-COOH | H | H |

TABLE 21
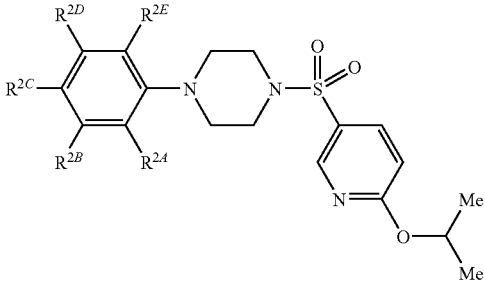
| Comd. No. | R²ᴬ | R²ᴮ | R²ᶜ | R²ᴰ | R²ᴱ |
|---|---|---|---|---|---|
| II-2 | ⌇O−CH₂−COOH | H | H | H | H |
| II-27 | H | ⌇O−CH₂−COOH | Cl | H | H |
| II-55 | H | ⌇O−CH₂−COOH | F | F | H |
| II-85 | H | ⌇O−CH₂−COOH | ⌇-oxazol-5-yl | H | H |
| II-94 | H | ⌇O−CH₂−COOH | ⌇-oxazol-2-yl | H | H |
TABLE 22
| Comd. No. | Structure |
|---|---|
| II-5 | 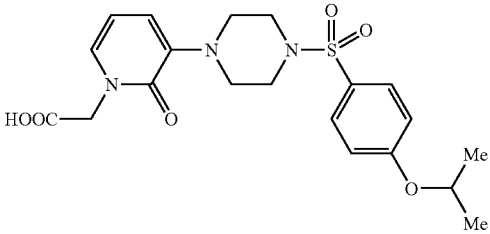 [SMILES: CC(C)Oc1ccc(S(=O)(=O)N2CCN(c3cccn(CC(=O)O)c3=O)CC2)cc1] |
TABLE 22-continued
| Comd. No. | Structure |
|---|---|
| II-29 | 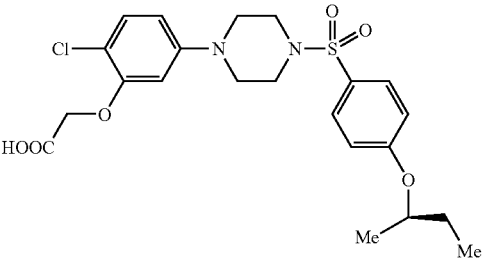 [SMILES: CC[C@@H](C)Oc1ccc(S(=O)(=O)N2CCN(c3ccc(Cl)c(OCC(=O)O)c3)CC2)cc1] |

TABLE 22-continued

| Comd. No. | Structure |
|---|---|
| II-30 | (structure) |
| II-31 | (structure) |
| II-34 | (structure) |
| II-35 | (structure) |
| II-36 | (structure) |

TABLE 23

| Comd. No. | Structure |
|---|---|
| II-43 | (structure) |
| II-44 | (structure) |
| II-103 | (structure) |
| II-116 | (structure) |
| II-117 | (structure) |

TABLE 24

| Comd. No. | Structure |
|---|---|
| II-128 | (structure) |

TABLE 24-continued

| Comd. No. | Structure |
|---|---|
| II-130 | 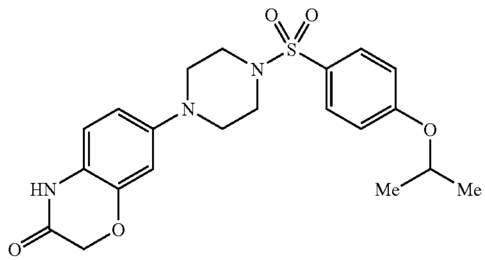 [SMILES: CC(C)Oc1ccc(S(=O)(=O)N2CCN(c3ccc4c(c3)OCC(=O)N4)CC2)cc1] |
| II-131 | 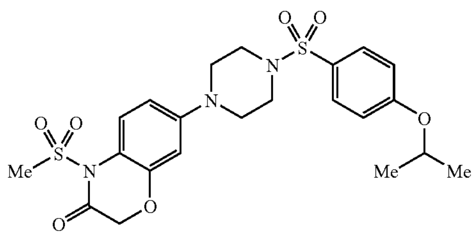 [SMILES: CC(C)Oc1ccc(S(=O)(=O)N2CCN(c3ccc4c(c3)OCC(=O)N4S(C)(=O)=O)CC2)cc1] |
| II-134 | 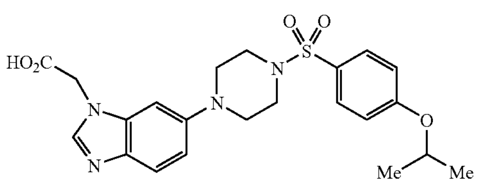 [SMILES: CC(C)Oc1ccc(S(=O)(=O)N2CCN(c3ccc4ncn(CC(=O)O)c4c3)CC2)cc1] |

TABLE 25

| Comd. No. | Structure |
|---|---|
| II-138 | 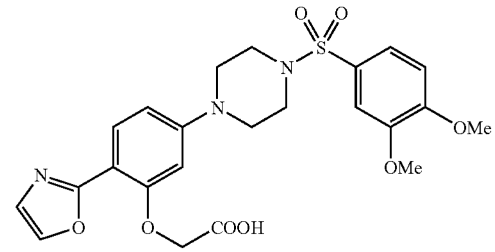 [SMILES: COc1ccc(S(=O)(=O)N2CCN(c3ccc(-c4ncco4)c(OCC(=O)O)c3)CC2)cc1OC] |
| II-139 | 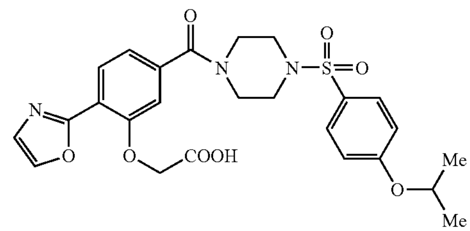 [SMILES: CC(C)Oc1ccc(S(=O)(=O)N2CCN(C(=O)c3ccc(-c4ncco4)c(OCC(=O)O)c3)CC2)cc1] |
| II-142 | 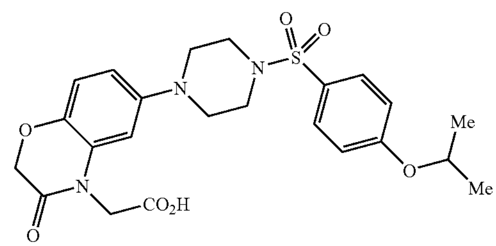 [SMILES: CC(C)Oc1ccc(S(=O)(=O)N2CCN(c3ccc4c(c3)N(CC(=O)O)C(=O)CO4)CC2)cc1] |

TABLE 26

| Comd. No. | $^1$H-NMR(Solvent)δ |
|---|---|
| I-1 | (CDCl3) 1.35 (d, 6H, J = 9.0 Hz), 2.01 (m, 4H), 2.28 (s, 3H), 3.15 (m, 4H), 4.62 (m, 1H), 6.38 (d, J = 16.2 Hz, 1H), 6.74 (d, J = 8.4 Hz, 1H), 6.96 (d, J = 9.0 Hz, 2H), 7.11 (dd, J = 1.8, 8.4 Hz, 1H), 7.31 (d, J = 1.8 Hz, 1H), 7.68 (d, J = 9.0 Hz, 2H), 7.89 (d, J = 16.2 Hz, 1H) |
| I-2 | (CDCl3) 1.35 (d, 6H, J = 9.0 Hz), 1.98 (m, 4H), 2.28 (s, 3H), 2.28 (m, 2H), 2.70 (m, 2H), 3.15 (m, 4H), 4.62 (m, 1H), 6.74 (d, J = 9.0 Hz, 1H), 6.94 (m, 4H), 7.68 (d, J = 9.0 Hz, 2H) |
| I-3 | (DMSO-d6) 1.30 (d, 6H, J = 4.5 Hz), 2.50 (brs, 2H), 3.14 (brs, 2H), 3.61 (brs, 2H), 4.63 (s, 2H), 4.74 (brs, 1H), 5.72 (s, 1H), 6.82-6.92 (m, 2H), 7.02-7.19 (m, 4H), 7.71 (d, 2H, J = 7.5 Hz), 13.01 (brs, 1H) |
| I-4 | (DMSO-d6) 1.32 (d, 6H, J = 6.0 Hz), 1.60-1.71 (m, 2H), 1.82 (d, 2H, J = 11.7 Hz), 2.26 (t, 2H, J = 10.5 Hz), 2.84 (t, 1H, J = 11.7 Hz), 3.75 (d, 2H, J = 11.4 Hz), 4.64 (s, 2H), 4.72-4.80 (m, 1H), 6.80 (d, 1H, J = 8.4 Hz), 6.90 (t, 1H, J = 7.2 Hz), 7.11-7.15 (m, 4H), 7.67 (d, 2H, J = 8.7 Hz), 13.00 (brs, 1H) |
| I-5 | (CDCl3) 1.37 (d, 6H, J = 6.3 Hz), 1.90-2.10 (m, 4H), 3.05-3.20 (m, 4H), 3.78 (s, 3H), 4.26-4.35 (m, 1H), 4.63-4.70 (m, 1H), 6.37 (d, 1H, J = 15.9 Hz), 6.80 (d, 1H, J = 9.0 Hz), 6.87 (dd, 1H, J = 9.0, 2.0 Hz), 6.95 (d, 2H, J = 9.0 Hz), 7.02 (d, 1H, J = 2.0 Hz), 7.67 (d, 2H, J = 9.0 Hz), 7.86 (d, 1H, J = 15.9 Hz) |
| I-6 | (CDCl3) 1.35 (d, 6H, J = 6.0 Hz), 1.90-2.10 (m, 4H), 3.05-3.20 (m, 4H), 4.36-4.45 (m, 1H), 4.63-4.70 (m, 1H), 6.37 (d, 1H, J = 15.9 Hz), 6.78 (d, 1H, J = 9.0 Hz), 6.95 (d, 2H, J = 9.0 Hz), 7.20-7.30 (m, 1H), 7.47 (d, 1H, J = 2.0 Hz), 7.67 (d, 2H, J = 9.0 Hz), 7.83 (d, 1H, J = 15.9 Hz) |
| I-7 | (CDCl3) 1.35 (d, 6H, J = 6.0 Hz), 1.90-2.10 (m, 4H), 3.05-3.20 (m, 4H), 4.40-4.48 (m, 1H), 4.63-4.70 (m, 1H), 6.37 (d, 1H, J = 15.9 Hz), 6.80 (d, 1H, J = 9.0 Hz), 6.92 (d, 1H, J = 9.0 Hz), 6.95 (d, 2H, J = 9.0 Hz), 7.33 (t, 1H, J = 9.0 Hz), 7.53 (d, 1H, J = 9.0 Hz), 7.70 (d, 2H, J = 9.0 Hz), 7.89 (d, 1H, J = 15.9 Hz) |

TABLE 26-continued

| Comd. No. | $^1$H-NMR(Solvent)δ |
|---|---|
| I-8 | (CDCl3) 1.33 (d, 6H, J = 6.3 Hz), 1.90-2.10 (m, 4H), 3.05-3.30 (m, 4H), 3.85 (s, 3H), 4.50-4.57 (m, 1H), 4.60-4.70 (m, 1H), 6.47 (d, 1H, J = 9.0 Hz), 6.52 (d, 1H, J = 9.0 Hz), 6.78 (d, 1H, J = 15.9 Hz), 6.95 (d, 2H, J = 9.0 Hz), 7.20 (t, 1H, J = 9.0 Hz), 7.67 (d, 2H, J = 9.0 Hz), 8.02 (d, 1H, J = 15.9 Hz) |
| I-9 | (CDCl3) 1.37 (d, 6H, J = 6.1 Hz), 1.85-2.05 (m, 4H), 2.49 (t, 2H, J = 7.5 Hz), 2.72 (t, 2H, J = 7.5 Hz), 3.05-3.20 (m, 4H), 3.74 (s, 3H), 4.26-4.35 (m, 1H), 4.63-4.70 (m, 1H), 6.65 (d, 1H, J = 2.0 Hz), 6.67 (s, 1H), 6.95 (d, 1H, J = 2.0 Hz), 6.95 (d, 2H, J = 9.0 Hz), 7.86 (d, 2H, J = 9.0 Hz). |

TABLE 27

| Comd. No. | $^1$H-NMR(Solvent)δ |
|---|---|
| I-10 | (CDCl3) 1.36 (d, 6H, J = 6.1 Hz), 1.85-2.05 (m, 4H), 2.46 (t, 2H, J = 7.5 Hz), 2.70 (t, 2H, J = 7.5 Hz), 3.05-3.20 (m, 4H), 4.35-4.42 (m, 1H), 4.60-4.70 (m, 1H), 6.65 (d, 1H, J = 8.0 Hz), 6.95 (d, 2H, J = 9.0 Hz), 7.05 (d, 1H, J = 8.0 Hz), 7.10 (s, 1H), 7.68 (d, 2H, J = 9.0 Hz). |
| I-11 | (CDCl3) 1.35 (d, 6H, J = 6.1 Hz), 1.85-2.05 (m, 4H), 2.47 (t, 2H, J = 7.5 Hz), 2.75 (t, 2H, J = 7.5 Hz), 3.00-3.20 (m, 4H), 4.40-4.50 (m, 1H), 4.63-4.70 (m, 1H), 6.75 (d, 1H, J = 8.0 Hz), 6.84 (t, 1H, J = 8.0 Hz), 6.95 (d, 2H, J = 9.0 Hz), 7.13 (d, 1H, J = 8.0 Hz), 7.15 (t, 1H, J = 8.0 Hz), 7.68 (d, 2H, J = 9.0 Hz). |
| I-12 | (CDCl3) 1.37 (d, 6H, J = 6.1 Hz), 1.85-2.05 (m, 4H), 2.38 (t, 2H, J = 7.5 Hz), 2.79 (t, 2H, J = 7.5 Hz), 3.00-3.20 (m, 4H), 3.78 (s, 3H), 4.40-4.50 (m, 1H), 4.63-4.70 (m, 1H), 6.43 (d, 1H, J = 8.0 Hz), 6.50 (d, 1H, J = 8.0 Hz), 6.95 (d, 2H, J = 9.0 Hz), 7.05 (t, 1H, J = 8.0 Hz), 7.68 (d, 2H, J = 9.0 Hz). |
| I-13 | (CDCl3) 1.33 (d, 6H, J = 6.0 Hz), 1.90-2.10 (m, 4H), 3.05-3.20 (m, 4H), 4.40-4.48 (m, 1H), 4.63-4.70 (m, 1H), 6.92 (d, 1H, J = 15.9 Hz), 6.95 (d, 2H, J = 9.0 Hz), 7.15-7.23 (m, 2H), 7.68 (d, 2H, J = 9.0 Hz), 7.95 (d, 1H, J = 15.9 Hz), 8.25(d, 1H, J = 3.4 Hz). |
| I-14 | (CDCl3) 1.33 (d, 6H, J = 6.0 Hz), 1.90-2.10 (m, 4H), 2.50 (s, 3H), 3.05-3.20 (m, 4H), 4.40-4.48 (m, 1H), 4.63-4.70 (m, 1H), 6.92 (d, 1H, J = 15.9 Hz), 6.95 (d, 2H, J = 9.0 Hz), 7.15 (s, 2H), 7.68 (d, 2H, J = 9.0 Hz), 7.95 (d, 1H, J = 15.9 Hz). |
| I-15 | (CDCl3) 1.37 (d, 6H, J = 6.1 Hz), 1.95-2.15 (m, 4H), 2.67 (t, 2H, J = 7.5 Hz), 2.95 (t, 2H, J = 7.5 Hz), 3.00-3.25 (m, 4H), 4.42-4.50 (m, 1H), 4.63-4.70 (m, 1H), 6.95 (d, 2H, J = 9.0 Hz), 7.15-7.22 (m, 2H), 7.68 (d, 2H, J = 9.0 Hz), 8.25(d, 1H, J = 3.4 Hz). |
| I-16 | (CDCl3) 1.37 (d, 6H, J = 6.1 Hz), 1.95-2.15 (m, 4H), 2.50 (s, 3H), 2.67 (t, 2H, J = 7.5 Hz), 2.95 (t, 2H, J = 7.5 Hz), 3.00-3.25 (m, 4H), 4.42-4.50 (m, 1H), 4.63-4.70 (m, 1H), 6.95 (d, 2H, J = 9.0 Hz), 7.05 (d, 1H, J = 8.8 Hz), 7.13 (d, 1H, J = 8.8 Hz), 7.68 (d, 2H, J = 9.0 Hz). |
| I-17 | (CDCl3) 1.37 (d, 6H, J = 6.1 Hz), 1.85-2.05 (m, 4H), 2.47 (t, 2H, J = 7.5 Hz), 2.72 (t, 2H, J = 7.5 Hz), 3.05-3.20 (m, 4H), 4.35-4.42 (m, 1H), 4.60-4.70 (m, 1H), 6.62-6.67 (m, 1H), 6.78-6.97 (m, 2H), 7.68 (d, 2H, J = 9.0 Hz). |
| I-18 | (CDCl3) 1.35 (d, 6H, J = 6.3 Hz), 1.90-2.10 (m, 4H), 3.05-3.20 (m, 4H), 3.80 (s, 3H), 4.40-4.45 (m, 1H), 4.63-4.70 (m, 1H), 6.37 (d, 1H, J = 15.9 Hz), 6.37 (d, 1H, J = 2.0 Hz), 6.55 (dd, 1H, J = 8.0, 2.0 Hz), 6.95 (d, 2H, J = 9.0 Hz), 7.45 (d, 1H, J = 8.0 Hz), 7.67 (d, 2H, J = 9.0 Hz), 7.82 (d, 1H, J = 15.9 Hz). |
| I-19 | (CDCl3) 1.35 (d, 6H, J = 6.3 Hz), 1.90-2.10 (m, 4H), 3.05-3.20 (m, 4H), 3.80 (s, 3H), 4.40-4.45 (m, 1H), 4.63-4.70 (m, 1H), 6.37 (d, 1H, J = 15.9 Hz), 6.37 (d, 1H, J = 2.0 Hz), 6.55 (dd, 1H, J = 8.0, 2.0 Hz), 6.95 (d, 2H, J = 9.0 Hz), 7.45 (d, 1H, J = 8.0 Hz), 7.67 (d, 2H, J = 9.0 Hz), 7.82 (d, 1H, J = 15.9 Hz). |

TABLE 28

| Comd. No. | ¹H-NMR(Solvent) δ |
|---|---|
| I-20 | (CDCl3) 1.37 (d, 6H, J = 6.1 Hz), 1.85-2.05 (m, 4H), 2.42 (t, 2H, J = 7.5 Hz), 2.66 (t, 2H, J = 7.5 Hz), 3.05-3.20 (m, 4H), 3.74 (s, 3H), 4.36-4.45 (m, 1H), 4.63-4.70 (m, 1H), 6.32 (d, 1H, J = 2.0 Hz), 6.38 (dd, 1H, J = 8.0, 2.0 Hz), 6.95 (d, 2H, J = 9.0 Hz), 7.02 (d, 1H, J = 8.0 Hz), 7.86 (d, 2H, J = 9.0 Hz). |
| I-21 | (CDCl3) 1.35 (d, 6H, J = 6.3 Hz), 1.90-2.10 (m, 4H), 2.85-2.95 (m, 2H), 3.35-3.45 (m, 2H), 3.80 (s, 3H), 4.06-4.15 (m, 1H), 4.60-4.71 (m, 1H), 6.37 (d, 1H, J = 16.2 Hz), 6.90 (t, 1H, J = 8.1 Hz), 6.95 (d, 2H, J = 9.0 Hz), 7.05 (t, 1H, J = 8.1 Hz), 7.17 (d, 1H, J = 8.1 Hz), 7.67 (d, 2H, J = 9.0 Hz), 7.82 (d, 1H, J = 16.2 Hz). |
| I-22 | (CDCl3) 1.37 (d, 6H, J = 6.1 Hz), 1.85-2.05 (m, 4H), 2.52 (t, 2H, J = 7.5 Hz), 2.76 (t, 2H, J = 7.5 Hz), 2.78-2.85 (m, 2H), 3.33-3.40 (m, 2H), 3.74 (s, 3H), 4.16-4.25 (m, 1H), 4.63-4.70 (m, 1H), 6.75 (d, 2H, J = 8.0 Hz), 6.95 (d, 2H, J = 9.0 Hz), 6.97 (t, 1H, J = 8.0 Hz), 7.67 (d, 2H, J = 9.0 Hz). |
| I-23 | (CDCl3) 1.35 (d, 6H, J = 6.0 Hz), 2.06-2.14 (m, 2H), 3.35-3.50 (m, 2H), 3.60-3.80 (m, 2H), 4.50-4.60 (m, 1H), 4.90-4.98 (m, 1H), 6.37 (d, 1H, J = 16.1 Hz), 6.72 (d, 1H, J = 9.0 Hz), 6.80 (d, 2H, J = 9.0 Hz), 6.99 (t, 1H, J = 9.0 Hz), 7.35 (t, 1H, J = 9.0 Hz), 7.53 (d, 1H, J = 9.0 Hz), 7.65 (d, 2H, J = 9.0 Hz), 7.67 (d, 1H, J = 16.1 Hz). |
| I-24 | (CDCl3) 1.35 (d, 6H, J = 6.0 Hz), 2.06-2.14 (m, 2H), 2.43 (t, 2H, J = 7.5 Hz), 2.60 (t, 2H, J = 7.5 Hz), 3.35-3.50 (m, 2H), 3.60-3.80 (m, 2H), 4.50-4.60 (m, 1H), 4.90-4.98 (m, 1H), 6.62 (d, 1H, J = 8.0 Hz), 6.85 (d, 2H, J = 9.0 Hz), 6.88 (t, 1H, J = 8.0 Hz), 7.15 (d, 1H, J = 8.0 Hz), 7.18 (d, 1H, J = 8.0 Hz), 7.71 (d, 2H, J = 9.0 Hz). |
| I-25 | (CDCl3) 1.39 (d, 6H, J = 6.0 Hz), 1.90-2.10 (m, 4H), 3.05-3.20 (m, 4H), 4.35-4.45 (m, 1H), 4.62-4.68 (m, 1H), 6.39 (d, 1H, J = 15.9 Hz), 6.84 (d, 1H, J = 8.0 Hz), 6.92 (d, 1H, J = 8.0 Hz), 6.95 (d, 2H, J = 9.0 Hz), 7.13 (d, 1H, J = 8.0 Hz), 7.33 (t, 1H, J = 8.0 Hz), 7.67 (d, 2H, J = 9.0 Hz), 7.70 (d, 1H, J = 15.9 Hz). |
| I-26 | (CDCl3) 1.35 (d, 6H, J = 6.1 Hz), 1.85-2.05 (m, 4H), 2.60 (t, 2H, J = 7.5 Hz), 2.85 (t, 2H, J = 7.5 Hz), 3.00-3.20 (m, 4H), 4.30-4.40 (m, 1H), 4.60-4.65 (m, 1H), 6.67 (d, 1H, J = 8.2 Hz), 6.69 (s, 1H), 6.95 (d, 2H, J = 9.0 Hz), 7.18 (t, 1H, J = 8.2 Hz), 7.68 (d, 2H, J = 9.0 Hz). |
| I-27 | (DMSO-d6) 1.35 (d, 6H, J = 6.0 Hz), 1.70-2.00 (m, 4H), 2.60-2.75 (m, 2H), 3.40-3.55 (m, 2H), 4.05-4.15 (m, 1H), 4.68-4.75 (m, 1H), 6.35 (d, 1H, J = 15.9 Hz), 7.50-7.70 (m, 4H), 7.33 (t, 1H, J = 8.0 Hz), 7.89 (d, 1H, J = 15.9 Hz). |
| I-28 | (CDCl3) 1.35 (d, 6H, J = 6.0 Hz), 1.90-2.10 (m, 4H), 2.60 (t, 2H, J = 7.5 Hz), 2.60-2.75 (m, 2H), 2.85 (t, 2H, J = 7.5 Hz), 3.45-3.55 (m, 2H), 4.05-4.15 (m, 1H), 4.68-4.75 (m, 1H), 6.95 (d, 2H, J = 9.0 Hz), 7.08 (d, 1H, J = 2.0 Hz), 7.20 (d, 1H, J = 2.0 Hz), 7.68 (d, 2H, J = 9.0 Hz). |

TABLE 29

| Comd. No. | ¹H-NMR (Solvent) δ |
|---|---|
| I-29 | (DMSO-d6) 1.32 (d, J = 6.0 Hz, 6H), 1.59 (brd, 2H), 1.94-2.08 (m, 2H), 2.54 (brt, 2H), 3.51 (brd, 2H), 4.76 (m, 1H), 4.82 (s, 2H), 5.06 (s, 1H), 7.04 (dd, J = 1.8, 8.1 Hz, 1H), 7.09 (d, J = 1.8 Hz, 1H), 7.15 (d-like, 2H), 7.35 (d, J = 8.1 Hz, 1H), 7.67 (d-like, 2H), 13.08 (br, 1H) |
| I-30 | (DMSO-d6) 1.28 (d, J = 6.0 Hz, 6H), 2.50 (brd, 2H), 3.18 (brt, 2H), 3.65 (brd, 2H), 4.73 (m, 1H), 4.83 (s, 2H), 6.11 (brt, 1H), 6.94 (dd, J = 1.8, 8.1 Hz, 1H), 7.00 (d, J = 1.8 Hz, 1H), 7.11 (d-like, 2H), 7.36 (d, J = 8.1 Hz, 1H), 7.71 (d-like, 2H), 13.06 (br, 1H) |
| I-31 | (DMSO-d6) 1.31 (d, J = 6.0 Hz, 6H), 1.60-1.80 (m, 4H), 2.20-2.29 (m, 2H), 2.47 (m, 1H), 3.72 (brd, 2H), 4.75 (m, 1H), 4.79 (s, 2H), 6.78 (dd, J = 1.8, 8.4 Hz, 1H), 6.90 (d, J = 1.8 Hz, 1H), 7.13 (d-like, 2H), 7.30 (d, J = 8.4 Hz, 1H), 7.66 (d-like, 2H), 13.04 (br, 1H) |
| II-1 | (DMSO-d6) 1.31 (d, 6H, J = 6.0 Hz), 2.99 (brs, 4H), 3.08 (brs, 4H), 4.61 (s, 2H), 4.72-4.80 (m, 1H), 6.78 (d, 1H, J = 6.9 Hz), 6.87-6.95 (m, 3H), 7.15 (d, 2H, J = 9.0 Hz), 7.67 (d, 2H, J = 9.0 Hz) |
| II-2 | (DMSO-d6) 1.34 (d, 6H, J = 6.3 Hz), 3.07 (brd, 8H, J = 5.4 Hz), 4.61 (s, 2H), 5.34-5.40 (m, 1H), 6.79 (d, 1H, J = 7.8 Hz), 6.85-6.95 (m, 3H), 6.98 (d, 1H, J = 9.0 Hz), 8.01 (dd, 2H, J = 2.4, 8.7 Hz), 8.55 (d, 1H, J = 2.1 Hz), 13.01 (brs, 1H) |
| II-3 | (DMSO-d6) 1.30 (d, 6H, J = 6.0 Hz), 2.93-2.99 (brm, 4H), 3.17-3.22 (brm, 4H), 4.59 (s, 2H), 4.71-4.79 (m, 1H), 6.33 (dd, 1H, J = 2.4, |

TABLE 29-continued

| Comd. No. | ¹H-NMR (Solvent) δ |
|---|---|
| | 8.1 Hz), 6.43 (t, 1H, J = 2.4 Hz), 6.50 (dd, 1H, J = 2.4, 8.1 Hz), 7.08 (t, 1H, J = 8.1 Hz), 7.14 (d, 2H, J = 9.0 Hz), 7.67 (d, 2H, J = 9.0 Hz), 12.90 (brs, 1H) |
| II-4 | (DMSO-d6) 1.30 (d, 6H, J = 6.3 Hz), 2.94-3.00 (brm, 4H), 3.02-3.08 (brm, 4H), 4.55 (s, 2H), 4.71-4.80 (m, 1H), 6.78 (d, 2H, J = 9.3 Hz), 6.85 (d, 2H, J = 9.3 Hz), 7.15 (d, 2H, J = 9.0 Hz), 7.67 (d, 2H, J = 9.0 Hz), 12.89 (brs, 1H) |
| II-5 | (DMSO-d6) 1.30 (d, 6H, J = 6.0 Hz), 2.94 (brs, 4H), 3.10 (brs, 4H), 4.55 (s, 2H), 4.72-4.81 (m, 1H), 6.16 (t, 1H, J = 7.2 Hz), 6.74 (dd, 1H, J = 1.5, 7.5 Hz), 7.15 (d, 2H, J = 9.0 Hz), 7.30 (dd, 1H, J = 1.5, 6.6 Hz), 7.67 (d, 2H, J = 9.0 Hz), 12.87 (brs, 1H) |
| II-6 | (DMSO-d6) 1.31 (d, 6H, J = 6.0 Hz), 2.99 (brs, 4H), 3.13 (brs, 4H), 4.72-4.79 (m, 3H), 6.92 (dd, 1H, J = 5.1, 7.5 Hz), 7.15 (d, 2H, J = 8.7 Hz), 7.23 (d, 1H, J = 7.8 Hz), 7.67-7.70 (m, 3H), 12.75 (brs, 1H) |
| II-7 | (DMSO-d6) 1.31 (d, 6H, J = 6.0 Hz), 2.98 (brs, 4H), 3.02 (brs, 4H), 4.67 (s, 2H), 4.72-4.80 (m, 1H), 6.66-6.76 (m, 2H), 6.90 (dd, 1H, J = 6.3, 8.7 Hz), 7.15 (d, 2H, J = 9.0 Hz), 7.67 (d, 2H, J = 8.7 Hz) |
| II-8 | (CDCl3) 1.37 (d, 6H, J = 6.3 Hz), 2.20 (s, 3H), 2.50 (brs, 1H), 3.20 (brs, 8H), 4.61-4.67 (m, 3H), 6.43 (s, 1H), 6.51 (d, 1H, J = 8.1 Hz), 6.97 (d, 2H, J = 9.0 Hz), 7.05 (d, 1H, J = 7.8 Hz), 7.69 (d, 2H, J = 9.0 Hz) |

TABLE 30

| Comd. No. | ¹H-NMR(Solvent)δ |
|---|---|
| II-9 | (CDCl3) 1.38 (d, 6H, J = 6.0 Hz), 1.95 (brs, 1H), 3.16 (brs, 8H), 3.86 (s, 3H), 4.60-4.69 (m, 3H), 6.60-6.63 (m, 2H), 6.85 (d, 1H, J = 9.0 Hz), 6.98 (d, 2H, J = 9.0 Hz), 7.70 (d, 2H, J = 9.0 Hz) |
| II-10 | (CDCl3) 1.37 (d, 6H, J = 6.0 Hz), 3.16-3.23 (brs, 8H), 3.73 (brs, 1H), 4.60-4.71 (m, 3H), 6.49-6.54 (m, 2H), 6.98 (d, 2H, J = 9.0 Hz), 7.24 (d, 1H, J = 8.7 Hz), 7.69 (d, 2H, J = 9.0 Hz) |
| II-11 | (CDCl3) 1.37 (d, J = 6.3 Hz, 6H), 3.00 (brs, 1H), 3.08 (brt, J = 4.8 Hz, 4H), 3.57 (brt, J = 4.8, 4H), 4.58-4.66 (m, 1H), 4.77 (s, 2H), 6.19-6.25 (m, 2H), 6.96 (d, J = 9.0 Hz, 2H), 7.44 (t, J = 7.8 Hz, 1H), 7.67 (d, J = 9.0 Hz, 2H) |
| II-12 | (CDCl3) 1.35 (d, J = 5.7 Hz, 6H), 3.08 (brs, 4H), 3.68 (brs, 4H), 4.58-4.66 (m, 1H), 4.79 (s, 2H), 5.64 (brs, 1H), 6.29 (brs, 1H), 6.39 (d, J = 6.0 Hz, 1H), 6.95 (d, J = 9.0 Hz, 2H), 7.63 (t, J = 9.0 Hz, 2H), 7.92 (d, J = 6.9 Hz, 1H) |
| II-13 | (CDCl3) 1.37 (d, 6H, J = 6.3 Hz), 3.15 (brt, 4H, J = 4.8 Hz), 3.50 (brt, 4H, J = 4.2 Hz), 4.60-4.70 (m, 1H), 4.75 (s, 2H), 6.24, (s, 1H), 6.49 (dd, 1H, J = 2.1, 9.3 Hz), 6.98 (d, 2H, J = 9.0 Hz), 7.69 (d, 2H, J = 8.7 Hz), 8.06 (d, 2H, J = 9.6 Hz) |
| II-14 | (CDCl3) 1.36 (d, J = 5.7 Hz, 6H), 3.10 (brs, 4H), 3.39 (brs, 1H), 3.74 (brs, 4H), 4.60-4.68 (m, 1H), 4.73 (s, 2H), 6.33 (brs, 1H), 6.43 (brs, 1H), 6.95 (brd, J = 8.7 Hz, 2H), 7.63 (brd, J = 7.8 Hz, 1H), 7.91 (brs, 1H) |
| II-15 | (CDCl3) 1.37 (d, 6H, J = 6.0 Hz), 3.17 (m, 4H), 3.25 (m, 4H), 4.63 (m, 1H), 6.92 (dd, 1H, J = 9.0, 3.0 Hz), 6.97 (d, 2H, J = 9.9 Hz), 7.26-7.30 (m, 2H), 7.69 (d, 2H). |
| II-16 | (CDCl3) 1.38 (d, J = 6.0 Hz, 6H), 3.00 (brs, 1H), 3.15 (s, 8H), 4.60-4.68 (m, 1H), 4.71 (s, 2H), 6.27 (brs, 1H), 6.32-6.39 (m, 1H), 6.98 (d, J = 8.7 Hz, 2H), 7.69 (d, J = 8.7 Hz, 2H) |
| II-17 | (CDCl3) 1.37 (d, 6H, J = 6.1 Hz), 3.09-3.13 (m, 4H), 4.62 (s, 2H), 4.63-4.69 (m, 1H), 6.35 (s, 1H), 6.51 (s, 1H), 6.65 (s, 1H), 6.98 (d, 2H, J = 8.7 Hz), 7.69 (d, 2H, J = 8.7 Hz) |
| II-18 | (DMSO-d6) 1.30 (d, 6H, J = 5.7 Hz), 2.97 (t, 4H), 3.38 (t, 4H), 4.75 (m, 1H), 6.65 (d, 1H, J = 16.2 Hz), 6.99 (dd, 1H, J = 9.0, 2.7 Hz), 7.14 (d, 2H, J = 9.0 Hz), 7.32 (d, 1H), 7.35 (d, 1H), 7.68 (d, 2H), 7.78 (d, 1H). |
| II-19 | (DMSO-d6) 1.38 (d, 6H, J = 5.7 Hz), 2.96 (brs, 4H), 3.29 (brs, 4H), 4.61 (s, 2H), 4.71-4.79 (m, 1H), 6.57 (s, 1H), 6.67 (s, 1H), 6.76 (s, 1H), 7.14 (d, J = 8.7 Hz, 2H), 7.66 (d, J = 8.7 Hz, 2H) |
| II-20 | (CDCl3) 1.38 (d, 6H, J = 6.3 Hz), 3.25-3.26 (m, 8H), 3.75 (s, 2H), 4.64 (m, 1H), 6.87-6.99 (m, 4H), 7.28 (d, 1H), 7.69 (d, 2H, J = 9.0 Hz). |
| II-21 | (CDCl3) 1.38 (d, 6H, J = 6.0 Hz), 2.67 (t, 2H, J = 7.8 Hz), 3.00 (t, 2H), 3.18-3.21 (m, 8H), 4.63 (m, 1H), 6.71-6.82 (m, 3H), 6.97 (d, 2H, J = 9.0 Hz), 7.21 (d, 1H, J = 8.4 Hz), 7.69 (d, 2H). |
| II-22 | (CDCl3) 1.38 (d, 6H, J = 6.3 Hz), 2.65 (t, 2H, J = 7.8 Hz), 2.92 (t, 2H), 3.29-3.30 (m, 8H), 4.64 (m, 1H), 6.86-6.99 (m, 5H), 7.23 (d, 1H, J = 7.8 Hz), 7.70 (d, 2H, J = 8.7 Hz). |

TABLE 31

| Comd. No. | $^1$H-NMR(Solvent)δ |
|---|---|
| II-23 | (DMSO-d6) 1.30 (d, J = 6.0 Hz, 6H), 2.02 (s, 3H), 2.96 (brs, 4H), 3.14 (brs, 4H), 4.69 (s, 2H), 4.71-4.79 (m, 1H), 6.45 (dd, J = 2.4, 9.0 Hz, 1H), 6.54 (d, J = 2.4 Hz, 1H), 7.14 (d, J = 8.7 Hz, 2H), 7.65-7.68 (m, 3H), 9.02 (s, 1H) |
| II-24 | (DMSO-d6) 1.30 (d, J = 6.0 Hz, 6H), 2.97 (brs, 4H), 3.20 (brs, 4H), 4.71-4.79 (m, 3H), 6.55 (dd, J = 2.4, 8.7 Hz, 1H), 6.68-6.70 (m, 2H), 7.15 (d, J = 8.7 Hz, 2H), 7.23 (dd, J = 0.6, 2.2 Hz, 1H), 7.68 (d, J = 9.0 Hz, 2H), 7.81 (d, J = 8.7 Hz, 1H), 7.89-7.90 (m, 1H), 9.30 (s, 1H) |
| II-25 | (CDCl3) 1.37 (d, 6H, J = 6.0 Hz), 3.08-3.17 (m, 4H), 3.20-3.30 (m, 4H), 4.59 (s, 2H), 4.57-4.65 (m, 1H), 6.07 (d, 1H, J = 8.8 Hz), 6.21 (s, 1H), 6.22 (d, 1H, J = 8.8 Hz), 6.98 (d, 2H, J = 9.0 Hz), 7.69 (d, 2H, J = 9.0 Hz) |
| II-26 | (CDCl3) 1.37 (d, 6H, J = 6.0 Hz), 3.08-3.17 (m, 4H), 3.20-3.30 (m, 4H), 4.60 (s, 2H), 4.58-4.65 (m, 1H), 6.31 (s, 1H), 6.33 (s, 1H), 6.49 (s, 1H), 6.98 (d, 2H, J = 9.0 Hz), 7.69 (d, 2H, J = 9.0 Hz) |
| II-27 | (CDCl3) 1.32 (d, J = 6.3 Hz, 6H), 3.01-3.04 (m, 4H), 3.20-3.23 (m, 4H), 4.76 (s, 2H), 5.34 (sep, J = 6.3 Hz, 1H), 6.48 (dd, J = 2.7, 8.7 Hz, 1H), 6.58 (d, J = 2.7 Hz, 1H), 6.96 (d, J = 8.7 Hz, 1H), 7.20 (d, J = 8.7 Hz, 1H), 8.00 (dd, J = 2.7, 8.7 Hz, 1H), 8.55 (d, J = 2.7 Hz, 1H), 13.03 (br, 1H) |
| II-28 | (DMSO-d6) 1.30 (d, J = 6.0 Hz, 6H), 2.98 (brs, 4H), 3.21 (brs, 4H), 4.72-4.80 (m, 3H), 6.57 (dd, J = 2.4, 8.7 Hz, 1H), 6.71 (d, J = 2.4 Hz, 1H), 7.15 (d, J = 8.7 Hz, 2H), 7.49-7.61 (m, 3H), 7.68 (d, J = 8.7 Hz, 2H), 7.74 (d, J = 8.7 Hz, 1H), 7.95 (d, J = 8.4 Hz, 2H), 9.51 (s, 1H) |
| II-29 | (DMSO-d6) 0.91 (t, J = 7.2 Hz, 3H), 1.26 (d, J = 6.0 Hz, 6H), 1.53-1.76 (m, 2H), 2.91-2.99 (m, 4H), 3.16-3.24 (m, 4H), 4.51 (m, 1H), 4.75 (s, 2H), 6.47 (dd, J = 2.4, 8.7 Hz, 1H), 6.58 (d, J = 2.4 Hz, 1H), 7.15 (d-like, 2H), 7.19 (d, J = 8.7 Hz, 1H), 7.66 (d-like, 2H), 13.02 (br, 1H) |
| II-30 | (DMSO-d6) 2.91-2.99 (m, 4H), 3.16-3.24 (m, 4H), 3.86 (s, 3H), 4.75 (s, 2H), 6.46 (dd, J = 2.4, 8.7 Hz, 1H), 6.57 (d, J = 2.4 Hz, 1H), 7.17 (d-like, 2H), 7.18 (d, J = 8.7 Hz, 1H), 7.70 (d-like, 2H), 13.01 (br, 1H) |
| II-31 | (DMSO-d6) 1.33 (d, J = 6.0 Hz, 6H), 2.95-3.04 (m, 4H), 3.16-3.24 (m, 4H), 4.76 (s, 2H), 4.81 (m, 1H), 6.47 (dd, J = 2.4, 8.7 Hz, 1H), 6.58 (d, J = 2.4 Hz, 1H), 7.20 (d, J = 8.7 Hz, 1H), 7.43 (t, J = 8.4 Hz, 1H), 7.54 (dd, J = 2.1, 9.0 Hz, 1H), 7.60 (dd, J = 2.1, 10.5 Hz, 1H), 13.01 (brs, 1H) |
| II-32 | (DMSO-d6) 1.30 (d, J = 6.0 Hz, 6H), 2.97 (brs, 4H), 3.16 (brs, 4H), 3.39 (s, 3H), 3.96 (s, 2H), 4.70-4.80 (m, 3H), 6.49 (d, J = 8.4 Hz, 1H), 6.64 (s, 1H), 7.14 (d, J = 8.7 Hz, 2H), 7.67 (d, J = 8.4 Hz, 2H), 7.91 (d, J = 8.7 Hz, 1H), 8.92 (s, 1H) |

TABLE 32

| Comd. No. | $^1$H-NMR(Solvent)δ |
|---|---|
| II-33 | (DMSO-d6) 1.30 (d, J = 6.0 Hz, 6H), 2.95 (brs, 4H), 3.02 (brs, 4H), 4.71-4.79 (m, 3H), 6.42 (dd, J = 2.4, 9.0 Hz, 1H), 6.54 (d, J = 2.4 Hz, 1H), 7.13 (d, J = 9.0 Hz, 2H), 7.32 (d, J = 8.7 Hz, 1H), 7.66 (d, J = 8.7 Hz, 2H) |
| II-34 | (DMSO-d6) 2.97-3.04 (m, 4H), 3.17-3.24 (m, 4H), 4.76 (s, 2H), 6.47 (dd, J = 2.7, 8.7 Hz, 1H), 6.58 (d, J = 2.7 Hz, 1H), 7.19 (d, J = 8.7 Hz, 1H), 7.47-7.55 (m, 2H), 7.82-7.89 (m, 2H), 13.00 (br, 1H) |
| II-35 | (DMSO-d6) 1.31 (d, J = 6.6 Hz, 6H), 2.94-3.03 (m, 4H), 3.15-3.23 (m, 4H), 3.73 (m, 1H), 4.75 (s, 2H), 6.47 (dd, J = 2.7, 8.7 Hz, 1H), 6.58 (d, J = 2.7 Hz, 1H), 7.19 (d, J = 8.7 Hz, 1H), 7.54 (d-like, 2H), 7.67 (d-like, 2H), 13.02 (br, 1H) |

TABLE 32-continued

| Comd. No. | $^1$H-NMR(Solvent)δ |
|---|---|
| II-36 | (DMSO-d6) 0.98 (d, J = 6.6 Hz, 6H), 2.04 (sep, J = 6.6 Hz, 1H), 2.91-2.99 (m, 4H), 3.16-3.24 (m, 4H), 3.85 (d, J = 6.6 Hz, 2H), 4.75 (s, 2H), 6.47 (dd, J = 2.4, 8.7 Hz, 1H), 6.57 (d, J = 2.4 Hz, 1H), 7.17 (d-like, 2H), 7.19 (d, J = 8.7 Hz, 1H), 7.65 (d-like, 2H), 13.00 (br, 1H) |
| II-37 | (CDCl3) 1.37 (d, 6H, J = 6.0 Hz), 3.08-3.17 (m, 4H), 3.20-3.30 (m, 4H), 3.43 (s, 3H), 4.29 (s, 2H), 4.60 (s, 2H), 4.58-4.65 (m, 1H), 6.31 (s, 1H), 6.33 (s, 1H), 6.49 (s, 1H), 6.98 (d, 2H, J = 9.0 Hz), 7.69 (d, 2H, J = 9.0 Hz) |
| II-38 | (CDCl3) 1.37 (d, 6H, J = 6.0 Hz), 3.18-3.22 (m, 4H), 3.25-3.30 (m, 4H), 4.58-4.65 (m, 1H), 4.70 (s, 2H), 6.44 (s, 1H), 6.57 (s, 1H), 6.61 (s, 1H), 6.68 (s, 1H), 6.98 (d, 2H, J = 8.6 Hz), 7.45 (s, 1H), 7.69 (d, 2H, J = 8.6 Hz). |
| II-39 | (DMSO-d6) 1.37 (d, 6H, J = 6.0 Hz), 2.98-3.07 (m, 4H), 3.20-3.30 (m, 4H), 4.60 (s, 2H), 4.58-4.65 (m, 1H), 6.55 (s, 1H), 6.75 (s, 1H), 6.95 (s, 1H), 7.18 (d, 2H, J = 9.0 Hz), 7.69 (d, 2H, J = 9.0 Hz), 7.65-7.75 (m, 2H), 8.60-8.64 (2H). |
| II-40 | (DMSO-d6) 1.37 (d, 6H, J = 6.0 Hz), 2.98-3.07 (m, 4H), 3.20-3.30 (m, 4H), 4.64 (s, 2H), 4.68-4.75 (m, 1H), 6.45 (s, 1H), 6.65 (s, 1H), 6.80 (s, 1H), 7.18 (d, 2H, J = 9.0 Hz), 7.39-7.45 (m, 1H), 7.69 (d, 2H, J = 9.0 Hz), 8.00 (d, 1H, J = 8.0 Hz), 8.53 (d, 1H, J = 4.8 Hz), 8.80 (brs, 1H). |
| II-41 | (CDCl3) 1.37 (d, 6H, J = 6.0 Hz), 2.23 (s, 3H), 3.08-3.17 (m, 4H), 3.20-3.30 (m, 4H), 4.60 (s, 2H), 4.58-4.65 (m, 1H), 6.47 (s, 2H), 6.65 (s, 1H), 6.98 (d, 2H, J = 9.0 Hz), 7.69 (d, 2H, J = 9.0 Hz). |
| II-42 | (DMSO-d6) 1.30 (d, 6H, J = 5.7 Hz), 2.96 (t, 4H), 3.28 (t, 4H), 4.71 (s, 2H), 4.75 (m, 1H), 6.87 (dd, 1H, J = 2.1 Hz), 7.14 (d, 2H, J = 9.0 Hz), 7.67 (d, 2H), 7.71 (d, 1H), 7.88 (d, 1H). |
| II-43 | (DMSO-d6) 1.08 (d, 3H, J = 6.6 Hz), 1.29 (d, 6H, J = 6.0 Hz), 2.42-2.76 (m, 2H), 3.20-3.59 (m, 4H), 4.01 (m, 1H), 4.68-4.76 (m, 3H), 6.43 (m, 2H), 7.08 (d, 2H, J = 9.0 Hz), 7.18 (d, 1H, J = 8.7 Hz), 7.73 (d, 2H). |
| II-44 | (DMSO-d6) 0.98 (d, 3H, J = 6.3 Hz), 1.30 (d, 6H, J = 6.0 Hz), 2.35-2.56 (m, 2H), 3.00-3.59 (m, 4H), 4.03 (m, 1H), 4.71-4.79 (m, 3H), 6.44 (dd, 1H, J = 8.7, 2.1 Hz), 6.53 (d, 1H), 7.14 (d, 2H, J = 9.0 Hz), 7.19 (d, 1H), 7.66 (d, 2H). |

TABLE 33

| Comd. No. | $^1$H-NMR(Solvent)δ |
|---|---|
| II-45 | (DMSO-d6) 1.31 (d, J = 6.0 Hz, 6H), 2.93-3.02 (m, 4H), 3.06-3.14 (m, 4H), 4.64 (s, 2H), 4.76 (m, 1H), 6.80 (d, J = 8.7 Hz, 1H), 6.88 (d, J = 2.7 Hz, 1H), 6.96 (dd, J = 2.7, 8.7 Hz, 1H), 7.15 (d-like, 2H), 7.67 (d-like, 2H), 13.01 (br, 1H) |
| II-46 | (CDCl3) 1.37 (d, 6H, J = 6.0 Hz), 3.17 (t, 4H), 3.46 (t, 4H), 4.63 (m, 1H), 4.76 (s, 2H), 6.38 (d, 1H, J = 2.4 Hz), 6.62 (dd, 1H, J = 9.0, 2.1 Hz), 6.98 (d, 2H), 7.67-7.75 (m, 3H), 8.39 (s, 1H). |
| II-47 | (DMSO-d6) 1.30 (d, J = 6.0 Hz, 6H), 2.98 (brs, 4H), 3.20 (brs, 4H), 4.70-4.79 (m, 1H), 4.85 (s, 2H), 6.55 (d, J = 9.0 Hz, 1H), 6.68 (s, 1H), 7.14 (d, J = 8.7 Hz, 2H), 7.64-7.69 (m, 3H), 8.06 (d, J = 9.3 Hz, 1H), 8.16 (d, J = 7.8 Hz, 1H), 8.24 (d, J = 7.8 Hz, 1H), 8.68 (d, J = 5.7 Hz, 1H), 10.40 (s, 1H), 13.05 (brs, 1H) |
| II-48 | (DMSO-d6) 1.30 (d, J = 6.0 Hz, 6H), 2.98 (brs, 4H), 3.22 (brs, 4H), 4.72-4.80 (m, 3H), 6.57 (dd, J = 2.1, 8.7 Hz, 1H), 6.68 (d, J = 2.4 Hz, 1H), 7.15 (d, J = 9.0 Hz, 2H), 7.53-7.57 (m, 1H), 7.64-7.70 (m, 3H), 8.29 (d, J = 8.1 Hz, 1H), 8.74 (s, 1H), 9.10 (s, 1H), 9.79 (s, 1H), 13.10 (brs, 1H) |
| II-49 | (DMSO-d6) 1.30 (d, J = 6.3 Hz, 6H), 2.98 (brs, 4H), 3.22 (brs, 4H), 4.73-4.80 (m, 3H), 6.57 (dd, J = 2.4, 9.0 Hz, 1H), 6.69 (d, J = 1.8 Hz, 1H), 7.15 (d, J = 9.0 Hz, 2H), 7.65-7.70 (m, 3H), 7.85 (d, J = 5.4 Hz, 2H), 8.76 (brs, 2H), 9.86 (brs, 1H), 13.16 (brs, 1H) |
| II-50 | (DMSO-d6) 1.37 (d, J = 6.0 Hz, 6H), 2.08 (quint, J = 5.7 Hz, 2H), 2.12 (br, 1H), 3.12-3.25 (m, 8H), 3.89 (t, J = 5.7 Hz, 2H), 4.14 (t, J = 5.7 Hz, 2H), 4.63 (sept, J = 6.0 Hz, 1H), 6.41 (dd, J = 2.7, 8.4 Hz, 1H), 6.47 (d, J = 2.7 Hz, 1H), 6.97 (d-like, 2H), 7.19 (d, J = 8.4 Hz, 1H), 7.69 (d-like, 2H) |
| II-51 | (CDCl3) 1.37 (d, 6H, J = 6.0 Hz), 3.18-3.22 (m, 4H), 3.25-3.30 (m, 4H), 4.58-4.65 (m, 1H), 4.70 (s, 2H), 6.41 (s, 1H), 6.65 (s, 1H), 6.77 (s, 1H), 6.98 (d, 2H, J = 8.6 Hz), 7.03-7.10 (m, 1H), 7.26-7.30 (m, 2H), 7.70 (d, 2H, J = 8.6 Hz). |

TABLE 33-continued

| Comd. No. | $^1$H-NMR(Solvent)δ |
|---|---|
| II-52 | (DMSO-d6) 1.30 (d, J = 6.0 Hz, 6H), 2.68 (t, J = 6.0, 2H), 2.92-3.00 (m, 4H), 3.19-3.27 (m, 4H), 4.19 (t, J = 6.0 Hz, 2H), 4.75 (sept, J = 6.0 Hz, 1H), 6.46 (dd, J = 2.4, 8.7 Hz, 1H), 6.66 (d, J = 2.4 Hz, 1H), 7.14 (d-like, 2H), 7.17 (d, J = 8.7 Hz, 1H), 7.67 (d-like, 2H), 12.37 (br, 1H) |
| II-53 | (DMSO-d6) 1.30 (d, J = 6.0 Hz, 6H), 2.99 (brs, 4H), 3.26 (brs, 4H), 4.78 (s, 2H), 4.72-4.79 (m, 1H), 6.55-6.57 (m, 2H), 7.14-7.17 (m, 3H), 7.23 (t, J = 7.2 Hz, 1H), 7.34 (t, J = 7.8 Hz, 2H), 7.51 (d, J = 7.8 Hz, 2H), 7.68 (d, J = 9.0 Hz, 2H) |
| II-54 | (DMSO-d6) 1.29 (d, J = 6.0 Hz, 6H), 2.97 (brs, 4H), 3.26 (brs, 4H), 4.79-4.70 (m, 3H), 6.52 (d, J = 9.0 Hz, 1H), 6.55 (s, 1H), 6.97 (s, 1H), 7.14 (d, J = 9.0 Hz, 2H), 7.44 (d, J = 9.0 Hz, 1H), 7.66 (s, 1H), 7.67 (d, J = 9.0 Hz, 2H), 8.36 (s, 1H) |
| II-55 | (DMSO-d6) 1.33 (d, J = 6.0 Hz, 6H), 2.98-3.05 (m, 4H), 3.16-3.23 (m, 4H), 4.79 (s, 2H), 5.34 (sep, J = 6.0 Hz, 1H), 6.48-6.56 (m, 2H), 6.97 (d, J = 8.7 Hz, 1H), 8.00 (dd, J = 2.4, 8.7 Hz, 1H), 8.55 (d, J = 2.4 Hz, 1H), 13.09 (br, 1H) |

TABLE 34

| Comd. No. | $^1$H-NMR(Solvent)δ |
|---|---|
| II-56 | (DMSO-d6) 1.37 (d, J = 6.0 Hz, 6H), 2.18 (br, 1H), 3.13-3.28 (m, 8H), 3.96 (brm, 2H), 4.10 (t, J = 4.5 Hz, 2H), 4.63 (sept, J = 6.0 Hz, 1H), 6.47 (dd, J = 2.4, 8.7 Hz, 1H), 6.54 (brs, 1H), 6.97 (d-like, 2H), 7.22 (d, J = 8.7 Hz, 1H), 7.69 (d-like, 2H) |
| II-57 | (CDCl3) 1.37 (d, 6H, J = 6.0 Hz), 3.18-3.22 (m, 4H), 3.25-3.30 (m, 4H), 4.58-4.65 (m, 1H), 4.70 (s, 2H), 6.53 (s, 1H), 6.65 (s, 1H), 6.77 (s, 1H), 6.98 (d, 2H, J = 8.6 Hz), 7.34-7.43 (m, 3H), 7.46-7.50 (m, 2H), 7.70 (d, 2H, J = 8.6 Hz). |
| II-58 | (DMSO-d6) 1.30 (d, J = 6.0 Hz, 6H), 2.97 (brs, 4H), 3.23 (brs, 4H), 4.70-4.80 (m, 3H), 6.48-6.65 (m, 3H), 7.03-7.16 (m, 3H), 7.65-7.78 (m, 3H), 9.60 (s, 1H), 12.98 (brs, 1H) |
| II-59 | (DMSO-d6) 1.30 (d, J = 6.0 Hz, 6H), 2.96 (brs, 4H), 3.15 (brs, 4H), 3.61 (s, 3H), 4.66-4.80 (m, 3H), 6.49 (d, J = 8.1 Hz, 1H), 6.58 (s, 1H), 7.14 (d, J = 9.0 Hz, 2H), 7.41 (s, 1H), 7.67 (d, J = 8.4 Hz, 2H), 8.29 (brs, 1H), 13.00 (brs, 1H) |
| II-60 | (DMSO-d6) 1.30 (d, J = 5.4 Hz, 6H), 2.50 (s, 3H), 2.97 (brs, 4H), 3.20 (brs, 4H), 4.65-4.85 (m, 3H), 6.54 (d, J = 7.5 Hz, 1H), 6.66-6.70 (m, 2H), 7.15 (d, J = 8.7 Hz, 2H), 7.68 (d, J = 8.4 Hz, 2H), 7.86 (d, J = 9.0 Hz, 1H), 9.47 (s, 1H), 13.11 (brs, 1H) |
| II-61 | (CDCl3) 1.37 (d, 6H, J = 6.0 Hz), 2.60 (s, 3H), 3.17 (t, 4H), 3.44 (t, 4H), 4.63 (m, 1H), 4.74 (s, 2H), 6.38 (d, 1H, J = 2.1 Hz), 6.60 (dd, 1H, J = 8.4, 1.8 Hz), 6.98 (d, 2H, J = 9.0 Hz), 7.67-7.71 (m, 3H) |
| II-62 | (CDCl3) 1.37 (d, 6H, J = 6.0 Hz), 3.21 (t, 4H), 3.41 (t, 4H), 4.63 (m, 1H), 4.79 (s, 2H), 6.37 (d, 1H), 6.63 (dd, 1H), 6.99 (d, 2H), 7.09 (t, 1H), 7.32 (t, 1H), 7.69 (d, 1H, J = 9.0 Hz), 7.79 (d, 2H, J = 8.1 Hz), 8.09 (d, 1H), 9.80 (s, 1H). |
| II-63 | (CDCl3) 1.24 (d, 6H, J = 6.3 Hz), 1.37 (d, 6H, J = 6.0 Hz), 3.14 (t, 4H), 3.35 (t, 4H), 4.65 (m, 1H), 4.71 (s, 2H), 6.29 (d, 1H, J = 2.4 Hz), 6.53 (dd, 1H, J = 8.7, 2.1 Hz), 6.97 (d, 2H, J = 3.0 Hz), 7.66-7.72 (m, 3H), 7.84 (d, 1H, J = 8.7 Hz). |
| II-64 | (CDCl3) 1.22 (d, 6H, J = 6.0 Hz), 1.37 (d, 6H, J = 6.0 Hz), 3.18-3.22 (m, 4H), 3.25-3.30 (m, 4H), 4.28-4.36 (m, 1H), 4.58-4.65 (m, 1H), 4.65 (s, 2H), 6.01 (brs, 1H), 6.57 (s, 1H), 6.75 (s, 1H), 6.89 (s, 1H), 6.98 (d, 2H, J = 8.6 Hz), 7.70 (d, 2H, J = 8.6 Hz). |
| II-65 | (DMSO-d6) 1.29 (d, J = 6.0 Hz, 6H), 2.97 (brs, 4H), 3.29 (brs, 4H), 4.71-4.80 (m, 3H), 6.52-6.57 (m, 3H), 7.11 (d, J = 3.0 Hz, 1H), 7.14 (d, J = 9.0 Hz, 2H), 7.56 (d, J = 9.3 Hz, 1H), 7.61 (d, J = 1.2 Hz, 1H), 7.67 (d, J = 9.0 Hz, 2H) |
| II-66 | (CDCl3) 1.37 (d, 6H, J = 6.0 Hz), 3.18-3.22 (m, 4H), 3.25-3.30 (m, 4H), 4.58-4.65 (m, 1H), 4.73 (s, 2H), 6.64 (s, 1H), 6.98 (d, 2H, J = 8.6 Hz), 7.07 (s, 1H), 7.24 (s, 1H), 7.28 (s, 1H), 7.70 (d, 2H, J = 8.6 Hz), 8.46 (s, 1H). |
| II-67 | (DMSO-d6) 1.21 (d, J = 6.3 Hz, 6H), 1.30 (d, J = 6.0 Hz, 6H), 2.96 (brs, 4H), 3.14 (brs, 4H), 4.62 (s, 2H), 4.71-4.85 (m, 2H), 6.48 (d, J = 9.9 Hz, 1H), 6.59 (s, 1H), 7.14 (d, J = 8.7 Hz, 2H), 7.47 (brd, J = 6.6 Hz, 1H), 7.67 (d, J = 8.7 Hz, 2H), 8.26 (brs, 1H) |

TABLE 35

| Comd. No. | ¹H-NMR(Solvent)δ |
|---|---|
| II-68 | (DMSO-d6) 1.06 (d, J = 6.6 Hz, 6H), 1.30 (d, J = 6.3 Hz, 6H), 2.96-2.97 (m, 4H), 3.06-3.08 (m, 4H), 3.65-3.76 (m, 1H), 4.71-4.79 (m, 3H), 6.39 (dd, J = 2.4, 8.7 Hz, 1H), 6.50 (d, J = 2.4 Hz, 1H), 6.62 (d, J = 7.5 Hz, 1H), 7.14 (d, J = 9.0 Hz, 2H), 7.52 (s, 1H), 7.67 (d, J = 9.0 Hz, 2H), 7.81 (d, J = 9.0 Hz, 1H), 13.02 (brs, 1H) |
| II-69 | (DMSO-d6) 1.31 (d, J = 6.0 Hz, 6H), 3.02 (brs, 8H), 4.67 (s, 1H), 4.73-4.80 (m, 2H), 6.59 (dd, J = 3.0, 9.0 Hz, 1H), 6.70 (d, J = 2.7 Hz, 1H), 7.16 (d, J = 8.7 Hz, 2H), 7.27 (d, J = 9.0 Hz, 1H), 7.68 (d, J = 8.7 Hz, 2H) |
| II-70 | (CDCl3) 1.35 (d, 6H, J = 6.0 Hz), 1.37 (d, 6H, J = 6.0 Hz), 3.18-3.22 (m, 8H), 4.48-4.56 (m, 1H), 4.52 (s, 2H), 4.58-4.65 (m, 1H), 6.58 (d, 1H, J = 8.5 Hz), 6.60 (s, 1H), 6.83 (d, 1H, J = 8.5 Hz), 6.96 (d, 2H, J = 8.5 Hz), 7.81 (d, 2H, J = 8.5 Hz). |
| II-71 | (CDCl3) 1.37 (d, 6H, J = 6.0 Hz), 3.18-3.22 (m, 8H), 4.52 (s, 2H), 4.58-4.65 (m, 1H), 5.10 (s, 2H), 6.58 (d, 1H, J = 8.5 Hz), 6.70 (s, 1H), 6.83 (d, 1H, J = 8.5 Hz), 6.96 (d, 2H, J = 8.5 Hz), 7.30-7.40 (m, 5H), 7.81 (d, 2H, J = 8.5 Hz). |
| II-72 | (DMSO-d6) 1.30 (d, J = 6.3 Hz, 6H), 2.97 (brs, 4H), 3.15 (s, 3H), 3.26 (brs, 4H), 4.58-4.80 (m, 3H), 5.71 (d, J = 3.3 Hz, 1H), 6.29 (s, 1H), 6.45 (dd, J = 2.1, 8.7 Hz, 1H), 6.59 (s, 1H), 6.99 (d, J = 8.4 Hz, 1H), 7.15 (d, J = 9.0 Hz, 2H), 7.62-7.69 (m, 3H) |
| II-73 | (CDCl3) 1.37 (d, 6H, J = 6.0 Hz), 2.43 (s, 3H), 3.16 (br, 4H), 3.45 (br, 4H), 4.63 (m, 1H), 4.85 (s, 2H), 6.43 (br, 1H), 6.57 (br, 1H), 6.96-7.01 (m, 3H), 7.68-7.75 (m, 3H). |
| II-74 | (CDCl3) 1.37 (d, 6H, J = 6.0 Hz), 3.16 (t, 4H), 3.42 (t, 4H), 4.63 (m, 1H), 4.77 (s, 2H), 6.40 (d, 1H, J = 2.7 Hz), 6.62 (dd, 1H, J = 9.0, 2.4 Hz), 6.98 (d, 2H, J = 3.0 Hz), 7.27 (d, 1H), 7.67-7.72 (m, 3H), 7.79 (d, 1H, J = 3.0 Hz). |
| II-75 | (CDCl3) 1.37 (d, 6H, J = 6.0 Hz), 2.79 (s, 3H), 3.16 (t, 4H), 3.43 (t, 4H), 4.63 (m, 1H), 4.82 (s, 2H), 6.41 (d, 1H, J = 2.1 Hz), 6.57 (dd, 1H, J = 8.4, 2.4 Hz), 6.98 (d, 2H, J = 8.7 Hz), 7.62 (d, 1H, J = 8.4 Hz), 7.69 (d, 2H). |
| II-76 | (DMSO-d6) 1.30 (d, 6H, J = 6.0 Hz), 3.18-3.22 (m, 8H), 4.59 (s, 2H), 4.58-4.65 (m, 1H), 6.38 (d, 1H, J = 8.5 Hz), 6.50 (s, 1H), 6.65 (d, 2H, J = 8.5 Hz), 7.12 (d, 1H, J = 8.5 Hz), 7.61 (d, 2H, J = 8.5 Hz). |
| II-77 | (CDCl3) 1.37 (d, 6H, J = 6.0 Hz), 3.18-3.22 (m, 8H), 4.52 (s, 2H), 4.58-4.65 (m, 1H), 5.10 (s, 2H), 6.58 (d, 1H, J = 7.5 Hz), 6.70 (s, 1H), 6.83 (d, 1H, J = 8.5 Hz), 6.96 (d, 2H, J = 8.5 Hz), 7.41 (s, 1H), 7.48 (s, 1H), 7.81 (d, 2H, J = 8.5 Hz). |
| II-78 | (CDCl3) 1.03 (d, 6H, J = 6.0 Hz), 1.37 (d, 6H, J = 6.0 Hz), 2.01-2.11 (m, 1H), 3.18-3.22 (m, 8H), 3.75 (d, 2H, J = 6.0), 4.62 (s, 2H), 4.60-4.69 (m, 1H), 6.58 (d, 1H, J = 7.5 Hz), 6.65 (s, 1H), 6.83 (d, 1H, J = 7.5 Hz), 6.96 (d, 2H, J = 8.5 Hz), 7.81 (d, 2H, J = 8.5 Hz). |

TABLE 36

| Comd. No. | ¹H-NMR(Solvent)δ |
|---|---|
| II-79 | (DMSO-d6) 1.31 (d, J = 6.0 Hz, 6H), 2.95-3.02 (m, 4H), 3.14-3.24 (m, 4H), 4.64 (s, 2H), 4.76 (sep, J = 6.0 Hz, 1H), 6.44 (dd, J = 2.4, 8.7 Hz, 1H), 6.63 (d, J = 2.4 Hz, 1H), 6.78-6.83 (m, 2H), 6.89 (d, J = 8.7 Hz, 1H), 6.96 (m, 1H), 7.15 (d-like, 2H), 7.22-7.29 (m, 2H), 7.68 (d-like, 2H), 12.88 (br, 1H) |
| II-80 | (DMSO-d6) 1.29 (d, 6H, J = 6.0 Hz), 2.93 (t, 4H), 3.43 (t, 4H), 4.74 (m, 1H), 4.83 (s, 2H), 6.50 (d, 1H), 6.54 (dd, 1H, J = 8.1, 1.8 Hz), 7.13 (d, 2H, J = 8.7 Hz), 7.44 (d, 1H, J = 8.7 Hz), 7.65 (d, 1H). |
| II-81 | (DMSO-d6) 1.30 (d, 6H, J = 6.0 Hz), 2.95 (t, 4H), 3.38 (t, 4H), 4.74 (m, 1H), 4.79 (s, 2H), 6.50 (d, 1H), 6.55 (dd, 1H, J = 8.7 Hz), 7.13 (d, 2H, J = 9.0 Hz), 7.32 (br, 1H), 7.67 (d, 2H), 7.77 (d, 1H), 8.01 (br, 1H). |
| II-82 | (DMSO-d6) 1.29 (d, 6H, J = 6.0 Hz), 2.78 (d, 3H, 4.5 Hz), 2.95 (t, 4H), 3.35 (t, 4H), 4.74 (m, 1H), 4.81 (s, 2H), 6.50 (d, 1H, J = 2.1 Hz), 6.56 (dd, 1H, J = 9.0, 2.1 Hz), 7.13 (d, 2H, J = 9.0 Hz), 7.67 (d, 2H), 7.75 (d, 1H), 8.54 (d, 1H). |
| II-83 | (DMSO-d6) 0.88 (t, 3H, J = 7.2 Hz), 1.29 (d, 6H, J = 6.0 Hz), 1.54 (m, 2H), 2.95 (t, 4H), 3.36 (t, 4H), 4.74 (m, 1H), 4.80 (s, 2H), 6.51 (d, 1H), 6.56 (dd, 1H, J = 8.4, 2.1 Hz), 7.13 (d, 2H, J = 8.7 Hz), 7.66 (d, 2H), 7.76 (d, 1H), 8.58 (t, 1H). |

TABLE 36-continued

| Comd. No. | ¹H-NMR(Solvent)δ |
|---|---|
| II-84 | (DMSO-d6) 1.29 (d, J = 6.0 Hz, 6H), 2.97 (brs, 4H), 3.33 (brs, 4H), 4.70-4.78 (m, 3H), 6.59-6.61 (m, 2H), 7.14 (d, J = 9.0 Hz, 2H), 7.52 (d, J = 9.0 Hz, 1H), 7.67 (d, J = 9.0 Hz, 2H), 7.74 (s, 1H), 8.29 (s, 1H) |
| II-85 | (DMSO-d6) 1.32 (d, J = 6.0 Hz, 6H), 3.05 (brs, 4H), 3.32 (brs, 4H), 4.79 (s, 2H), 5.30-5.40 (m, 1H), 6.61-6.63 (m, 2H), 6.96 (d, J = 8.7 Hz, 1H), 7.52 (d, J = 8.7 Hz, 1H), 7.73 (s, 1H), 8.00 (dd, J = 2.7, 8.7 Hz, 1H), 8.29 (s, 1H), 8.55 (d, J = 2.4 Hz, 1H), 13.11 (brs, 1H) |
| II-86 | (CDCl3) 1.37 (d, 6H, J = 6.0 Hz), 3.18-3.22 (m, 8H), 4.58-4.65 (m, 1H), 6.58 (d, 1H, J = 15.5 Hz), 6.70-6.90 (m, 3H), 6.96 (d, 2H, J = 8.5 Hz), 7.61 (d, 2H, J = 8.5 Hz), 8.96 (d, 1H, J = 15.5 Hz). |
| II-87 | (CDCl3) 1.37 (d, 6H, J = 6.0 Hz), 3.18-3.22 (m, 8H), 4.58-4.65 (m, 1H), 5.10 (s, 2H), 6.58 (d, 1H, J = 15.5 Hz), 6.70-6.90 (m, 3H), 6.96 (d, 2H, J = 8.5 Hz), 7.30-7.40 (m, 5H), 7.81 (d, 2H, J = 8.5 Hz), 8.96 (d, 1H, J = 15.5 Hz). |
| II-88 | (DMSO-d6) 1.29 (d, 6H, J = 6.0 Hz), 2.97 (t, 4H), 3.41 (t, 4H), 4.74 (m, 1H), 4.91 (s, 2H), 6.64 (d, 1H), 6.68 (dd, 1H, J = 9.0 Hz), 7.14 (d, 2H, J = 9.0 Hz), 7.67 (d, 2H), 8.14 (d, 1H, J = 9.0 Hz), 9.49 (s, 1H). |
| II-89 | (DMSO-d6) 0.55 (m, 2H), 0.68 (m, 2H), 1.29 (d, 6H, J = 6.3 Hz), 2.90 (t, 4H), 3.37 (t, 4H), 4.74 (m, 1H), 4.76 (s, 2H), 6.48 (d, 1H, J = 1.8 Hz), 6.56 (dd, 1H, J = 9.0 Hz), 7.13 (d, 2H, J = 8.7 Hz), 7.66 (d, 2H), 7.77 (d, 1H), 8.61 (d, 1H, J = 4.8 Hz). |
| II-90 | (DMSO-d6) 1.28 (d, J = 6.0 Hz, 6H), 2.88 (brs, 4H), 3.53 (brs, 4H), 4.66-4.76 (m, 3H), 6.30 (d, J = 8.4 Hz, 1H), 7.09 (d, J = 9.0 Hz, 2H), 7.64 (d, J = 9.0 Hz, 3H) |

TABLE 37

| Comd. No. | ¹H-NMR(Solvent)δ |
|---|---|
| II-91 | (DMSO-d6) 1.29 (d, J = 6.0 Hz, 6H), 2.50 (s, 3H), 2.94 (brs, 4H), 3.42 (brs, 4H), 4.70-4.79 (m, 3H), 6.45 (d, J = 2.4 Hz, 1H), 6.52 (dd, J = 2.4, 8.4 Hz, 1H), 7.13 (d, J = 9.0 Hz, 2H), 7.55 (d, J = 9.0 Hz, 1H), 7.66 (d, J = 8.7 Hz, 2H), 13.07 (brs, 1H) |
| II-92 | (DMSO-d6) 1.29 (d, 6H, J = 6.0 Hz), 2.97 (t, 4H), 3.38 (t, 4H), 4.74 (m, 1H), 4.93 (s, 2H), 6.61 (d, 1H), 6.64 (dd, 1H, J = 9.3 Hz), 7.14 (d, 2H, J = 9.0 Hz), 7.63-7.69 (m, 3H), 7.83 (d, 1H, J = 3.0 Hz), 8.08 (d, 1H). |
| II-93 | (DMSO-d6) 1.29 (d, 6H, J = 6.0 Hz), 2.95 (t, 4H), 3.23 (s, 3H), 3.43 (t, 4H), 4.74 (m, 1H), 4.86 (s, 2H), 6.54-6.59 (m, 2H), 6.68 (dd, 1H, J = 9.0 Hz), 7.14 (d, 2H, J = 9.0 Hz), 7.54 (d, 1H, J = 9.3 Hz), 7.67 (d, 2H). |
| II-94 | (DMSO-d6) 1.32 (d, J = 6.3 Hz, 6H), 3.05 (brs, 4H), 3.39 (brs, 4H), 4.82 (s, 2H), 5.29-5.38 (m, 1H), 6.59 (s, 1H), 6.64 (d, J = 8.4 Hz, 1H), 6.96 (d, J = 8.7 Hz, 1H), 7.37 (s, 1H), 7.69 (d, J = 9.0 Hz, 1H), 8.00 (dd, J = 2.7, 8.7 Hz, 1H), 8.13 (s, 1H), 8.55 (d, J = 2.7 Hz, 1H) |
| II-95 | 1H NMR (DMSO-d6) 1.30 (d, J = 6.0 Hz, 6H), 2.97 (brs, 4H), 3.25 (brs, 4H), 4.70-4.80 (m, 3H), 6.41 (s, 1H), 6.57 (d, 1H), 6.66 (s, 1H), 7.14 (d, J = 8.7 Hz, 2H), 7.47 (d, J = 8.4 Hz, 1H), 7.61 (s, 1H), 7.67 (d, J = 8.7 Hz, 2H), 8.36 (s, 1H) |
| II-96 | 1H NMR (DMSO-d6) 1.29 (d, J = 6.0 Hz, 6H), 2.96 (brs, 4H), 3.26 (brs, 4H), 4.30 (s, 2H), 4.69-4.77 (m, 1H), 6.50 (s, 1H), 6.53 (d, J = 9.0 Hz, 1H), 7.12 (d, J = 8.7 Hz, 2H), 7.65 (d, J = 9.0 Hz, 2H), 7.78 (d, J = 8.7 Hz, 1H), 8.31 (s, 1H), 9.13 (s, 1H) |
| II-99 | 1H NMR (CDCl3) 1.36 (d, 6H, J = 6.0 Hz), 3.08-3.15 (m, 4H), 3.25-3.35 (m, 4H), 4.58-4.65 (m, 1H), 4.69 (s, 2H), 4.78 (d, 2H, J = 6.0 Hz), 6.24 (s, 1H), 6.52 (d, 1H, J = 8.5 Hz), 6.87-6.91 (m, 1H), 6.96 (d, 2H, J = 8.5 Hz), 6.96-6.98 (m, 1H), 7.14 (d, 1H, J = 8.5 Hz), 7.68 (d, 2H, J = 8.5 Hz), 7.90 (d, 1H, J = 8.5 Hz), 8.30-8.35 (m, 1H). |
| II-100 | 1H NMR (DMSO-d6) 1.30 (d, 6H, J = 6.0 Hz), 3.08-3.15 (m, 4H), 3.25-3.35 (m, 4H), 4.55 (d, 2H, J = 6.0 Hz), 4.74-4.84 (m, 1H), 4.79 (s, 2H), 6.53 (s, 1H), 6.58 (d, 1H, J = 8.5 Hz), 7.14 (d, 2H, J = 8.5 Hz), 7.20-7.24 (m, 1H), 7.32 (d, 1H, J = 8.5 Hz), 7.64 (d, 2H, J = 8.5 Hz), 7.69-7.72 (m, 1H), 7.79 (d, 1H, J = 8.5 Hz), 8.48 (d, 1H, J = 4.5 Hz), 9.30-9.35 (m, 1H). |

TABLE 38

| Comd. No. | ¹H-NMR(Solvent)δ |
|---|---|
| II-101 | 1H NMR (DMSO-d6) 1.30 (d, 6H, J = 6.0 Hz), 3.08-3.15 (m, 4H), 3.25-3.35 (m, 4H), 4.35 (s, 2H), 4.74-4.84 (m, 1H), 6.12 (d, 1H, J = 8.5 Hz), 6.53 (s, 1H), 6.58-6.70 (m, 2H), 7.00 (t, 1H, J = 7.6 Hz), 7.13 (t, 1H, J = 7.6 Hz), 7.15 (d, 2H, J = 8.5 Hz), 7.28 (d, 1H, J = 7.6 Hz), 7.64 (d, 2H, J = 8.5 Hz). |
| II-102 | 1H-NMR (DMSO-d6) 8.13 (1H, d, J = 0.8 Hz), 7.67 (2H, d, J = 8.9 Hz), 7.51 (1H, dd, J = 8.2, 1.8 Hz), 7.30-7.30 (2H, m), 7.15 (2H, d, J = 9.0 Hz), 7.01 (1H, d, J = 8.4 Hz), 4.77-4.75 (3H, m), 3.19-3.16 (4H, m), 3.02-2.99 (4H, m), 1.31 (6H, d, J = 6.0 Hz). |
| II-103 | 1H-NMR (CDCl3) 1.38 (6H, d, J = 6.1 Hz), 3.20 (8H, s), 4.51 (2H, s), 4.61-4.69 (1H, m), 6.56 (1H, s), 6.67 (1H, d, J = 9.0 Hz), 6.98 (2H, d, J = 8.9 Hz), 7.11 (1H, d, J = 9.0 Hz), 7.69 (2H, d, J = 8.9 Hz). |
| II-105 | 1H-NMR (CDCl3) 8.04 (0.5H, s), 7.85 (1H, d, J = 8.7 Hz), 7.73 (2H, d, J = 8.9 Hz), 7.01 (2H, d, J = 8.9 Hz), 6.64-6.61 (1H, m), 4.78 (2H, s), 4.71-4.63 (1H, m), 4.12-4.04 (1H, m), 3.42-3.32 (6H, m), 3.23 (4H, brs), 1.41 (6H, d, J = 6.0 Hz), 1.26 (6H, d, J = 6.0 Hz), 1.14-1.07 (1H, m), 0.58-0.53 (2H, m), 0.32-0.24 (2H, m). |
| II-106 | 1H NMR (DMSO-d6) 1.29 (d, 6H, J = 6.0 Hz), 3.08-3.15 (m, 4H), 3.25-3.35 (m, 4H), 4.45 (d, 2H, J = 6.0 Hz), 4.74-4.84 (m, 1H), 4.81 (s, 2H), 6.22 (d, 1H, J = 2.3 Hz), 6.32 (d, 1H, J = 2.3 Hz), 6.50 (s, 1H), 6.58 (d, 1H, J = 8.5 Hz), 7.14 (d, 2H, J = 8.5 Hz), 7.52 (d, 1H, J = 2.3 Hz), 7.64 (d, 2H, J = 8.5 Hz), 7.76 (d, 1H, J = 8.5 Hz), 8.90-8.95 (m, 1H). |
| II-108 | 1H-NMR (DMSO-d6) 1.29 (6H, d, J = 6.0 Hz), 2.96 (4H, m), 3.48 (4H, m), 4.74 (1H, tt, J = 6.0, 6.0 Hz), 4.96 (2H, s), 6.60 (1H, d, J = 2.1 Hz), 6.66 (1H, d, J = 2.1, 9.0 Hz), 7.13 (2H, d, J = 9.0 Hz), 7.22 (1H, d, J = 3.6 Hz), 7.47 (1H, d, J = 3.6 Hz), 7.66 (2H, d, J = 9.0 Hz), 7.84 (1H, d, J = 9.0 Hz), 11.56 (1H, brs). |
| II-109 | 1H-NMR (DMSO-d6) 1.29 (6H, d, J = 6.0 Hz), 2.95 (4H, m), 3.39 (4H, m), 4.74 (1H, tt, J = 6.0, 6.0 Hz), 4.77 (2H, s), 6.47 (1H, d, J = 2.4 Hz), 6.54 (1H, d, J = 2.4, 9.0 Hz), 7.13 (2H, d, J = 9.0 Hz), 7.62 (1H, d, J = 9.0 Hz), 7.66 (2H, d, J = 9.0 Hz), 11.8 (1H, br), 13.0 (1H, br). |
| II-110 | 1H-NMR (DMSO-d6) 1.28 (6H, d, J = 6.0 Hz), 2.96 (4H, m), 3.50 (4H, m), 4.73 (1H, tt, J = 6.0, 6.0 Hz), 4.96 (2H, s), 6.61 (1H, d, J = 2.1 Hz), 6.67 (1H, dd, J = 2.1, 9.0 Hz), 7.13 (2H, d, J = 9.0 Hz), 7.67 (2H, d, J = 9.0 Hz), 7.84 (1H, d, J = 9.0 Hz), 9.16 (1H, s), 11.88 (1H, brs), 13.5 (1H, br). |

TABLE 39

| Comd. No. | ¹H-NMR(Solvent)δ or [M + H]+ |
|---|---|
| II-111 | 1H-NMR (DMSO-d6) 1.28 (6H, d, J = 6.0 Hz), 2.96 (4H, m), 3.42 (4H, m), 3.73 (3H, s), 4.74 (1H, tt, J = 6.0, 6.0 Hz), 4.93 (2H, s), 6.54 (1H, d, J = 2.4 Hz), 6.57 (1H, d, J = 2.4 Hz), 6.61 (1H, dd, J = 2.4, 9.0 Hz), 7.13 (2H, d, J = 9.0 Hz), 7.55 (1H, d, J = 2.4 Hz), 7.67 (2H, d, J = 9.0 Hz), 7.81 (1H, d, J = 9.0 Hz), 10.32 (1H, s), 13.35 (1H, brs). |
| II-112 | 1H NMR (DMSO-d6) 0.63-0.68 (m, 2H), 0.88-0.92 (m, 2H), 1.30 (d, 6H, J = 6.0 Hz), 1.93-1.96 (m, 1H), 3.08-3.15 (m, 4H), 3.25-3.35 (m, 4H), 4.74-4.84 (m, 1H), 4.90 (s, 2H), 6.18 (s, 1H), 6.53 (s, 1H), 6.58 (d, 1H, J = 8.5 Hz), 7.14 (d, 2H, J = 8.5 Hz), 7.64 (d, 2H, J = 8.5 Hz), 7.79 (d, 1H, J = 8.5 Hz), 9.80-9.85 (m, 1H). |
| II-113 | 1H-NMR (CDCl3) 7.69 (2H, d, J = 6.9 Hz), 7.07 (1H, d, J = 9.0 Hz), 6.97 (2H, d, J = 6.9 Hz), 6.54 (2H, d, J = 6.7 Hz), 4.77 (2H, s), 4.67-4.59 (1H, m), 3.72-3.60 (4H, m), 3.35-3.33 (4H, m), 3.18-3.16 (4H, m), 1.38 (6H, d, J = 6.1 Hz). |
| II-114 | 1H-NMR (CDCl3) 7.73 (2H, d, J = 8.9 Hz), 7.25 (1H, d, J = 9.1 Hz), 7.02 (2H, d, J = 8.9 Hz), 6.60 (2H, s), 4.82 (2H, s), 4.72-4.64 (1H, m), 3.71 (4H, m), 3.40-3.38 (4H, m), 3.24-3.22 (4H, m), 1.99 (4H, m), 1.42 (6H, d, J = 6.0 Hz). |
| II-115 | 1H-NMR (CDCl3) 7.73 (2H, d, J = 9.4 Hz), 7.16 (1H, d, J = 9.1 Hz), 7.02 (2H, d, J = 8.9 Hz), 6.59-6.57 (2H, m), 4.81 (2H, s), 4.72-4.64 (1H, m), 3.40-3.38 (4H, m), 3.22-3.17 (10H, m), 1.42 (6H, d, J = 6.0 Hz). |
| II-116 | [M + H]+ = 494 |
| II-117 | [M + H]+ = 480 |
| II-118 | 1H NMR (CDCl3) 1.36 (d, 6H, J = 6.0 Hz), 3.08-3.15 (m, 4H), 3.25-3.35 (m, 4H), 4.58-4.65 (m, 1H), 4.78 (s, 2H), 6.42 (s, 1H), |

TABLE 39-continued

| Comd. No. | $^1$H-NMR(Solvent)δ or [M + H]+ |
|---|---|
| | 6.45 (d, 1H, J = 8.5 Hz), 6.96 (d, 2H, J = 8.5 Hz), 7.32 (d, 1H, J = 8.5 Hz), 7.44 (t, 2H, J = 8.0 Hz), 7.60 (t, 1H, J = 8.0 Hz), 7.74 (d, 2H, J = 8.5 Hz), 7.79 (d, 2H, J = 8.0 Hz). |

TABLE 40

| Comd. No. | $^1$H-NMR(Solvent)δ or [M + H]+ |
|---|---|
| II-122 | 1H NMR (CDCl3) 1.36 (d, 6H, J = 6.0 Hz), 3.15-3.35 (m, 8H), 3.94 (s, 2H), 4.52 (s, 2H), 4.60-4.66 (m, 1H), 6.42 (s, 1H), 6.45 (d, 1H, J = 8.5 Hz), 6.96 (d, 2H, J = 8.5 Hz), 7.08 (d, 1H, J = 8.5 Hz), 7.16-7.30 (m, 5H), 7.74 (d, 2H, J = 8.5 Hz), 7.70 (d, 2H, J = 8.0 Hz). |
| II-123 | 1H NMR (CDCl3) 1.36 (d, 6H, J = 6.0 Hz), 3.08-3.15 (m, 4H), 3.25-3.35 (m, 4H), 4.61-4.67 (m, 1H), 4.78 (s, 2H), 6.45 (s, 1H), 6.52 (d, 1H, J = 8.5 Hz), 6.97 (d, 2H, J = 8.5 Hz), 7.15 (t, 1H, J = 4.0 Hz), 7.56 (d, 2H, J = 8.5 Hz), 7.60 (s, 1H), 7.74 (d, 2H, J = 8.5 Hz), 7.70 (d, 2H, J = 4.0 Hz). |
| II-127 | 1H-NMR (CDCl3) 8.09 (0.5H, s), 7.80-7.69 (4H, m), 7.57-7.52 (1H, m), 7.45-7.39 (3H, m), 7.00 (2H, d, J = 8.9 Hz), 6.59 (1H, d, J = 10.0 Hz), 6.39 (1H, s), 4.68-4.64 (1H, m), 4.36 (2H, s), 3.23 (8H, br s), 1.41 (6H, d, J = 6.0 Hz). |
| II-128 | [M + H]+ = 440 |
| II-129 | 1H NMR (CDCl3) 1.36 (d, 6H, J = 6.0 Hz), 3.08-3.15 (m, 4H), 3.25-3.35 (m, 4H), 4.61-4.67 (m, 1H), 4.76 (s, 2H), 6.40 (s, 1H), 6.52 (d, 1H, J = 8.5 Hz), 6.65 (d, 1H, J = 4.0 Hz), 6.97 (d, 2H, J = 8.5 Hz), 7.20 (d, 2H, J = 4.0 Hz), 7.60-7.70 (m, 3H). |
| II-130 | 1H-NMR (DMSO-d6) 10.48 (1H, s), 7.65 (2H, d, J = 8.5 Hz), 7.14 (2H, d, J = 8.4 Hz), 6.72 (1H, d, J = 7.8 Hz), 6.53-6.49 (2H, m), 4.79-4.71 (1H, m), 4.48 (2H, s), 3.12-3.09 (4H, m), 2.96-2.93 (4H, m), 1.30 (6H, d, J = 6.1 Hz). |
| II-131 | 1H-NMR (CDCl3) 7.76-7.71 (2H, m), 7.53-7.51 (1H, m), 7.03-7.00 (2H, m), 6.66 (2H, td, J = 5.0, 2.6 Hz), 4.74-4.62 (1H, m), 4.57 (2H, s), 3.55 (3H, s), 3.31-3.22 (8H, m), 1.42 (6H, d, J = 6.0 Hz). |
| II-133 | 1H-NMR (DMSO-d6) 8.31 (0.5H, s), 7.66 (2H, d, J = 8.9 Hz), 7.14 (2H, d, J = 8.9 Hz), 7.03 (1H, d, J = 8.7 Hz), 6.58 (1H, d, J = 2.6 Hz), 6.50 (1H, dd, J = 8.8, 2.4 Hz), 4.79-4.71 (1H, m), 4.48 (2H, s), 3.19-3.17 (4H, m), 2.97-2.94 (4H, m), 2.85 (3H, s), 1.30 (6H, d, J = 6.0 Hz). |
| II-134 | [M + H]+ = 459 |
| II-135 | [M + H]+ = 479 |

TABLE 41

| Comd. No. | $^1$H-NMR(Solvent)δ or [M + H]+ |
|---|---|
| II-140 | 1H NMR (CDCl3) 1.37 (d, J = 6.0 Hz, 6H), 3.23 (brs, 4H), 3.37 (brs, 4H), 4.09 (brs, 2H), 4.63 (m, 1H), 6.16 (brs, 1H), 6.39 (m, 1H), 6.97 (d, J = 9.0 Hz, 2H), 7.19 (s, 1H), 7.60 (s, 1H), 7.69 (d, J = 9.0 Hz, 2H), 7.80 (d, J = 9.0 Hz, 1H) |
| II-141 | 1H-NMR (CDCl3) 1.37 (6H, d, J = 6.0 Hz), 3.06-3.19 (8H, m), 3.40-3.46 (4H, m), 3.69-3.75 (4H, m), 4.59-4.67 (1H, m), 4.70 (2H, s), 6.27 (1H, d, J = 1.9 Hz), 6.53 (1H, dd, J = 8.9, 1.9 Hz), 6.98 (2H, d, J = 8.8 Hz), 7.63 (1H, d, J = 8.9 Hz), 7.69 (2H, d, J = 8.8 Hz). |
| II-142 | 1H-NMR (DMSO-d6) 1.33 (6H, d, J = 5.8 Hz), 2.96-3.02 (4H, m), 3.11-3.16 (4H, m), 4.59 (2H, s), 4.62 (2H, s), 4.72-4.84 (1H, m), 6.56 (1H, dd, J = 8.8, 2.2 Hz), 6.67 (1H, d, J = 2.2 Hz), 6.90 (1H, d, J = 8.8 Hz), 7.17 (2H, d, J = 8.8 Hz), 7.70 (2H, d, J = 8.8 Hz). |
| II-143 | [M + H]+ = 492 |

Moreover, compounds in Tables 42-47 can be prepared in the same manner as set forth above.

TABLE 42

| Comd. No. | Structure |
|---|---|
| IV-1 | (structure) |
| IV-2 | (structure) |
| IV-3 | (structure) |
| IV-4 | (structure) |
| IV-5 | (structure) |

TABLE 43

| Comd. No. | Structure |
|---|---|
| IV-6 | (structure) |
| IV-7 | (structure) |
| IV-8 | (structure) |
| IV-9 | (structure) |
| IV-10 | (structure) |

TABLE 44

| Comd. No. | Structure |
|---|---|
| IV-11 | 4-[4-[(4-isopropoxyphenyl)sulfonyl]piperazin-1-yl]-2-[(benzyloxycarbamoyl)methoxy]-1-nitrobenzene |
| IV-12 | 2-[5-[4-[(3,4-dimethoxyphenyl)sulfonyl]piperazin-1-yl]-2-bromophenoxy]acetic acid |
| IV-13 | 2-[5-[4-[(4-isopropoxyphenyl)sulfonyl]piperazine-1-carbonyl]-2-bromophenoxy]acetic acid |
| IV-14 | 2-[N-methyl-N-[5-[4-[(4-isopropoxyphenyl)sulfonyl]piperazin-1-yl]-2-nitrophenyl]amino]acetic acid |
| IV-15 | 2-[N,N-dimethyl-N-[5-[4-[(4-isopropoxyphenyl)sulfonyl]piperazin-1-yl]-2-nitrophenyl]ammonio]acetic acid iodide |

TABLE 45

| Comd. No. | Structure |
|---|---|
| V-1 | methyl 2-(2,5-dibromophenoxy)acetate |
| V-2 | methyl 2-(5-chloro-2-methylphenoxy)acetate |
| V-3 | methyl 2-(5-chloro-2-methoxyphenoxy)acetate |
| V-4 | methyl 2-[5-chloro-2-(dimethylamino)phenoxy]acetate |
| V-5 | methyl 2-(2-acetamido-5-bromophenoxy)acetate |
| V-6 | methyl 2-[5-chloro-2-(methoxycarbonyl)phenoxy]acetate |
| V-7 | methyl 2-[5-chloro-2-(methylcarbamoyl)phenoxy]acetate |
| V-8 | methyl 2-(5-chloro-2-cyanophenoxy)acetate |

TABLE 45-continued
| Comd. No. | Structure |
|---|---|
| V-9 | 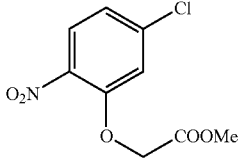 [SMILES: COC(=O)COc1cc(Cl)ccc1[N+](=O)[O-]] |
| V-10 | 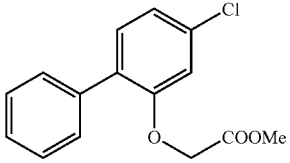 [SMILES: COC(=O)COc1cc(Cl)ccc1-c1ccccc1] |
| V-11 | 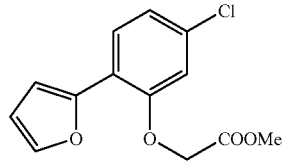 [SMILES: COC(=O)COc1cc(Cl)ccc1-c1ccco1] |
| V-12 | 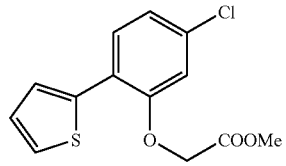 |
| V-13 | 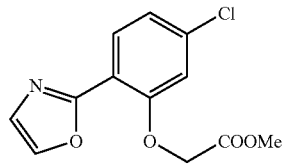 [SMILES: COC(=O)COc1cc(Cl)ccc1-c1ncco1] |
| V-14 | 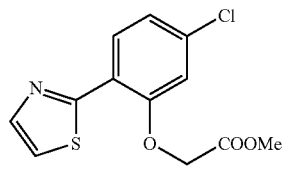 [SMILES: COC(=O)COc1cc(Cl)ccc1-c1nccs1] |
| V-15 | 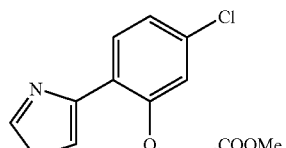 |
| V-16 | 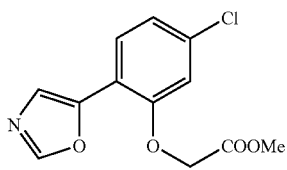 |
| V-17 | 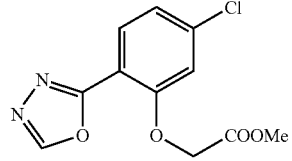 [SMILES: COC(=O)COc1cc(Cl)ccc1-c1nnco1] |
| V-18 | 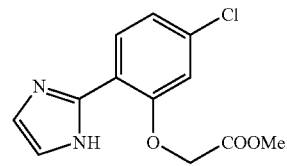 [SMILES: COC(=O)COc1cc(Cl)ccc1-c1ncc[nH]1] |
TABLE 46
| Comd. No. | Structure |
|---|---|
| V-19 | 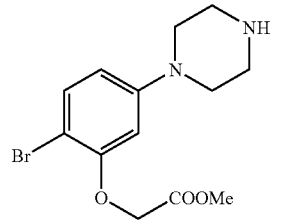 [SMILES: COC(=O)COc1cc(N2CCNCC2)ccc1Br] |
| V-20 | 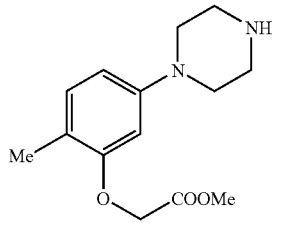 |
| V-21 | 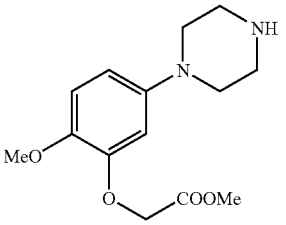 [SMILES: COC(=O)COc1cc(N2CCNCC2)ccc1OC] |
| V-22 | 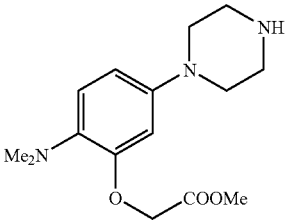 [SMILES: COC(=O)COc1cc(N2CCNCC2)ccc1N(C)C] |

TABLE 46-continued

| Comd. No. | Structure |
|---|---|
| V-23 | 4-(piperazin-1-yl)-2-(methoxycarbonylmethoxy)-N-acetyl-aniline derivative (MeC(O)NH-, -O-CH2-COOMe) |
| V-24 | methyl 4-(piperazin-1-yl)-2-(methoxycarbonylmethoxy)benzoate (MeO-C(O)-, -O-CH2-COOMe) |
| V-25 | 4-(piperazin-1-yl)-2-(methoxycarbonylmethoxy)-N-methylbenzamide (MeNH-C(O)-, -O-CH2-COOMe) |
| V-26 | 4-(piperazin-1-yl)-2-(methoxycarbonylmethoxy)benzonitrile (NC-, -O-CH2-COOMe) |
| V-27 | 4-(piperazin-1-yl)-2-(methoxycarbonylmethoxy)nitrobenzene (O2N-, -O-CH2-COOMe) |
| V-28 | 4-(piperazin-1-yl)-2-(methoxycarbonylmethoxy)biphenyl (Ph-, -O-CH2-COOMe) |
| V-29 | 4-(piperazin-1-yl)-2-(methoxycarbonylmethoxy)phenyl furan-2-yl |
| V-30 | 4-(piperazin-1-yl)-2-(methoxycarbonylmethoxy)phenyl thiophen-2-yl |
| V-31 | 4-(piperazin-1-yl)-2-(methoxycarbonylmethoxy)phenyl oxazol-2-yl |
| V-32 | 4-(piperazin-1-yl)-2-(methoxycarbonylmethoxy)phenyl thiazol-2-yl |

TABLE 47

| Comd. No. | Structure |
|---|---|
| V-33 | 4-(piperazin-1-yl)-2-(methoxycarbonylmethoxy)phenyl oxazol-4-yl |
| V-34 | 4-(piperazin-1-yl)-2-(methoxycarbonylmethoxy)phenyl oxazol-5-yl |

TABLE 47-continued

| Comd. No. | Structure |
|---|---|
| V-35 | (structure) |
| V-36 | (structure) |

Also, compounds of the formula (IA):

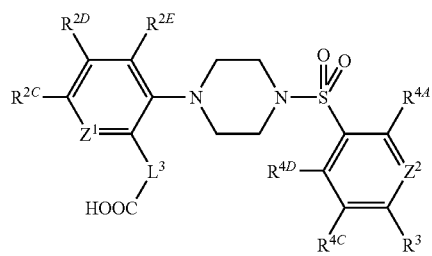

(IA)

wherein $Z^1$ is $CR^{2B}$ or N; $Z^2$ is $CR^{4B}$ or N; $R^{2B}$, $R^{2C}$, $R^{2D}$ and $R^{2E}$ are independently a hydrogen atom, a fluorine atom, a chlorine atom, a bromine atom, methyl, ethyl, allyl, propargyl, trifluoromethyl, methyloxy, difluoromethyloxy, methylthio, methylsulfonyl, phenyl, phenoxy, phenylthio, amino, methylamino, dimethylamino, methylcarbonylamino, methylsulfonylamino, nitro, cyano, methylcarbonyl, N-methylcarbamoyl, N-phenylcarbamoyl, 2-furyl, 2-thenyl, 2-pyridyl, 1,3-oxazol-2-yl, 1,3-oxazol-4-yl, 1,3-oxazol-5-yl, 1,3-thiazol-2-yl, 1,3-thiazol-4-yl, 1,3-thiazol-5-yl, 1,3,4-oxadiazol-2-yl, 1,3,4-thiadiazol-2-yl, imidazol-1-yl, pyrazol-1-yl, morpholino, pyrrolidino or piperizino; $R^3$ is methyloxy, ethyloxy, isopropyloxy, sec-butyloxy, difluoromethyloxy, 1-phenylethyloxy, phenoxy, methylthio, ethylthio, isopropylthio, sec-butylthio, difluoromethylthio, 1-phenylethylthio or phenylthio; $R^{4A}$, $R^{4B}$, $R^{4C}$ and $R^{4D}$ are independently a hydrogen atom, a fluorine atom, a chlorine atom, methyl or methyloxy; $L^3$ is a single bond, methylene, 1,1-dimethylmethylene, ethylene, —CH=CH—CH$_2$—, 1-propylene-1,3-diynel, —O—CH$_2$—, —O—CH(Me)—, —O—C(Me)$_2$—, —S—CH$_2$— or —NH—CH$_2$—; can be prepared in the same manner as set forth above.

A combination of $Z^1$, $R^{2C}$, $R^{2D}$ and $R^{2E}$ (part A) is shown in Tables 48-53. -$L^3$-COOH (part B) is shown in Table 54. A combination of $R^{4A}$, $Z^2$, $R^{4C}$, $R^{4D}$ (part C) is shown in Tables 55-60.

TABLE 48

| No. | $Z^1$ | $R^{2C}$ | $R^{2D}$ | $R^{2E}$ |
|---|---|---|---|---|
| A-1 | CH | H | H | H |
| A-2 | CH | F | H | H |
| A-3 | CH | Cl | H | H |
| A-4 | CH | Br | H | H |
| A-5 | CH | Me | H | H |
| A-6 | CH | Et | H | H |
| A-7 | CH | allyl | H | H |
| A-8 | CH | propargyl | H | H |
| A-9 | CH | CF3 | H | H |
| A-10 | CH | OMe | H | H |
| A-11 | CH | OCHF2 | H | H |
| A-12 | CH | SMe | H | H |
| A-13 | CH | SO2Me | H | H |
| A-14 | CH | Ph | H | H |
| A-15 | CH | OPh | H | H |
| A-16 | CH | SPh | H | H |
| A-17 | CH | NH2 | H | H |
| A-18 | CH | NHMe | H | H |
| A-19 | CH | NMe2 | H | H |
| A-20 | CH | NHCOMe | H | H |
| A-21 | CH | NHSO2Me | H | H |
| A-22 | CH | NO2 | H | H |
| A-23 | CH | CN | H | H |
| A-24 | CH | COMe | H | H |
| A-25 | CH | CONHMe | H | H |
| A-26 | CH | CONHPh | H | H |
| A-27 | CH | 2-furyl | H | H |
| A-28 | CH | 2-thienyl | H | H |
| A-29 | CH | 2-pyridyl | H | H |
| A-30 | CH | 1,3-oxazol-2-yl | H | H |
| A-31 | CH | 1,3-oxazol-4-yl | H | H |
| A-32 | CH | 1,3-oxazol-5-yl | H | H |
| A-33 | CH | 1,3-thiazol-2-yl | H | H |
| A-34 | CH | 1,3-thiazol-4-yl | H | H |
| A-35 | CH | 1,3-thiazol-5-yl | H | H |
| A-36 | CH | 1,3,4-oxadiazol-2-yl | H | H |
| A-37 | CH | 1,3,4-thiadiazol-2-yl | H | H |
| A-38 | CH | imidazol-1-yl | H | H |
| A-39 | CH | pyrazol-1-yl | H | H |
| A-40 | CH | morpholino | H | H |
| A-41 | CH | pyrrolidino | H | H |
| A-42 | CH | piperidino | H | H |
| A-43 | CH | piperazino | H | H |
| A-44 | CH | H | F | H |
| A-45 | CH | H | Cl | H |

TABLE 49

| No. | $Z^1$ | $R^{2C}$ | $R^{2D}$ | $R^{2E}$ |
|---|---|---|---|---|
| A-46 | CH | H | Br | H |
| A-47 | CH | H | Me | H |
| A-48 | CH | H | Et | H |
| A-49 | CH | H | allyl | H |
| A-50 | CH | H | propargyl | H |
| A-51 | CH | H | CF3 | H |
| A-52 | CH | H | OMe | H |
| A-53 | CH | H | OCHF2 | H |
| A-54 | CH | H | SMe | H |
| A-55 | CH | H | SO2Me | H |
| A-56 | CH | H | Ph | H |
| A-57 | CH | H | OPh | H |
| A-58 | CH | H | SPh | H |
| A-59 | CH | H | NH2 | H |
| A-60 | CH | H | NMe2 | H |
| A-61 | CH | H | NHCOMe | H |
| A-62 | CH | H | NHSO2Me | H |
| A-63 | CH | H | NO2 | H |
| A-64 | CH | H | CN | H |
| A-65 | CH | H | COMe | H |
| A-66 | CH | H | CONHMe | H |
| A-67 | CH | H | CONHPh | H |
| A-68 | CH | H | 2-furyl | H |
| A-69 | CH | H | 2-thienyl | H |
| A-70 | CH | H | 2-pyridyl | H |

TABLE 49-continued

| No. | $Z^1$ | $R^{2C}$ | $R^{2D}$ | $R^{2E}$ |
|---|---|---|---|---|
| A-71 | CH | H | 1,3-oxazol-2-yl | H |
| A-72 | CH | H | 1,3-oxazol-4-yl | H |
| A-73 | CH | H | 1,3-oxazol-5-yl | H |
| A-74 | CH | H | 1,3-thiazol-2-yl | H |
| A-75 | CH | H | 1,3-thiazol-4-yl | H |
| A-76 | CH | H | 1,3-thiazol-5-yl | H |
| A-77 | CH | H | 1,3,4-oxadiazol-2-yl | H |
| A-78 | CH | H | 1,3,4-thiadiazol-2-yl | H |
| A-79 | CH | H | imidazol-1-yl | H |
| A-80 | CH | H | pyrazol-1-yl | H |
| A-81 | CH | H | morpholino | H |
| A-82 | CH | H | pyrrolidino | H |
| A-83 | CH | H | piperidino | H |
| A-84 | CH | H | piperazino | H |
| A-85 | CH | H | H | F |
| A-86 | CH | H | H | Cl |
| A-87 | CH | H | H | Br |
| A-88 | CH | H | H | Me |
| A-89 | CH | H | H | Et |
| A-90 | CH | H | H | allyl |

TABLE 50

| No. | $Z^1$ | $R^{2C}$ | $R^{2D}$ | $R^{2E}$ |
|---|---|---|---|---|
| A-91 | CH | H | H | propargyl |
| A-92 | CH | H | H | CF3 |
| A-93 | CH | H | H | OMe |
| A-94 | CH | H | H | OCHF2 |
| A-95 | CH | H | H | SMe |
| A-96 | CH | H | H | SO2Me |
| A-97 | CH | H | H | Ph |
| A-98 | CH | H | H | OPh |
| A-99 | CH | H | H | SPh |
| A-100 | CH | H | H | NH2 |
| A-101 | CH | H | H | NHMe |
| A-102 | CH | H | H | NMe2 |
| A-103 | CH | H | H | NHCOMe |
| A-104 | CH | H | H | NHSO2Me |
| A-105 | CH | H | H | NO2 |
| A-106 | CH | H | H | CN |
| A-107 | CH | H | H | COMe |
| A-108 | CH | H | H | CONHMe |
| A-109 | CH | H | H | CONHPh |
| A-110 | CH | H | H | 2-furyl |
| A-111 | CH | H | H | 2-thienyl |
| A-112 | CH | H | H | 2-pyridyl |
| A-113 | CH | H | H | 1,3-oxazol-2-yl |
| A-114 | CH | H | H | 1,3-oxazol-4-yl |
| A-115 | CH | H | H | 1,3-oxazol-5-yl |
| A-116 | CH | H | H | 1,3-thiazol-2-yl |
| A-117 | CH | H | H | 1,3-thiazol-4-yl |
| A-118 | CH | H | H | 1,3-thiazol-5-yl |
| A-119 | CH | H | H | 1,3,4-oxadiazol-2-yl |
| A-120 | CH | H | H | 1,3,4-thiadiazol-2-yl |
| A-121 | CH | H | H | imidazol-1-yl |
| A-122 | CH | H | H | pyrazol-1-yl |
| A-123 | CH | H | H | morpholino |
| A-124 | CH | H | H | pyrrolidino |
| A-125 | CH | H | H | piperidino |
| A-126 | CH | H | H | piperazino |
| A-127 | N | Cl | H | H |
| A-128 | N | Br | H | H |
| A-129 | N | OMe | H | H |
| A-130 | N | NO2 | H | H |
| A-131 | N | CN | H | H |
| A-132 | N | CONHMe | H | H |
| A-133 | N | 2-furyl | H | H |
| A-134 | N | 2-thienyl | H | H |
| A-135 | N | 1,3-oxazol-2-yl | H | H |

TABLE 51

| No. | $Z^1$ | $R^{2C}$ | $R^{2D}$ | $R^{2E}$ |
|---|---|---|---|---|
| A-136 | N | 1,3-oxazol-4-yl | H | H |
| A-137 | N | 1,3-oxazol-5-yl | H | H |
| A-138 | N | 1,3-thiazol-2-yl | H | H |
| A-139 | N | 1,3-thiazol-4-yl | H | H |
| A-140 | N | 1,3-thiazol-5-yl | H | H |
| A-141 | N | 1,3,4-oxadiazol-2-yl | H | H |
| A-142 | N | 1,3,4-thiadiazol-2-yl | H | H |
| A-143 | N | imidazol-1-yl | H | H |
| A-144 | N | pyrazol-1-yl | H | H |
| A-145 | N | morpholino | H | H |
| A-146 | N | pyrrolidino | H | H |
| A-147 | N | piperidino | H | H |
| A-148 | N | piperazino | H | H |
| A-149 | N | 2-thienyl | H | H |
| A-150 | N | 2-pyridyl | H | H |
| A-151 | N | morpholino | H | H |
| A-152 | N | pyrrolidino | H | H |
| A-153 | N | piperidino | H | H |
| A-154 | CH | Cl | Cl | H |
| A-155 | CH | Br | Cl | H |
| A-156 | CH | OMe | Cl | H |
| A-157 | CH | NO2 | Cl | H |
| A-158 | CH | CN | Cl | H |
| A-159 | CH | CONHMe | Cl | H |
| A-160 | CH | 2-furyl | Cl | H |
| A-161 | CH | 2-thienyl | Cl | H |
| A-162 | CH | 1,3-oxazol-2-yl | Cl | H |
| A-163 | CH | 1,3-oxazol-4-yl | Cl | H |
| A-164 | CH | 1,3-oxazol-5-yl | Cl | H |
| A-165 | CH | 1,3-thiazol-2-yl | Cl | H |
| A-166 | CH | 1,3-thiazol-4-yl | Cl | H |
| A-167 | CH | 1,3-thiazol-5-yl | Cl | H |
| A-168 | CH | 1,3,4-oxadiazol-2-yl | Cl | H |
| A-169 | CH | 1,3,4-thiadiazol-2-yl | Cl | H |
| A-170 | CH | imidazol-1-yl | Cl | H |
| A-171 | CH | pyrazol-1-yl | Cl | H |
| A-172 | CH | morpholino | Cl | H |
| A-173 | CH | pyrrolidino | Cl | H |
| A-174 | CH | piperidino | Cl | H |
| A-175 | CH | piperazino | Cl | H |
| A-176 | CH | Cl | Cl | H |
| A-177 | CH | Br | Cl | H |
| A-178 | CH | OMe | Cl | H |
| A-179 | CH | NO2 | Cl | |
| A-180 | CH | CN | Cl | H |

TABLE 52

| No. | $Z^1$ | $R^{2C}$ | $R^{2D}$ | $R^{2E}$ |
|---|---|---|---|---|
| A-181 | CH | CONHMe | Cl | H |
| A-182 | CH | 2-furyl | Cl | H |
| A-183 | CH | 2-thienyl | Cl | H |
| A-184 | CH | 1,3-oxazol-2-yl | Cl | H |
| A-185 | CH | 1,3-oxazol-4-yl | Cl | H |
| A-186 | CH | 1,3-oxazol-5-yl | Cl | H |
| A-187 | CH | 1,3-thiazol-2-yl | Cl | H |
| A-188 | CH | 1,3-thiazol-4-yl | Cl | H |
| A-189 | CH | 1,3-thiazol-5-yl | Cl | H |
| A-190 | CH | 1,3,4-oxadiazol-2-yl | Cl | H |
| A-191 | CH | 1,3,4-thiadiazol-2-yl | Cl | H |
| A-192 | CH | imidazol-1-yl | Cl | H |
| A-193 | CH | pyrazol-1-yl | Cl | H |
| A-194 | CH | morpholino | Cl | H |
| A-195 | CH | pyrrolidino | Cl | H |
| A-196 | CH | piperidino | Cl | H |
| A-197 | CH | piperazino | Cl | H |
| A-198 | CH | Cl | H | Cl |
| A-199 | CH | Br | H | Cl |
| A-200 | CH | OMe | H | Cl |
| A-201 | CH | NO2 | H | Cl |
| A-202 | CH | CN | H | Cl |
| A-203 | CH | CONHMe | H | Cl |
| A-204 | CH | 2-furyl | H | Cl |
| A-205 | CH | 2-thienyl | H | Cl |

TABLE 52-continued

| No. | $Z^1$ | $R^{2C}$ | $R^{2D}$ | $R^{2E}$ |
|---|---|---|---|---|
| A-206 | CH | 1,3-oxazol-2-yl | H | Cl |
| A-207 | CH | 1,3-oxazol-4-yl | H | Cl |
| A-208 | CH | 1,3-oxazol-5-yl | H | Cl |
| A-209 | CH | 1,3-thiazol-2-yl | H | Cl |
| A-210 | CH | 1,3-thiazol-4-yl | H | Cl |
| A-211 | CH | 1,3-thiazol-5-yl | H | Cl |
| A-212 | CH | 1,3,4-oxadiazol-2-yl | H | Cl |
| A-213 | CH | 1,3,4-thiadiazol-2-yl | H | Cl |
| A-214 | CH | imidazol-1-yl | H | Cl |
| A-215 | CH | pyrazol-1-yl | H | Cl |
| A-216 | CH | morpholino | H | Cl |
| A-217 | CH | pyrrolidino | H | Cl |
| A-218 | CH | piperidino | H | Cl |
| A-219 | CH | piperazino | H | Cl |
| A-220 | CH | Cl | Me | H |
| A-221 | CH | Br | Me | H |
| A-222 | CH | OMe | Me | H |
| A-223 | CH | NO2 | Me | H |
| A-224 | CH | CN | Me | H |
| A-225 | CH | CONHMe | Me | H |

TABLE 53

| No. | $Z^1$ | $R^{2C}$ | $R^{2D}$ | $R^{2E}$ |
|---|---|---|---|---|
| A-226 | CH | 2-furyl | Me | H |
| A-227 | CH | 2-thienyl | Me | H |
| A-228 | CH | 1,3-oxazol-2-yl | Me | H |
| A-229 | CH | 1,3-oxazol-4-yl | Me | H |
| A-230 | CH | 1,3-oxazol-5-yl | Me | H |
| A-231 | CH | 1,3-thiazol-2-yl | Me | H |
| A-232 | CH | 1,3-thiazol-4-yl | Me | H |
| A-233 | CH | 1,3-thiazol-5-yl | Me | H |
| A-234 | CH | 1,3,4-oxadiazol-2-yl | Me | H |
| A-235 | CH | 1,3,4-thiadiazol-2-yl | Me | H |
| A-236 | CH | imidazol-1-yl | Me | H |
| A-237 | CH | pyrazol-1-yl | Me | H |
| A-238 | CH | morpholino | Me | H |
| A-239 | CH | pyrrolidino | Me | H |
| A-240 | CH | piperidino | Me | H |
| A-241 | CH | piperazino | Me | H |
| A-242 | CH | Cl | H | Me |
| A-243 | CH | Br | H | Me |
| A-244 | CH | OMe | H | Me |
| A-245 | CH | NO2 | H | Me |
| A-246 | CH | CN | H | Me |
| A-247 | CH | CONHMe | H | Me |
| A-248 | CH | 2-furyl | H | Me |
| A-249 | CH | 2-thienyl | H | Me |
| A-250 | CH | 1,3-oxazol-2-yl | H | Me |
| A-251 | CH | 1,3-oxazol-4-yl | H | Me |
| A-252 | CH | 1,3-oxazol-5-yl | H | Me |
| A-253 | CH | 1,3-thiazol-2-yl | H | Me |
| A-254 | CH | 1,3-thiazol-4-yl | H | Me |
| A-255 | CH | 1,3-thiazol-5-yl | H | Me |
| A-256 | CH | 1,3,4-oxadiazol-2-yl | H | Me |
| A-257 | CH | 1,3,4-thiadiazol-2-yl | H | Me |
| A-258 | CH | imidazol-1-yl | H | Me |
| A-259 | CH | pyrazol-1-yl | H | Me |
| A-260 | CH | morpholino | H | Me |
| A-261 | CH | pyrrolidino | H | Me |
| A-262 | CH | 4-Me-1,3-oxazol-2-yl | H | Me |
| A-263 | CH | 5-Me-1,3-oxazol-4-yl | H | Me |
| A-264 | CH | 2-Me-1,3-oxazol-5-yl | H | Me |
| A-265 | CH | 4-Me-1,3-thiazol-2-yl | H | Me |
| A-266 | CH | 5-Me-1,3-thiazol-4-yl | H | Me |
| A-267 | CH | 2-Me-1,3-thiazol-5-yl | H | Me |
| A-268 | CH | 5-Me-1,3,4-oxadiazol-2-yl | H | Me |
| A-269 | CH | 5-Me-1,3,4-thiadiazol-2-yl | H | Me |
| A-270 | CH | 5-Me-1,3-oxazol-2-yl | H | Me |

TABLE 54

| No. | $L^3$-COOH | No. | $L^3$-COOH |
|---|---|---|---|
| B-1 | —COOH | B-2 | —CH$_2$COOH |
| B-3 | —C(Me)$_2$COOH | B-4 | —CH$_2$CH$_2$COOH |
| B-5 | —CH═CH—COOH | B-6 | —C≡C—COOH |
| B-7 | —OCH$_2$COOH | B-8 | —OC(Me)$_2$COOH |
| B-9 | —SCH$_2$COOH | B-10 | —NHCH$_2$COOH |

TABLE 55

| No. | $R^3$ | $R^{4A}$ | $Z^2$ | $R^{4C}$ | $R^{4D}$ |
|---|---|---|---|---|---|
| C-1 | OMe | H | C—H | H | H |
| C-2 | OMe | H | C—H | H | F |
| C-3 | OMe | H | C—H | H | Cl |
| C-4 | OMe | H | C—H | H | Me |
| C-5 | OMe | H | C—H | F | H |
| C-6 | OMe | H | C—H | Cl | H |
| C-7 | OMe | H | C—H | Me | H |
| C-8 | OEt | H | C—H | H | H |
| C-9 | OEt | H | C—H | H | F |
| C-10 | OEt | H | C—H | H | Cl |
| C-11 | OEt | H | C—H | H | Me |
| C-12 | OEt | H | C—H | F | H |
| C-13 | OEt | H | C—H | Cl | H |
| C-14 | OEt | H | C—H | Me | H |
| C-15 | OCHMe$_2$ | H | C—H | H | H |
| C-16 | OCHMe$_2$ | H | C—H | H | F |
| C-17 | OCHMe$_2$ | H | C—H | H | Cl |
| C-18 | OCHMe$_2$ | H | C—H | H | Me |
| C-19 | OCHMe$_2$ | H | C—H | F | H |
| C-20 | OCHMe$_2$ | H | C—H | F | F |
| C-21 | OCHMe$_2$ | H | C—H | F | Cl |
| C-22 | OCHMe$_2$ | H | C—H | F | Me |
| C-23 | OCHMe$_2$ | H | C—H | Cl | H |
| C-24 | OCHMe$_2$ | H | C—H | Cl | F |
| C-25 | OCHMe$_2$ | H | C—H | Cl | Cl |
| C-26 | OCHMe$_2$ | H | C—H | Cl | Me |
| C-27 | OCHMe$_2$ | H | C—H | Me | H |
| C-28 | OCHMe$_2$ | H | C—H | Me | F |
| C-29 | OCHMe$_2$ | H | C—H | Me | Cl |
| C-30 | OCHMe$_2$ | H | C—H | Me | Me |
| C-31 | OCHMe$_2$ | H | C—F | H | F |
| C-32 | OCHMe$_2$ | H | C—F | H | Cl |
| C-33 | OCHMe$_2$ | H | C—F | H | Me |
| C-34 | OCHMe$_2$ | H | C—F | F | H |
| C-35 | OCHMe$_2$ | H | C—F | Cl | H |
| C-36 | OCHMe$_2$ | H | C—F | Me | H |
| C-37 | OCHMe$_2$ | H | C—Cl | H | F |
| C-38 | OCHMe$_2$ | H | C—Cl | H | Cl |
| C-39 | OCHMe$_2$ | H | C—Cl | H | Me |
| C-40 | OCHMe$_2$ | H | C—Cl | Cl | H |

TABLE 56

| No. | $R^3$ | $R^{4A}$ | $Z^2$ | $R^{4C}$ | $R^{4D}$ |
|---|---|---|---|---|---|
| C-41 | OCHMe$_2$ | H | C—Cl | Me | H |
| C-42 | OCHMe$_2$ | H | C-Me | H | F |
| C-43 | OCHMe$_2$ | H | C-Me | H | Cl |
| C-44 | OCHMe$_2$ | H | C-Me | H | Me |
| C-45 | OCHMe$_2$ | H | C-Me | Me | H |
| C-46 | OCHMe$_2$ | F | C—H | H | F |
| C-47 | OCHMe$_2$ | F | C—H | H | Cl |
| C-48 | OCHMe$_2$ | F | C—H | H | Me |
| C-49 | OCHMe$_2$ | Cl | C—H | H | Cl |
| C-50 | OCHMe$_2$ | Cl | C—H | H | Me |
| C-51 | OCHMe$_2$ | Me | C—H | H | Me |
| C-52 | OCHMe$_2$ | H | N | H | H |
| C-53 | OCHMe$_2$ | H | N | H | F |
| C-54 | OCHMe$_2$ | H | N | H | Cl |
| C-55 | OCHMe$_2$ | H | N | H | Me |
| C-56 | OCHMe$_2$ | H | N | F | H |
| C-57 | OCHMe$_2$ | H | N | Cl | H |
| C-58 | OCHMe$_2$ | H | N | Me | H |

TABLE 56-continued

| No. | $R^3$ | $R^{4A}$ | $Z^2$ | $R^{4C}$ | $R^{4D}$ |
|---|---|---|---|---|---|
| C-59 | OCHMe$_2$ | F | N | H | H |
| C-60 | OCHMe$_2$ | Cl | N | H | H |
| C-61 | OCHMe$_2$ | Me | N | H | H |
| C-62 | OCHMe(Et) | H | C—H | H | H |
| C-63 | OCHMe(Et) | H | C—H | H | F |
| C-64 | OCHMe(Et) | H | C—H | H | Cl |
| C-65 | OCHMe(Et) | H | C—H | H | Me |
| C-66 | OCHMe(Et) | H | C—H | F | H |
| C-67 | OCHMe(Et) | H | C—H | F | F |
| C-68 | OCHMe(Et) | H | C—H | F | Cl |
| C-69 | OCHMe(Et) | H | C—H | F | Me |
| C-70 | OCHMe(Et) | H | C—H | Cl | H |
| C-71 | OCHMe(Et) | H | C—H | Cl | F |
| C-72 | OCHMe(Et) | H | C—H | Cl | Cl |
| C-73 | OCHMe(Et) | H | C—H | Cl | Me |
| C-74 | OCHMe(Et) | H | C—H | Me | H |
| C-75 | OCHMe(Et) | H | C—H | Me | F |
| C-76 | OCHMe(Et) | H | C—H | Me | Cl |
| C-77 | OCHMe(Et) | H | C—H | Me | Me |
| C-78 | OCHMe(Et) | H | C—F | H | F |
| C-79 | OCHMe(Et) | H | C—F | H | Cl |
| C-80 | OCHMe(Et) | H | C—F | H | Me |

TABLE 57

| No. | $R^3$ | $R^{4A}$ | $Z^2$ | $R^{4C}$ | $R^{4D}$ |
|---|---|---|---|---|---|
| C-81 | OCHMe(Et) | H | C—F | F | H |
| C-82 | OCHMe(Et) | H | C—F | Cl | H |
| C-83 | OCHMe(Et) | H | C—F | Me | H |
| C-84 | OCHMe(Et) | H | C—Cl | H | F |
| C-85 | OCHMe(Et) | H | C—Cl | H | Cl |
| C-86 | OCHMe(Et) | H | C—Cl | H | Me |
| C-87 | OCHMe(Et) | H | C—Cl | Cl | H |
| C-88 | OCHMe(Et) | H | C—Cl | Me | H |
| C-89 | OCHMe(Et) | H | C-Me | H | F |
| C-90 | OCHMe(Et) | H | C-Me | H | Cl |
| C-91 | OCHMe(Et) | H | C-Me | H | Me |
| C-92 | OCHMe(Et) | H | C-Me | Me | H |
| C-93 | OCHMe(Et) | F | C—H | H | F |
| C-94 | OCHMe(Et) | F | C—H | H | Cl |
| C-95 | OCHMe(Et) | F | C—H | H | Me |
| C-96 | OCHMe(Et) | Cl | C—H | H | Cl |
| C-97 | OCHMe(Et) | Cl | C—H | H | Me |
| C-98 | OCHMe(Et) | H | C—H | Me | Cl |
| C-99 | OCHMe(Et) | H | C—H | Me | Me |
| C-100 | OCHMe(Et) | H | C—F | H | F |
| C-101 | OCHMe(Et) | H | C—F | H | Cl |
| C-102 | OCHMe(Et) | H | C—F | H | Me |
| C-103 | OCHMe(Et) | H | C—F | F | H |
| C-104 | OCHMe(Et) | H | C—F | Cl | H |
| C-105 | OCHMe(Et) | H | C—F | Me | H |
| C-106 | OCHMe(Et) | H | C—Cl | H | F |
| C-107 | OCHMe(Et) | H | C—Cl | H | Cl |
| C-108 | OCHMe(Et) | H | C—Cl | H | Me |
| C-109 | OCHMe(Et) | H | C—Cl | Cl | H |
| C-110 | OCHMe(Et) | H | C—Cl | Me | H |
| C-111 | OCHMe(Et) | H | C-Me | H | F |
| C-112 | OCHMe(Et) | H | C-Me | H | Cl |
| C-113 | OCHMe(Et) | H | C-Me | H | Me |
| C-114 | OCHMe(Et) | H | C-Me | Me | H |
| C-115 | OCHMe(Et) | F | C—H | H | F |
| C-116 | OCHMe(Et) | F | C—H | H | Cl |
| C-117 | OCHMe(Et) | F | C—H | H | Me |
| C-118 | OCHMe(Et) | Cl | C—H | H | Cl |
| C-119 | OCHMe(Et) | Cl | C—H | H | Me |
| C-120 | OCHMe(Et) | Me | C—H | H | Me |

TABLE 58

| No. | $R^3$ | $R^{4A}$ | $Z^2$ | $R^{4C}$ | $R^{4D}$ |
|---|---|---|---|---|---|
| C-121 | OCHMe(Et) | H | N | H | H |
| C-122 | OCHMe(Et) | H | N | H | F |

TABLE 58-continued

| No. | $R^3$ | $R^{4A}$ | $Z^2$ | $R^{4C}$ | $R^{4D}$ |
|---|---|---|---|---|---|
| C-123 | OCHMe(Et) | H | N | H | Cl |
| C-124 | OCHMe(Et) | H | N | H | Me |
| C-125 | OCHMe(Et) | H | N | F | H |
| C-126 | OCHMe(Et) | H | N | Cl | H |
| C-127 | OCHMe(Et) | H | N | Me | H |
| C-128 | OCHMe(Et) | F | N | H | H |
| C-129 | OCHMe(Et) | Cl | N | H | H |
| C-130 | OCHMe(Et) | Me | N | H | H |
| C-131 | OCHF$_2$ | H | C—H | H | H |
| C-132 | OCHF$_2$ | H | C—H | H | F |
| C-133 | OCHF$_2$ | H | C—H | H | Cl |
| C-134 | OCHF$_2$ | H | C—H | H | Me |
| C-135 | OCHF$_2$ | H | C—H | F | H |
| C-136 | OCHF$_2$ | H | C—H | Cl | H |
| C-137 | OCHF$_2$ | H | C—H | Me | H |
| C-138 | OCHMe(Ph) | H | C—H | H | H |
| C-139 | OCHMe(Ph) | H | C—H | H | F |
| C-140 | OCHMe(Ph) | H | C—H | H | Cl |
| C-141 | OCHMe(Ph) | H | C—H | H | Me |
| C-142 | OCHMe(Ph) | H | C—H | F | H |
| C-143 | OCHMe(Ph) | H | C—H | Cl | H |
| C-144 | OCHMe(Ph) | H | C—H | Me | H |
| C-145 | OPh | H | C—H | H | H |
| C-146 | OPh | H | C—H | H | F |
| C-147 | OPh | H | C—H | H | Cl |
| C-148 | OPh | H | C—H | H | Me |
| C-149 | OPh | H | C—H | F | H |
| C-150 | OPh | H | C—H | Cl | H |
| C-151 | OPh | H | C—H | Me | H |
| C-152 | SMe | H | C—H | H | H |
| C-153 | SMe | H | C—H | H | F |
| C-154 | SMe | H | C—H | H | Cl |
| C-155 | SMe | H | C—H | H | Me |
| C-156 | SMe | H | C—H | F | H |
| C-157 | SMe | H | C—H | Cl | H |
| C-158 | SMe | H | C—H | Me | H |
| C-159 | SEt | H | C—H | H | H |
| C-160 | SEt | H | C—H | H | F |

TABLE 59

| No. | $R^3$ | $R^{4A}$ | $Z^2$ | $R^{4C}$ | $R^{4D}$ |
|---|---|---|---|---|---|
| C-161 | SEt | H | C—H | H | Cl |
| C-162 | SEt | H | C—H | H | Me |
| C-163 | SEt | H | C—H | F | H |
| C-164 | SEt | H | C—H | Cl | H |
| C-165 | SEt | H | C—H | Me | H |
| C-166 | SCHMe$_2$ | H | C—H | H | H |
| C-167 | SCHMe$_2$ | H | C—H | H | F |
| C-168 | SCHMe$_2$ | H | C—H | H | Cl |
| C-169 | SCHMe$_2$ | H | C—H | H | Me |
| C-170 | SCHMe$_2$ | H | C—H | F | H |
| C-171 | SCHMe$_2$ | H | C—H | Cl | H |
| C-172 | SCHMe$_2$ | H | C—H | Me | H |
| C-173 | SCHMe(Et) | H | C—H | H | H |
| C-174 | SCHMe(Et) | H | C—H | H | F |
| C-175 | SCHMe(Et) | H | C—H | H | Cl |
| C-176 | SCHMe(Et) | H | C—H | H | Me |
| C-177 | SCHMe(Et) | H | C—H | F | H |
| C-178 | SCHMe(Et) | H | C—H | Cl | H |
| C-179 | SCHMe(Et) | H | C—H | Me | H |
| C-180 | SCHF$_2$ | H | C—H | H | H |
| C-181 | SCHF$_2$ | H | C—H | H | F |
| C-182 | SCHF$_2$ | H | C—H | H | Cl |
| C-183 | SCHF$_2$ | H | C—H | H | Me |
| C-184 | SCHF$_2$ | H | C—H | F | H |
| C-185 | SCHF$_2$ | H | C—H | Cl | H |
| C-186 | SCHF$_2$ | H | C—H | Me | H |
| C-187 | SCHMe(Ph) | H | C—H | H | H |
| C-188 | SCHMe(Ph) | H | C—H | H | F |
| C-189 | SCHMe(Ph) | H | C—H | H | Cl |
| C-190 | SCHMe(Ph) | H | C—H | H | Me |
| C-191 | SCHMe(Ph) | H | C—H | F | H |

TABLE 59-continued

| No. | R³ | R⁴⁴ | Z² | R⁴ᶜ | R⁴ᴰ |
|---|---|---|---|---|---|
| C-192 | SCHMe(Ph) | H | C—H | Cl | H |
| C-193 | SCHMe(Ph) | H | C—H | Me | H |
| C-194 | SPh | H | C—H | H | H |
| C-195 | SPh | H | C—H | H | F |
| C-196 | SPh | H | C—H | H | Cl |
| C-197 | SPh | H | C—H | H | Me |
| C-198 | SPh | H | C—H | F | H |
| C-199 | SPh | H | C—H | Cl | H |
| C-200 | SPh | H | C—H | Me | H |

TABLE 60

| No. | R³ | R⁴⁴ | Z² | R⁴ᶜ | R⁴ᴰ |
|---|---|---|---|---|---|
| C-201 | OCHMe₂ | H | N | H | H |
| C-202 | OCHMe₂ | H | N | H | F |
| C-203 | OCHMe₂ | H | N | H | Cl |
| C-204 | OCHMe₂ | H | N | H | Me |
| C-205 | OCHMe₂ | H | N | F | H |
| C-206 | OCHMe₂ | H | N | Cl | H |
| C-207 | OCHMe₂ | H | N | Me | H |
| C-208 | SCHMe₂ | H | N | H | H |
| C-209 | SCHMe₂ | H | N | H | F |
| C-210 | SCHMe₂ | H | N | H | Cl |
| C-211 | SCHMe₂ | H | N | H | Me |
| C-212 | SCHMe₂ | H | N | F | H |
| C-213 | SCHMe₂ | H | N | Cl | H |
| C-214 | SCHMe₂ | H | N | Me | H |

A compound of the formula (IA) is shown below. (Compound No., part A, part B, part C), (IA-1,A-1,B-7,C-15),(IA-2,A-1,B-7,C-52),(IA-3,A-1,B-10,C-15),(IA-4,A-1,B-10,C-52),(IA-5,A-2,B-7,C-15),(IA-6,A-2,B-7,C-52),(IA-7,A-2,B-10,C-15),(IA-8,A-2,B-10,C-52),(IA-9,A-3,B-7,C-15),(IA-10,A-3,B-7,C-52),(IA-11,A-3,B-10,C-15),(IA-12,A-3,B-10,C-52),(IA-13,A-4,B-7,C-15),(IA-14,A-4,B-7,C-52),(IA-15,A-4,B-10,C-15),(IA-16,A-4,B-10,C-52),(IA-17,A-5,B-7,C-15),(IA-18,A-5,B-7,C-52),(IA-19,A-5,B-10,C-15),(IA-20,A-5,B-10,C-52),(IA-21,A-6,B-7,C-15),(IA-22,A-6,B-7,C-52),(IA-23,A-6,B-10,C-15),(IA-24,A-6,B-10,C-52),(IA-25,A-7,B-7,C-15),(IA-26,A-7,B-7,C-52),(IA-27,A-7,B-10,C-15),(IA-28,A-7,B-10,C-52),(IA-29,A-8,B-7,C-15),(IA-30,A-8,B-7,C-52),(IA-31,A-8,B-10,C-15),(IA-32,A-8,B-10,C-52),(IA-33,A-9,B-7,C-15),(IA-34,A-9,B-7,C-52),(IA-35,A-9,B-10,C-15),(IA-36,A-9,B-10,C-52),(IA-37,A-10,B-7,C-15),(IA-38,A-10,B-7,C-52),(IA-39,A-10,B-10,C-15),(IA-40,A-10,B-10,C-52),(IA-41,A-11,B-7,C-15),(IA-42,A-11,B-7,C-52),(IA-43,A-11,B-10,C-15),(IA-44,A-11,B-10,C-52),(IA-45,A-12,B-7,C-15),(IA-46,A-12,B-7,C-52),(IA-47,A-12,B-10,C-15),(IA-48,A-12,B-10,C-52),(IA-49,A-13,B-7,C-15),(IA-50,A-13,B-7,C-52),(I A-51,A-13,B-10,C-15),(IA-52,A-13,B-10,C-52),(IA-53,A-14,B-7,C-15),(IA-54,A-14,B-7,C-52),(IA-55,A-14,B-10,C-15),(IA-56,A-14,B-10,C-52),(IA-57,A-15,B-7,C-15),(IA-58,A-15,B-7,C-52),(IA-59,A-15,B-10,C-15),(IA-60,A-15,B-10,C-52),(IA-61,A-16,B-7,C-15),(IA-62,A-16,B-7,C-52),(IA-63,A-16,B-10,C-15),(IA-64,A-16,B-10,C-52),(IA-65,A-17,B-7,C-15),(IA-66,A-17,B-7,C-52),(IA-67,A-17,B-10,C-15),(IA-68,A-17,B-10,C-52),(IA-69,A-18,B-7,C-15),(IA-70,A-18,B-7,C-52),(I A-71,A-18,B-10,C-15),(IA-72,A-18,B-10,C-52),(IA-73,A-19,B-7,C-15),(IA-74,A-19,B-7,C-52),(IA-75,A-19,B-10,C-15),(IA-76,A-19,B-10,C-52),(IA-77,A-20,B-7,C-15),(IA-78,A-20,B-7,C-52),(IA-79,A-20,B-10,C-15),(IA-80,A-20,B-10,C-52),(IA-81,A-21,B-7,C-15),(IA-82,A-21,B-7,C-52),(IA-83,A-21,B-10,C-15),(IA-84,A-21,B-10,C-52),(IA-85,A-22,B-7,C-15),(IA-86,A-22,B-7,C-52),(IA-87,A-22,B-10,C-15),(IA-88,A-22,B-10,C-52),(IA-89,A-23,B-7,C-15),(IA-90,A-23,B-7,C-52),(IA-91,A-23,B-10,C-15),(IA-92,A-23,B-10,C-52),(IA-93,A-24,B-7,C-15),(IA-94,A-24,B-7,C-52),(IA-95,A-24,B-10,C-15),(IA-96,A-24,B-10,C-52),(IA-97,A-25,B-7,C-15),(IA-98,A-25,B-7,C-52),(IA-99,A-25,B-10,C-15),(IA-100,A-25,B-10,C-52),(IA-101,A-26,B-7,C-15),(IA-102,A-26,B-7,C-52),(IA-103,A-26,B-10,C-15),(IA-104,A-26,B-10,C-52),(IA-105,A-27,B-7,C-15),(IA-106,A-27,B-7,C-52),(IA-107,A-27,B-10,C-15),(IA-108,A-27,B-10,C-52),(IA-109,A-28,B-7,C-15),(IA-110,A-28,B-7,C-52),(IA-111,A-28,B-10,C-15),(IA-112,A-28,B-10,C-52),(IA-113,A-29,B-7,C-15),(IA-114,A-29,B-7,C-52),(IA-115,A-29,B-10,C-15),(IA-116,A-29,B-10,C-52),(IA-117,A-30,B-7,C-15),(IA-118,A-30,B-7,C-52),(IA-119,A-30,B-10,C-15),(IA-120,A-30,B-10,C-52),(IA-121,A-31,B-7,C-15),(IA-122,A-31,B-7,C-52),(IA-123,A-31,B-10,C-15),(IA-124,A-31,B-10,C-52),(IA-125,A-32,B-7,C-15),(IA-126,A-32,B-7,C-52),(IA-127,A-32,B-10,C-15),(IA-128,A-32,B-10,C-52),(IA-129,A-33,B-7,C-15),(IA-130,A-33,B-7,C-52),(IA-131,A-33,B-10,C-15),(IA-132,A-33,B-10,C-52),(IA-133,A-34,B-7,C-15),(IA-134,A-34,B-7,C-52),(IA-135,A-34,B-10,C-15),(IA-136,A-34,B-10,C-52),(IA-137,A-35,B-7,C-15),(IA-138,A-35,B-7,C-52),(IA-139,A-35,B-10,C-15),(IA-140,A-35,B-10,C-52),(IA-141,A-36,B-7,C-15),(IA-142,A-36,B-7,C-52),(IA-143,A-36,B-10,C-15),(IA-144,A-36,B-10,C-52),(IA-145,A-37,B-7,C-15),(IA-146,A-37,B-7,C-52),(IA-147,A-37,B-10,C-15),(IA-148,A-37,B-10,C-52),(IA-149,A-38,B-7,C-15),(IA-150,A-38,B-7,C-52),(IA-151,A-38,B-10,C-15),(IA-152,A-38,B-10,C-52),(IA-153,A-39,B-7,C-15),(IA-154,A-39,B-7,C-52),(IA-155,A-39,B-10,C-15),(IA-156,A-39,B-10,C-52),(IA-157,A-40,B-7,C-15),(IA-158,A-40,B-7,C-52),(IA-159,A-40,B-10,C-15),(IA-160,A-40,B-10,C-52),(IA-161,A-41,B-7,C-15),(IA-162,A-41,B-7,C-52),(IA-163,A-41,B-10,C-15),(IA-164,A-41,B-10,C-52),(IA-165,A-42,B-7,C-15),(IA-166,A-42,B-7,C-52),(IA-167,A-42,B-10,C-15),(IA-168,A-42,B-10,C-52),(IA-169,A-43,B-7,C-15),(IA-170,A-43,B-7,C-52),(IA-171,A-43,B-10,C-15),(IA-172,A-43,B-10,C-52),(IA-173,A-44,B-7,C-15),(IA-174,A-44,B-10,C-15),(IA-175,A-45,B-7,C-15),(IA-176,A-45,B-10,C-15),(IA-177,A-46,B-7,C-15),(IA-178,A-46,B-10,C-15),(IA-179,A-47,B-7,C-15),(IA-180,A-47,B-10,C-15),(I A-181,A-48,B-7,C-15),(IA-182,A-48,B-10,C-15),(IA-183,A-49,B-7,C-15),(IA-184,A-49,B-10,C-15),(IA-185,A-50,B-7,C-15),(IA-186,A-50,B-10,C-15),(IA-187,A-51,B-7,C-15),(IA-188,A-51,B-10,C-15),(IA-189,A-52,B-7,C-15),(IA-190,A-52,B-10,C-15),(IA-191,A-53,B-7,C-15),(IA-192,A-53,B-10,C-15),(IA-193,A-54,B-7,C-15),(IA-194,A-54,B-10,C-15),(IA-195,A-55,B-7,C-15),(IA-196,A-55,B-10,C-15),(IA-197,A-56,B-7,C-15),(IA-198,A-56,B-10,C-15),(IA-199,A-57,B-7,C-15),(IA-200,A-57,B-10,C-15),(IA-201,A-58,B-7,C-15),(IA-202,A-58,B-10,C-15),(IA-203,A-59,B-7,C-15),(IA-204,A-59,B-10,C-15),(IA-205,A-60,B-7,C-15),(IA-206,A-60,B-10,C-15),(IA-207,A-61,B-7,C-15),(IA-208,A-61,B-10,C-15),(IA-209,A-62,B-7,C-15),(IA-210,A-62,B-10,C-15),(IA-211,A-63,B-7,C-15),(IA-212,A-63,B-10,C-15),(IA-213,A-64,B-7,C-15),(IA-214,A-64,B-10,C-15),(IA-215,A-65,B-7,C-15),(I A-216,A-65,B-10,C-15),(IA-217,A-66,B-7,C-15),(IA-218,A-66,B-10,C-15),(IA-219,A-67,B-7,C-15),(IA-220,A-67,B-10,C-15),(IA-221,A-68,B-7,C-15),(IA-222,A-68,B-10,C-15),(IA-223,A-69,B-7,C-15),(IA-224,A-69,B-10,C-15),(IA-225,A-70,B-7,C-15),(IA-226,A-70,B-10,C-15),(IA-227,A-71,B-7,C-15),(IA-228,A-71,B-10,C-15),(IA-229,A-72,B-7,C-15),(IA-230,A-72,B-10,C-15),(IA-231,A-73,B-7,C-15),(IA-232,A-73,B-10,C-15),(IA-233,A-74,B-7,C-15),(IA-234,A-74,B-10,C-15),(IA-235,A-75,B-7,C-15),(IA-236,A-75,B-10,C-15),(IA-237,A-

76,B-7,C-15),(IA-238,A-76,B-10,C-15),(IA-239,A-77,B-7,C-15),(IA-240,A-77,B-10,C-15),(IA-241,A-78,B-7,C-15),(IA-242,A-78,B-10,C-15),(IA-243,A-79,B-7,C-15),(IA-244,A-79,B-10,C-15),(IA-245,A-80,B-7,C-15),(IA-246,A-80,B-10,C-15),(IA-247,A-81,B-7,C-15),(IA-248,A-81,B-10,C-15),(IA-249,A-82,B-7,C-15),(IA-250,A-82,B-10,C-15),(IA-251,A-83,B-7,C-15),(IA-252,A-83,B-10,C-15),(IA-253,A-84,B-7,C-15),(IA-254,A-84,B-10,C-15),(IA-255,A-85,B-7,C-15),(IA-256,A-85,B-10,C-15),(IA-257,A-86,B-7,C-15),(IA-258,A-86,B-10,C-15),(IA-259,A-87,B-7,C-15),(IA-260,A-87,B-10,C-15),(IA-261,A-88,B-7,C-15),(IA-262,A-88,B-10,C-15),(IA-263,A-89,B-7,C-15),(IA-264,A-89,B-10,C-15),(IA-265,A-90,B-7,C-15),(IA-266,A-90,B-10,C-15),(IA-267,A-91,B-7,C-15),(IA-268,A-91,B-10,C-15),(IA-269,A-92,B-7,C-15),(IA-270,A-92,B-10,C-15),(IA-271,A-93,B-7,C-15),(IA-272,A-93,B-10,C-15),(IA-273,A-94,B-7,C-15),(IA-274,A-94,B-10,C-15),(IA-275,A-95,B-7,C-15),(IA-276,A-95,B-10,C-15),(IA-277,A-96,B-7,C-15),(IA-278,A-96,B-10,C-15),(IA-279,A-97,B-7,C-15),(IA-280,A-97,B-10,C-15),(IA-281,A-98,B-7,C-15),(IA-282,A-98,B-10,C-15),(IA-283,A-99,B-7,C-15),(IA-284,A-99,B-10,C-15),(IA-285,A-100,B-7,C-15),(IA-286,A-100,B-10,C-15),(IA-287,A-101,B-7,C-15),(IA-288,A-101,B-10,C-15),(IA-289,A-102,B-7,C-15),(IA-290,A-102,B-10,C-15),(IA-291,A-103,B-7,C-15),(IA-292,A-103,B-10,C-15),(IA-293,A-104,B-7,C-15),(IA-294,A-104,B-10,C-15),(IA-295,A-105,B-7,C-15),(IA-296,A-105,B-10,C-15),(IA-297,A-106,B-7,C-15),(IA-298,A-106,B-10,C-15),(IA-299,A-107,B-7,C-15),(IA-300,A-107,B-10,C-15),(IA-301,A-108,B-7,C-15),(IA-302,A-108,B-10,C-15),(IA-303,A-109,B-7,C15),(IA-304,A-109,B-10,C-15),(IA-305,A-110,B-7,C-15),(IA-306,A-110,B-10,C-15),(IA-307,A-111,B-7,C-15),(IA-308,A-111,B-10,C-15),(IA-309,A-112,B-7,C-15),(IA-310,A-112,B-10,C-15),(IA-311,A-113,B-7,C-15),(IA-312,A-113,B-10,C-15),(IA-313,A-114,B-7,C-15),(IA-314,A-114,B-10,C-15),(IA-315,A-115,B-7,C-15),(IA-316,A-115,B-10,C-15),(IA-317,A-116,B-7,C-15),(IA-318,A-116,B-10,C-15),(IA-319,A-117,B-7,C-15),(IA-320,A-117,B-10,C-15),(IA-321,A-118,B-7,C-15),(IA-322,A-118,B-10,C-15),(IA-323,A-119,B-7,C-15),(IA-324,A-119,B-10,C-15),(IA-325,A-120,B-7,C-15),(IA-326,A-120,B-10,C-15),(IA-327,A-121,B-7,C-15),(IA-328,A-121,B-10,C-15),(IA-329,A-122,B-7,C-15),(IA-330,A-122,B-10,C-15),(IA-331,A-123,B-7,C-15),(IA-332,A-123,B-10,C-15),(IA-333,A-124,B-7,C-15),(IA-334,A-124,B-10,C-15),(IA-335,A-125,B-7,C-15),(IA-336,A-125,B-10,C-15),(IA-337,A-126,B-7,C-15),(IA-338,A-126,B-10,C-15),(IA-339,A-127,B-7,C-15),(IA-340,A-127,B-10,C-15),(IA-341,A-128,B-7,C-15),(IA-342,A-128,B-10,C-15),(IA-343,A-129,B-7,C-15),(IA-344,A-129,B-10,C-15),(IA-345,A-130,B-7,C-15),(IA-346,A-130,B-10,C-15),(IA-347,A-131,B-7,C-15),(IA-348,A-131,B-10,C-15),(IA-349,A-132,B-7,C-15),(IA-350,A-132,B-10,C-15),(IA-351,A-133,B-7,C-15),(IA-352,A-133,B-10,C-15),(IA-353,A-134,B-7,C-15),(IA-354,A-134,B-10,C-15),(IA-355,A-135,B-7,C-15),(IA-356,A-135,B-10,C-15),(IA-357,A-136,B-7,C-15),(IA-358,A-136,B-10,C-15),(IA-359,A-137,B-7,C-15),(IA-360,A-137,B-10,C-15),(IA-361,A-138,B-7,C-15),(IA-362,A-138,B-10,C-15),(IA-363,A-139,B-7,C-15),(IA-364,A-139,B-10,C-15),(IA-365,A-140,B-7,C-15),(IA-366,A-140,B-10,C-15),(IA-367,A-141,B-7,C-15),(IA-368,A-141,B-10,C-15),(IA-369,A-142,B-7,C-15),(IA-370,A-142,B-10,C-15),(IA-371,A-143,B-7,C-15),(IA-372,A-143,B-10,C-15),(IA-373,A-144,B-7,C-15),(IA-374,A-144,B-10,C-15),(IA-375,A-145,B-7,C-15),(IA-376,A-145,B-10,C-15),(IA-377,A-146,B-7,C-15),(IA-378,A-146,B-10,C-15),(IA-379,A-147,B-7,C-15),(IA-380,A-147,B-10,C-15),(IA-381,A-148,B-7,C-15),(IA-382,A-148,B-10,C-15),(IA-383,A-149,B-7,C-15),(IA-384,A-149,B-10,C-15),(IA-385,A-150,B-7,C-15),(IA-386,A-150,B-10,C-15),(IA-387,A-151,B-7,C-15),(IA-388,A-151,B-10,C-15),(IA-389,A-152,B-7,C-15),(IA-390,A-152,B-10,C-15),(IA-391,A-153,B-7,C-15),(IA-392,A-153,B-10,C-15),(IA-393,A-154,B-7,C-15),(IA-394,A-154,B-10,C-15),(IA-395,A-155,B-7,C-15),(IA-396,A-155,B-10,C-15),(IA-397,A-156,B-7,C-15),(IA-398,A-156,B-10,C-15),(IA-399,A-157,B-7,C-15),(IA-400,A-157,B-10,C-15),(IA-401,A-158,B-7,C-15),(IA-402,A-158,B-10,C-15),(IA-403,A-159,B-7,C-15),(IA-404,A-159,B-10,C-15),(IA-405,A-160,B-7,C-15),(IA-406,A-160,B-10,C-15),(IA-407,A-161,B-7,C-15),(IA-408,A-161,B-10,C-15),(IA-409,A-162,B-7,C-15),(IA-410,A-162,B-10,C-15),(IA-411,A-163,B-7,C-15),(IA-412,A-163,B-10,C-15),(IA-413,A-164,B-7,C-15),(IA-414,A-164,B-10,C-15),(IA-415,A-165,B-7,C-15),(IA-416,A-165,B-10,C-15),(IA-417,A-166,B-7,C-15),(IA-418,A-166,B-10,C-15),(IA-419,A-167,B-7,C-15),(IA-420,A-167,B-10,C-15),(IA-421,A-168,B-7,C-15),(IA-422,A-168,B-10,C-15),(IA-423,A-169,B-7,C-15),(IA-424,A-169,B-10,C-15),(IA-425,A-170,B-7,C-15),(IA-426,A-170,B-10,C-15),(IA-427,A-171,B-7,C-15),(IA-428,A-171,B-10,C-15),(IA-429,A-172,B-7,C-15),(IA-430,A-172,B-10,C-15),(IA-431,A-173,B-7,C-15),(IA-432,A-173,B-10,C-15),(IA-433,A-174,B-7,C-15),(IA-434,A-174,B-10,C-15),(IA-435,A-175,B-7,C-15),(IA-436,A-175,B-10,C-15),(IA-437,A-176,B-7,C-15),(IA-438,A-176,B-10,C-15),(IA-439,A-177,B-7,C-15),(IA-440,A-177,B-10,C-15),(IA-441,A-178,B-7,C-15),(IA-442,A-178,B-10,C-15),(IA-443,A-179,B-7,C-15),(IA-444,A-179,B-10,C-15),(IA-445,A-180,B-7,C-15),(IA-446,A-180,B-10,C-15),(IA-447,A-181,B-7,C-15),(IA-448,A-181,B-10,C-15),(IA-449,A-182,B-7,C-15),(IA-450,A-182,B-10,C-15),(IA-451,A-183,B-7,C-15),(IA-452,A-183,B-10,C-15),(IA-453,A-184,B-7,C-15),(IA-454,A-184,B-10,C-15),(IA-455,A-185,B-7,C-15),(IA-456,A-185,B-10,C-15),(IA-457,A-186,B-7,C-15),(IA-458,A-186,B-10,C-15),(IA-459,A-187,B-7,C-15),(IA-460,A-187,B-10,C-15),(IA-461,A-188,B-7,C-15),(IA-462,A-188,B-10,C-15),(IA-463,A-189,B-7,C-15),(IA-464,A-189,B-10,C-15),(IA-465,A-190,B-7,C-15),(IA-466,A-190,B-10,C-15),(IA-467,A-191,B-7,C-15),(IA-468,A-191,B-10,C-15),(IA-469,A-192,B-7,C-15),(IA-470,A-192,B-10,C-15),(IA-471,A-193,B-7,C-15),(IA-472,A-193,B-10,C-15),(IA-473,A-194,B-7,C-15),(IA-474,A-194,B-10,C-15),(IA-475,A-195,B-7,C-15),(IA-476,A-195,B-10,C-15),(IA-477,A-196,B-7,C-15),(IA-478,A-196,B-10,C-15),(IA-479,A-197,B-7,C-15),(IA-480,A-197,B-10,C-15),(IA-481,A-198,B-7,C-15),(IA-482,A-198,B-10,C-15),(IA-483,A-199,B-7,C-15),(IA-484,A-199,B-10,C-15),(IA-485,A-200,B-7,C-15),(IA-486,A-200,B-10,C-15),(IA-487,A-201,B-7,C-15),(IA-488,A-201,B-10,C-15),(IA-489,A-202,B-7,C-15),(IA-490,A-202,B-10,C-15),(IA-491,A-203,B-7,C-15),(IA-492,A-203,B-10,C-15),(IA-493,A-204,B-7,C-15),(IA-494,A-204,B-10, C-15),(IA-495,A-205,B-7,C-15),(IA-496,A-205,B-10,C-15),(IA-497,A-206,B-7,C-15),(IA-498,A-206,B-10,C-15),(IA-499,A-207,B-7,C-15),(IA-500,A-207,B-10,C-15),(IA-501,A-208,B-7,C-15),(IA-502,A-208,B-10,C-15),(IA-503,A-209,B-7,C-15),(IA-504,A-209,B-10,C-15),(IA-505,A-210,B-7,C-15),(IA-506,A-210,B-10,C-15),(IA-507,A-211,B-7,C-15),(IA-508,A-211,B-10,C-15),(IA-509,A-212,B-7,C-15),(IA-510,A-212,B-10,C-15),(IA-511,A-213,B-7,C-15),(IA-512,A-213,B-10,C-15),(IA-513,A-214,B-7,C-15),(IA-514,A-214,B-10,C-15),(IA-515,A-215,B-7,C-15),(IA-516,A-215,B-10,C-15),(IA-517,A-216,B-7,C-15),(IA-518,A-216,B-10,C-15),(IA-519,A-217,B-7,C-15),(IA-520,A-217,B-10,C-15),(IA-521,A-218,B-7,C-15),(IA-522,A-218,B-10,C-15),(IA-523,A-219,B-7,C-15),(IA-524,A-219,B-10,C-15),(IA-525,A-220,B-7,C-15),(IA-526,

A-220,B-10,C-15),(IA-527,A-221,B-7,C-15),(IA-528,A-221,B-10,C-15),(IA-529,A-222,B-7,C-15),(IA-530,A-222,B-10,C-15),(IA-531,A-223,B-7,C-15),(IA-532,A-223,B-10,C-15),(IA-533,A-224,B-7,C-15),(IA-534,A-224,B-10,C-15),(IA-535,A-225,B-7,C-15),(IA-536,A-225,B-10, C-15),(IA-537,A-226,B-7,C-15),(IA-538,A-226,B-10,C-15),(IA-539,A-227,B-7,C-15),(IA-540,A-227,B-10,C-15),(IA-541,A-228,B-7,C-15),(IA-542,A-228,B-10,C-15),(IA-543,A-229,B-7,C-15),(IA-544,A-229,B-10,C-15),(IA-545,A-230,B-7,C-15),(IA-546,A-230,B-10,C-15),(IA-547,A-231,B-7,C-15),(IA-548,A-231,B-10,C-15),(IA-549,A-232,B-7,C-15),(IA-550,A-232,B-10,C-15),(IA-551,A-233,B-7,C-15),(IA-552,A-233,B-10,C-15),(IA-553,A-234,B-7,C-15),(IA-554,A-234,B-10,C-15),(IA-555,A-235,B-7,C-15),(IA-556,A-235,B-10,C-15),(IA-557,A-236,B-7,C-15),(IA-558,A-236,B-10,C-15),(IA-559,A-237,B-7,C-15),(IA-560,A-237,B-10,C-15),(IA-561,A-238,B-7,C-15),(IA-562,A-238,B-10,C-15),(IA-563,A-239,B-7,C-15),(IA-564,A-239,B-10,C-15),(IA-565,A-240,B-7,C-15),(IA-566,A-240,B-10,C-15),(IA-567,A-241,B-7,C-15),(IA-568,A-241,B-10,C-15),(IA-569,A-242,B-7,C-15),(IA-570,A-242,B-10,C-15),(IA-571,A-243,B-7,C-15),(IA-572,A-243,B-10,C-15),(IA-573,A-244,B-7,C-15),(IA-574,A-244,B-10,C-15),(IA-575,A-245,B-7,C-15),(IA-576,A-245,B-10,C-15),(IA-577,A-246,B-7,C-15),(IA-578,A-246,B-10,C-15),(IA-579,A-247,B-7,C-15),(IA-580,A-247,B-10,C-15),(IA-581,A-248,B-7,C-15),(IA-582,A-248,B-10,C-15),(IA-583,A-249,B-7,C-15),(IA-584,A-249,B-10,C-15),(IA-585,A-250,B-7,C-15),(IA-586,A-250,B-10,C-15),(IA-587,A-251,B-7,C-15),(IA-588,A-251,B-10,C-15),(IA-589,A-252,B-7,C-15),(IA-590,A-252,B-10,C-15),(IA-591,A-253,B-7,C-15),(IA-592,A-253,B-10,C-15),(IA-593,A-254,B-7,C-15),(IA-594,A-254,B-10,C-15),(IA-595,A-255,B-7,C-15),(IA-596,A-255,B-10,C-15),(IA-597,A-256,B-7,C-15),(IA-598,A-256,B-10,C-15),(IA-599,A-257,B-7,C-15),(IA-600,A-257,B-10,C-15),(IA-601,A-258,B-7,C-15),(IA-602,A-258,B-10,C-15),(IA-603,A-259,B-7,C-15),(IA-604,A-259,B-10,C-15),(IA-605,A-260,B-7,C-15),(IA-606,A-260,B-10,C-15),(IA-607,A-261,B-7,C-15),(IA-608,A-261,B-10,C-15),(IA-609,A-262,B-7,C-15),(IA-610,A-262,B-10,C-15),(IA-611,A-263,B-7,C-15),(IA-612,A-263,B-10,C-15),(IA-613,A-264,B-7,C-15),(IA-614,A-264,B-10,C-15),(IA-615,A-265,B-7,C-15),(IA-616,A-265,B-10,C-15),(IA-617,A-266,B-7,C-15),(IA-618,A-266,B-10,C-15),(IA-619,A-267,B-7,C-15),(IA-620,A-267,B-10,C-15),(IA-621,A-268,B-7,C-15),(IA-622,A-268,B-10,C-15),(IA-623,A-269,B-7,C-15),(IA-624,A-269,B-10,C-15),(IA-625,A-270,B-7,C-15),(IA-626,A-270,B-10,C-15)

A compound of the formula (IB)

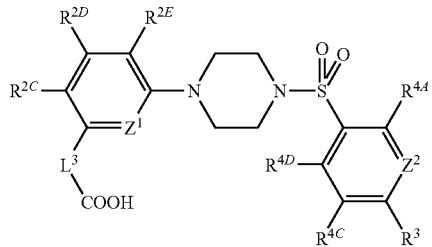

(IB)

wherein $Z^1$ is $CR^{2B}$ or N; $Z^2$ is $CR^{4B}$ or N; $R^{2B}$, $R^{2C}$, $R^{2D}$ and $R^{2E}$ are independently a hydrogen atom, a fluorine atom, a chlorine atom, a bromine atom, a iodine atom, methyl, ethyl, allyl, propargyl, trifluoromethyl, methyloxy, difluoromethyloxy, methylthio, methylsulfonyl, phenyl, phenoxy, phenylthio, amino, methylamino, dimethylamino, methylcarbonylamino, methylsulfonylamino, nitro, cyano, 2-furyl, 2-thenyl, 2-pyridyl, 1,3-oxazol-2-yl, 1,3-oxazol-4-yl, 1,3-oxazol-5-yl, 1,3-thiazol-2-yl, 1,3-thiazol-4-yl, 1,3-thiazol-5-yl, 1,3,4-oxdiazol-2-yl, 1,3,4-thiadiazol-2-yl, imidazol-1-yl, pyrazol-1-yl, morpholino, pyrrolidino or piperizino; $R^3$ is methyloxy, ethyloxy, isopropyloxy, sec-butyloxy, difluoromethyloxy, 1-phenylethyloxy, phenoxy, methylthio, ethylthio, isopropylthio, sec-butylthio, difluoromethylthio, 1-phenylethylthio or phenylthio; $R^{4A}$, $R^{4B}$, $R^{4C}$ and $R^{4D}$ are independently a hydrogen atom, a fluorine atom, a chlorine atom, methyl or methyloxy; $L^3$ is a single bond, methylene, 1,1-dimethylmethylene, ethylene, —CH=CH—CH$_2$—, 1-propylene-1,3-diynel, —O—CH$_2$—, —O—CH(Me)-, —O—C(Me)$_2$—, —S—CH$_2$— or —NH—CH$_2$—; can be prepared in the same manner as set forth above.

Hereinafter, a table for combination of part A, part B and part C is the same as that of the formula (IA).

A compound of the formula (IB) is shown below;
(Compound No., part A, part B, part C), (IB-1,A-1,B-1,C-15),(IB-2,A-1,B-2,C-15),(IB-3,A-1,B-3,C-15),(IB-4,A-1,B-4,C-15),(IB-5,A-1,B-5,C-15),(IB-6,A-1,B-6,C-15),(IB-7,A-1,B-7,C-15),(IB-8,A-1,B-7,C-52),(IB-9,A-1,B-8,C-15),(IB-10,A-1,B-9,C-15),(IB-11,A-1,B-10,C-15),(IB-12,A-1,B-10,C-52),(IB-13,A-2,B-1,C-15),(IB-14,A-2,B-2,C-15),(IB-15,A-2,B-3,C-15),(IB-16,A-2,B-4,C-15),(IB-17,A-2,B-5,C-15),(IB-18,A-2,B-6,C-15),(IB-19,A-2,B-7,C-15),(IB-20,A-2,B-7,C-52),(IB-21,A-2,B-8,C-15),(IB-22,A-2,B-9,C-15),(IB-23,A-2,B-10,C-15),(IB-24,A-2,B-10,C-52),(IB-25,A-3,B-1,C-15),(IB-26,A-3,B-2,C-15),(IB-27,A-3,B-3,C-15),(IB-28,A-3,B-4,C-15),(IB-29,A-3,B-5,C-15),(IB-30,A-3,B-6,C-15),(IB-31,A-3,B-7,C-1),(IB-32,A-3,B-7,C-2),(IB-33,A-3,B-7,C-3),(IB-34,A-3,B-7,C-4),(IB-35,A-3,B-7,C-5),(IB-36,A-3,B-7,C-6),(IB-37,A-3,B-7,C-7),(IB-38,A-3,B-7,C-8),(IB-39,A-3,B-7,C-9),(IB-40,A-3,B-7,C-10),(IB-41,A-3,B-7,C-11),(IB-42,A-3,B-7,C-12),(IB-43,A-3,B-7,C-13),(IB-44,A-3,B-7,C-14),(IB-45,A-3,B-7,C-15),(IB-46,A-3,B-7,C-16),(IB-47,A-3,B-7,C-17),(IB-48,A-3,B-7,C-18),(IB-49,A-3,B-7,C-19),(IB-50,A-3,B-7,C-20),(IB-51,A-3,B-7,C-21),(IB-52,A-3,B-7,C-22),(IB-53,A-3,B-7,C-23),(IB-54,A-3,B-7,C-24),(IB-55,A-3,B-7,C-25),(IB-56,A-3,B-7,C-26),(IB-57,A-3,B-7,C-27),(IB-58,A-3,B-7,C-28),(IB-59,A-3,B-7,C-29),(IB-60,A-3,B-7,C-30),(IB-61,A-3,B-7,C-31),(IB-62,A-3,B-7,C-32),(IB-63,A-3,B-7,C-33),(IB-64,A-3,B-7,C-34),(IB-65,A-3,B-7,C-35),(IB-66,A-3,B-7,C-36),(IB-67,A-3,B-7,C-37),(IB-68,A-3,B-7,C-38),(IB-69,A-3,B-7,C-39),(IB-70,A-3,B-7,C-40),(IB-71,A-3,B-7,C-41),(IB-72,A-3,B-7,C-42),(IB-73,A-3,B-7,C-43),(IB-74,A-3,B-7,C-44),(IB-75,A-3,B-7,C-45),(IB-76,A-3,B-7,C-46),(IB-77,A-3,B-7,C-47),(IB-78,A-3,B-7,C-48),(IB-79,A-3,B-7,C-49),(IB-80,A-3,B-7,C-50),(IB-81,A-3,B-7,C-51),(IB-82,A-3,B-7,C-52),(IB-83,A-3,B-7,C-53),(IB-84,A-3,B-7,C-54),(IB-85,A-3,B-7,C-55),(IB-86,A-3,B-7,C-56),(IB-87,A-3,B-7,C-57),(IB-88,A-3,B-7,C-58),(IB-89,A-3,B-7,C-59),(IB-90,A-3,B-7,C-60),(IB-91,A-3,B-7,C-61),(IB-92,A-3,B-7,C-62),(IB-93,A-3,B-7,C-63),(IB-94,A-3,B-7,C-64),(IB-95,A-3,B-7,C-65),(IB-96,A-3,B-7,C-66),(IB-97,A-3,B-7,C-67),(IB-98,A-3,B-7,C-68),(IB-99,A-3,B-7,C-69),(IB-100,A-3,B-7,C-70),(IB-101,A-3,B-7,C-71),(IB-102,A-3,B-7,C-72),(IB-103,A-3,B-7,C-73),(IB-104,A-3,B-7,C-74),(IB-105,A-3,B-7,C-75),(IB-106,A-3,B-7,C-76),(IB-107,A-3,B-7,C-77),(IB-108,A-3,B-7,C-78),(IB-109,A-3,B-7,C-79),(IB-110,A-3,B-7,C-80),(IB-111,A-3,B-7,C-81),(IB-112,A-3,B-7,C-82),(IB-113,A-3,B-7,C-83),(IB-114,A-3,B-7,C-84),(I B-115,A-3,B-7,C-85),(IB-116,A-3,B-7,C-86),(IB-117,A-3,B-7,C-87),(IB-118,A-3,B-7,C-88),(IB-119,A-3,B-7,C-89),(IB-120,A-3,B-7,C-90),(IB-121,A-3,B-7,C-91),(IB-122,A-3,B-7,C-

92),(IB-123,A-3,B-7,C-93),(IB-124,A-3,B-7,C-94),(IB-125,A-3,B-7,C-95),(IB-126,A-3,B-7,C-96),(IB-127,A-3,B-7,C-97),(IB-128,A-3,B-7,C-98),(IB-129,A-3,B-7,C-99), (IB-130,A-3,B-7,C-100),(IB-131,A-3,B-7,C-101),(IB-132,A-3,B-7,C-102),(IB-133,A-3,B-7,C-103),(IB-134,A-3,B-7,C-104),(IB-135,A-3,B-7,C-105),(IB-136,A-3,B-7,C-106),(IB-137,A-3,B-7,C-107),(IB-138,A-3,B-7,C-108),(IB-139,A-3,B-7,C-109),(IB-140,A-3,B-7,C-110),(IB-141,A-3,B-7,C-111),(IB-142,A-3,B-7,C-112),(IB-143,A-3,B-7,C-113),(IB-144,A-3,B-7,C-114),(IB-145,A-3,B-7,C-115),(IB-146,A-3,B-7,C-116),(IB-147,A-3,B-7,C-117),(IB-148,A-3,B-7,C-118),(IB-149,A-3,B-7,C-119),(IB-150,A-3,B-7,C-120),(IB-151,A-3,B-7,C-121),(IB-152,A-3,B-7,C-122),(IB-153,A-3,B-7,C-123),(IB-154,A-3,B-7,C-124),(IB-155,A-3,B-7,C-125),(IB-156,A-3,B-7,C-126),(IB-157,A-3,B-7,C-127),(IB-158,A-3,B-7,C-128),(IB-159,A-3,B-7,C-129),(IB-160,A-3,B-7,C-130),(IB-161,A-3,B-7,C-131),(IB-162,A-3,B-7,C-132),(IB-163,A-3,B-7,C-133),(IB-164,A-3,B-7,C-134),(IB-165,A-3,B-7,C-135),(IB-166,A-3,B-7,C-136),(IB-167,A-3,B-7,C-137),(IB-168,A-3,B-7,C-138),(IB-169,A-3,B-7,C-139),(IB-170,A-3,B-7,C-140),(IB-171,A-3,B-7,C-141),(IB-172,A-3,3-7,C-142),(13-173,A-3,B-7,C-143),(IB-174,A-3,B-7,C-144),(IB-175,A-3,B-7,C-145),(IB-176,A-3,B-7,C-146),(IB-177,A-3,B-7,C-147),(IB-178,A-3,B-7,C-148),(IB-179,A-3,B-7,C-149),(IB-180,A-3,B-7,C-150),(IB-181,A-3,B-7,C-151),(IB-182,A-3,B-7,C-152),(IB-183,A-3,B-7,C-153),(IB-184,A-3,B-7,C-154),(IB-185,A-3,B-7,C-155),(IB-186,A-3,B-7,C-156),(IB-187,A-3,B-7,C-157),(IB-188,A-3,B-7,C-158),(IB-189,A-3,B-7,C-159),(IB-190,A-3,B-7,C-160),(IB-191,A-3,B-7,C-161),(IB-192,A-3,B-7,C-162),(IB-193,A-3,B-7,C-163),(IB-194,A-3,B-7,C-164),(IB-195,A-3,B-7,C-165),(IB-196,A-3,B-7,C-166),(IB-197,A-3,B-7,C-167),(IB-198,A-3,B-7,C-168),(IB-199,A-3,B-7,C-169),(IB-200,A-3,B-7,C-170),(IB-201,A-3,B-7,C-171),(IB-202,A3-C7-C-172),(IB-203,A-3,B-7,C-173),(IB-204,A-3,B-7,C-174),(IB-205,A-3,B-7,C-175),(IB-206,A-3,B-7,C-176),(IB-207,A-3,B-7,C-177),(IB-208,A-3,B-7,C-178),(IB-209,A-3,B-7,C-179),(IB-210,A-3,B-7,C-180),(IB-211,A-3,B-7,C-181),(IB-212,A-3,B-7,C-182),(113-213,A-3,B-7,C-183),(IB-214,A-3,B-7,C-184),(IB-215,A-3,B-7,C-185),(IB-216,A-3,B-7,C-186), (IB-217,A-3,B-7,C-187),(IB-218,A-3,B-7,C-188),(IB-219,A-3,B-7,C-189),(IB-220,A-3,B-7,C-190),(IB-221,A-3,B-7,C-191),(IB-222,A-3,B-7,C-192),(IB-223,A-3,B-7,C-193),(IB-224,A-3,B-7,C-194),(IB-225,A-3,B-7,C-195),(IB-226,A-3,B-7,C-196),(IB-227,A-3,B-7,C-197),(IB-228,A-3,B-7,C-198),(IB-229,A-3,B-7,C-199),(13-230,A-3,B-7,C-200),(IB-231,A-3,B-7,C-201),(IB-232,A-3,B-7,C-202),(IB-233,A-3,B-7,C-203),(IB-234,A-3,B-7,C-204),(IB-235,A-3,B-7,C-205),(IB-236,A-303-7,C-206),(IB-237,A-3,B-7,C-207),(IB-238,A-3,B-7,C-208),(I B-239,A-3,B-7,C-209),(IB-240,A-3,B-7,C-210),(IB-241,A-3,B-7,C-211),(IB-242,A-3,B-7,C-212),(IB-243,A-3,B-7,C-213),(IB-244,A-3,B-7,C-214),(IB-245,A-3,B-8,C-15),(IB-246,A-3,B-9,C-15),(IB-247,A-3,B-10,C-15),(IB-248,A-3,B-10,C-52), (IB-249,A-4,B-1,C-15),(IB-250,A-4,B-2,C-15),(IB-251,A-4,B-3,C-15),(IB-252,A-4,B-4,C-15),(IB-253,A-4,B-5,C-15),(IB-254,A-4,B-6,C-15),(IB-255,A-4,B-7,C-1),(IB-256,A-4,B-7,C-2),(IB-257,A-4,B-7,C-3),(IB-258,A-4,B-7,C-4),(IB-259,A-4,B-7,C-5),(IB-260,A-4,B-7,C-6),(IB-261,A-4,B-7,C-7),(IB-262,A-4,B-7,C-8),(IB-263,A-4,B-7,C-9),(IB-264,A-4,B-7,C-10),(IB-265,A-4,B-7,C-11),(IB-266,A-4,B-7,C-12),(IB-267,A-4,B-7,C-13),(IB-268,A-4,B-7,C-14),(IB-269,A-4,B-7,C-15),(IB-270,A-4,B-7,C-16),(IB-271,A-4,B-7,C-17),(IB-272,A-4,B-7,C-18),(IB-273,A-4,B-7,C-19),(IB-274,A-4,B-7,C-20),(IB-275,A-4,B-7,C-21),(IB-276,A-4,B-7,C-22),(IB-277,A-4,B-7,C-23),(IB-278,A-4,B-7,C-24),(IB-279,A-4,B-7,C-25),(IB-280,A-4,B-7,C-26), (IB-281,A-4,B-7,C-27),(IB-282,A-4,B-7,C-28),(IB-283,A-4,B-7,C-29),(IB-284,A-4,B-7,C-30),(IB-285,A-4,B-7,C-31),(IB-286,A-4,B-7,C-32),(IB-287,A-4,B-7,C-33),(IB-288,A-4,B-7,C-34),(IB-289,A-4,B-7,C-35),(IB-290,A-4,B-7,C-36),(IB-291,A-4,B-7,C-37),(IB-292,A-4,B-7,C-38),(IB-293,A-4,B-7,C-39),(IB-294,A-4,B-7,C-40),(IB-295,A-4,B-7,C-41),(IB-296,A-4,B-7,C-42),(IB-297,A-4,B-7,C-43),(IB-298,A-4,B-7,C-44),(16-299,A-4,B-7,C-45),(IB-300,A-4,B-7,C-46),(IB-301,A-4,B-7,C-47),(IB-302,A-4,B-7,C-48),(IB-303,A-4,B-7,C-49),(IB-304,A-4,B-7,C-50),(IB-305,A-4,B-7,C-51),(IB-306,A-4,B-7,C-52),(IB-307,A-4,B-7,C-53),(IB-308,A-4,B-7,C-54),(IB-309,A-4,B-7,C-55),(IB-310,A-4,B-7,C-56),(IB-311,A-4,B-7,C-57),(IB-312,A-4,B-7,C-58),(IB-313,A-4,B-7,C-59),(IB-314,A-4,B-7,C-60),(IB-315,A-4,B-7,C-61),(IB-316,A-4,B-7,C-62),(IB-317,A-4,B-7,C-63),(IB-318,A-4,B-7,C-64),(IB-319,A-4,B-7,C-65),(IB-320,A-4,B-7,C-66),(IB-321,A-4,B-7,C-67),(IB-322,A-4,B-7,C-68),(IB-323,A-4,B-7,C-69),(IB-324,A-4,B-7,C-70),(IB-325,A-4,B-7,C-71),(IB-326,A-4,B-7,C-72),(IB-327,A-4,B-7,C-73),(IB-328,A-4,B-7,C-74),(IB-329,A-4,B-7,C-75),(IB-330,A-4,B-7,C-76),(IB-331,A-4,B-7,C-77),(IB-332,A-4,B-7,C-78), (IB-333,A-4,B-7,C-79),(IB-334,A-4,B-7,C-80),(IB-335,A-4,B-7,C-81),(IB-336,A-4,B-7,C-82),(IB-337,A-4,B-7,C-83),(IB-338,A-4,B-7,C-84),(IB-339,A-4,B-7,C-85), (IB-340,A-4,B-7,C-86),(IB-341,A-4,B-7,C-87),(IB-342,A-4,B-7,C-88),(IB-343,A-4,B-7,C-89),(IB-344,A-4,B-7,C-90),(IB-345,A-4,B-7,C-91),(IB-346,A-4,B-7,C-92),(IB-347,A-4,B-7,C-93),(IB-348,A-4,B-7,C-94),(IB-349,A-4,B-7,C-95),(IB-350,A-4,B-7,C-96),(IB-351,A-4,B-7,C-97),(IB-352,A-4,B-7,C-98),(IB-353,A-4,B-7,C-99),(IB-354,A-4,B-7,C-100),(IB-355,A-4,B-7,C-101),(IB-356,A-4,B-7,C-102),(IB-357,A-4,B-7,C-103),(IB-358,A-4,B-7,C-104),(IB-359,A-4,B-7,C-105),(IB-360,A-4,B-7,C-106),(IB-361,A-4,B-7,C-107),(IB-362,A-4,B-7,C-108),(IB-363,A-4,B-7,C-109),(IB-364,A-4,B-7,C-110),(IB-365,A-4,B-7,C-111),(IB-366,A-4,B-7,C-112),(IB-367,A-4,B-7,C-113),(IB-368,A-4,B-7,C-114),(IB-369,A-4,B-7,C-115),(IB-370,A-4,B-7,C-116),(IB-371,A-4,B-7,C-117),(IB-372,A-4,B-7,C-118),(IB-373,A-4,B-7,C-119),(IB-374,A-4,B-7,C-120),(IB-375,A-4,B-7,C-121),(IB-376,A-4,B-7,C-122),(IB-377,A-4,B-7,C-123),(IB-378,A-4,B-7,C-124),(IB-379,A-4,B-7,C-125),(IB-380,A-4,B-7,C-126),(IB-381,A-4,B-7,C-127),(IB-382,A-4,B-7,C-128),(IB-383,A-4,B-7,C-129),(IB-384,A-4,B-7,C-130),(IB-385,A-4,B-7,C-131),(IB-386,A-4,B-7,C-132),(IB-387,A-4,B-7,C-133),(IB-388,A-4,B-7,C-134),(IB-389,A-4,B-7,C-135),(IB-390,A-4,B-7,C-136),(IB-391,A-4,B-7,C-137),(IB-392,A-4,B-7,C-138),(IB-393,A-4,B-7,C-139),(IB-394,A-4,B-7,C-140),(IB-395,A-4,B-7,C-141),(IB-396,A-4,B-7,C-142),(IB-397,A-4,B-7,C-143),(IB-398,A-4,B-7,C-144),(IB-399,A-4,B-7,C-145),(IB-400,A-4,B-7,C-146),(IB-401,A-4,B-7,C-147),(IB-402,A-4,B-7,C-148),(IB-403,A-4,B-7,C-149),(IB-404,A-4,B-7,C-150),(IB-405,A-4,B-7,C-151),(IB-406,A-4,B-7,C-152),(IB-407,A-4,B-7,C-153),(IB-408,A-4,B-7,C-154), (IB-409,A-4,B-7,C-155),(IB-410,A-4,B-7,C-156),(IB-411,A-4,B-7,C-157),(IB-412,A-4,B-7,C-158),(IB-413,A-4,B-7,C-159),(IB-414,A-4,B-7,C-160),(IB-415,A-4,B-7,C-161),(IB-416,A-4,B-7,C-162),(IB-417,A-4,B-7,C-163),(IB-418,A-4,B-7,C-164),(IB-419,A-4,B-7,C-165),(IB-420,A-4,B-7,C-166),(IB-421,A-4,B-7,C-167),(IB-422,A-4,B-7,C-168),(IB-423,A-4,B-7,C-169),(IB-424,A-4,B-7,C-170),(IB-425,A-4,B-7,C-171),(IB-426,A-4,B-7,C-172),(I B-427,A-4,B-7,C-173),(IB-428,A-4,B-7,C-174),(IB-429,A-4,B-7,C-175),(IB-430,A-4,B-7,C-176),(IB-431,A-4,B-7,C-177),(IB-432,A-4,B-7,C-178),(IB-433,A-4,B-7,C-179),(IB-434,A-4,B-7,C-180),(IB-435,A-4,B-7,C-181),(IB-436,A-4,B-7,C-182),(IB-437,A-4,B-7,C-183),(IB-438,A-4,B-7,C-184),(IB-439,

A-4,B-7,C-185),(IB-440,A-4,B-7,C-186),(IB-441,A-4,B-7,C-187),(IB-442,A-4,B-7,C-188),(IB-443,A-4,B-7,C-189),(IB-444,A-4,B-7,C-190),(IB-445,A-4,B-7,C-191),(IB-446,A-4,B-7,C-192),(IB-447,A-4,B-7,C-193),(IB-448,A-4,B-7,C-194),(IB-449,A-4,B-7,C-195),(IB-450,A-4,B-7,C-196),(IB-451,A-4,B-7,C-197),(IB-452,A-4,B-7,C-198),(IB-453,A-4,B-7,C-199),(IB-454,A-4,B-7,C-200),(IB-455,A-4,B-7,C-201),(IB-456,A-4,B-7,C-202),(IB-457,A-4,B-7,C-203),(IB-458,A-4,B-7, C-204),(IB-459,A-4,B-7,C-205),(IB-460,A-4,B-7,C-206),(IB-461,A-4,B-7,C-207),(IB-462,A-4,B-7,C-208),(IB-463,A-4,B-7,C-209),(IB-464,A-4,B-7,C-210),(IB-465,A-4,B-7,C-211),(IB-466,A-4,B-7,C-212),(IB-467,A-4,B-7,C-213),(IB-468,A-4,B-7,C-214),(IB-469,A-4,B-8,C-15),(IB-470,A-4,B-9,C-15),(IB-471,A-4,B-10,C-15),(IB-472,A-4,B-10,C-52),(IB-473,A-5,B-1,C-15),(IB-474,A-5,B-2,C-15),(IB-475,A-5,B-3,C-15),(IB-476,A-5,B-4,C-15),(IB-477,A-5,B-5,C-15),(IB-478,A-5,B-6,C-15),(IB-479,A-5,B-7,C-15),(IB-480,A-5,B-7,C-52),(IB-481,A-5,B-8,C-15),(IB-482,A-5,B-9,C-15),(IB-483,A-5,B-10,C-15),(IB-484,A-5,B-10,C-52),(IB-485,A-6,B-1,C-15),(IB-486,A-6,B-2,C-15),(IB-487,A-6,B-3,C-15),(IB-488,A-6,B-4,C-15),(IB-489,A-6,B-5,C-15),(IB-490,A-6,B-6,C-15),(IB-491,A-6,B-7,C-15),(IB-492,A-6,B-7,C-52),(IB-493,A-6,B-8,C-15),(IB-494,A-6,B-9,C-15),(IB-495,A-6,B-10,C-15),(IB-496,A-6,B-10,C-52),(IB-497,A-7,B-1,C-15),(IB-498,A-7,B-2,C-15),(IB-499,A-7,B-3,C-15),(IB-500,A-7,B-4,C-15),(IB-501,A-7,B-5,C-15),(IB-502,A-7,B-6,C-15),(IB-503,A-7,B-7,C-15),(IB-504,A-7,B-7,C-52),(IB-505,A-7,B-8,C-15),(IB-506,A-7,B-9,C-15),(IB-507,A-7,B-10,C-15),(IB-508,A-7,B-10,C-52),(IB-509,A-8,B-1,C-15),(IB-510,A-8,B-2,C-15),(IB-511,A-8,B-3,C-15),(IB-512,A-8,B-4,C-15),(IB-513,A-8,B-5,C-15),(IB-514,A-8,B-6,C-15),(IB-515,A-8,B-7,C-15),(IB-516,A-8,B-7,C-52),(IB-517,A-8,B-8,C-15),(IB-518,A-8,B-9,C-15),(IB-519,A-8,B-10,C-15),(1I3-520,A-8,B-10,C-52),(IB-521,A-9,B-1,C-15),(IB-522,A-9,B-2,C-15),(IB-523,A-9,B-3,C-15),(IB-524,A-9,B-4,C-15),(IB-525,A-9,B-5,C-15),(IB-526,A-9,B-6,C-15),(IB-527,A-9,B-7,C-15),(IB-528,A-9,B-7,C-52),(IB-529,A-9,B-8,C-15),(IB-530,A-9,B-9,C-15),(IB-531,A-9,B-10,C-15),(IB-532,A-9,B-10,C-52),(IB-533,A-10,B-1,C-15),(IB-534,A-10,B-2,C-15),(IB-535,A-10,B-3,C-15),(IB-536,A-10,B-4,C-15),(IB-537,A-10,B-5,C-15),(IB-538,A-10,B-6,C-15),(IB-539,A-10,B-7,C-1),(IB-540,A-10,B-7,C-2),(IB-541,A-10,B-7,C-3),(IB-542,A-10,B-7,C-4),(IB-543,A-10,B-7,C-5),(1B-544,A-10,B-7,C-6),(IB-545,A-10,B-7,C-7),(IB-546,A-10,B-7,C-8),(IB-547,A-10,B-7,C-9),(IB-548,A-10,B-7,C-10),(IB-549,A-10,B-7,C-11),(IB-550,A-10,B-7,C-12),(IB-551,A-10,B-7,C-13),(IB-552,A-10,B-7,C-14),(IB-553,A-10,B-7,C-15),(IB-554,A-10,B-7,C-16),(IB-555,A-10,B-7,C-17),(IB-556,A-10,B-7,C-18),(IB-557,A-10,B-7,C-19),(IB-558,A-10,B-7,C-20),(IB-559,A-10,B-7,C-21),(IB-560,A-10,B-7,C-22),(IB-561,A-10,B-7,C-23),(IB-562,A-10,B-7,C-24),(IB-563,A-10,B-7,C-25),(IB-564,A-10,B-7,C-26),(IB-565,A-10,B-7,C-27),(IB-566,A-10,B-7,C-28),(IB-567,A-10,B-7,C-29),(IB-568,A-10,B-7,C-30),(IB-569,A-10,B-7,C-31),(IB-570,A-10,B-7,C-32),(IB-571,A-10,B-7,C-33),(IB-572,A-10,B-7,C-34),(IB-573,A-10,B-7,C-35),(IB-574,A-10,B-7,C-36),(IB-575,A-10,B-7,C-37),(IB-576,A-10,B-7,C-38),(IB-577,A-10,B-7,C-39),(IB-578,A-10,B-7,C-40),(IB-579,A-10,B-7,C-41),(I B-580,A-10,B-7,C-42),(IB-581,A-10,B-7,C-43),(IB-582,A-10,B-7,C-44),(IB-583,A-10,B-7,C-45),(IB-584,A-10,B-7,C-46),(IB-585,A-10,B-7,C-47),(IB-586,A-10,B-7,C-48),(IB-587,A-10,B-7,C-49),(IB-588,A-10,B-7,C-50),(IB-589,A-10,B-7,C-51),(IB-590,A-10,B-7,C-52),(IB-591,A-10,B-7,C-53),(IB-592,A-10,B-7,C-54),(IB-593,A-10,B-7,C-55),(IB-594,A-10,B-7,C-56),(IB-595,A-10,B-7,C-57),(IB-596,A-10,B-7,C-58),(IB-597,A-10,B-7,C-59),(IB-598,A-10,B-7,C-60),(IB-599,A-10,B-7,C-61),(IB-600,A-10,B-7,C-62),(IB-601,A-10,B-7,C-63),(IB-602,A-10,B-7,C-64),(IB-603,A-10,B-7,C-65),(IB-604,A-10,B-7,C-66),(IB-605,A-10,B-7,C-67),(IB-606,A-10,B-7,C-68),(IB-607,A-10,B-7,C-69),(IB-608,A-10,B-7,C-70),(IB-609,A-10,B-7,C-71),(IB-610,A-10,B-7,C-72),(IB-611,A-10,B-7,C-73),(IB-612,A-10,B-7,C-74),(IB-613,A-10,B-7,C-75),(IB-614,A-10,B-7,C-76),(IB-615,A-10,B-7,C-77),(IB-616,A-10,B-7,C-78),(IB-617,A-10,B-7,C-79),(IB-618,A-10,B-7,C-80),(IB-619,A-10,B-7,C-81),(IB-620,A-10,B-7,C-82),(IB-621,A-10,B-7,C-83),(IB-622,A-10,B-7,C-84),(IB-623,A-10,B-7,C-85),(IB-624,A-10,B-7,C-86),(IB-625,A-10,B-7,C-87),(IB-626,A-10,B-7,C-88),(IB-627,A-10,B-7,C-89),(IB-628,A-10,B-7,C-90),(IB-629,A-10,B-7,C-91),(IB-630,A-10,B-7,C-92),(IB-631,A-10,B-7,C-93),(IB-632,A-10,B-7,C-94),(IB-633,A-10,B-7,C-95),(IB-634,A-10,B-7,C-96),(IB-635,A-10,B-7,C-97),(IB-636,A-10,B-7,C-98),(IB-637,A-10,B-7,C-99),(IB-638,A-10,B-7,C-100),(IB-639,A-10,B-7,C-101),(IB-640,A-10,B-7,C-102),(IB-641,A-10,B-7,C-103),(IB-642,A-10,B-7,C-104),(IB-643,A-10,B-7,C-105),(IB-644,A-10,B-7,C-106),(IB-645,A-10,B-7,C-107),(IB-646,A-10,B-7,C-108),(IB-647,A-10,B-7,C-109),(IB-648,A-10,B-7,C-110),(IB-649,A-10,B-7,C-111),(IB-650,A-10,B-7,C-112),(IB-651,A-10,B-7,C-113),(IB-652,A-10,B-7,C-114),(IB-653,A-10,B-7,C-115),(IB-654,A-10,B-7,C-116),(IB-655,A-10,B-7,C-117),(IB-656,A-10,B-7,C-118),(IB-657,A-10,B-7,C-119),(IB-658,A-10,B-7,C-120),(IB-659,A-10,B-7,C-121),(IB-660,A-10,B-7,C-122),(IB-661,A-10,B-7,C-123),(IB-662,A-10,B-7,C-124),(IB-663,A-10,B-7,C-125),(IB-664,A-10,B-7,C-126),(IB-665,A-10,B-7,C-127),(IB-666,A-10,B-7,C-128),(IB-667,A-10,B-7,C-129),(IB-668,A-10,B-7,C-130),(IB-669,A-10,B-7,C-131),(IB-670,A-10,B-7,C-132),(IB-671,A-10,B-7,C-133),(IB-672,A-10,B-7,C-134),(IB-673,A-10,B-7,C-135),(IB-674,A-10,B-7,C-136),(IB-675,A-10,B-7,C-137),(IB-676,A-10,B-7,C-138),(IB-677,A-10,B-7,C-139),(IB-678,A-10,B-7,C-140),(IB-679,A-10,B-7,C-141),(IB-680,A-10,B-7,C-142),(IB-681,A-10,B-7,C-143),(IB-682,A-10,B-7,C-144),(IB-683,A-10,3-7,C-145),(IB-684,A-10,B-7,C-146),(IB-685,A-10,B-7,C-147),(IB-686,A-10,B-7,C-148),(IB-687,A-10,B-7,C-149),(IB-688,A-10,B-7,C-150),(IB-689,A-10,B-7,C-151),(IB-690,A-10,B-7,C-152),(IB-691,A-10,B-7,C-153),(IB-692,A-10,B-7,C-154),(IB-693,A-10,B-7,C-155),(IB-694,A-10,B-7,C-156),(IB-695,A-10,B-7,C-157),(IB-696,A-10,B-7,C-158),(IB-697,A-10,B-7,C-159),(IB-698,A-10,B-7,C-160),(IB-699,A-10,B-7,C-161),(IB-700,A-10,B-7,C-162),(IB-701,A-10,B-7,C-163),(IB-702,A-10,B-7,C-164),(IB-703,A-10,B-7,C-165),(IB-704,A-10,B-7,C-166),(IB-705,A-10,B-7,C-167),(IB-706,A-10,B-7,C-168),(IB-707,A-10,B-7,C-169),(IB-708,A-10,B-7,C-170),(IB-709,A-10,B-7,C-171),(IB-710,A-10,B-7,C-172),(IB-711,A-10,B-7,C-173),(IB-712,A-10,B-7,C-174),(IB-713,A-10,B-7,C-175),(IB-714,A-10,B-7,C-176),(IB-715,A-10,B-7,C-177),(IB-716,A-10,B-7,C-178),(IB-717,A-10,B-7,C-179),(IB-718,A-10,B-7,C-180),(IB-719,A-10,B-7,C-181),(IB-720,A-10,B-7,C-182),(IB-721,A-10,B-7,C-183),(IB-722,A-10,B-7,C-184),(IB-723,A-10,B-7,C-185),(IB-724,A-10,B-7,C-186),(IB-725,A-10,B-7,C-187),(IB-726,A-10,B-7,C-188),(IB-727,A-10,B-7,C-189),(IB-728,A-10,B-7,C-190),(IB-729,A-10,B-7,C-191),(IB-730,A-10,B-7,C-192),(IB-731,A-10,B-7,C-193),(IB-732,A-10,B-7,C-194),(IB-733,A-10,B-7,C-195),(IB-734,A-10,B-7,C-196),(IB-735,A-10,B-7,C-197),(IB-736,A-10,B-7,C-198),(IB-737,A-10,B-7,C-199),(IB-738,A-10,B-7,C-200),(IB-739,A-10,B-7,C-201),(IB-740,A-10,B-7,C-202),(IB-741,A-10,B-7,C-203),(IB-742,A-10,B-7,C-204),(IB-743,A-10,B-7,C-205),(IB-744,A-10,B-7,C-206),(IB-745,A-10,B-7,C-207),(IB-746,A-10,B-7,C-208),(IB-747,A-

10,B-7,C-209),(IB-748,A-10,B-7,C-210),(IB-749,A-10,B-7,C-211),(IB-750,A-10,B-7,C-212),(IB-751,A-10,B-7,C-213),(IB-752,A-10,B-7,C-214),(IB-753,A-11,B-1,C-15),(IB-754,A-11,B-2,C-15),(IB-755,A-11,B-3,C-15),(IB-756,A-11,B-4,C-15),(IB-757,A-11,B-5,C-15),(IB-758,A-11,B-6,C-15),(IB-759,A-11,B-7,C-15),(IB-760,A-11,B-7,C-52),(13-761,A-11,B-8,C-15),(IB-762,A-11,B-9,C-15),(IB-763,A-11,B-10,C-15),(IB-764,A-11,B-10,C-52),(IB-765,A-12,B-1,B-15),(IB-766,A-12,B-2,C-15),(IB-767,A-12,B-3,C-15),(IB-768,A-12,B-4,C-15),(IB-769,A-12,B-5,C-15),(IB-770,A-12,B-6,C-15),(IB-771,A-12,B-7,C-15),(IB-772,A-12,B-7,C-52),(IB-773,A-12,B-8,C-15),(IB-774,A-12,B-9,C-15),(IB-775,A-12,B-10,C-15),(IB-776,A-12,B-10,C-52),(IB-777,A-13,B-1,C-15),(IB-778,A-13,B-2,C-15),(IB-779,A-13,B-3,C-15),(IB-780,A-13,B-4,C-15),(IB-781,A-13,B-5,C-15),(IB-782,A-13,B-6,C-15),(IB-783,A-13,B-7,C-15),(IB-784,A-13,B-7,C-52),(IB-785,A-13,B-8,C-15),(IB-786,A-13,B-9,C-15),(IB-787,A-13,B-10,C-15),(IB-788,A-13,B-10,C-52),(IB-789,A-14,B-1,C-15),(IB-790,A-14,B-2,C-15),(IB-791,A-14,B-3,C-15),(IB-792,A-14,B-4,C-15),(IB-793,A-14,B-5,C-15),(IB-794,A-14,B-6,C-15),(IB-795,A-14,B-7,C-15),(IB-796,A-14,B-7,C-52),(IB-797,A-14,B-8,C-15),(IB-798,A-14,B-9,C-15),(IB-799,A-14,B-10,C-15),(IB-800,A-14,B-10,C-52),(IB-801,A-15,B-1,C-15),(IB-802,A-15,B-2,C-15),(IB-803,A-15,B-3,C-15),(IB-804,A-15,B-4,C-15),(IB-805,A-15,B-5,C-15),(IB-806,A-15,B-6,C-15),(IB-807,A-15,B-7,C-15),(IB-808,A-15,B-7,C-52),(IB-809,A-15,B-8,C-15),(IB-810,A-15,B-9,C-15),(IB-811,A-15,B-10,C-15),(IB-812,A-15,B-10,C-52),(IB-813,A-16,B-1,C-15),(IB-814,A-16,B-2,C-15),(IB-815,A-16,B-3,C-15),(IB-816,A-16,B-4,C-15),(IB-817,A-16,B-5,C-15),(IB-818,A-16,B-6,C-15),(IB-819,A-16,B-7,C-15),(IB-820,A-16,B-7,C-52),(IB-821,A-16,B-8,C-15),(IB-822,A-16,B-9,C-15),(IB-823,A-16,B-10,C-15),(IB-824,A-16,B-10,C-52),(IB-825,A-17,B-1,C-15),(IB-826,A-17,B-2,C-15),(IB-827,A-17,B-3,C-15),(IB-828,A-17,B-4,C-15),(IB-829,A-17,B-5,C-15),(IB-830,A-17,B-6,C-15),(IB-831,A-17,B-7,C-15),(IB-832,A-17,B-7,C-52),(IB-833,A-17,B-8,C-15),(IB-834,A-17,B-9,C-15),(IB-835,A-17,B-10,C-15),(IB-836,A-17,B-10,C-52),(IB-837,A-18,B-1,C-15),(IB-838,A-18,B-2,C-15),(IB-839,A-18,B-3,C-15),(IB-840,A-18,B-4,C-15),(IB-841,A-18,B-5,C-15),(IB-842,A-18,B-6,C-15),(IB-843,A-18,B-7,C-15),(IB-844,A-18,B-7,C-52),(IB-845,A-18,B-8,C-15),(IB-846,A-18,B-9,C-15),(IB-847,A-18,B-10,C-15),(IB-848,A-18,B-10,C-52),(IB-849,A-19,B-1,C-15),(IB-850,A-19,B-2,C-15),(IB-851,A-19,B-3,C-15),(IB-852,A-19,B-4,C-15),(IB-853,A-19,B-5,C-15),(IB-854,A-19,B-6,C-15),(IB-855,A-19,B-7,C-15),(IB-856,A-19,B-7,C-52),(IB-857,A-19,B-8,C-15),(IB-858,A-19,B-9,C-15),(IB-859,A-19,B-10,C-15),(IB-860,A-19,B-10,C-52),(IB-861,A-20,B-1,C-15),(IB-862,A-20,B-2,C-15),(IB-863,A-20,B-3,C-15),(IB-864,A-20,B-4,C-15),(IB-865,A-20,B-5,C-15),(IB-866,A-20,B-6,C-15),(IB-867,A-20,B-7,C-1),(IB-868,A-20,B-7,C-2),(IB-869,A-20,B-7,C-3),(IB-870,A-20,B-7,C-4),(IB-871,A-20,B-7,C-5),(IB-872,A-20,B-7,C-6),(IB-873,A-20,B-7,C-7),(IB-874,A-20,B-7,C-8),(IB-875,A-20,B-7,C-9),(IB-876,A-20,B-7,C-10),(IB-877,A-20,B-7,C-11),(IB-878,A-20,B-7,C-12),(IB-879,A-20,B-7,C-13),(IB-880,A-20,B-7,C-14),(IB-881,A-20,B-7,C-15),(IB-882,A-20,B-7,C-16),(IB-883,A-20,B-7,C-17),(IB-884,A-20,B-7,C-18),(IB-885,A-20,B-7,C-19),(IB-886,A-20,B-7,C-20),(IB-887,A-20,B-7,C-21),(IB-888,A-20,B-7,C-22),(IB-889,A-20,B-7,C-23),(IB-890,A-20,B-7,C-24),(IB-891,A-20,B-7,C-25),(IB-892,A-20,B-7,C-26),(IB-893,A-20,B-7,C-27),(IB-894,A-20,B-7,C-28),(IB-895,A-20,B-7,C-29),(IB-896,A-20,B-7,C-30),(IB-897,A-20,B-7,C-31),(IB-898,A-20,B-7,C-32),(IB-899,A-20,B-7,C-33),(IB-900,A-20,B-7,C-34),(IB-901,A-20,B-7,C-35),(IB-902,A-20,B-7,C-36),(IB-903,A-20,B-7,C-37),(IB-904,A-20,B-7,C-38),(IB-905,A-20,B-7,C-39),(IB-906,A-20,B-7,C-40),(IB-907,A-20,B-7,C-41),(IB-908,A-20,B-7,C-42),(IB-909,A-20,B-7,C-43),(IB-910,A-20,B-7,C-44),(IB-911,A-20,B-7,C-45),(IB-912,A-20,B-7,C-46),(IB-913,A-20,B-7,C-47),(IB-914,A-20,B-7,C-48),(IB-915,A-20,B-7,C-49),(IB-916,A-20,B-7,C-50),(IB-917,A-20,B-7,C-51),(IB-918,A-20,B-7,C-52),(IB-919,A-20,B-7,C-53),(IB-920,A-20,B-7,C-54),(IB-921,A-20,B-7,C-55),(IB-922,A-20,B-7,C-56),(IB-923,A-20,B-7,C-57),(IB-924,A-20,B-7,C-58),(IB-925,A-20,B-7,C-59),(IB-926,A-20,B-7,C-60),(IB-927,A-20,B-7,C-61),(IB-928,A-20,B-7,C-62),(IB-929,A-20,B-7,C-63),(IB-930,A-20,B-7,C-64),(IB-931,A-20,B-7,C-65),(IB-932,A-20,B-7,C-66),(IB-933,A-20,B-7,C-67),(IB-934,A-20,B-7,C-68),(IB-935,A-20,B-7,C-69),(IB-936,A-20,B-7,C-70),(IB-937,A-20,B-7,C-71),(IB-938,A-20,B-7,C-72),(IB-939,A-20,B-7,C-73),(IB-940,A-20,B-7,C-74),(IB-941,A-20,B-7,C-75),(IB-942,A-20,B-7,C-76),(IB-943,A-20,B-7,C-77),(IB-944,A-20,B-7,C-78),(IB-945,A-20,B-7,C-79),(IB-946,A-20,B-7,C-80),(IB-947,A-20,B-7,C-81),(IB-948,A-20,B-7,C-82),(IB-949,A-20,B-7,C-83),(IB-950,A-20,B-7,C-84),(IB-951,A-20,B-7,C-85),(IB-952,A-20,B-7,C-86),(IB-953,A-20,B-7,C-87),(IB-954,A-20,B-7,C-88),(IB-955,A-20,B-7,C-89),(IB-956,A-20,B-7,C-90),(IB-957,A-20,B-7,C-91),(IB-958,A-20,B-7,C-92),(IB-959,A-20,B-7,C-93),(IB-960,A-20,B-7,C-94),(IB-961,A-20,B-7,C-95),(IB-962,A-20,B-7,C-96),(IB-963,A-20,B-7,C-97),(IB-964,A-20,B-7,C-98),(IB-965,A-20,B-7,C-99),(IB-966,A-20,B-7,C-100),(IB-967,A-20,B-7,C-101),(IB-968,A-20,B-7,C-102),(IB-969,A-20,B-7,C-103),(IB-970,A-20,B-7,C-104),(IB-971,A-20,B-7,C-105),(IB-972,A-20,B-7,C-106),(IB-973,A-20,B-7,C-107),(IB-974,A-20,B-7,C-108),(IB-975,A-20,B-7,C-109),(IB-976,A-20,B-7,C-110),(IB-977,A-20,B-7,C-111),(IB-978,A-20,B-7,C-112),(IB-979,A-20,B-7,C-113),(IB-980,A-20,B-7,C-114),(IB-981,A-20,B-7,C-115),(IB-982,A-20,B-7,C-116),(IB-983,A-20,B-7,C-117),(IB-984,A-20,B-7,C-118),(IB-985,A-20,B-7,C-119),(IB-986,A-20,B-7,C-120),(IB-987,A-20,B-7,C-121),(IB-988,A-20,B-7,C-122),(IB-989,A-20,B-7,C-123),(IB-990,A-20,B-7,C-124),(IB-991,A-20,B-7,C-125),(IB-992,A-20,B-7,C-126),(IB-993,A-20,B-7,C-127),(IB-994,A-20,B-7,C-128),(IB-995,A-20,B-7,C-129),(IB-996,A-20,B-7,C-130),(IB-997,A-20,B-7,C-131),(IB-998,A-20,B-7,C-132),(IB-999,A-20,B-7,C-133),(IB-1000,A-20,B-7,C-134),(IB-1001,A-20,B-7,C-135),(IB-1002,A-20,B-7,C-136),(IB-1003,A-20,B-7,C-137),(IB-1004,A-20,B-7,C-138),(IB-1005,A-20,B-7,C-139),(IB-1006,A-20,B-7,C-140),(IB-1007,A-20,B-7,C-141),(IB-1008,A-20,B-7,C-142),(IB-1009,A-20,B-7,C-143),(IB-1010,A-20,B-7,C-144),(IB-1011,A-20,B-7,C-145),(IB-1012,A-20,B-7,C-146),(IB-1013,A-20,B-7,C-147),(IB-1014,A-20,B-7,C-148),(IB-1015,A-20,B-7,C-149),(IB-1016,A-20,B-7,C-150),(IB-1017,A-20,B-7,C-151),(IB-1018,A-20,B-7,C-152),(IB-1019,A-20,B-7,C-153),(IB-1020,A-20,B-7,C-154),(IB-1021,A-20,B-7,C-155),(IB-1022,A-20,B-7,C-156),(IB-1023,A-20,B-7,C-157),(IB-1024,A-20,B-7,C-158),(IB-1025,A-20,B-7,C-159),(IB-1026,A-20,B-7,C-160),(IB-1027,A-20,B-7,C-161),(IB-1028,A-20,B-7,C-162),(IB-1029,A-20,B-7,C-163),(IB-1030,A-20,B-7,C-164),(IB-1031,A-20,B-7,C-165),(IB-1032,A-20,B-7,C-166),(IB-1033,A-20,B-7,C-167),(IB-1034,A-20,B-7,C-168),(IB-1035,A-20,B-7,C-169),(IB-1036,A-20,B-7,C-170),(IB-1037,A-20,B-7,C-171),(IB-1038,A-20,B-7,C-172),(IB-1039,A-20,B-7,C-173),(IB-1040,A-20,B-7,C-174),(IB-1041,A-20,B-7,C-175),(IB-1042,A-20,B-7,C-176),(IB-1043,A-20,B-7,C-177),(IB-1044,A-20,B-7,C-178),(IB-1045,A-20,B-7,C-179),(IB-1046,A-20,B-7,C-180),(IB-1047,A-20,B-7,C-181),(IB-

1048,A-20,B-7,C-182),(IB-1049,A-20,B-7,C-183),(IB-1050,A-20,B-7,C-184),(IB-1051,A-20,B-7,C-185),(IB-1052,A-20,B-7,C-186),(IB-1053,A-20,B-7,C-187),(IB-1054,A-20,B-7,C-188),(IB-1055,A-20,B-7,C-189),(IB-1056,A-20,B-7,C-190),(IB-1057,A-20,B-7,C-191),(IB-1058,A-20,B-7,C-192),(IB-1059,A-20,B-7,C-193),(IB-1060,A-20,B-7,C-194),(IB-1061,A-20,B-7,C-195),(IB-1062,A-20,B-7,C-196),(IB-1063,A-20,B-7,C-197),(IB-1064,A-20,B-7,C-198),(IB-1065,A-20,B-7,C-199),(IB-1066,A-20,B-7,C-200),(IB-1067,A-20,B-7,C-201),(IB-1068,A-20,B-7,C-202),(IB-1069,A-20,B-7,C-203),(IB-1070,A-20,B-7,C-204),(IB-1071,A-20,B-7,C-205),(IB-1072,A-20,B-7,C-206),(IB-1073,A-20,B-7,C-207),(IB-1074,A-20,B-7,C-208),(IB-1075,A-20,B-7,C-209),(IB-1076,A-20,B-7,C-210),(IB-1077,A-20,B-7,C-211),(IB-1078,A-20,B-7,C-212),(IB-1079,A-20,B-7,C-213),(IB-1080,A-20,B-7,C-214),(IB-1081,A-21,B-1,C-15),(IB-1082,A-21,B-2,C-15),(IB-1083,A-21,B-3,C-15),(IB-1084,A-21,B-4,C-15),(IB-1085,A-21,B-5,C-15),(IB-1086,A-21,B-6,C-15),(IB-1087,A-21,B-7,C-15),(IB-1088,A-21,B-7,C-52),(IB-1089,A-21,B-8,C-15),(IB-1090,A-21,B-9,0-15),(IB-1091,A-21,B-10,C-15),(IB-1092,A-21,B-10,C-52),(IB-1093,A-22,B-1,C-15),(IB-1094,A-22,B-2,C-15),(IB-1095,A-22,B-3,C-15),(IB-1096,A-22,B-4,C-15),(IB-1097,A-22,B-5,C-15),(IB-1098,A-22,B-6,C-15),(IB-1099,A-22,B-7,C-1),(IB-1100,A-22,B-7,C-2),(IB-1101,A-22,B-7,C-3),(IB-1102,A-22,B-7,C-4),(IB-1103,A-22,B-7,C-5),(IB-1104,A-22,B-7,C-6),(IB-1105,A-22,B-7,C-7),(IB-1106,A-22,B-7,C-8),(IB-1107,A-22,B-7,C-9),(IB-1108,A-22,B-7,C-10),(IB-1109,A-22,B-7,C-11),(IB-1110,A-22,B-7,C-12),(IB-1111,A-22,B-7,C-13),(IB-1112,A-22,B-7,C-14),(IB-1113,A-22,B-7,C-15),(IB-1114,A-22,B-7,C-16),(IB-1115,A-22,B-7,C-17),(IB-1116,A-22,B-7,C-18),(IB-1117,A-22,B-7,C-19),(IB-1118,A-22,B-7,C-20),(IB-1119,A-22,B-7,C-21),(IB-1120,A-22,B-7,C-22),(IB-1121,A-22,B-7,C-23),(IB-1122,A-22,B-7,C-24),(IB-1123,A-22,B-7,C-25),(IB-1124,A-22,B-7,C-26),(IB-1125,A-22,B-7,C-27),(IB-1126,A-22,B-7,C-28),(IB-1127,A-22,B-7,C-29),(IB-1128,A-22,B-7,C-30),(IB-1129,A-22,B-7,C-31),(IB-1130,A-22,B-7,C-32),(IB-1131,A-22,B-7,C-33),(IB-1132,A-22,B-7,C-34),(IB-1133,A-22,B-7,C-35),(IB-1134,A-22,B-7,C-36),(IB-1135,A-22,B-7,C-37),(IB-1136,A-22,B-7,C-38),(IB-1137,A-22,B-7,C-39),(IB-1138,A-22,B-7,C-40),(IB-1139,A-22,B-7,C-41),(IB-1140,A-22,B-7,C-42),(IB-1141,A-22,B-7,C-43),(IB-1142,A-22,B-7,C-44),(IB-1143,A-22,B-7,C-45),(IB-1144,A-22,B-7,C-46),(IB-1145,A-22,B-7,C-47),(IB-1146,A-22,B-7,C-48),(IB-1147,A-22,B-7,C-49),(IB-1148,A-22,B-7,C-50),(IB-1149,A-22,B-7,C-51),(IB-1150,A-22,B-7,C-52),(IB-1151,A-22,B-7,C-53),(IB-1152,A-22,B-7,C-54),(IB-1153,A-22,B-7,C-55),(IB-1154,A-22,B-7,C-56),(IB-1155,A-22,B-7,C-57),(IB-1156,A-22,B-7,C-58),(IB-1157,A-22,B-7,C-59),(IB-1158,A-22,B-7,C-60),(IB-1159,A-22,B-7,C-61),(IB-1160,A-22,B-7,C-62),(IB-1161,A-22,B-7,C-63),(IB-1162,A-22,B-7,C-64),(IB-1163,A-22,B-7,C-65),(IB-1164,A-22,B-7,C-66),(IB-1165,A-22,B-7,C-67),(IB-1166,A-22,B-7,C-68),(IB-1167,A-22,B-7,C-69),(IB-1168,A-22,B-7,C-70),(IB-1169,A-22,B-7,C-71),(IB-1170,A-22,B-7,C-72),(IB-1171,A-22,B-7,C-73),(IB-1172,A-22,B-7,C-74),(IB-1173,A-22,B-7,C-75),(IB-1174,A-22,B-7,C-76),(IB-1175,A-22,B-7,C-77),(IB-1176,A-22,B-7,C-78),(IB-1177,A-22,B-7,C-79),(IB-1178,A-22,B-7,C-80),(IB-1179,A-22,B-7,C-81),(IB-1180,A-22,B-7,C-82),(IB-1181,A-22,B-7,C-83),(IB-1182,A-22,B-7,C-84),(IB-1183,A-22,B-7,C-85),(IB-1184,A-22,B-7,C-86),(IB-1185,A-22,B-7,C-87),(IB-1186,A-22,B-7,C-88),(IB-1187,A-22,B-7,C-89),(IB-1188,A-22,B-7,C-90),(IB-1189,A-22,B-7,C-91),(IB-1190,A-22,B-7,C-92),(IB-1191,A-22,B-7,C-93),(IB-1192,A-22,B-7,C-94),(IB-1193,A-22,B-7,C-95),(IB-1194,A-22,B-7,C-96),(IB-1195,A-22,B-7,C-97),(IB-1196,A-22,B-7,C-98),(IB-1197,A-22,B-7,C-99),(IB-1198,A-22,B-7,C-100),(IB-1199,A-22,B-7,C-101),(IB-1200,A-22,B-7,C-102),(IB-1201,A-22,B-7,C-103),(IB-1202,A-22,B-7,C-104),(IB-1203,A-22,B-7,C-105),(IB-1204,A-22,B-7,C-106),(IB-1205,A-22,B-7,C-107),(IB-1206,A-22,B-7,C-108),(IB-1207,A-22,B-7,C-109),(IB-1208,A-22,B-7,C-110),(IB-1209,A-22,B-7,C-111),(IB-1210,A-22,B-7,C-112),(IB-1211,A-22,B-7,C-113),(IB-1212,A-22,B-7,C-114),(IB-1213,A-22,B-7,C-115),(IB-1214,A-22,B-7,C-116),(IB-1215,A-22,B-7,C-117),(IB-1216,A-22,B-7,C-118),(IB-1217,A-22,B-7,C-119),(IB-1218,A-22,B-7,C-120),(IB-1219,A-22,B-7,C-121),(IB-1220,A-22,B-7,C-122),(IB-1221,A-22,B-7,C-123),(IB-1222,A-22,B-7,C-124),(IB-1223,A-22,B-7,C-125),(IB-1224,A-22,B-7,C-126),(IB-1225,A-22,B-7,C-127),(IB-1226,A-22,B-7,C-128),(IB-1227,A-22,B-7,C-129),(IB-1228,A-22,B-7,C-130),(IB-1229,A-22,B-7,C-131),(IB-1230,A-22,B-7,C-132),(IB-1231,A-22,B-7,C-133),(IB-1232,A-22,B-7,C-134),(IB-1233,A-22,B-7,C-135),(IB-1234,A-22,B-7,C-136),(IB-1235,A-22,B-7,C-137),(IB-1236,A-22,B-7,C-138),(IB-1237,A-22,B-7,C-139),(IB-1238,A-22,B-7,C-140),(IB-1239,A-22,B-7,C-141),(IB-1240,A-22,B-7,C-142),(IB-1241,A-22,B-7,C-143),(IB-1242,A-22,B-7,C-144),(IB-1243,A-22,B-7,C-145),(IB-1244,A-22,B-7,C-146),(IB-1245,A-22,B-7,C-147),(IB-1246,A-22,B-7,C-148),(IB-1247,A-22,B-7,C-149),(IB-1248,A-22,B-7,C-150),(IB-1249,A-22,B-7,C-151),(IB-1250,A-22,B-7,C-152),(IB-1251,A-22,B-7,C-153),(IB-1252,A-22,B-7,C-154),(IB-1253,A-22,B-7,C-155),(IB-1254,A-22,B-7,C-156),(IB-1255,A-22,B-7,C-157),(IB-1256,A-22,B-7,C-158),(IB-1257,A-22,B-7,C-159),(IB-1258,A-22,B-7,C-160),(IB-1259,A-22,B-7,C-161),(IB-1260,A-22,B-7,C-162),(IB-1261,A-22,B-7,C-163),(IB-1262,A-22,B-7,C-164),(IB-1263,A-22,B-7,C-165),(IB-1264,A-22,B-7,C-166),(IB-1265,A-22,B-7,C-167),(IB-1266,A-22,B-7,C-168),(IB-1267,A-22,B-7,C-169),(IB-1268,A-22,B-7,C-170),(IB-1269,A-22,B-7,C-171),(IB-1270,A-22,B-7,C-172),(IB-1271,A-22,B-7,C-173),(IB-1272,A-22,B-7,C-174),(IB-1273,A-22,B-7,C-175),(IB-1274,A-22,B-7,C-176),(IB-1275,A-22,B-7,C-177),(IB-1276,A-22,B-7,C-178),(IB-1277,A-22,B-7,C-179),(IB-1278,A-22,B-7,C-180),(IB-1279,A-22,B-7,C-181),(IB-1280,A-22,B-7,C-182),(IB-1281,A-22,B-7,C-183),(IB-1282,A-22,B-7,C-184),(IB-1283,A-22,B-7,C-185),(IB-1284,A-22,B-7,C-186),(IB-1285,A-22,B-7,C-187),(IB-1286,A-22,B-7,C-188),(IB-1287,A-22,B-7,C-189),(IB-1288,A-22,B-7,C-190),(IB-1289,A-22,B-7,C-191),(IB-1290,A-22,B-7,C-192),(IB-1291,A-22,B-7,C-193),(IB-1292,A-22,B-7,C-194),(IB-1293,A-22,B-7,C-195),(IB-1294,A-22,B-7,C-196),(IB-1295,A-22,B-7,C-197),(IB-1296,A-22,B-7,C-198),(IB-1297,A-22,B-7,C-199),(IB-1298,A-22,B-7,C-200),(IB-1299,A-22,B-7,C-201),(IB-1300,A-22,B-7,C-202),(IB-1301,A-22,B-7,C-203),(IB-1302,A-22,B-7,C-204),(IB-1303,A-22,B-7,C-205),(IB-1304,A-22,B-7,C-206),(IB-1305,A-22,B-7,C-207),(IB-1306,A-22,B-7,C-208),(IB-1307,A-22,B-7,C-209),(IB-1308,A-22,B-7,C-210),(IB-1309,A-22,B-7,C-211),(IB-1310,A-22,B-7,C-212),(IB-1311,A-22,B-7,C-213),(IB-1312,A-22,B-7,C-214),(IB-1313,A-23,B-1,C-15),(IB-1314,A-23,B-2,C-15),(IB-1315,A-23,B-3,C-15),(IB-1316,A-23,B-4,C-15),(IB-1317,A-23,B-5,C-15),(IB-1318,A-23,B-6,C-15),(IB-1319,A-23,B-7,C-15),(IB-1320,A-23,B-7,C-52),(IB-1321,A-23,B-8,C-15),(IB-1322,A-23,B-9,C-15),(IB-1323,A-23,B-10,C-15),(IB-1324,A-23,B-10,C-52),(IB-1325,A-24,B-1,C-15),(IB-1326,A-24,B-2,C-15),(IB-1327,A-24,B-3,C-15),(IB-1328,A-24,

B-4,C-15),(IB-1329,A-24,B-5,C-15),(IB-1330,A-24,B-6,C-15),(IB-1331,A-24,B-7,C-15),(IB-1332,A-24,B-7,C-52),(IB-1333,A-24,B-8,C-15),(IB-1334,A-24,B-9,C-15),(IB-1335,A-24,B-10,C-15),(IB-1336,A-24,B-10,C-52),(IB-1337,A-25,B-1,C-15),(IB-1338,A-25,B-2,C-15),(IB-1339,A-25,B-3,C-15),(IB-1340,A-25,B-4,C-15),(IB-1341,A-25,B-5,C-15),(IB-1342,A-25,B-6,C-15),(IB-1343,A-25,B-7,C-15),(IB-1344,A-25,B-7,C-52),(IB-1345,A-25,B-8,C-15),(IB-1346,A-25,B-9,C-15),(IB-1347,A-25,B-10,C-15),(IB-1348,A-25,B-10,C-52),(IB-1349,A-26,B-1,C-15),(IB-1350,A-26,B-2,C-15),(IB-1351,A-26,B-3,C-15),(IB-1352,A-26,B-4,C-15),(IB-1353,A-26,B-5,C-15),(IB-1354,A-26,B-6,C-15),(IB-1355,A-26,B-7,C-15),(IB-1356,A-26,B-7,C-52),(IB-1357,A-26,B-8,C-15),(IB-1358,A-26,B-9,C-15),(IB-1359,A-26,B-10,C-15),(IB-1360,A-26,B-10,C-52),(IB-1361,A-27,B-1,C-15),(IB-1362,A-27,B-2,C-15),(IB-1363,A-27,B-3,C-15),(IB-1364,A-27,B-4,C-15),(IB-1365,A-27,B-5,C-15),(IB-1366,A-27,B-6,C-15),(IB-1367,A-27,B-7,C-1),(IB-1368,A-27,B-7,C-2),(IB-1369,A-27,B-7,C-3),(IB-1370,A-27,B-7,C-4),(IB-1371,A-27,B-7,C-5),(IB-1372,A-27,B-7,C-6),(IB-1373,A-27,B-7,C-7),(IB-1374,A-27,B-7,C-8),(IB-1375,A-27,B-7,C-9),(IB-1376,A-27,B-7,C-10),(IB-1377,A-27,B-7,C-11),(IB-1378,A-27,B-7,C-12),(IB-1379,A-27,B-7,C-13),(IB-1380,A-27,B-7,C-14),(IB-1381,A-27,B-7,C-15),(IB-1382,A-27,B-7,C-16),(IB-1383,A-27,B-7,C-17),(IB-1384,A-27,B-7,C-18),(IB-1385,A-27,B-7,C-19),(IB-1386,A-27,B-7,C-20),(IB-1387,A-27,B-7,C-21),(IB-1388,A-27,B-7,C-22),(IB-1389,A-27,B-7,C-23),(IB-1390,A-27,B-7,C-24),(IB-1391,A-27,B-7,C-25),(IB-1392,A-27,B-7,C-26),(IB-1393,A-27,B-7,C-27),(IB-1394,A-27,B-7,C-28),(IB-1395,A-27,B-7,C-29),(IB-1396,A-27,B-7,C-30),(IB-1397,A-27,B-7,C-31),(IB-1398,A-27,B-7,C-32),(IB-1399,A-27,B-7,C-33),(IB-1400,A-27,B-7,C-34),(IB-1401,A-27,B-7,C-35),(IB-1402,A-27,B-7,C-36),(IB-1403,A-27,B-7,C-37),(IB-1404,A-27,B-7,C-38),(IB-1405,A-27,B-7,C-39),(IB-1406,A-27,B-7,C-40),(IB-1407,A-27,B-7,C-41),(IB-1408,A-27,B-7,C-42),(IB-1409,A-27,B-7,C-43),(IB-1410,A-27,B-7,C-44),(IB-1411,A-27,B-7,C-45),(IB-1412,A-27,B-7,C-46),(IB-1413,A-27,B-7,C-47),(IB-1414,A-27,B-7,C-48),(IB-1415,A-27,B-7,C-49),(IB-1416,A-27,B-7,C-50),(IB-1417,A-27,B-7,C-51),(IB-1418,A-27,B-7,C-52),(IB-1419,A-27,B-7,C-53),(IB-1420,A-27,B-7,C-54),(IB-1421,A-27,B-7,C-55),(IB-1422,A-27,B-7,C-56),(IB-1423,A-27,B-7,C-57),(IB-1424,A-27,B-7,C-58),(IB-1425,A-27,B-7,C-59),(IB-1426,A-27,B-7,C-60),(IB-1427,A-27,B-7,C-61),(IB-1428,A-27,B-7,C-62),(IB-1429,A-27,B-7,C-63),(IB-1430,A-27,B-7,C-64),(IB-1431,A-27,B-7,C-65),(IB-1432,A-27,B-7,C-66),(IB-1433,A-27,B-7,C-67),(IB-1434,A-27,B-7,C-68),(IB-1435,A-27,B-7,C-69),(IB-1436,A-27,B-7,C-70),(IB-1437,A-27,B-7,C-71),(IB-1438,A-27,B-7,C-72),(IB-1439,A-27,B-7,C-73),(IB-1440,A-27,B-7,C-74),(IB-1441,A-27,B-7,C-75),(IB-1442,A-27,B-7,C-76),(IB-1443,A-27,B-7,C-77),(IB-1444,A-27,B-7,C-78),(IB-1445,A-27,B-7,C-79),(IB-1446,A-27,B-7,C-80),(IB-1447,A-27,B-7,C-81),(IB-1448,A-27,B-7,C-82),(IB-1449,A-27,B-7,C-83),(IB-1450,A-27,B-7,C-84),(IB-1451,A-27,B-7,C-85),(IB-1452,A-27,B-7,C-86),(IB-1453,A-27,B-7,C-87),(IB-1454,A-27,B-7,C-88),(IB-1455,A-27,B-7,C-89),(IB-1456,A-27,B-7,C-90),(IB-1457,A-27,B-7,C-91),(IB-1458,A-27,B-7,C-92),(IB-1459,A-27,B-7,C-93),(IB-1460,A-27,B-7,C-94),(IB-1461,A-27,B-7,C-95),(IB-1462,A-27,B-7,C-96),(IB-1463,A-27,B-7,C-97),(IB-1464,A-27,B-7,C-98),(IB-1465,A-27,B-7,C-99),(IB-1466,A-27,B-7,C-100),(IB-1467,A-27,B-7,C-101),(IB-1468,A-27,B-7,C-102),(IB-1469,A-27,B-7,C-103),(IB-1470,A-27,B-7,C-104),(IB-1471,A-27,B-7,C-105),(IB-1472,A-27,B-7,C-106),(IB-1473,A-27,B-7,C-107),(IB-1474,A-27,B-7,C-108),(IB-1475,A-27,B-7,C-109),(IB-1476,A-27,B-7,C-110),(IB-1477,A-27,B-7,C-111),(IB-1478,A-27,B-7,C-112),(IB-1479,A-27,B-7,C-113),(IB-1480,A-27,B-7,C-114),(IB-1481,A-27,B-7,C-115),(IB-1482,A-27,B-7,C-116),(IB-1483,A-27,B-7,C-117),(IB-1484,A-27,B-7,C-118),(IB-1485,A-27,B-7,C-119),(IB-1486,A-27,B-7,C-120),(IB-1487,A-27,B-7,C-121),(IB-1488,A-27,B-7,C-122),(IB-1489,A-27,B-7,C-123),(IB-1490,A-27,B-7,C-124),(IB-1491,A-27,B-7,C-125),(IB-1492,A-27,B-7,C-126),(IB-1493,A-27,B-7,C-127),(IB-1494,A-27,B-7,C-128),(IB-1495,A-27,B-7,C-129),(IB-1496,A-27,B-7,C-130),(IB-1497,A-27,B-7,C-131),(IB-1498,A-27,B-7,C-132),(IB-1499,A-27,B-7,C-133),(IB-1500,A-27,B-7,C-134),(IB-1501,A-27,B-7,C-135),(IB-1502,A-27,B-7,C-136),(IB-1503,A-27,B-7,C-137),(IB-1504,A-27,B-7,C-138),(IB-1505,A-27,B-7,C-139),(IB-1506,A-27,B-7,C-140),(IB-1507,A-27,B-7,C-141),(IB-1508,A-27,B-7,C-142),(IB-1509,A-27,B-7,C-143),(IB-1510,A-27,B-7,C-144),(IB-1511,A-27,B-7,C-145),(IB-1512,A-27,B-7,C-146),(IB-1513,A-27,B-7,C-147),(IB-1514,A-27,B-7,C-148),(IB-1515,A-27,B-7,C-149),(IB-1516,A-27,B-7,C-150),(IB-1517,A-27,B-7,C-151),(IB-1518,A-27,B-7,C-152),(IB-1519,A-27,B-7,C-153),(IB-1520,A-27,B-7,C-154),(IB-1521,A-27,B-7,C-155),(IB-1522,A-27,B-7,C-156),(IB-1523,A-27,B-7,C-157),(IB-1524,A-27,B-7,C-158),(IB-1525,A-27,B-7,C-159),(IB-1526,A-27,B-7,C-160),(IB-1527,A-27,B-7,C-161),(IB-1528,A-27,B-7,C-162),(IB-1529,A-27,B-7,C-163),(IB-1530,A-27,B-7,C-164),(IB-1531,A-27,B-7,C-165),(IB-1532,A-27,B-7,C-166),(IB-1533,A-27,B-7,C-167),(IB-1534,A-27,B-7,C-168),(IB-1535,A-27,B-7,C-169),(IB-1536,A-27,B-7,C-170),(IB-1537,A-27,B-7,C-171),(IB-1538,A-27,B-7,C-172),(IB-1539,A-27,B-7,C-173),(IB-1540,A-27,B-7,C-174),(IB-1541,A-27,B-7,C-175),(IB-1542,A-27,B-7,C-176),(IB-1543,A-27,B-7,C-177),(IB-1544,A-27,B-7,C-178),(IB-1545,A-27,B-7,C-179),(IB-1546,A-27,B-7,C-180),(IB-1547,A-27,B-7,C-181),(IB-1548,A-27,B-7,C-182),(IB-1549,A-27,B-7,C-183),(IB-1550,A-27,B-7,C-184),(IB-1551,A-27,B-7,C-185),(IB-1552,A-27,B-7,C-186),(IB-1553,A-27,B-7,C-187),(IB-1554,A-27,B-7,C-188),(IB-1555,A-27,B-7,C-189),(IB-1556,A-27,B-7,C-190),(IB-1557,A-27,B-7,C-191),(IB-1558,A-27,B-7,C-192),(IB-1559,A-27,B-7,C-193),(IB-1560,A-27,B-7,C-194),(IB-1561,A-27,B-7,C-195),(IB-1562,A-27,B-7,C-196),(IB-1563,A-27,B-7,C-197),(IB-1564,A-27,B-7,C-198),(IB-1565,A-27,B-7,C-199),(IB-1566,A-27,B-7,C-200),(IB-1567,A-27,B-7,C-201),(IB-1568,A-27,B-7,C-202),(IB-1569,A-27,B-7,C-203),(IB-1570,A-27,B-7,C-204),(IB-1571,A-27,B-7,C-205),(IB-1572,A-27,B-7,C-206),(IB-1573,A-27,B-7,C-207),(IB-1574,A-27,B-7,C-208),(IB-1575,A-27,B-7,C-209),(IB-1576,A-27,B-7,C-210),(IB-1577,A-27,B-7,C-211),(IB-1578,A-27,B-7,C-212),(IB-1579,A-27,B-7,C-213),(IB-1580,A-27,B-7,C-214),(IB-1581,A-27,B-8,C-15),(IB-1582,A-27,B-9,C-15),(IB-1583,A-27,B-10,C-15),(IB-1584,A-27,B-10,C-52),(IB-1585,A-28,B-1,C-15),(IB-1586,A-28,B-2,C-15),(IB-1587,A-28,B-3,C-15),(IB-1588,A-28,B-4,C-15),(IB-1589,A-28,B-5,C-15),(IB-1590,A-28,B-6,C-15),(IB-1591,A-28,B-7,C-1),(IB-1592,A-28,B-7,C-2),(IB-1593,A-28,B-7,C-3),(IB-1594,A-28,B-7,C-4),(IB-1595,A-28,B-7,C-5),(IB-1596,A-28,B-7,C-6),(IB-1597,A-28,B-7,C-7),(IB-1598,A-28,B-7,C-8),(IB-1599,A-28,B-7,C-9),(IB-1600,A-7,C-10),(IB-1601,A-28,B-7,C-11),(IB-1602,A-28,B-7,C-12),(IB-1603,A-28,B-7,C-13),(IB-1604,A-28,B-7,C-14),(IB-1605,A-28,B-7,C-15),(IB-1606,A-28,B-7,C-16),(IB-1607,A-28,B-7,C-17),(IB-1608,A-28,B-7,C-18),(IB-1609,A-28,B-7,C-19),(IB-1610,A-28,B-7,C-20),(IB-1611,A-28,B-7,C-21),(IB-1612,A-28,

B-7,C-22),(IB-1613,A-28,B-7,C-23),(IB-1614,A-28,B-7,C-24),(IB-1615,A-28,B-7,C-25),(IB-1616,A-28,B-7,C-26), (IB-1617,A-28,B-7,C-27),(IB-1618,A-28,B-7,C-28),(IB-1619,A-28,B-7,C-29),(IB-1620,A-28,B-7,C-30),(IB-1621, A-28,B-7,C-31),(IB-1622,A-28,B-7,C-32),(IB-1623,A-28, B-7,C-33),(IB-1624,A-28,B-7,C-34),(IB-1625,A-28,B-7,C-35),(IB-1626,A-28,B-7,C-36),(IB-1627,A-28,B-7,C-37), (IB-1628,A-28,B-7,C-38),(IB-1629,A-28,B-7,C-39),(IB-1630,A-28,B-7,C-40),(IB-1631,A-28,B-7,C-41),(IB-1632, A-28,B-7,C-42),(IB-1633,A-28,B-7,C-43),(IB-1634,A-28, B-7,C-44),(IB-1635,A-28,B-7,C-45),(IB-1636,A-28,B-7,C-46),(IB-1637,A-28,B-7,C-47),(IB-1638,A-28,B-7,C-48), (IB-1639,A-28,B-7,C-49),(IB-1640,A-28,B-7,C-50),(IB-1641,A-28,B-7,C-51),(IB-1642,A-28,B-7,C-52),(IB-1643, A-28,B-7,C-53),(IB-1644,A-28,B-7,C-54),(IB-1645,A-28, B-7,C-55),(IB-1646,A-28,B-7,C-56),(IB-1647,A-28,B-7,C-57),(IB-1648,A-28,B-7,C-58),(IB-1649,A-28,B-7,C-59), (IB-1650,A-28,B-7,C-60),(IB-1651,A-28,B-7,C-61),(IB-1652,A-28,B-7,C-62),(IB-1653,A-28,B-7,C-63),(IB-1654, A-28,B-7,C-64),(IB-1655,A-28,B-7,C-65),(IB-1656,A-28, B-7,C-66),(IB-1657,A-28,B-7,C-67),(IB-1658,A-28,B-7,C-68),(IB-1659,A-28,B-7,C-69),(IB-1660,A-28,B-7,C-70), (IB-1661,A-28,B-7,C-71),(IB-1662,A-28,B-7,C-72),(IB-1663,A-28,B-7,C-73),(IB-1664,A-28,B-7,C-74),(IB-1665, A-28,B-7,C-75),(IB-1666,A-28,B-7,C-76),(IB-1667,A-28, B-7,C-77),(IB-1668,A-28,B-7,C-78),(IB-1669,A-28,B-7,C-79),(IB-1670,A-28,B-7,C-80),(IB-1671,A-28,B-7,C-81), (IB-1672,A-28,B-7,C-82),(IB-1673,A-28,B-7,C-83),(IB-1674,A-28,B-7,C-84),(IB-1675,A-28,B-7,C-85),(IB-1676, A-28,B-7,C-86),(IB-1677,A-28,B-7,C-87),(IB-1678,A-28, B-7,C-88),(IB-1679,A-28,B-7,C-89),(IB-1680,A-28,B-7,C-90),(IB-1681,A-28,B-7,C-91),(IB-1682,A-28,B-7,C-92), (IB-1683,A-28,B-7,C-93),(IB-1684,A-28,B-7,C-94),(IB-1685,A-28,B-7,C-95),(IB-1686,A-28,B-7,C-96),(IB-1687, A-28,B-7,C-97),(IB-1688,A-28,B-7,C-98),(IB-1689,A-28, B-7,C-99),(IB-1690,A-28,B-7,C-100),(IB-1691,A-28,B-7, C-101),(IB-1692,A-28,B-7,C-102),(IB-1693,A-28,B-7,C-103),(IB-1694,A-28,B-7,C-104),(IB-1695,A-28,B-7,C-105),(IB-1696,A-28,B-7,C-106),(IB-1697,A-28,B-7,C-107),(IB-1698,A-28,B-7,C-108),(IB-1699,A-28,B-7,C-109),(IB-1700,A-28,B-7,C-110),(IB-1701,A-28,B-7,C-111),(IB-1702,A-28,B-7,C-112),(IB-1703,A-28,B-7,C-113),(IB-1704,A-28,B-7,C-114),(IB-1705,A-28,B-7,C-115),(IB-1706,A-28,B-7,C-116),(IB-1707,A-28,B-7,C-117),(IB-1708,A-28,B-7,C-118),(IB-1709,A-28,B-7,C-119),(IB-1710,A-28,B-7,C-120),(IB-1711,A-28,B-7,C-121),(IB-1712,A-28,B-7,C-122),(IB-1713,A-28,B-7,C-123),(IB-1714,A-28,B-7,C-124),(IB-1715,A-28,B-7,C-125),(IB-1716,A-28,B-7,C-126),(IB-1717,A-28,B-7,C-127),(IB-1718,A-28,B-7,C-128),(IB-1719,A-28,B-7,C-129),(IB-1720,A-28,B-7,C-130),(IB-1721,A-28,B-7,C-131),(IB-1722,A-28,B-7,C-132),(IB-1723,A-28,B-7,C-133),(IB-1724,A-28,B-7,C-134),(IB-1725,A-28,B-7,C-135),(IB-1726,A-28,B-7,C-136),(IB-1727,A-28,B-7,C-137),(IB-1728,A-28,B-7,C-138),(IB-1729,A-28,B-7,C-139),(IB-1730,A-28,B-7,C-140),(IB-1731,A-28,B-7,C-141),(IB-1732,A-28,B-7,C-142),(IB-1733,A-28,B-7,C-143),(IB-1734,A-28,B-7,C-144),(IB-1735,A-28,B-7,C-145),(IB-1736,A-28,B-7,C-146),(IB-1737,A-28,B-7,C-147),(IB-1738,A-28,B-7,C-148),(IB-1739,A-28,B-7,C-149),(IB-1740,A-28,B-7,C-150),(IB-1741,A-28,B-7,C-151),(IB-1742,A-28,B-7,C-152),(IB-1743,A-28,B-7,C-153),(IB-1744,A-28,B-7,C-154),(IB-1745,A-28,B-7,C-155),(IB-1746,A-28,B-7,C-156),(IB-1747,A-28,B-7,C-157),(IB-1748,A-28,B-7,C-158),(IB-1749,A-28,B-7,C-159),(IB-1750,A-28,B-7,C-160),(IB-1751,A-28,B-7,C-161),(IB-1752,A-28,B-7,C-162),(IB-1753,A-28,B-7,C-163),(IB-1754,A-28,B-7,C-164),(IB-1755,A-28,B-7,C-165),(IB-1756,A-28,B-7,C-166),(IB-1757,A-28,B-7,C-167),(IB-1758,A-28,B-7,C-168),(IB-1759,A-28,B-7,C-169),(IB-1760,A-28,B-7,C-170),(IB-1761,A-28,B-7,C-171),(IB-1762,A-28,B-7,C-172),(IB-1763,A-28,B-7,C-173),(IB-1764,A-28,B-7,C-174),(IB-1765,A-28,B-7,C-175),(IB-1766,A-28,B-7,C-176),(IB-1767,A-28,B-7,C-177),(IB-1768,A-28,B-7,C-178),(IB-1769,A-28,B-7,C-179),(IB-1770,A-28,B-7,C-180),(IB-1771,A-28,B-7,C-181),(IB-1772,A-28,B-7,C-182),(IB-1773,A-28,B-7,C-183),(IB-1774,A-28,B-7,C-184),(IB-1775,A-28,B-7,C-185),(IB-1776,A-28,B-7,C-186),(IB-1777,A-28,B-7,C-187),(IB-1778,A-28,B-7,C-188),(IB-1779,A-28,B-7,C-189),(IB-1780,A-28,B-7,C-190),(IB-1781,A-28,B-7,C-191),(IB-1782,A-28,B-7,C-192),(IB-1783,A-28,B-7,C-193),(IB-1784,A-28,B-7,C-194),(IB-1785,A-28,B-7,C-195),(IB-1786,A-28,B-7,C-196),(IB-1787,A-28,B-7,C-197),(IB-1788,A-28,B-7,C-198),(IB-1789,A-28,B-7,C-199),(IB-1790,A-28,B-7,C-200),(IB-1791,A-28,B-7,C-201),(IB-1792,A-28,B-7,C-202),(IB-1793,A-28,B-7,C-203),(IB-1794,A-28,B-7,C-204),(IB-1795,A-28,B-7,C-205),(IB-1796,A-28,B-7,C-206),(IB-1797,A-28,B-7,C-207),(IB-1798,A-28,B-7,C-208),(IB-1799,A-28,B-7,C-209),(IB-1800,A-28,B-7,C-210),(IB-1801,A-28,B-7,C-211),(IB-1802,A-28,B-7,C-212),(IB-1803,A-28,B-7,C-213),(IB-1804,A-28,B-7,C-214),(IB-1805,A-28,B-8,C-15), (IB-1806,A-28,B-9,C-15),(IB-1807,A-28,B-10,C-15),(IB-1808,A-28,B-10,C-52),(IB-1809,A-29,B-1,C-15),(IB-1810, A-29,B-2,C-15),(IB-1811,A-29,B-3,C-15),(IB-1812,A-29, B-4,C-15),(IB-1813,A-29,B-5,C-5),(IB-1814,A-29,B-6,C-15),(IB-1815,A-29,B-7,C-1),(IB-1816,A-29,B-7,C-2),(IB-1817,A-29,B-7,C-3),(IB-1818,A-29,B-7,C-4),(IB-1819,A-29,B-7,C-5),(IB-1820,A-29,B-7,C-6),(IB-1821,A-29,B-7, C-7),(IB-1822,A-29,B-7,C-8),(IB-1823,A-29,B-7,C-9),(IB-1824,A-29,B-7,C-10),(IB-1825,A-29,B-7,C-11),(IB-1826, A-29,B-7,C-12),(IB-1827,A-29,B-7,C-13),(IB-1828,A-29, B-7,C-14),(IB-1829,A-29,B-7,C-15),(IB-1830,A-29,B-7,C-16),(IB-1831,A-29,B-7,C-17),(IB-1832,A-29,B-7,C-18), (IB-1833,A-29,B-7,C-19),(IB-1834,A-29,B-7,C-20),(IB-1835,A-29,B-7,C-21),(IB-1836,A-29,B-7,C-22),(IB-1837, A-29,B-7,C-23),(IB-1838,A-29,B-7,C-24),(IB-1839,A-29, B-7,C-25),(IB-1840,A-29,B-7,C-26),(IB-1841,A-29,B-7,C-27),(IB-1842,A-29,B-7,C-28),(IB-1843,A-29,B-7,C-29), (IB-1844,A-29,B-7,C-30),(IB-1845,A-29,B-7,C-31),(IB-1846,A-29,B-7,C-32),(IB-1847,A-29,B-7,C-33),(IB-1848, A-29,B-7,C-34),(IB-1849,A-29,B-7,C-35),(IB-1850,A-29, B-7,C-36),(IB-1851,A-29,B-7,C-37),(IB-1852,A-29,B-7,C-38),(IB-1853,A-29,B-7,C-39),(IB-1854,A-29,B-7,C-40), (IB-1855,A-29,B-7,C-41),(IB-1856,A-29,B-7,C-42),(IB-1857,A-29,B-7,C-43),(IB-1858,A-29,B-7,C-44),(IB-1859, A-29,B-7,C-45),(IB-1860,A-29,B-7,C-46),(IB-1861,A-29, B-7,C-47),(IB-1862,A-29,B-7,C-48),(IB-1863,A-29,B-7,C-49),(IB-1864,A-29,B-7,C-50),(IB-1865,A-29,B-7,C-51), (IB-1866,A-29,B-7,C-52),(IB-1867,A-29,B-7,C-53),(IB-1868,A-29,B-7,C-54),(IB-1869,A-29,B-7,C-55),(IB-1870, A-29,B-7,C-56),(IB-1871,A-29,B-7,C-57),(IB-1872,A-29, B-7,C-58),(IB-1873,A-29,B-7,C-59),(IB-1874,A-29,B-7,C-60),(IB-1875,A-29,B-7,C-61),(IB-1876,A-29,B-7,C-62), (IB-1877,A-29,B-7,C-63),(IB-1878,A-29,B-7,C-64),(IB-1879,A-29,B-7,C-65),(IB-1880,A-29,B-7,C-66),(IB-1881, A-29,B-7,C-67),(IB-1882,A-29,B-7,C-68),(IB-1883,A-29, B-7,C-69),(IB-1884,A-29,B-7,C-70),(IB-1885,A-29,B-7,C-71),(IB-1886,A-29,B-7,C-72),(IB-1887,A-29,B-7,C-73), (IB-1888,A-29,B-7,C-74),(IB-1889,A-29,B-7,C-75),(IB-1890,A-29,B-7,C-76),(IB-1891,A-29,B-7,C-77),(IB-1892, A-29,B-7,C-78),(IB-1893,A-29,B-7,C-79),(IB-1894,A-29, B-7,C-80),(IB-1895,A-29,B-7,C-81),(IB-1896,A-29,B-7,C-

82),(IB-1897,A-29,B-7,C-83),(IB-1898,A-29,B-7,C-84),(IB-1899,A-29,B-7,C-85),(IB-1900,A-29,B-7,C-86),(IB-1901,A-29,B-7,C-87),(IB-1902,A-29,B-7,C-88),(IB-1903,A-29,B-7,C-89),(IB-1904,A-29,B-7,C-90),(IB-1905,A-29,B-7,C-91),(IB-1906,A-29,B-7,C-92),(IB-1907,A-29,B-7,C-93),(IB-1908,A-29,B-7,C-94),(IB-1909,A-29,B-7,C-95),(IB-1910,A-29,B-7,C-96),(IB-1911,A-29,B-7,C-97),(IB-1912,A-29,B-7,C-98),(IB-1913,A-29,B-7,C-99),(IB-1914,A-29,B-7,C-100),(IB-1915,A-29,B-7,C-101),(IB-1916,A-29,B-7,C-102),(IB-1917,A-29,B-7,C-103),(IB-1918,A-29,B-7,C-104),(IB-1919,A-29,B-7,C-105),(IB-1920,A-29,B-7,C-106),(IB-1921,A-29,B-7,C-107),(IB-1922,A-29,B-7,C-108),(IB-1923,A-29,B-7,C-109),(IB-1924,A-29,B-7,C-110),(IB-1925,A-29,B-7,C-111),(IB-1926,A-29,B-7,C-112),(IB-1927,A-29,B-7,C-113),(IB-1928,A-29,B-7,C-114),(IB-1929,A-29,B-7,C-115),(IB-1930,A-29,B-7,C-116),(IB-1931,A-29,B-7,C-117),(IB-1932,A-29,B-7,C-118),(IB-1933,A-29,B-7,C-119),(IB-1934,A-29,B-7,C-120),(IB-1935,A-29,B-7,C-121),(IB-1936,A-29,B-7,C-122),(IB-1937,A-29,B-7,C-123),(IB-1938,A-29,B-7,C-124),(IB-1939,A-29,B-7,C-125),(IB-1940,A-29,B-7,C-126),(IB-1941,A-29,B-7,C-127),(IB-1942,A-29,B-7,C-128),(IB-1943,A-29,B-7,C-129),(IB-1944,A-29,B-7,C-130),(IB-1945,A-29,B-7,C-131),(IB-1946,A-29,B-7,C-132),(IB-1947,A-29,B-7,C-133),(IB-1948,A-29,B-7,C-134),(IB-1949,A-29,B-7,C-135),(IB-1950,A-29,B-7,C-136),(IB-1951,A-29,B-7,C-137),(IB-1952,A-29,B-7,C-138),(IB-1953,A-29,B-7,C-139),(IB-1954,A-29,B-7,C-140),(IB-1955,A-29,B-7,C-141),(IB-1956,A-29,B-7,C-142),(IB-1957,A-29,B-7,C-143),(IB-1958,A-29,B-7,C-144),(IB-1959,A-29,B-7,C-145),(IB-1960,A-29,B-7,C-146),(IB-1961,A-29,B-7,C-147),(IB-1962,A-29,B-7,C-148),(IB-1963,A-29,B-7,C-149),(IB-1964,A-29,B-7,C-150),(IB-1965,A-29,B-7,C-151),(IB-1966,A-29,B-7,C-152),(IB-1967,A-29,B-7,C-153),(IB-1968,A-29,B-7,C-154),(IB-1969,A-29,B-7,C-155),(IB-1970,A-29,B-7,C-156),(IB-1971,A-29,B-7,C-157),(IB-1972,A-29,B-7,C-158),(IB-1973,A-29,B-7,C-159),(IB-1974,A-29,B-7,C-160),(IB-1975,A-29,B-7,C-161),(IB-1976,A-29,B-7,C-162),(IB-1977,A-29,B-7,C-163),(IB-1978,A-29,B-7,C-164),(IB-1979,A-29,B-7,C-165),(IB-1980,A-29,B-7,C-166),(IB-1981,A-29,B-7,C-167),(IB-1982,A-29,B-7,C-168),(IB-1983,A-29,B-7,C-169),(IB-1984,A-29,B-7,C-170),(IB-1985,A-29,B-7,C-171),(IB-1986,A-29,B-7,C-172),(IB-1987,A-29,B-7,C-173),(IB-1988,A-29,B-7,C-174),(IB-1989,A-29,B-7,C-175),(IB-1990,A-29,B-7,C-176),(IB-1991,A-29,B-7,C-177),(IB-1992,A-29,B-7,C-178),(IB-1993,A-29,B-7,C-179),(IB-1994,A-29,B-7,C-180),(IB-1995,A-29,B-7,C-181),(IB-1996,A-29,B-7,C-182),(IB-1997,A-29,B-7,C-183),(IB-1998,A-29,B-7,C-184),(IB-1999,A-29,B-7,C-185),(IB-2000,A-29,B-7,C-186),(IB-2001,A-29,B-7,C-187),(IB-2002,A-29,B-7,C-188),(IB-2003,A-29,B-7,C-189),(IB-2004,A-29,B-7,C-190),(IB-2005,A-29,B-7,C-191),(IB-2006,A-29,B-7,C-192),(IB-2007,A-29,B-7,C-193),(IB-2008,A-29,B-7,C-194),(IB-2009,A-29,B-7,C-195),(IB-2010,A-29,B-7,C-196),(IB-2011,A-29,B-7,C-197),(IB-2012,A-29,B-7,C-198),(IB-2013,A-29,B-7,C-199),(IB-2014,A-29,B-7,C-200),(IB-2015,A-29,B-7,C-201),(IB-2016,A-29,B-7,C-202),(IB-2017,A-29,B-7,C-203),(IB-2018,A-29,B-7,C-204),(IB-2019,A-29,B-7,C-205),(IB-2020,A-29,B-7,C-206),(IB-2021,A-29,B-7,C-207),(IB-2022,A-29,B-7,C-208),(IB-2023,A-29,B-7,C-209),(IB-2024,A-29,B-7,C-210),(IB-2025,A-29,B-7,C-211),(IB-2026,A-29,B-7,C-212),(IB-2027,A-29,B-7,C-213),(IB-2028,A-29,B-7,C-214),(IB-2029,A-29,B-8,C-15),(IB-2030,A-29,B-9,C-15),(IB-2031,A-29,B-10,C-15),(IB-2032,A-29,B-10,C-52),(IB-2033,A-30,B-1,C-15),(IB-2034,A-30,B-2,C-15),(IB-2035,A-30,B-3,C-15),(IB-2036,A-30,B-4,C-15),(IB-2037,A-30,B-5,C-15),(IB-2038,A-30,B-6,C-15),(IB-2039,A-30,B-7,C-1),(IB-2040,A-30,B-7,C-2),(IB-2041,A-30,B-7,C-3),(IB-2042,A-30,B-7,C-4),(IB-2043,A-30,B-7,C-5),(IB-2044,A-30,B-7,C-6),(IB-2045,A-30,B-7,C-7),(IB-2046,A-30,B-7,C-8),(IB-2047,A-30,B-7,C-9),(IB-2048,A-30,B-7,C-10),(IB-2049,A-30,B-7,C-11),(IB-2050,A-30,B-7,C-12),(IB-2051,A-30,B-7,C-13),(IB-2052,A-30,B-7,C-14),(IB-2053,A-30,B-7,C-15),(IB-2054,A-30,B-7,C-16),(IB-2055,A-30,B-7,C-17),(IB-2056,A-30,B-7,C-18),(IB-2057,A-30,B-7,C-19),(IB-2058,A-30,B-7,C-20),(IB-2059,A-30,B-7,C-21),(IB-2060,A-30,B-7,C-22),(IB-2061,A-30,B-7,C-23),(IB-2062,A-30,B-7,C-24),(IB-2063,A-30,B-7,C-25),(IB-2064,A-30,B-7,C-26),(IB-2065,A-30,B-7,C-27),(IB-2066,A-30,B-7,C-28),(IB-2067,A-30,B-7,C-29),(IB-2068,A-30,B-7,C-30),(IB-2069,A-30,B-7,C-31),(IB-2070,A-30,B-7,C-32),(IB-2071,A-30,B-7,C-33),(IB-2072,A-30,B-7,C-34),(IB-2073,A-30,B-7,C-35),(IB-2074,A-30,B-7,C-36),(IB-2075,A-30,B-7,C-37),(IB-2076,A-30,B-7,C-38),(IB-2077,A-30,B-7,C-39),(IB-2078,A-30,B-7,C-40),(IB-2079,A-30,B-7,C-41),(IB-2080,A-30,B-7,C-42),(IB-2081,A-30,B-7,C-43),(IB-2082,A-30,B-7,C-44),(IB-2083,A-30,B-7,C-45),(IB-2084,A-30,B-7,C-46),(IB-2085,A-30,B-7,C-47),(IB-2086,A-30,B-7,C-48),(IB-2087,A-30,B-7,C-49),(IB-2088,A-30,B-7,C-50),(IB-2089,A-30,B-7,C-51),(IB-2090,A-30,B-7,C-52),(IB-2091,A-30,B-7,C-53),(IB-2092,A-30,B-7,C-54),(IB-2093,A-30,B-7,C-55),(IB-2094,A-30,B-7,C-56),(IB-2095,A-30,B-7,C-57),(IB-2096,A-30,B-7,C-58),(IB-2097,A-30,B-7,C-59),(IB-2098,A-30,B-7,C-60),(IB-2099,A-30,B-7,C-61),(IB-2100,A-30,B-7,C-62),(IB-2101,A-30,B-7,C-63),(IB-2102,A-30,B-7,C-64),(IB-2103,A-30,B-7,C-65),(IB-2104,A-30,B-7,C-66),(IB-2105,A-30,B-7,C-67),(IB-2106,A-30,B-7,C-68),(IB-2107,A-30,B-7,C-69),(IB-2108,A-30,B-7,C-70),(IB-2109,A-30,B-7,C-71),(IB-2110,A-30,B-7,C-72),(IB-2111,A-30,B-7,C-73),(IB-2112,A-30,B-7,C-74),(IB-2113,A-30,B-7,C-75),(IB-2114,A-30,B-7,C-76),(IB-2115,A-30,B-7,C-77),(IB-2116,A-30,B-7,C-78),(IB-2117,A-30,B-7,C-79),(IB-2118,A-30,B-7,C-80),(IB-2119,A-30,B-7,C-81),(IB-2120,A-30,B-7,C-82),(IB-2121,A-30,B-7,C-83),(IB-2122,A-30,B-7,C-84),(IB-2123,A-30,B-7,C-85),(IB-2124,A-30,B-7,C-86),(IB-2125,A-30,B-7,C-87),(IB-2126,A-30,B-7,C-88),(IB-2127,A-30,B-7,C-89),(IB-2128,A-30,B-7,C-90),(IB-2129,A-30,B-7,C-91),(IB-2130,A-30,B-7,C-92),(IB-2131,A-30,B-7,C-93),(IB-2132,A-30,B-7,C-94),(IB-2133,A-30,B-7,C-95),(IB-2134,A-30,B-7,C-96),(IB-2135,A-30,B-7,C-97),(IB-2136,A-30,B-7,C-98),(IB-2137,A-30,B-7,C-99),(IB-2138,A-30,B-7,C-100),(IB-2139,A-30,B-7,C-101),(IB-2140,A-30,B-7,C-102),(IB-2141,A-30,B-7,C-103),(IB-2142,A-30,B-7,C-104),(IB-2143,A-30,B-7,C-105),(IB-2144,A-30,B-7,C-106),(IB-2145,A-30,B-7,C-107),(IB-2146,A-30,B-7,C-108),(IB-2147,A-30,B-7,C-109),(IB-2148,A-30,B-7,C-110),(IB-2149,A-30,B-7,C-111),(IB-2150,A-30,B-7,C-112),(IB-2151,A-30,B-7,C-113),(IB-2152,A-30,B-7,C-114),(IB-2153,A-30,B-7,C-115),(IB-2154,A-30,B-7,C-116),(IB-2155,A-30,B-7,C-117),(IB-2156,A-30,B-7,C-118),(IB-2157,A-30,B-7,C-119),(IB-2158,A-30,B-7,C-120),(IB-2159,A-30,B-7,C-121),(IB-2160,A-30,B-7,C-122),(IB-2161,A-30,B-7,C-123),(IB-2162,A-30,B-7,C-124),(IB-2163,A-30,B-7,C-125),(IB-2164,A-30,B-7,C-126),(IB-2165,A-30,B-7,C-127),(IB-2166,A-30,B-7,C-128),(IB-2167,A-30,B-7,C-129),(IB-2168,A-30,B-7,C-130),(IB-2169,A-30,B-7,C-131),(IB-2170,A-30,B-7,C-132),(IB-2171,A-30,B-7,C-133),(IB-2172,A-30,B-7,C-134),(IB-2173,A-30,B-7,C-135),(IB-2174,A-30,B-7,C-136),(IB-2175,A-30,B-7,C-137),(IB-2176,A-30,B-7,C-138),(IB-

2177,A-30,B-7,C-139),(IB-2178,A-30,B-7,C-140),(IB-2179,A-30,B-7,C-141),(IB-2180,A-30,B-7,C-142),(IB-2181,A-30,B-7,C-143),(IB-2182,A-30,B-7,C-144),(IB-2183,A-30,B-7,C-145),(IB-2184,A-30,B-7,C-146),(IB-2185,A-30,B-7,C-147),(IB-2186,A-30,B-7,C-148),(IB-2187,A-30,B-7,C-149),(IB-2188,A-30,B-7,C-150),(IB-2189,A-30,B-7,C-151),(IB-2190,A-30,B-7,C-152),(IB-2191,A-30,B-7,C-153),(IB-2192,A-30,B-7,C-154),(IB-2193,A-30,B-7,C-155),(IB-2194,A-30,B-7,C-156),(IB-2195,A-30,B-7,C-157),(IB-2196,A-30,B-7,C-158),(IB-2197,A-30,B-7,C-159),(IB-2198,A-30,B-7,C-160),(IB-2199,A-30,B-7,C-161),(IB-2200,A-30,B-7,C-162),(IB-2201,A-30,B-7,C-163),(IB-2202,A-30,B-7,C-164),(IB-2203,A-30,B-7,C-165),(IB-2204,A-30,B-7,C-166),(IB-2205,A-30,B-7,C-167),(IB-2206,A-30,B-7,C-168),(IB-2207,A-30,B-7,C-169),(IB-2208,A-30,B-7,C-170),(IB-2209,A-30,B-7,C-171),(IB-2210,A-30,B-7,C-172),(IB-2211,A-30,B-7,C-173),(IB-2212,A-30,B-7,C-174),(IB-2213,A-30,B-7,C-175),(IB-2214,A-30,B-7,C-176),(IB-2215,A-30,B-7,C-177),(IB-2216,A-30,B-7,C-178),(IB-2217,A-30,B-7,C-179),(IB-2218,A-30,B-7,C-180),(IB-2219,A-30,B-7,C-181),(IB-2220,A-30,B-7,C-182),(IB-2221,A-30,B-7,C-183),(IB-2222,A-30,B-7,C-184),(IB-2223,A-30,B-7,C-185),(IB-2224,A-30,B-7,C-186),(IB-2225,A-30,B-7,C-187),(IB-2226,A-30,B-7,C-188),(IB-2227,A-30,B-7,C-189),(IB-2228,A-30,B-7,C-190),(IB-2229,A-30,B-7,C-191),(IB-2230,A-30,B-7,C-192),(IB-2231,A-30,B-7,C-193),(IB-2232,A-30,B-7,C-194),(IB-2233,A-30,B-7,C-195),(IB-2234,A-30,B-7,C-196),(IB-2235,A-30,B-7,C-197),(IB-2236,A-30,B-7,C-198),(IB-2237,A-30,B-7,C-199),(IB-2238,A-30,B-7,C-200),(IB-2239,A-30,B-7,C-201),(IB-2240,A-30,B-7,C-202),(IB-2241,A-30,B-7,C-203),(IB-2242,A-30,B-7,C-204),(IB-2243,A-30,B-7,C-205),(IB-2244,A-30,B-7,C-206),(IB-2245,A-30,B-7,C-207),(IB-2246,A-30,B-7,C-208),(IB-2247,A-30,B-7,C-209),(IB-2248,A-30,B-7,C-210),(IB-2249,A-30,B-7,C-211),(IB-2250,A-30,B-7,C-212),(IB-2251,A-30,B-7,C-213),(IB-2252,A-3003-7,C-214),(IB-2253,A-30,B-8,C-15),(IB-2254,A-30,B-9,C-15),(IB-2255,A-30,B-10,C-15),(IB-2256,A-30,B-10,C-52),(IB-2257,A-31,B-1,C-15),(IB-2258,A-31,B-2,C-15),(IB-2259,A-31,B-3,C-15),(IB-2260,A-31,B-4,C-15),(IB-2261,A-31,B-5,C-15),(IB-2262,A-31,B-6,C-15),(IB-2263,A-31,B-7,C-1),(IB-2264,A-31,B-7,C-2),(IB-2265,A-31,B-7,C-3),(IB-2266,A-31,B-7,C-4),(IB-2267,A-31,B-7,C-5),(I B-2268,A-31,B-7,C-6),(IB-2269,A-31,B-7,C-7),(IB-2270,A-31,B-7,C-8),(IB-2271,A-31,B-7,C-9),(IB-2272,A-31,B-7,C-10),(IB-2273,A-31,B-7,C-11),(IB-2274,A-31,B-7,C-12),(IB-2275,A-31,B-7,C-13),(IB-2276,A-31,B-7,C-14),(IB-2277,A-31,B-7,C-15),(IB-2278,A-31,B-7,C-16),(IB-2279,A-31,B-7,C-17),(IB-2280,A-31,B-7,C-18),(IB-2281,A-31,B-7,C-19),(IB-2282,A-31,B-7,C-20),(IB-2283,A-31,B-7,C-21),(IB-2284,A-31,B-7,C-22),(IB-2285,A-31,B-7,C-23),(IB-2286,A-31,B-7,C-24),(IB-2287,A-31,B-7,C-25),(IB-2288,A-31,B-7,C-26),(IB-2289,A-31,B-7,C-27),(IB-2290,A-31,B-7,C-28),(IB-2291,A-31,B-7,C-29),(IB-2292,A-31,B-7,C-30),(IB-2293,A-31,B-7,C-31),(IB-2294,A-31,B-7,C-32),(IB-2295,A-31,B-7,C-33),(IB-2296,A-31,B-7,C-34),(IB-2297,A-31,B-7,C-35),(IB-2298,A-31,B-7,C-36),(IB-2299,A-31,B-7,C-37),(IB-2300,A-31,B-7,C-38),(IB-2301,A-31,B-7,C-39),(IB-2302,A-31,B-7,C-40),(IB-2303,A-31,B-7,C-41),(IB-2304,A-31,B-7,C-42),(IB-2305,A-31,B-7,C-43),(IB-2306,A-31,B-7,C-44),(IB-2307,A-31,B-7,C-45),(IB-2308,A-31,B-7,C-46),(IB-2309,A-31,B-7,C-47),(IB-2310,A-31,B-7,C-48),(IB-2311,A-31,B-7,C-49),(IB-2312,A-31,B-7,C-50),(IB-2313,A-31,B-7,C-51),(IB-2314,A-31,B-7,C-52),(IB-2315,A-31,B-7,C-53),(IB-2316,A-31,B-7,C-54),(IB-2317,A-31,B-7,C-55),(IB-2318,A-31,B-7,C-56),(IB-2319,A-31,B-7,C-57),(IB-2320,A-31,B-7,C-58),(IB-2321,A-31,B-7,C-59),(IB-2322,A-31,B-7,C-60),(IB-2323,A-31,B-7,C-61),(IB-2324,A-31,B-7,C-62),(IB-2325,A-31,B-7,C-63),(IB-2326,A-31,B-7,C-64),(IB-2327,A-31,B-7,C-65),(IB-2328,A-31,B-7,C-66),(IB-2329,A-31,B-7,C-67),(IB-2330,A-31,B-7,C-68),(IB-2331,A-31,B-7,C-69),(IB-2332,A-31,B-7,C-70),(IB-2333,A-31,B-7,C-71),(IB-2334,A-31,B-7,C-72),(IB-2335,A-31,B-7,C-73),(IB-2336,A-31,B-7,C-74),(IB-2337,A-31,B-7,C-75),(IB-2338,A-31,B-7,C-76),(IB-2339,A-31,B-7,C-77),(IB-2340,A-31,B-7,C-78),(IB-2341,A-31,B-7,C-79),(IB-2342,A-31,B-7,C-80),(IB-2343,A-31,B-7,C-81),(IB-2344,A-31,B-7,C-82),(IB-2345,A-31,B-7,C-83),(IB-2346,A-31,B-7,C-84),(IB-2347,A-31,B-7,C-85),(IB-2348,A-31,B-7,C-86),(IB-2349,A-31,B-7,C-87),(IB-2350,A-31,B-7,C-88),(IB-2351,A-31,B-7,C-89),(IB-2352,A-31,B-7,C-90),(IB-2353,A-31,B-7,C-91),(IB-2354,A-31,B-7,C-92),(IB-2355,A-31,B-7,C-93),(IB-2356,A-31,B-7,C-94),(IB-2357,A-31,B-7,C-95),(IB-2358,A-31,B-7,C-96),(IB-2359,A-31,B-7,C-97),(IB-2360,A-31,B-7,C-98),(IB-2361,A-31,B-7,C-99),(IB-2362,A-31,B-7,C-100),(IB-2363,A-31,B-7,C-101),(IB-2364,A-31,B-7,C-102),(IB-2365,A-31,B-7,C-103),(IB-2366,A-31,B-7,C-104),(IB-2367,A-31,B-7,C-105),(IB-2368,A-31,B-7,C-106),(IB-2369,A-31,B-7,C-107),(IB-2370,A-31,B-7,C-108),(IB-2371,A-31,B-7,C-109),(IB-2372,A-31,B-7,C-110),(IB-2373,A-31,B-7,C-111),(IB-2374,A-31,B-7,C-112),(IB-2375,A-31,B-7,C-113),(IB-2376,A-31,B-7,C-114),(IB-2377,A-31,B-7,C-115),(IB-2378,A-31,B-7,C-116),(IB-2379,A-31,B-7,C-117),(IB-2380,A-31,B-7,C-118),(IB-2381,A-31,B-7,C-119),(IB-2382,A-31,B-7,C-120),(IB-2383,A-31,B-7,C-121),(IB-2384,A-31,B-7,C-122),(IB-2385,A-31,B-7,C-123),(IB-2386,A-31,B-7,C-124),(IB-2387,A-31,B-7,C-125),(IB-2388,A-31,B-7,C-126),(IB-2389,A-31,B-7,C-127),(IB-2390,A-31,B-7,C-128),(IB-2391,A-31,B-7,C-129),(IB-2392,A-31,B-7,C-130),(IB-2393,A-31,B-7,C-131),(IB-2394,A-31,B-7,C-132),(IB-2395,A-31,B-7,C-133),(IB-2396,A-31,B-7,C-134),(IB-2397,A-31,B-7,C-135),(IB-2398,A-31,B-7,C-136),(IB-2399,A-31,B-7,C-137),(IB-2400,A-31,B-7,C-138),(IB-2401,A-31,B-7,C-139),(IB-2402,A-31,B-7,C-140),(IB-2403,A-31,B-7,C-141),(IB-2404,A-31,B-7,C-142),(IB-2405,A-31,B-7,C-143),(IB-2406,A-31,B-7,C-144),(IB-2407,A-31,B-7,C-145),(IB-2408,A-31,B-7,C-146),(IB-2409,A-31,B-7,C-147),(IB-2410,A-31,B-7,C-148),(IB-2411,A-31,B-7,C-149),(IB-2412,A-31,B-7,C-150),(IB-2413,A-31,B-7,C-151),(IB-2414,A-31,B-7,C-152),(IB-2415,A-31,B-7,C-153),(IB-2416,A-31,B-7,C-154),(IB-2417,A-31,B-7,C-155),(IB-2418,A-31,B-7,C-156),(IB-2419,A-31,B-7,C-157),(IB-2420,A-31,B-7,C-158),(IB-2421,A-31,B-7,C-159),(IB-2422,A-31,B-7,C-160),(IB-2423,A-31,B-7,C-161),(IB-2424,A-31,B-7,C-162),(IB-2425,A-31,B-7,C-163),(IB-2426,A-31,B-7,C-164),(IB-2427,A-31,B-7,C-165),(IB-2428,A-31,B-7,C-166),(IB-2429,A-31,B-7,C-167),(IB-2430,A-31,B-7,C-168),(IB-2431,A-31,B-7,C-169),(IB-2432,A-31,B-7,C-170),(IB-2433,A-31,B-7,0-171),(IB-2434,A-31,B-7,C-172),(IB-2435,A-31,B-7,C-173),(IB-2436,A-31,B-7,C-174),(IB-2437,A-31,B-7,C-175),(IB-2438,A-31,B-7,C-176),(IB-2439,A-31,B-7,C-177),(IB-2440,A-31,B-7,C-178),(IB-2441,A-31,B-7,C-179),(IB-2442,A-31,B-7,C-180),(IB-2443,A-31,B-7,C-181),(IB-2444,A-31,B-7,C-182),(IB-2445,A-31,B-7,C-183),(IB-2446,A-31,B-7,C-184),(IB-2447,A-31,B-7,C-185),(IB-2448,A-31,B-7,C-186),(IB-2449,A-31,B-7,C-187),(IB-2450,A-31,B-7,C-188),(IB-2451,A-31,B-7,C-189),(IB-2452,A-31,B-7,C-190),(IB-2453,A-31,B-7,C-191),(IB-2454,A-31,B-7,C-192),(IB-2455,A-31,B-7,C-

193),(IB-2456,A-31,B-7,C-194),(IB-2457,A-31,B-7,C-195),(IB-2458,A-31,B-7,C-196),(IB-2459,A-31,B-7,C-197),(IB-2460,A-31,B-7,C-198),(IB-2461,A-31,B-7,C-199),(IB-2462,A-31,B-7,C-200),(IB-2463,A-31,B-7,C-201),(IB-2464,A-31,B-7,C-202),(IB-2465,A-31,B-7,C-203),(IB-2466,A-31,B-7,C-204),(IB-2467,A-31,B-7,C-205),(IB-2468,A-31,B-7,C-206),(IB-2469,A-31,B-7,C-207),(IB-2470,A-31,B-7,C-208),(IB-2471,A-31,B-7,C-209),(IB-2472,A-31,B-7,C-210),(IB-2473,A-31,B-7,C-211),(IB-2474,A-31,B-7,C-212),(IB-2475,A-31,B-7,C-213),(IB-2476,A-31,B-7,C-214),(IB-2477,A-31,B-8,C-15),(IB-2478,A-31,B-9,C-15),(IB-2479,A-31,B-10,C-15),(IB-2480,A-31,B-10,C-52),(IB-2481,A-32,B-1,C-15),(IB-2482,A-32,B-2,C-15),(IB-2483,A-32,B-3,C-15),(IB-2484,A-32,B-4,C-15),(IB-2485,A-32,B-5,C-15),(IB-2486,A-32,B-6,C-15),(IB-2487,A-32,B-7,C-1),(IB-2488,A-32,B-7,C-2),(IB-2489,A-3203-7,C-3),(IB-2490,A-32,B-7,C-4),(IB-2491,A-32,B-7,C-5),(IB-2492,A-32,B-7,C-6),(IB-2493,A-32,B-7,C-7),(IB-2494,A-32,B-7,C-8),(IB-2495,A-32,B-7,C-9),(IB-2496,A-32,B-7,C-10),(IB-2497,A-32,B-7,C-11),(IB-2498,A-32,B-7,C-12),(IB-2499,A-32,B-7,C-13),(IB-2500,A-32,B-7,C-14),(IB-2501,A-32,B-7,C-15),(IB-2502,A-32,B-7,C-16),(IB-2503,A-32,B-7,C-17),(IB-2504,A-32,B-7,C-18),(IB-2505,A-32,B-7,C-19),(IB-2506,A-32,B-7,C-20),(IB-2507,A-32,B-7,C-21),(IB-2508,A-32,B-7,C-22),(IB-2509,A-32,B-7,C-23),(IB-2510,A-32,B-7,C-24),(IB-2511,A-32,B-7,C-25),(IB-2512,A-32,B-7,C-26),(IB-2513,A-32,B-7,C-27),(IB-2514,A-32,B-7,C-28),(IB-2515,A-32,B-7,C-29),(IB-2516,A-32,B-7,C-30),(IB-2517,A-32,B-7,C-31),(IB-2518,A-32,B-7,C-32),(IB-2519,A-32,B-7,C-33),(IB-2520,A-32,B-7,C-34),(IB-2521,A-32,B-7,C-35),(IB-2522,A-32,B-7,C-36),(IB-2523,A-32,B-7,C-37),(IB-2524,A-32,B-7,C-38),(IB-2525,A-32,B-7,C-39),(IB-2526,A-32,B-7,C-40),(IB-2527,A-32,B-7,C-41),(IB-2528,A-32,B-7,C-42),(IB-2529,A-32,B-7,C-43),(IB-2530,A-32,B-7,C-44),(IB-2531,A-32,B-7,C-45),(IB-2532,A-32,B-7,C-46),(IB-2533,A-32,B-7,C-47),(IB-2534,A-32,B-7,C-48),(IB-2535,A-32,B-7,C-49),(IB-2536,A-32,B-7,C-50),(IB-2537,A-32,B-7,C-51),(IB-2538,A-32,B-7,C-52),(IB-2539,A-32,B-7,C-53),(IB-2540,A-32,B-7,C-54),(IB-2541,A-32,B-7,C-55),(IB-2542,A-32,B-7,C-56),(IB-2543,A-32,B-7,C-57),(IB-2544,A-32,B-7,C-58),(IB-2545,A-32,B-7,C-59),(IB-2546,A-32,B-7,C-60),(IB-2547,A-32,B-7,C-61),(IB-2548,A-32,B-7,C-62),(IB-2549,A-32,B-7,C-63),(IB-2550,A-32,B-7,C-64),(IB-2551,A-32,B-7,C-65),(IB-2552,A-32,B-7,C-66),(IB-2553,A-32,B-7,C-67),(IB-2554,A-32,B-7,C-68),(IB-2555,A-32,B-7,C-69),(IB-2556,A-32,B-7,C-70),(IB-2557,A-32,B-7,C-71),(IB-2558,A-32,B-7,C-72),(IB-2559,A-32,B-7,C-73),(IB-2560,A-32,B-7,C-74),(IB-2561,A-32,B-7,C-75),(IB-2562,A-32,B-7,C-76),(IB-2563,A-32,B-7,C-77),(IB-2564,A-32,B-7,C-78),(IB-2565,A-32,B-7,C-79),(IB-2566,A-32,B-7,C-80),(IB-2567,A-32,B-7,C-81),(IB-2568,A-32,B-7,C-82),(IB-2569,A-32,B-7,C-83),(IB-2570,A-32,B-7,C-84),(IB-2571,A-32,B-7,C-85),(IB-2572,A-32,B-7,C-86),(IB-2573,A-32,B-7,C-87),(IB-2574,A-32,B-7,C-88),(IB-2575,A-32,B-7,C-89),(IB-2576,A-32,B-7,C-90),(IB-2577,A-32,B-7,C-91),(IB-2578,A-32,B-7,C-92),(IB-2579,A-32,B-7,C-93),(IB-2580,A-32,B-7,C-94),(IB-2581,A-32,B-7,C-95),(IB-2582,A-32,B-7,C-96),(IB-2583,A-32,B-7,C-97),(IB-2584,A-32,B-7,C-98),(IB-2585,A-32,B-7,C-99),(IB-2586,A-32,B-7,C-100),(IB-2587,A-32,B-7,C-101),(IB-2588,A-32,B-7,C-102),(IB-2589,A-32,B-7,C-103),(IB-2590,A-32,B-7,C-104),(IB-2591,A-32,B-7,C-105),(IB-2592,A-32,B-7,C-106),(IB-2593,A-32,B-7,C-107),(IB-2594,A-32,B-7,C-108),(IB-2595,A-32,B-7,C-109),(IB-2596,A-32,B-7,C-110),(IB-2597,A-32,B-7,C-111),(IB-2598,A-32,B-7,C-112),(IB-2599,A-32,B-7,C-113),(IB-2600,A-32,B-7,C-114),(IB-2601,A-32,B-7,C-115),(IB-2602,A-32,B-7,C-116),(IB-2603,A-32,B-7,C-117),(IB-2604,A-32,B-7,C-118),(IB-2605,A-32,B-7,C-119),(IB-2606,A-32,B-7,C-120),(IB-2607,A-32,B-7,C-121),(IB-2608,A-32,B-7,C-122),(IB-2609,A-32,B-7,C-123),(IB-2610,A-32,B-7,C-124),(IB-2611,A-32,B-7,C-125),(IB-2612,A-32,B-7,C-126),(IB-2613,A-32,B-7,C-127),(IB-2614,A-32,B-7,C-128),(IB-2615,A-32,B-7,C-129),(IB-2616,A-32,B-7,C-130),(IB-2617,A-32,B-7,C-131),(IB-2618,A-32,B-7,C-132),(IB-2619,A-32,B-7,C-133),(IB-2620,A-32,B-7,C-134),(IB-2621,A-32,B-7,C-135),(IB-2622,A-32,B-7,C-136),(IB-2623,A-32,B-7,C-137),(IB-2624,A-32,B-7,C-138),(IB-2625,A-32,B-7,C-139),(IB-2626,A-32,B-7,C-140),(IB-2627,A-32,B-7,C-141),(IB-2628,A-32,B-7,C-142),(IB-2629,A-32,B-7,C-143),(IB-2630,A-32,B-7,C-144),(IB-2631,A-32,B-7,C-145),(IB-2632,A-32,B-7,C-146),(IB-2633,A-32,B-7,C-147),(IB-2634,A-32,B-7,C-148),(IB-2635,A-32,B-7,C-149),(IB-2636,A-32,B-7,C-150),(IB-2637,A-32,B-7,C-151),(IB-2638,A-32,B-7,C-152),(IB-2639,A-32,B-7,C-153),(IB-2640,A-32,B-7,C-154),(IB-2641,A-32,B-7,C-155),(IB-2642,A-32,B-7,C-156),(IB-2643,A-32,B-7,C-157),(IB-2644,A-32,B-7,C-158),(IB-2645,A-32,B-7,C-159),(IB-2646,A-32,B-7,C-160),(IB-2647,A-32,B-7,C-161),(IB-2648,A-32,B-7,C-162),(IB-2649,A-32,B-7,C-163),(IB-2650,A-32,B-7,C-164),(IB-2651,A-32,B-7,C-165),(IB-2652,A-32,B-7,C-166),(IB-2653,A-32,B-7,C-167),(IB-2654,A-32,B-7,C-168),(IB-2655,A-32,B-7,C-169),(IB-2656,A-32,B-7,C-170),(IB-2657,A-32,B-7,C-171),(IB-2658,A-32,B-7,C-172),(IB-2659,A-32,B-7,C-173),(IB-2660,A-32,B-7,C-174),(IB-2661,A-32,B-7,C-175),(IB-2662,A-32,B-7,C-176),(IB-2663,A-32,B-7,C-177),(IB-2664,A-32,B-7,C-178),(IB-2665,A-32,B-7,C-179),(IB-2666,A-32,B-7,C-180),(IB-2667,A-32,B-7,C-181),(IB-2668,A-32,B-7,C-182),(IB-2669,A-32,B-7,C-183),(IB-2670,A-32,B-7,C-184),(IB-2671,A-32,B-7,C-185),(IB-2672,A-32,B-7,C-186),(IB-2673,A-32,B-7,C-187),(IB-2674,A-32,B-7,C-188),(IB-2675,A-32,B-7,C-189),(IB-2676,A-32,B-7,C-190),(IB-2677,A-32,B-7,C-191),(IB-2678,A-32,B-7,C-192),(IB-2679,A-32,B-7,C-193),(IB-2680,A-32,B-7,C-194),(IB-2681,A-32,B-7,C-195),(IB-2682,A-32,B-7,C-196),(IB-2683,A-32,B-7,C-197),(IB-2684,A-32,B-7,C-198),(IB-2685,A-32,B-7,C-199),(IB-2686,A-32,B-7,C-200),(IB-2687,A-32,B-7,C-201),(IB-2688,A-32,B-7,C-202),(IB-2689,A-32,B-7,C-203),(IB-2690,A-32,B-7,C-204),(IB-2691,A-32,B-7,C-205),(IB-2692,A-32,B-7,C-206),(IB-2693,A-32,B-7,C-207),(IB-2694,A-32,B-7,C-208),(IB-2695,A-32,B-7,C-209),(IB-2696,A-32,B-7,C-210),(IB-2697,A-32,B-7,C-211),(IB-2698,A-32,B-7,C-212),(IB-2699,A-32,B-7,C-213),(IB-2700,A-32,B-7,C-214),(IB-2701,A-32,B-8,C-15),(IB-2702,A-32,B-9,C-15),(IB-2703,A-32,B-10,C-15),(IB-2704,A-32,B-10,C-52),(IB-2705,A-33,B-1,C-15),(IB-2706,A-33,B-2,C-15),(IB-2707,A-33,B-3,C-15),(IB-2708,A-33,B-4,C-15),(IB-2709,A-33,B-5,C-15),(IB-2710,A-33,B-6,C-15),(IB-2711,A-33,B-7,C-1),(IB-2712,A-33,B-7,C-2),(IB-2713,A-33,B-7,C-3),(IB-2714,A-33,B-7,C-4),(IB-2715,A-33,B-7,C-5),(IB-2716,A-33,B-7,C-6),(IB-2717,A-33,B-7,C-7),(IB-2718,A-33,B-7,C-8),(IB-2719,A-33,B-7,C-9),(IB-2720,A-33,B-7,C-10),(IB-2721,A-33,B-7,C-11),(IB-2722,A-33,B-7,C-12),(IB-2723,A-33,B-7,C-13),(IB-2724,A-33,B-7,C-14),(IB-2725,A-33,B-7,C-15),(IB-2726,A-33,B-7,C-16),(IB-2727,A-33,B-7,C-17),(IB-2728,A-33,B-7,C-18),(IB-2729,A-33,B-7,C-19),(IB-2730,A-33,B-7,C-20),(IB-2731,A-33,B-7,C-21),(IB-2732,A-33,B-7,C-22),(IB-2733,A-33,B-7,C-23),(IB-2734,A-33,B-7,C-24),(IB-2735,A-33,B-7,C-25),(IB-2736,A-33,B-7,C-26),(IB-2737,A-33,B-7,C-27),(IB-2738,A-33,

B-7,C-28),(IB-2739,A-33,B-7,C-29),(IB-2740,A-33,B-7,C-30),(IB-2741,A-33,B-7,C-31),(IB-2742,A-33,B-7,C-32), (IB-2743,A-33,B-7,C-33),(IB-2744,A-33,B-7,C-34),(IB-2745,A-33,B-7,C-35),(IB-2746,A-33,B-7,C-36),(IB-2747,A-33,B-7,C-37),(IB-2748,A-33,B-7,C-38),(IB-2749,A-33,B-7,C-39),(IB-2750,A-33,B-7,C-40),(IB-2751,A-33,B-7,C-41),(IB-2752,A-33,B-7,C-42),(IB-2753,A-33,B-7,C-43), (IB-2754,A-33,B-7,C-44),(IB-2755,A-33,B-7,C-45),(IB-2756,A-33,B-7,C-46),(IB-2757,A-33,B-7,C-47),(IB-2758,A-33,B-7,C-48),(IB-2759,A-33,B-7,C-49),(IB-2760,A-33,B-7,C-50),(IB-2761,A-33,B-7,C-51),(IB-2762,A-33,B-7,C-52),(IB-2763,A-33,B-7,C-53),(IB-2764,A-33,B-7,C-54), (IB-2765,A-33,B-7,C-55),(IB-2766,A-33,B-7,C-56),(IB-2767,A-33,B-7,C-57),(IB-2768,A-33,B-7,C-58),(IB-2769,A-33,B-7,C-59),(IB-2770,A-33,B-7,C-60),(IB-2771,A-33,B-7,C-61),(IB-2772,A-33,B-7,C-62),(IB-2773,A-33,B-7,C-63),(IB-2774,A-33,B-7,C-64),(IB-2775,A-33,B-7,C-65), (IB-2776,A-33,B-7,C-66),(IB-2777,A-33,B-7,C-67),(IB-2778,A-33,B-7,C-68),(IB-2779,A-33,B-7,C-69),(IB-2780,A-33,B-7,C-70),(IB-2781,A-33,B-7,C-71),(IB-2782,A-33,B-7,C-72),(IB-2783,A-33,B-7,C-73),(IB-2784,A-33,B-7,C-74),(IB-2785,A-33,B-7,C-75),(IB-2786,A-33,B-7,C-76), (IB-2787,A-33,B-7,C-77),(IB-2788,A-33,B-7,C-78),(IB-2789,A-33,B-7,C-79),(IB-2790,A-33,B-7,C-80),(IB-2791,A-33,B-7,C-81),(IB-2792,A-33,B-7,C-82),(IB-2793,A-33,B-7,C-83),(IB-2794,A-33,B-7,C-84),(IB-2795,A-33,B-7,C-85),(IB-2796,A-33,B-7,C-86),(IB-2797,A-33,B-7,C-87), (IB-2798,A-33,B-7,C-88),(IB-2799,A-33,B-7,C-89),(IB-2800,A-33,B-7,C-90),(IB-2801,A-33,B-7,C-91),(IB-2802,A-33,B-7,C-92),(IB-2803,A-33,B-7,C-93),(IB-2804,A-33,B-7,C-94),(IB-2805,A-33,B-7,C-95),(IB-2806,A-33,B-7,C-96),(IB-2807,A-33,B-7,C-97),(IB-2808,A-33,B-7,C-98), (IB-2809,A-33,B-7,C-99),(IB-2810,A-33,B-7,C-100),(IB-2811,A-33,B-7,C-101),(IB-2812,A-33,B-7,C-102),(IB-2813,A-33,B-7,C-103),(IB-2814,A-33,B-7,C-104),(IB-2815,A-33,B-7,C-105),(IB-2816,A-33,B-7,C-106),(IB-2817,A-33,B-7,C-107),(IB-2818,A-33,B-7,C-108),(IB-2819,A-33,B-7,C-109),(IB-2820,A-33,B-7,C-110),(IB-2821,A-33,B-7,C-111),(IB-2822,A-33,B-7,C-112),(IB-2823,A-33,B-7,C-113),(IB-2824,A-33,B-7,C-114),(IB-2825,A-33,B-7,C-115),(IB-2826,A-33,B-7,C-116),(IB-2827,A-33,B-7,C-117),(IB-2828,A-33,B-7,C-118),(IB-2829,A-33,B-7,C-119),(IB-2830,A-33,B-7,C-120),(IB-2831,A-33,B-7,C-121),(IB-2832,A-33,B-7,C-122),(IB-2833,A-33,B-7,C-123),(IB-2834,A-33,B-7,C-124),(IB-2835,A-33,B-7,C-125),(IB-2836,A-33,B-7,C-126),(IB-2837,A-33,B-7,C-127),(IB-2838,A-33,B-7,C-128),(IB-2839,A-33,B-7,C-129),(IB-2840,A-33,B-7,C-130),(IB-2841,A-33,B-7,C-131),(IB-2842,A-33,B-7,C-132),(IB-2843,A-33,B-7,C-133),(IB-2844,A-33,B-7,C-134),(IB-2845,A-33,B-7,C-135),(IB-2846,A-33,B-7,C-136),(IB-2847,A-33,B-7,C-137),(IB-2848,A-33,B-7,C-138),(IB-2849,A-33,B-7,C-139),(IB-2850,A-33,B-7,C-140),(IB-2851,A-33,B-7,C-141),(IB-2852,A-33,B-7,C-142),(IB-2853,A-33,B-7,C-143),(IB-2854,A-33,B-7,C-144),(IB-2855,A-33,B-7,C-145),(IB-2856,A-33,B-7,C-146),(IB-2857,A-33,B-7,C-147),(IB-2858,A-33,B-7,C-148),(IB-2859,A-33,B-7,C-149),(IB-2860,A-33,B-7,C-150),(IB-2861,A-33,B-7,C-151),(IB-2862,A-33,B-7,C-152),(IB-2863,A-33,B-7,C-153),(IB-2864,A-33,B-7,C-154),(IB-2865,A-33,B-7,C-155),(IB-2866,A-33,B-7,C-156),(IB-2867,A-33,B-7,C-157),(IB-2868,A-33,B-7,C-158),(IB-2869,A-33,B-7,C-159),(IB-2870,A-33,B-7,C-160),(IB-2871,A-33,B-7,C-161),(IB-2872,A-33,B-7,C-162),(IB-2873,A-33,B-7,C-163),(IB-2874,A-33,B-7,C-164),(IB-2875,A-33,B-7,C-165),(IB-2876,A-33,B-7,C-166),(IB-2877,A-33,B-7,C-167),(IB-2878,A-33,B-7,C-168),(IB-2879,A-33,B-7,C-169),(IB-2880,A-33,B-7,C-170),(IB-2881,A-33,B-7,C-171),(IB-2882,A-33,B-7,C-172),(IB-2883,A-33,B-7,C-173),(IB-2884,A-33,B-7,C-174),(IB-2885,A-33,B-7,C-175),(IB-2886,A-33,B-7,C-176),(IB-2887,A-33,B-7,C-177),(IB-2888,A-33,B-7,C-178),(IB-2889,A-33,B-7,C-179),(IB-2890,A-33,B-7,C-180),(IB-2891,A-33,B-7,C-181),(IB-2892,A-33,B-7,C-182),(IB-2893,A-33,B-7,C-183),(IB-2894,A-33,B-7,C-184),(IB-2895,A-33,B-7,C-185),(IB-2896,A-33,B-7,C-186),(IB-2897,A-33,B-7,C-187),(IB-2898,A-33,B-7,C-188),(IB-2899,A-33,B-7,C-189),(IB-2900,A-33,B-7,C-190),(IB-2901,A-33,B-7,C-191),(IB-2902,A-33,B-7,C-192),(IB-2903,A-33,B-7,C-193),(IB-2904,A-33,B-7,C-194),(IB-2905,A-33,B-7,C-195),(IB-2906,A-33,B-7,C-196),(IB-2907,A-33,B-7,C-197),(IB-2908,A-33,B-7,C-198),(IB-2909,A-33,B-7,C-199),(IB-2910,A-33,B-7,C-200),(IB-2911,A-33,B-7,C-201),(IB-2912,A-33,B-7,C-202),(IB-2913,A-33,B-7,C-203),(IB-2914,A-33,B-7,C-204),(IB-2915,A-33,B-7,C-205),(IB-2916,A-33,B-7,C-206),(IB-2917,A-33,B-7,C-207),(IB-2918,A-33,B-7,C-208),(IB-2919,A-33,B-7,C-209),(IB-2920,A-33,B-7,C-210),(IB-2921,A-33,B-7,C-211),(IB-2922,A-33,B-7,C-212),(IB-2923,A-33,B-7,C-213),(IB-2924,A-33,B-7,C-214),(IB-2925,A-33,B-8,C-15),(IB-2926,A-33,B-9,C-15),(IB-2927,A-33,B-10,C-15),(IB-2928,A-33,B-10,C-52),(IB-2929,A-34,B-1,C-15),(IB-2930,A-34,B-2,C-15),(IB-2931,A-34,B-3,C-15),(IB-2932,A-34,B-4,C-15),(IB-2933,A-34,B-5,C-15),(IB-2934,A-34,B-6,C-15),(IB-2935,A-34,B-7,C-1),(IB-2936,A-34,B-7,C-2),(IB-2937,A-34,B-7,C-3),(IB-2938,A-34,B-7,C-4),(IB-2939,A-34,B-7,C-5),(IB-2940,A-34,B-7,C-6),(IB-2941,A-34,B-7,C-7),(IB-2942,A-34,B-7,C-8),(IB-2943,A-34,B-7,C-9),(IB-2944,A-34,B-7,C-10),(IB-2945,A-34,B-7,C-11),(IB-2946,A-34,B-7,C-12),(IB-2947,A-34,B-7,C-13),(IB-2948,A-34,B-7,C-14),(IB-2949,A-34,B-7,C-15),(IB-2950,A-34,B-7,C-16),(IB-2951,A-34,B-7,C-17), (IB-2952,A-34,B-7,C-18),(IB-2953,A-34,B-7,C-19),(IB-2954,A-34,B-7,C-20),(IB-2955,A-34,B-7,C-21),(IB-2956,A-34,B-7,C-22),(IB-2957,A-34,B-7,C-23),(IB-2958,A-34,B-7,C-24),(IB-2959,A-34,B-7,C-25),(IB-2960,A-34,B-7,C-26),(IB-2961,A-34,B-7,C-27),(IB-2962,A-34,B-7,C-28), (IB-2963,A-34,B-7,C-29),(IB-2964,A-34,B-7,C-30),(IB-2965,A-34,B-7,C-31),(IB-2966,A-34,B-7,C-32),(IB-2967,A-34,B-7,C-33),(IB-2968,A-34,B-7,C-34),(IB-2969,A-34,B-7,C-35),(IB-2970,A-34,B-7,C-36),(IB-2971,A-34,B-7,C-37),(IB-2972,A-34,B-7,C-38),(IB-2973,A-34,B-7,C-39), (IB-2974,A-34,B-7,C-40),(IB-2975,A-34,B-7,C-41),(IB-2976,A-34,B-7,C-42),(IB-2977,A-34,B-7,C-43),(IB-2978,A-34,B-7,C-44),(IB-2979,A-34,B-7,C-45),(IB-2980,A-34,B-7,C-46),(IB-2981,A-34,B-7,C-47),(IB-2982,A-34,B-7,C-48),(IB-2983,A-34,B-7,C-49),(IB-2984,A-34,B-7,C-50), (IB-2985,A-34,B-7,C-51),(IB-2986,A-34,B-7,C-52),(IB-2987,A-34,B-7,C-53),(IB-2988,A-34,B-7,C-54),(IB-2989,A-34,B-7,C-55),(IB-2990,A-34,B-7,C-56),(IB-2991,A-34,B-7,C-57),(IB-2992,A-34,B-7,C-58),(IB-2993,A-34,B-7,C-59),(IB-2994,A-34,B-7,C-60),(IB-2995,A-34,B-7,C-61), (IB-2996,A-34,B-7,C-62),(IB-2997,A-34,B-7,C-63),(IB-2998,A-34,B-7,C-64),(IB-2999,A-34,B-7,C-65),(IB-3000,A-34,B-7,C-66),(IB-3001,A-34,B-7,C-67),(IB-3002,A-34,B-7,C-68),(IB-3003,A-34,B-7,C-69),(IB-3004,A-34,B-7,C-70),(IB-3005,A-34,B-7,C-71),(IB-3006,A-34,B-7,C-72), (IB-3007,A-34,B-7,C-73),(IB-3008,A-34,B-7,C-74),(IB-3009,A-34,B-7,C-75),(IB-3010,A-34,B-7,C-76),(IB-3011,A-34,B-7,C-77),(IB-3012,A-34,B-7,C-78),(IB-3013,A-34,B-7,C-79),(IB-3014,A-34,B-7,C-80),(IB-3015,A-34,B-7,C-81),(IB-3016,A-34,B-7,C-82),(IB-3017,A-34,B-7,C-83), (IB-3018,A-34,B-7,C-84),(IB-3019,A-34,B-7,C-85),(IB-3020,A-34,B-7,C-86),(IB-3021,A-34,B-7,C-87),(IB-3022,

A-34,B-7,C-88),(IB-3023,A-34,B-7,C-89),(IB-3024,A-34,B-7,C-90),(IB-3025,A-34,B-7,C-91),(IB-3026,A-34,B-7,C-92),(IB-3027,A-34,B-7,C-93),(IB-3028,A-34,B-7,C-94),(IB-3029,A-34,B-7,C-95),(IB-3030,A-34,B-7,C-96),(IB-3031,A-34,B-7,C-97),(IB-3032,A-34,B-7,C-98),(IB-3033,A-34,B-7,C-99),(IB-3034,A-34,B-7,C-100),(IB-3035,A-34,B-7,C-101),(IB-3036,A-34,B-7,C-102),(IB-3037,A-34,B-7,C-103),(IB-3038,A-34,B-7,C-104),(IB-3039,A-34,B-7,C-105),(IB-3040,A-34,B-7,C-106),(IB-3041,A-34,B-7,C-107),(IB-3042,A-34,B-7,C-108),(IB-3043,A-34,B-7,C-109),(IB-3044,A-34,B-7,C-110),(IB-3045,A-34,B-7,C-111),(IB-3046,A-34,B-7,C-112),(IB-3047,A-34,B-7,C-113),(IB-3048,A-34,B-7,C-114),(IB-3049,A-34,B-7,C-115),(IB-3050,A-34,B-7,C-116),(IB-3051,A-34,B-7,C-117),(IB-3052,A-34,B-7,C-118),(IB-3053,A-34,B-7,C-119),(IB-3054,A-34,B-7,C-120),(IB-3055,A-34,B-7,C-121),(IB-3056,A-34,B-7,C-122),(IB-3057,A-34,B-7,C-123),(IB-3058,A-34,B-7,C-124),(IB-3059,A-34,B-7,C-125),(IB-3060,A-34,B-7,C-126),(IB-3061,A-34,B-7,C-127),(IB-3062,A-34,B-7,C-128),(IB-3063,A-34,B-7,C-129),(IB-3064,A-34,B-7,C-130),(IB-3065,A-34,B-7,C-131),(IB-3066,A-34,B-7,C-132),(IB-3067,A-34,B-7,C-133),(IB-3068,A-34,B-7,C-134),(IB-3069,A-34,B-7,C-135),(IB-3070,A-34,B-7,C-136),(IB-3071,A-34,B-7,C-137),(IB-3072,A-34,B-7,C-138),(IB-3073,A-34,B-7,C-139),(IB-3074,A-34,B-7,C-140),(IB-3075,A-34,B-7,C-141),(IB-3076,A-34,B-7,C-142),(IB-3077,A-34,B-7,C-143),(IB-3078,A-34,B-7,C-144),(IB-3079,A-34,B-7,C-145),(IB-3080,A-34,B-7,C-146),(IB-3081,A-34,B-7,C-147),(IB-3082,A-34,B-7,C-148),(IB-3083,A-34,B-7,C-149),(IB-3084,A-34,B-7,C-150),(IB-3085,A-34,B-7,C-151),(IB-3086,A-34,B-7,C-152),(IB-3087,A-34,B-7,C-153),(IB-3088,A-34,B-7,C-154),(IB-3089,A-34,B-7,C-155),(IB-3090,A-34,B-7,C-156),(IB-3091,A-34,B-7,C-157),(IB-3092,A-34,B-7,C-158),(IB-3093,A-34,B-7,C-159),(IB-3094,A-34,B-7,C-160),(IB-3095,A-34,B-7,C-161),(IB-3096,A-34,B-7,C-162),(IB-3097,A-34,B-7,C-163),(IB-3098,A-34,B-7,C-164),(IB-3099,A-34,B-7,C-165),(IB-3100,A-34,B-7,C-166),(IB-3101,A-34,B-7,C-167),(IB-3102,A-34,B-7,C-168),(IB-3103,A-34,B-7,C-169),(IB-3104,A-34,B-7,C-170),(IB-3105,A-34,B-7,C-171),(IB-3106,A-34,B-7,C-172),(IB-3107,A-34,B-7,C-173),(IB-3108,A-34,B-7,C-174),(IB-3109,A-34,B-7,C-175),(IB-3110,A-34,B-7,C-176),(IB-3111,A-34,B-7,C-177),(IB-3112,A-34,B-7,C-178),(IB-3113,A-34,B-7,C-179),(IB-3114,A-34,B-7,C-180),(IB-3115,A-34,B-7,C-181),(IB-3116,A-34,B-7,C-182),(IB-3117,A-34,B-7,C-183),(IB-3118,A-34,B-7,C-184),(IB-3119,A-34,B-7,C-185),(IB-3120,A-34,B-7,C-186),(IB-3121,A-34,B-7,C-187),(IB-3122,A-34,B-7,C-188),(IB-3123,A-34,B-7,C-189),(IB-3124,A-34,B-7,C-190),(IB-3125,A-34,B-7,C-191),(IB-3126,A-34,B-7,C-192),(IB-3127,A-34,B-7,C-193),(IB-3128,A-34,B-7,C-194),(IB-3129,A-34,B-7,C-195),(IB-3130,A-34,B-7,C-196),(IB-3131,A-34,B-7,C-197),(IB-3132,A-34,B-7,C-198),(IB-3133,A-34,B-7,C-199),(IB-3134,A-34,B-7,C-200),(IB-3135,A-34,B-7,C-201),(IB-3136,A-34,B-7,C-202),(IB-3137,A-34,B-7,C-203),(IB-3138,A-34,B-7,C-204),(IB-3139,A-34,B-7,C-205),(IB-3140,A-34,B-7,C-206),(IB-3141,A-34,B-7,C-207),(IB-3142,A-34,B-7,C-208),(IB-3143,A-34,B-7,C-209),(IB-3144,A-34,B-7,C-210),(IB-3145,A-34,B-7,C-211),(IB-3146,A-34,B-7,C-212),(IB-3147,A-34,B-7,C-213),(IB-3148,A-34,B-7,C-214),(IB-3149,A-34,B-8,C-15),(IB-3150,A-34,B-9,C-15),(IB-3151,A-34,B-10,C-15),(IB-3152,A-34,B-10,C-52),(IB-3153,A-35,B-1,C-15),(IB-3154,A-35,B-2,C-15),(IB-3155,A-35,B-3,C-15),(IB-3156,A-35,B-4,C-15),(IB-3157,A-35,B-5,C-15),(IB-3158,A-35,B-6,C-15),(IB-3159,A-35,B-7,C-1),(IB-3160,A-35,B-7,C-2),(IB-3161,A-35,B-7,C-3),(IB-3162,A-35,B-7,C-4),(IB-3163,A-35,B-7,C-5),(IB-3164,A-35,B-7,C-6),(IB-3165,A-35,B-7,C-7),(IB-3166,A-35,B-7,C-8),(IB-3167,A-35,B-7,C-9),(IB-3168,A-35,B-7,C-10),(IB-3169,A-35,B-7,C-11),(IB-3170,A-35,B-7,C-12),(IB-3171,A-35,B-7,C-13),(IB-3172,A-35,B-7,C-14),(IB-3173,A-35,B-7,C-15),(IB-3174,A-35,B-7,C-16),(IB-3175,A-35,B-7,C-17),(IB-3176,A-35,B-7,C-18),(IB-3177,A-35,B-7,C-19),(IB-3178,A-35,B-7,C-20),(IB-3179,A-35,B-7,C-21),(IB-3180,A-35,B-7,C-22),(IB-3181,A-35,B-7,C-23),(IB-3182,A-35,B-7,C-24),(IB-3183,A-35,B-7,C-25),(IB-3184,A-35,B-7,C-26),(IB-3185,A-35,B-7,C-27),(IB-3186,A-35,B-7,C-28),(IB-3187,A-35,B-7,C-29),(IB-3188,A-35,B-7,C-30),(IB-3189,A-35,B-7,C-31),(IB-3190,A-35,B-7,C-32),(IB-3191,A-35,B-7,C-33),(IB-3192,A-35,B-7,C-34),(IB-3193,A-35,B-7,C-35),(IB-3194,A-35,B-7,C-36),(IB-3195,A-35,B-7,C-37),(IB-3196,A-35,B-7,C-38),(IB-3197,A-35,B-7,C-39),(IB-3198,A-35,B-7,C-40),(IB-3199,A-35,B-7,C-41),(IB-3200,A-35,B-7,C-42),(IB-3201,A-35,B-7,C-43),(IB-3202,A-35,B-7,C-44),(IB-3203,A-35,B-7,C-45),(IB-3204,A-35,B-7,C-46),(IB-3205,A-35,B-7,C-47),(IB-3206,A-35,B-7,C-48),(IB-3207,A-35,B-7,C-49),(IB-3208,A-35,B-7,C-50),(IB-3209,A-35,B-7,C-51),(IB-3210,A-35,B-7,C-52),(IB-3211,A-35,B-7,C-53),(IB-3212,A-35,B-7,C-54),(IB-3213,A-35,B-7,C-55),(IB-3214,A-35,B-7,C-56),(IB-3215,A-35,B-7,C-57),(IB-3216,A-35,B-7,C-58),(IB-3217,A-35,B-7,C-59),(IB-3218,A-35,B-7,C-60),(IB-3219,A-35,B-7,C-61),(IB-3220,A-35,B-7,C-62),(IB-3221,A-35,B-7,C-63),(IB-3222,A-35,B-7,C-64),(IB-3223,A-35,B-7,C-65),(IB-3224,A-35,B-7,C-66),(IB-3225,A-35,B-7,C-67),(IB-3226,A-35,B-7,C-68),(IB-3227,A-35,B-7,C-69),(IB-3228,A-35,B-7,C-70),(IB-3229,A-35,B-7,C-71),(IB-3230,A-35,B-7,C-72),(IB-3231,A-35,B-7,C-73),(IB-3232,A-35,B-7,C-74),(IB-3233,A-35,B-7,C-75),(IB-3234,A-35,B-7,C-76),(IB-3235,A-35,B-7,C-77),(IB-3236,A-35,B-7,C-78),(IB-3237,A-35,B-7,C-79),(IB-3238,A-35,B-7,C-80),(IB-3239,A-35,B-7,C-81),(IB-3240,A-35,B-7,C-82),(IB-3241,A-35,B-7,C-83),(IB-3242,A-35,B-7,C-84),(IB-3243,A-35,B-7,C-85),(IB-3244,A-35,B-7,C-86),(IB-3245,A-35,B-7,C-87),(IB-3246,A-35,B-7,C-88),(IB-3247,A-35,B-7,C-89),(IB-3248,A-35,B-7,C-90),(IB-3249,A-35,B-7,C-91),(IB-3250,A-35,B-7,C-92),(IB-3251,A-35,B-7,C-93),(IB-3252,A-35,B-7,C-94),(IB-3253,A-35,B-7,C-95),(IB-3254,A-35,B-7,C-96),(IB-3255,A-35,B-7,C-97),(IB-3256,A-35,B-7,C-98),(IB-3257,A-35,B-7,C-99),(IB-3258,A-35,B-7,C-100),(IB-3259,A-35,B-7,C-101),(IB-3260,A-35,B-7,C-102),(IB-3261,A-35,B-7,C-103),(IB-3262,A-35,B-7,C-104),(IB-3263,A-35,B-7,C-105),(IB-3264,A-35,B-7,C-106),(IB-3265,A-35,B-7,C-107),(IB-3266,A-35,B-7,C-108),(IB-3267,A-35,B-7,C-109),(IB-3268,A-35,B-7,C-110),(IB-3269,A-35,B-7,C-111),(IB-3270,A-35,B-7,C-112),(IB-3271,A-35,B-7,C-113),(IB-3272,A-35,B-7,C-114),(IB-3273,A-35,B-7,C-115),(IB-3274,A-35,B-7,C-116),(IB-3275,A-35,B-7,C-117),(IB-3276,A-35,B-7,C-118),(IB-3277,A-35,B-7,C-119),(IB-3278,A-35,B-7,C-120),(IB-3279,A-35,B-7,C-121),(IB-3280,A-35,B-7,C-122),(IB-3281,A-35,B-7,C-123),(IB-3282,A-35,B-7,C-124),(IB-3283,A-35,B-7,C-125),(IB-3284,A-35,B-7,C-126),(IB-3285,A-35,B-7,C-127),(IB-3286,A-35,B-7,C-128),(IB-3287,A-35,B-7,C-129),(IB-3288,A-35,B-7,C-130),(IB-3289,A-35,B-7,C-131),(IB-3290,A-35,B-7,C-132),(IB-3291,A-35,B-7,C-133),(IB-3292,A-35,B-7,C-134),(IB-3293,A-35,B-7,C-135),(IB-3294,A-35,B-7,C-136),(IB-3295,A-35,B-7,C-137),(IB-3296,A-35,B-7,C-138),(IB-3297,A-35,B-7,C-139),(IB-3298,A-35,B-7,C-140),(IB-3299,A-35,B-7,C-141),(IB-3300,A-35,B-7,C-142),(IB-3301,A-35,B-7,C-143),(IB-3302,A-35,B-7,C-

144),(IB-3303,A-35,B-7,C-145),(IB-3304,A-35,B-7,C-146),(IB-3305,A-35,B-7,C-147),(IB-3306,A-35,B-7,C-148),(IB-3307,A-35,B-7,C-149),(IB-3308,A-35,B-7,C-150),(IB-3309,A-35,B-7,C-151),(IB-3310,A-35,B-7,C-152),(IB-3311,A-35,B-7,C-153),(IB-3312,A-35,B-7,C-154),(IB-3313,A-35,B-7,C-155),(IB-3314,A-35,B-7,C-156),(IB-3315,A-35,B-7,C-157),(IB-3316,A-35,B-7,C-158),(IB-3317,A-35,B-7,C-159),(IB-3318,A-35,B-7,C-160),(IB-3319,A-35,B-7,C-161),(IB-3320,A-35,B-7,C-162),(IB-3321,A-35,B-7,C-163),(IB-3322,A-35,B-7,C-164),(IB-3323,A-35,B-7,C-165),(IB-3324,A-35,B-7,C-166),(IB-3325,A-35,B-7,C-167),(IB-3326,A-35,B-7,C-168),(IB-3327,A-35,B-7,C-169),(IB-3328,A-35,B-7,C-170),(IB-3329,A-35,B-7,C-171),(IB-3330,A-35,B-7,C-172),(IB-3331,A-35,B-7,C-173),(IB-3332,A-35,B-7,C-174),(IB-3333,A-35,B-7,C-175),(IB-3334,A-35,B-7,C-176),(IB-3335,A-35,B-7,C-177),(IB-3336,A-35,B-7,C-178),(IB-3337,A-35,B-7,C-179),(IB-3338,A-35,B-7,C-180),(IB-3339,A-35,B-7,C-181),(IB-3340,A-35,B-7,C-182),(IB-3341,A-35,B-7,C-183),(IB-3342,A-35,B-7,C-184),(IB-3343,A-35,B-7,C-185),(IB-3344,A-35,B-7,C-186),(IB-3345,A-35,B-7,C-187),(IB-3346,A-35,B-7,C-188),(IB-3347,A-35,B-7,C-189),(IB-3348,A-35,B-7,C-190),(IB-3349,A-35,B-7,C-191),(IB-3350,A-35,B-7,C-192),(IB-3351,A-35,B-7,C-193),(IB-3352,A-35,B-7,C-194),(IB-3353,A-35,B-7,C-195),(IB-3354,A-35,B-7,C-196),(IB-3355,A-35,B-7,C-197),(IB-3356,A-35,B-7,C-198),(IB-3357,A-35,B-7,C-199),(IB-3358,A-35,B-7,C-200),(IB-3359,A-35,B-7,C-201),(IB-3360,A-35,B-7,C-202),(IB-3361,A-35,B-7,C-203),(IB-3362,A-35,B-7,C-204),(IB-3363,A-35,B-7,C-202),(IB-3364,A-35,B-7,C-206),(IB-3365,A-35,B-7,C-207),(IB-3366,A-35,B-7,C-208),(IB-3367,A-35,B-7,C-209),(IB-3368,A-35,B-7,C-210),(IB-3369,A-35,B-7,C-211),(IB-3370,A-35,B-7,C-212),(IB-3371,A-35,B-7,C-213),(IB-3372,A-35,B-7,C-214),(IB-3373,A-35,B-8,C-15),(IB-3374,A-35,B-9,C-15),(IB-3375,A-35,B-10,C-15),(IB-3376,A-35,B-10,C-52),(IB-3377,A-36,B-1,C-15),(IB-3378,A-36,B-2,C-15),(IB-3379,A-36,B-3,C-15),(IB-3380,A-36,B-4,C-15),(IB-3381,A-36,B-5,C-15),(IB-3382,A-36,B-6,C-15),(IB-3383,A-36,B-7,C-1),(IB-3384,A-36,B-7,C-2),(IB-3385,A-36,B-7,C-3),(IB-3386,A-36,B-7,C-4),(IB-3387,A-36,B-7,C-5),(IB-3388,A-36,B-7,C-6),(1B-3389,A-36,B-7,C-7),(IB-3390,A-36,B-7,C-8),(IB-3391,A-36,B-7,C-9),(IB-3392,A-36,B-7,C-10),(IB-3393,A-36,B-7,C-11),(IB-3394,A-36,B-7,C-12),(IB-3395,A-36,B-7,C-13),(IB-3396,A-36,B-7,C-14),(IB-3397,A-36,B-7,C-15),(IB-3398,A-36,B-7,C-16),(IB-3399,A-36,B-7,C-17),(IB-3400,A-36,B-7,C-18),(IB-3401,A-36,B-7,C-19),(IB-3402,A-36,B-7,C-20),(IB-3403,A-36,B-7,C-21),(IB-3404,A-36,B-7,C-22),(IB-3405,A-36,B-7,C-23),(IB-3406,A-36,B-7,C-24),(IB-3407,A-36,B-7,C-25),(IB-3408,A-36,B-7,C-26),(IB-3409,A-36,B-7,C-27),(IB-3410,A-36,B-7,C-28),(IB-3411,A-36,B-7,C-29),(IB-3412,A-36,B-7,C-30),(IB-3413,A-36,B-7,C-31),(IB-3414,A-36,B-7,C-32),(IB-3415,A-36,B-7,C-33),(IB-3416,A-36,B-7,C-34),(IB-3417,A-36,B-7,C-35),(IB-3418,A-36,B-7,C-36),(IB-3419,A-36,B-7,C-37),(IB-3420,A-36,B-7,C-38),(IB-3421,A-36,B-7,C-39),(IB-3422,A-36,B-7,C-40),(IB-3423,A-36,B-7,C-41),(IB-3424,A-36,B-7,C-42),(IB-3425,A-36,B-7,C-43),(IB-3426,A-36,B-7,C-44),(IB-3427,A-36,B-7,C-45),(IB-3428,A-36,B-7,C-46),(IB-3429,A-36,B-7,C-47),(IB-3430,A-36,B-7,C-48),(IB-3431,A-36,B-7,C-49),(IB-3432,A-36,B-7,C-50),(IB-3433,A-36,B-7,C-51),(IB-3434,A-36,B-7,C-52),(IB-3435,A-36,B-7,C-53),(IB-3436,A-36,B-7,C-54),(IB-3437,A-36,B-7,C-55),(IB-3438,A-36,B-7,C-56),(IB-3439,A-36,B-7,C-57),(IB-3440,A-36,B-7,C-58),(IB-3441,A-36,B-7,C-59),(IB-3442,A-36,B-7,C-60),(IB-3443,A-36,B-7,C-61),(IB-3444,A-36,B-7,C-62),(IB-3445,A-36,B-7,C-63),(IB-3446,A-36,B-7,C-64),(IB-3447,A-36,B-7,C-65),(IB-3448,A-36,B-7,C-66),(IB-3449,A-36,B-7,C-67),(IB-3450,A-36,B-7,C-68),(IB-3451,A-36,B-7,C-69),(IB-3452,A-36,B-7,C-70),(IB-3453,A-36,B-7,C-71),(IB-3454,A-36,B-7,C-72),(IB-3455,A-36,B-7,C-73),(IB-3456,A-36,B-7,C-74),(IB-3457,A-36,B-7,C-75),(IB-3458,A-36,B-7,C-76),(IB-3459,A-36,B-7,C-77),(IB-3460,A-36,B-7,C-78),(IB-3461,A-36,B-7,C-79),(IB-3462,A-36,B-7,C-80),(IB-3463,A-36,B-7,C-81),(IB-3464,A-36,B-7,C-82),(IB-3465,A-36,B-7,C-83),(IB-3466,A-36,B-7,C-84),(IB-3467,A-36,B-7,C-85),(IB-3468,A-36,B-7,C-86),(IB-3469,A-36,B-7,C-87),(IB-3470,A-36,B-7,C-88),(IB-3471,A-36,B-7,C-89),(IB-3472,A-36,B-7,C-90),(IB-3473,A-36,B-7,C-91),(IB-3474,A-36,B-7,C-92),(IB-3475,A-36,B-7,C-93),(IB-3476,A-36,B-7,C-94),(IB-3477,A-36,B-7,C-95),(IB-3478,A-36,B-7,C-96),(IB-3479,A-36,B-7,C-97),(IB-3480,A-36,B-7,C-98),(IB-3481,A-36,B-7,C-99),(IB-3482,A-36,B-7,C-100),(IB-3483,A-36,B-7,C-101),(IB-3484,A-36,B-7,C-102),(IB-3485,A-36,B-7,C-103),(IB-3486,A-36,B-7,C-104),(IB-3487,A-36,B-7,C-105),(IB-3488,A-36,B-7,C-106),(IB-3489,A-36,B-7,C-107),(IB-3490,A-36,B-7,C-108),(IB-3491,A-36,B-7,C-109),(IB-3492,A-36,B-7,C-110),(IB-3493,A-36,B-7,C-111),(IB-3494,A-36,B-7,C-112),(IB-3495,A-36,B-7,C-113),(IB-3496,A-36,B-7,C-114),(IB-3497,A-36,B-7,C-115),(IB-3498,A-36,B-7,C-116),(IB-3499,A-36,B-7,C-117),(IB-3500,A-36,B-7,C-118),(IB-3501,A-36,B-7,C-119),(IB-3502,A-36,B-7,C-120),(IB-3503,A-36,B-7,C-121),(IB-3504,A-36,B-7,C-122),(IB-3505,A-36,B-7,C-123),(IB-3506,A-36,B-7,C-124),(IB-3507,A-36,B-7,C-125),(IB-3508,A-36,B-7,C-126),(IB-3509,A-36,B-7,C-127),(IB-3510,A-36,B-7,C-128),(IB-3511,A-36,B-7,C-129),(IB-3512,A-36,B-7,C-130),(IB-3513,A-36,B-7,C-131),(IB-3514,A-36,B-7,C-132),(IB-3515,A-36,B-7,C-133),(IB-3516,A-36,B-7,C-134),(IB-3517,A-36,B-7,C-135),(IB-3518,A-36,B-7,C-136),(IB-3519,A-36,B-7,C-137),(IB-3520,A-36,B-7,C-138),(IB-3521,A-36,B-7,C-139),(IB-3522,A-36,B-7,C-140),(IB-3523,A-36,B-7,C-141),(IB-3524,A-36,B-7,C-142),(IB-3525,A-36,B-7,C-143),(IB-3526,A-36,B-7,C-144),(IB-3527,A-36,B-7,C-145),(IB-3528,A-36,B-7,C-146),(IB-3529,A-36,B-7,C-147),(IB-3530,A-36,B-7,C-148),(IB-3531,A-36,B-7,C-149),(IB-3532,A-36,B-7,C-150),(IB-3533,A-36,B-7,C-151),(IB-3534,A-36,B-7,C-152),(IB-3535,A-36,B-7,C-153),(IB-3536,A-36,B-7,C-154),(IB-3537,A-36,B-7,C-155),(IB-3538,A-36,B-7,C-156),(IB-3539,A-36,B-7,C-157),(IB-3540,A-36,B-7,C-158),(IB-3541,A-36,B-7,C-159),(IB-3542,A-36,B-7,C-160),(IB-3543,A-36,B-7,C-161),(IB-3544,A-36,B-7,C-162),(IB-3545,A-36,B-7,C-163),(IB-3546,A-36,B-7,C-164),(IB-3547,A-36,B-7,C-165),(IB-3548,A-36,B-7,C-166),(IB-3549,A-36,B-7,C-167),(IB-3550,A-36,B-7,C-168),(IB-3551,A-36,B-7,C-169),(IB-3552,A-36,B-7,C-170),(IB-3553,A-36,B-7,C-171),(IB-3554,A-36,B-7,C-172),(IB-3555,A-36,B-7,C-173),(IB-3556,A-36,B-7,C-174),(IB-3557,A-36,B-7,C-175),(IB-3558,A-36,B-7,C-176),(IB-3559,A-36,B-7,C-177),(IB-3560,A-36,B-7,C-178),(IB-3561,A-36,B-7,C-179),(IB-3562,A-36,B-7,C-180),(IB-3563,A-36,B-7,C-181),(IB-3564,A-36,B-7,C-182),(IB-3565,A-36,B-7,C-183),(IB-3566,A-36,B-7,C-184),(IB-3567,A-36,B-7,C-185),(IB-3568,A-36,B-7,C-186),(IB-3569,A-36,B-7,C-187),(IB-3570,A-36,B-7,C-188),(IB-3571,A-36,B-7,C-1 89),(IB-3572,A-36,B-7,C-190),(IB-3573,A-36,B-7,C-191),(IB-3574,A-36,B-7,C-192),(IB-3575,A-36,B-7,C-193),(IB-3576,A-36,B-7,C-194),(IB-3577,A-36,B-7,C-195),(IB-3578,A-36,B-7,C-196),(IB-3579,A-36,B-7,C-197),(IB-3580,A-36,B-7,C-198),(IB-

3581,A-36,B-7,C-199),(IB-3582,A-36,B-7,C-200),(IB-3583,A-36,B-7,C-201),(IB-3584,A-36,B-7,C-202),(IB-3585,A-36,B-7,C-203),(IB-3586,A-36,B-7,C-204),(IB-3587,A-36,B-7,C-205),(IB-3588,A-36,B-7,C-206),(IB-3589,A-36,B-7,C-207),(IB-3590,A-36,B-7,C-208),(IB-3591,A-36,B-7,C-209),(IB-3592,A-36,B-7,C-210),(IB-3593,A-36,B-7,C-211),(IB-3594,A-36,B-7,C-212),(IB-3595,A-36,B-7,C-213),(IB-3596,A-36,B-7,C-214),(IB-3597,A-36,B-8,C-15),(IB-3598,A-36,B-9,C-15),(IB-3599,A-36,B-10,C-15),(IB-3600,A-36,B-10,C-52),(IB-3601,A-37,B-1,C-15),(IB-3602,A-37,B-2,C-15),(IB-3603,A-37,B-3,C-15),(IB-3604,A-37,B-4,C-15),(IB-3605,A-37,B-5,C-15),(IB-3606,A-37,B-6,C-15),(IB-3607,A-37,B-7,C-1),(IB-3608,A-37,B-7,C-2),(IB-3609,A-37,B-7,C-3),(IB-3610,A-37,B-7,C-4),(IB-3611,A-37,B-7,C-5),(IB-3612,A-37,B-7,C-6),(IB-3613,A-37,B-7,C-7),(IB-3614,A-37,B-7,C-8),(IB-3615,A-37,B-7,C-9),(IB-3616,A-37,B-7,C-10),(IB-3617,A-37,B-7,C-11),(IB-3618,A-37,B-7,C-12),(IB-3619,A-37,B-7,C-13),(IB-3620,A-37,B-7,C-14),(IB-3621,A-37,B-7,C-15),(IB-3622,A-37,B-7,C-16),(IB-3623,A-37,B-7,C-17),(IB-3624,A-37,B-7,C-18),(IB-3625,A-37,B-7,C-19),(IB-3626,A-37,B-7,C-20),(IB-3627,A-37,B-7,C-21),(IB-3628,A-37,B-7,C-22),(IB-3629,A-37,B-7,C-23),(IB-3630,A-37,B-7,C-24),(IB-3631,A-37,B-7,C-25),(IB-3632,A-37,B-7,C-26),(IB-3633,A-37,B-7,C-27),(IB-3634,A-37,B-7,C-28),(IB-3635,A-37,B-7,C-29),(IB-3636,A-37,B-7,C-30),(IB-3637,A-37,B-7,C-31),(IB-3638,A-37,B-7,C-32),(IB-3639,A-37,B-7,C-33),(IB-3640,A-37,B-7,C-34),(IB-3641,A-37,B-7,C-35),(IB-3642,A-37,B-7,C-36),(IB-3643,A-37,B-7,C-37),(IB-3644,A-37,B-7,C-38),(IB-3645,A-37,B-7,C-39),(IB-3646,A-37,B-7,C-40),(IB-3647,A-37,B-7,C-41),(IB-3648,A-37,B-7,C-42),(IB-3649,A-37,B-7,C-43),(IB-3650,A-37,B-7,C-44),(IB-3651,A-37,B-7,C-45),(IB-3652,A-37,B-7,C-46),(IB-3653,A-37,B-7,C-47),(IB-3654,A-37,B-7,C-48),(IB-3655,A-37,B-7,C-49),(IB-3656,A-37,B-7,C-50),(IB-3657,A-37,B-7,C-51),(IB-3658,A-37,B-7,C-52),(IB-3659,A-37,B-7,C-53),(IB-3660,A-37,B-7,C-54),(IB-3661,A-37,B-7,C-55),(IB-3662,A-37,B-7,C-56),(IB-3663,A-37,B-7,C-57),(IB-3664,A-37,B-7,C-58),(IB-3665,A-37,B-7,C-59),(IB-3666,A-37,B-7,C-60),(IB-3667,A-37,B-7,C-61),(IB-3668,A-37,B-7,C-62),(IB-3669,A-37,B-7,C-63),(IB-3670,A-37,B-7,C-64),(IB-3671,A-37,B-7,C-65),(IB-3672,A-37,B-7,C-66),(IB-3673,A-37,B-7,C-67),(IB-3674,A-37,B-7,C-68),(IB-3675,A-37,B-7,C-69),(IB-3676,A-37,B-7,C-70),(IB-3677,A-37,B-7,C-71),(IB-3678,A-37,B-7,C-72),(IB-3679,A-37,B-7,C-73),(IB-3680,A-37,B-7,C-74),(IB-3681,A-37,B-7,C-75),(IB-3682,A-37,B-7,C-76),(IB-3683,A-37,B-7,C-77),(IB-3684,A-37,B-7,C-78),(IB-3685,A-37,B-7,C-79),(IB-3686,A-37,B-7,C-80),(IB-3687,A-37,B-7,C-81),(IB-3688,A-37,B-7,C-82),(IB-3689,A-37,B-7,C-83),(IB-3690,A-37,B-7,C-84),(IB-3691,A-37,B-7,C-85),(IB-3692,A-37,B-7,C-86),(IB-3693,A-37,B-7,C-87),(IB-3694,A-37,B-7,C-88),(IB-3695,A-37,B-7,C-89),(IB-3696,A-37,B-7,C-90),(IB-3697,A-37,B-7,C-91),(IB-3698,A-37,B-7,C-92),(IB-3699,A-37,B-7,C-93),(IB-3700,A-37,B-7,C-94),(IB-3701,A-37,B-7,C-95),(IB-3702,A-37,B-7,C-96),(IB-3703,A-37,B-7,C-97),(IB-3704,A-37,B-7,C-98),(IB-3705,A-37,B-7,C-99),(IB-3706,A-37,B-7,C-100),(IB-3707,A-37,B-7,C-101),(IB-3708,A-37,B-7,C-102),(IB-3709,A-37,B-7,C-103),(IB-3710,A-37,B-7,C-104),(IB-3711,A-37,B-7,C-105),(IB-3712,A-37,B-7,C-106),(IB-3713,A-37,B-7,C-107),(IB-3714,A-37,B-7,C-108),(IB-3715,A-37,B-7,C-109),(IB-3716,A-37,B-7,C-110),(IB-3717,A-37,B-7,C-111),(IB-3718,A-37,B-7,C-112),(IB-3719,A-37,B-7,C-113),(IB-3720,A-37,B-7,C-114),(IB-3721,A-37,B-7,C-115),(IB-3722,A-37,B-7,C-116),(IB-3723,A-37,B-7,C-117),(IB-3724,A-37,B-7,C-118),(IB-3725,A-37,B-7,C-119),(IB-3726,A-37,B-7,C-120),(IB-3727,A-37,B-7,C-121),(IB-3728,A-37,B-7,C-122),(IB-3729,A-37,B-7,C-123),(IB-3730,A-37,B-7,C-124),(IB-3731,A-37,B-7,C-125),(IB-3732,A-37,B-7,C-126),(IB-3733,A-37,B-7,C-127),(IB-3734,A-37,B-7,C-128),(IB-3735,A-37,B-7,C-129),(IB-3736,A-37,B-7,C-130),(IB-3737,A-37,B-7,C-131),(IB-3738,A-37,B-7,C-132),(IB-3739,A-37,B-7,C-133),(IB-3740,A-37,B-7,C-134),(IB-3741,A-37,B-7,C-135),(IB-3742,A-37,B-7,C-136),(IB-3743,A-37,B-7,C-137),(IB-3744,A-37,B-7,C-138),(IB-3745,A-37,B-7,C-139),(IB-3746,A-37,B-7,C-140),(IB-3747,A-37,B-7,C-141),(IB-3748,A-37,B-7,C-142),(IB-3749,A-37,B-7,C-143),(IB-3750,A-37,B-7,C-144),(IB-3751,A-37,B-7,C-145),(IB-3752,A-37,B-7,C-146),(IB-3753,A-37,B-7,C-147),(IB-3754,A-37,B-7,C-148),(IB-3755,A-37,B-7,C-149),(IB-3756,A-37,B-7,C-150),(IB-3757,A-37,B-7,C-151),(IB-3758,A-37,B-7,C-152),(IB-3759,A-37,B-7,C-153),(IB-3760,A-37,B-7,C-154),(IB-3761,A-37,B-7,C-155),(IB-3762,A-37,B-7,C-156),(IB-3763,A-37,B-7,C-157),(IB-3764,A-37,B-7,C-158),(IB-3765,A-37,B-7,C-159),(IB-3766,A-37,B-7,C-160),(IB-3767,A-37,B-7,C-161),(IB-3768,A-37,B-7,C-162),(IB-3769,A-37,B-7,C-163),(IB-3770,A-37,B-7,C-164),(IB-3771,A-37,B-7,C-165),(IB-3772,A-37,B-7,C-166),(IB-3773,A-37,B-7,C-167),(IB-3774,A-37,B-7,C-168),(IB-3775,A-37,B-7,C-169),(IB-3776,A-37,B-7,C-170),(IB-3777,A-37,B-7,C-171),(IB-3778,A-37,B-7,C-172),(IB-3779,A-37,B-7,C-173),(IB-3780,A-37,B-7,C-174),(IB-3781,A-37,B-7,C-175),(IB-3782,A-37,B-7,C-176),(IB-3783,A-37,B-7,C-177),(IB-3784,A-37,B-7,C-178),(IB-3785,A-37,B-7,C-179),(IB-3786,A-37,B-7,C-180),(IB-3787,A-37,B-7,C-181),(IB-3788,A-37,B-7,C-182),(IB-3789,A-37,B-7,C-183),(IB-3790,A-37,B-7,C-184),(IB-3791,A-37,B-7,C-185),(IB-3792,A-37,B-7,C-186),(IB-3793,A-37,B-7,C-187),(IB-3794,A-37,B-7,C-188),(IB-3795,A-37,B-7,C-189),(IB-3796,A-37,B-7,C-190),(IB-3797,A-37,B-7,C-191),(IB-3798,A-37,B-7,C-192),(IB-3799,A-37,B-7,C-193),(IB-3800,A-37,B-7,C-194),(IB-3801,A-37,B-7,C-195),(IB-3802,A-37,B-7,C-196),(IB-3803,A-37,B-7,C-197),(IB-3804,A-37,B-7,C-198),(IB-3805,A-37,B-7,C-199),(IB-3806,A-37,B-7,C-200),(IB-3807,A-37,B-7,C-201),(IB-3808,A-37,B-7,C-202),(IB-3809,A-37,B-7,C-203),(IB-3810,A-37,B-7,C-204),(IB-3811,A-37,B-7,C-205),(IB-3812,A-37,B-7,C-206),(IB-3813,A-37,B-7,C-207),(IB-3814,A-37,B-7,C-208),(IB-3815,A-37,B-7,C-209),(IB-3816,A-37,B-7,C-210),(IB-3817,A-37,B-7,C-211),(IB-3818,A-37,B-7,C-212),(IB-3819,A-37,B-7,C-213),(IB-3820,A-37,B-7,C-214),(IB-3821,A-37,B-8,C-15),(IB-3822,A-37,B-9,C-15),(IB-3823,A-37,B-10,C-15),(IB-3824,A-37,B-10,C-52),(IB-3825,A-38,B-1,C-15),(IB-3826,A-38,B-2,C-15),(IB-3827,A-38,B-3,C-15),(IB-3828,A-38,B-4,C-15),(IB-3829,A-38,B-5,C-15),(IB-3830,A-38,B-6,C-15),(IB-3831,A-38,B-7,C-1),(IB-3832,A-38,B-7,C-2),(IB-3833,A-38,B-7,C-3),(IB-3834,A-38,B-7,C-4),(IB-3835,A-38,B-7,C-5),(IB-3836,A-38,B-7,C-6),(IB-3837,A-38,B-7,C-7),(IB-3838,A-38,B-7,C-8),(IB-3839,A-38,B-7,C-9),(IB-3840,A-38,B-7,C-10),(IB-3841,A-38,B-7,C-11),(IB-3842,A-38,B-7,C-12),(IB-3843,A-38,B-7,C-13),(IB-3844,A-38,B-7,C-14),(IB-3845,A-38,B-7,C-15),(IB-3846,A-38,B-7,C-16),(IB-3847,A-38,B-7,C-17),(IB-3848,A-38,B-7,C-18),(IB-3849,A-38,B-7,C-19),(IB-3850,A-38,B-7,C-20),(IB-3851,A-38,B-7,C-21),(IB-3852,A-38,B-7,C-22),(IB-3853,A-38,B-7,C-23),(IB-3854,A-38,B-7,C-24),(IB-3855,A-38,B-7,C-25),(IB-3856,A-38,B-7,C-26),(IB-3857,A-38,B-7,C-27),(IB-3858,A-38,B-7,C-28),(IB-3859,A-38,B-7,C-29),(IB-3860,A-38,B-7,C-30),(IB-3861,A-38,B-7,C-31),(IB-3862,A-38,B-7,C-32),(IB-3863,A-38,B-7,C-33),(IB-3864,

A-38,B-7,C-34),(IB-3865,A-38,B-7,C-35),(IB-3866,A-38, B-7,C-36),(IB-3867,A-38,B-7,C-37),(IB-3868,A-38,B-7,C-38),(IB-3869,A-38,B-7,C-39),(IB-3870,A-38,B-7,C-40), (IB-3871,A-38,B-7,C-41),(IB-3872,A-38,B-7,C-42),(IB-3873,A-38,B-7,C-43),(IB-3874,A-38,B-7,C-44),(IB-3875, A-38,B-7,C-45),(IB-3876,A-38,B-7,C-46),(IB-3877,A-38, B-7,C-47),(IB-3878,A-38,B-7,C-48),(IB-3879,A-38,B-7,C-49),(IB-3880,A-38,B-7,C-50),(IB-3881,A-38,B-7,C-51), (IB-3882,A-38,B-7,C-52),(IB-3883,A-38,B-7,C-53),(IB-3884,A-38,B-7,C-54),(IB-3885,A-38,B-7,C-55),(IB-3886, A-38,B-7,C-56),(IB-3887,A-38,B-7,C-57),(IB-3888,A-38, B-7,C-58),(IB-3889,A-38,B-7,C-59),(IB-3890,A-38,B-7,C-60),(IB-3891,A-38,B-7,C-61),(IB-3892,A-38,B-7,C-62), (IB-3893,A-38,B-7,C-63),(IB-3894,A-38,B-7,C-64),(IB-3895,A-38,B-7,C-65),(IB-3896,A-38,B-7,C-66),(IB-3897, A-38,B-7,C-67),(IB-3898,A-38,B-7,C-68),(IB-3899,A-38, B-7,C-69),(IB-3900,A-38,B-7,C-70),(IB-3901,A-38,B-7,C-71),(IB-3902,A-38,B-7,C-72),(IB-3903,A-38,B-7,C-73), (IB-3904,A-38,B-7,C-74),(IB-3905,A-38,B-7,C-75),(IB-3906,A-38,B-7,C-76),(IB-3907,A-38,B-7,C-77),(IB-3908, A-3803-7,C-78),(IB-3909,A-38,B-7,C-79),(IB-3910,A-38, B-7,C-80),(IB-3911,A-38,B-7,C-81),(IB-3912,A-38,B-7,C-82),(IB-3913,A-38,B-7,C-83),(IB-3914,A-38,B-7,C-84), (IB-3915,A-38,B-7,C-85),(IB-3916,A-38,B-7,C-86),(IB-3917,A-38,B-7,C-87),(IB-3918,A-38,B-7,C-88),(IB-3919, A-38,B-7,C-89),(IB-3920,A-38,B-7,C-90),(IB-3921,A-38, B-7,C-91),(IB-3922,A-38,B-7,C-92),(IB-3923,A-38,B-7,C-93),(IB-3924,A-38,B-7,C-94),(IB-3925,A-38,B-7,C-95), (IB-3926,A-38,B-7,C-96),(IB-3927,A-38,B-7,C-97),(IB-3928,A-38,B-7,C-98),(IB-3929,A-38,B-7,C-99),(IB-3930, A-38,B-7,C-100),(IB-3931,A-38,B-7,C-101),(IB-3932,A-38,B-7,C-102),(IB-3933,A-38,B-7,C-103),(IB-3934,A-38, B-7,C-104),(IB-3935,A-38,B-7,C-105),(IB-3936,A-38,B-7, C-106),(IB-3937,A-38,B-7,C-107),(IB-3938,A-38,B-7,C-108),(IB-3939,A-38,B-7,C-109),(IB-3940,A-38,B-7,C-110),(IB-3941,A-38,B-7,C-111),(IB-3942,A-38,B-7,C-112),(IB-3943,A-38,B-7,C-113),(IB-3944,A-38,B-7,C-114),(IB-3945,A-38,B-7,C-115),(IB-3946,A-38,B-7,C-116),(IB-3947,A-38,B-7,C-117),(IB-3948,A-38,B-7,C-118),(IB-3949,A-38,B-7,C-119),(IB-3950,A-38,B-7,C-120),(IB-3951,A-38,B-7,C-121),(IB-3952,A-38,B-7,C-122),(IB-3953,A-38,B-7,C-123),(IB-3954,A-38,B-7,C-124),(IB-3955,A-38,B-7,C-125),(IB-3956,A-38,B-7,C-126),(IB-3957,A-38,B-7,C-127),(IB-3958,A-38,B-7,C-128),(IB-3959,A-38,B-7,C-129),(IB-3960,A-38,B-7,C-130),(IB-3961,A-38,B-7,C-131),(IB-3962,A-38,B-7,C-132),(IB-3963,A-38,B-7,C-133),(IB-3964,A-38,B-7,C-134),(IB-3965,A-38,B-7,C-135),(IB-3966,A-38,B-7,C-136),(IB-3967,A-38,B-7,C-137),(IB-3968,A-38,B-7,C-138),(IB-3969,A-38,B-7,C-139),(IB-3970,A-38,B-7,C-140),(IB-3971,A-38,B-7,C-141),(IB-3972,A-38,B-7,C-142),(IB-3973,A-38,B-7,C-143),(IB-3974,A-38,B-7,C-144),(IB-3975,A-38,B-7,C-145),(IB-3976,A-38,B-7,C-146),(IB-3977,A-38,B-7,C-147),(IB-3978,A-38,B-7,C-148),(IB-3979,A-38,B-7,C-149),(IB-3980,A-38,B-7,C-150),(IB-3981,A-38,B-7,C-151),(IB-3982,A-38,B-7,C-152),(IB-3983,A-38,B-7,C-153),(IB-3984,A-38,B-7,C-154),(IB-3985,A-38,B-7,C-155),(IB-3986,A-38,B-7,C-156),(IB-3987,A-38,B-7,C-157),(IB-3988,A-38,B-7,C-158),(IB-3989,A-38,B-7,C-159),(IB-3990,A-38,B-7,C-160),(IB-3991,A-38,B-7,C-161),(IB-3992,A-38,B-7,C-162),(IB-3993,A-38,B-7,C-163),(IB-3994,A-38,B-7,C-164),(IB-3995,A-38,B-7,C-165),(IB-3996,A-38,B-7,C-166),(IB-3997,A-38,B-7,C-167),(IB-3998,A-38,B-7,C-168),(IB-3999,A-38,B-7,C-169),(IB-4000,A-38,B-7,C-170),(IB-4001,A-38,B-7,C-171),(IB-4002,A-38,B-7,C-172),(IB-4003,A-38,B-7,C-173),(IB-4004,A-38,B-7,C-174),(IB-4005,A-38,B-7,C-175),(IB-4006,A-38,B-7,C-176),(IB-4007,A-38,B-7,C-177),(IB-4008,A-38,B-7,C-178),(IB-4009,A-38,B-7,C-179),(IB-4010,A-38,B-7,C-180),(IB-4011,A-38,B-7,C-181),(IB-4012,A-38,B-7,C-182),(IB-4013,A-38,B-7,C-183),(IB-4014,A-38,B-7,C-184),(IB-4015,A-38,B-7,C-185),(IB-4016,A-38,B-7,C-186),(IB-4017,A-38,B-7,C-187),(IB-4018,A-38,B-7,C-188),(IB-4019,A-38,B-7,C-189),(IB-4020,A-38,B-7,C-190),(IB-4021,A-38,B-7,C-191),(IB-4022,A-38,B-7,C-192),(IB-4023,A-38,B-7,C-193),(IB-4024,A-38,B-7,C-194),(IB-4025,A-38,B-7,C-195),(IB-4026,A-38,B-7,C-196),(IB-4027,A-38,B-7,C-197),(IB-4028,A-38,B-7,C-198),(IB-4029,A-38,B-7,C-199),(IB-4030,A-38,B-7,C-200),(IB-4031,A-38,B-7,C-201),(IB-4032,A-38,B-7,C-202),(IB-4033,A-38,B-7,C-203),(IB-4034,A-38,B-7,C-204),(IB-4035,A-38,B-7,C-205),(IB-4036,A-38,B-7,C-206),(IB-4037,A-38,B-7,C-207),(IB-4038,A-38,B-7,C-208),(IB-4039,A-38,B-7,C-209),(IB-4040,A-38,B-7,C-210),(IB-4041,A-38,B-7,C-211),(IB-4042,A-38,B-7,C-212),(IB-4043,A-38,B-7,C-213),(IB-4044,A-38,B-7,C-214),(IB-4045,A-38,B-8,C-15),(IB-4046,A-38,B-9,C-15), (IB-4047,A-38,B-10,C-15),(IB-4048,A-38,B-10,C-52),(IB-4049,A-39,B-1,C-15),(IB-4050,A-39,B-2,C-15),(IB-4051, A-39,B-3,C-15),(IB-4052,A-39,B-4,C-15),(IB-4053,A-39, B-5,C-15),(IB-4054,A-39,B-6,C-15),(IB-4055,A-39,B-7,C-1),(IB-4056,A-39,B-7,C-2),(IB-4057,A-39,B-7,C-3),(IB-4058,A-39,B-7,C-4),(IB-4059,A-39,B-7,C-5),(IB-4060,A-39,B-7,C-6),(IB-4061,A-39,B-7,C-7),(IB-4062,A-39,B-7, C-8),(IB-4063,A-39,B-7,C-9),(IB-4064,A-39,B-7,C-10), (IB-4065,A-39,B-7,C-11),(IB-4066,A-39,B-7,C-12),(IB-4067,A-39,B-7,C-13),(IB-4068,A-39,B-7,C-14),(IB-4069, A-39,B-7,C-15),(IB-4070,A-39,B-7,C-16),(IB-4071,A-39, B-7,C-17),(IB-4072,A-39,B-7,C-18),(IB-4073,A-39,B-7,C-19),(IB-4074,A-39,B-7,C-20),(IB-4075,A-39,B-7,C-21), (IB-4076,A-39,B-7,C-22),(IB-4077,A-39,B-7,C-23),(IB-4078,A-39,B-7,C-24),(IB-4079,A-39,B-7,C-25),(IB-4080, A-39,B-7,C-26),(IB-4081,A-39,B-7,C-27),(IB-4082,A-39, B-7,C-28),(IB-4083,A-39,B-7,C-29),(IB-4084,A-39,B-7,C-30),(IB-4085,A-39,B-7,C-31),(IB-4086,A-39,B-7,C-32), (IB-4087,A-39,B-7,C-33),(IB-4088,A-39,B-7,C-34),(IB-4089,A-39,B-7,C-35),(IB-4090,A-39,B-7,C-36),(IB-4091, A-39,B-7,C-37),(IB-4092,A-39,B-7,C-38),(IB-4093,A-39, B-7,C-39),(IB-4094,A-39,B-7,C-40),(IB-4095,A-39,B-7,C-41),(IB-4096,A-39,B-7,C-42),(IB-4097,A-39,B-7,C-43), (IB-4098,A-39,B-7,C-44),(IB-4099,A-39,B-7,C-45),(IB-4100,A-39,B-7,C-46),(IB-4101,A-39,B-7,C-47),(IB-4102, A-39,B-7,C-48),(IB-4103,A-39,B-7,C-49),(IB-4104,A-39, B-7,C-50),(IB-4105,A-39,B-7,C-51),(IB-4106,A-39,B-7,C-52),(IB-4107,A-39,B-7,C-53),(IB-4108,A-39,B-7,C-54), (IB-4109,A-39,B-7,C-55),(IB-4110,A-39,B-7,C-56),(IB-4111,A-39,B-7,C-57),(IB-4112,A-39,B-7,C-58),(IB-4113, A-39,B-7,C-59),(IB-4114,A-39,B-7,C-60),(IB-4115,A-39, B-7,C-61),(IB-4116,A-39,B-7,C-62),(IB-4117,A-39,B-7,C-63),(IB-4118,A-39,B-7,C-64),(IB-4119,A-39,B-7,C-65), (IB-4120,A-39,B-7,C-66),(IB-4121,A-39,B-7,C-67),(IB-4122,A-39,B-7,C-68),(IB-4123,A-39,B-7,C-69),(IB-4124, A-39,B-7,C-70),(IB-4125,A-39,B-7,C-71),(IB-4126,A-39, B-7,C-72),(IB-4127,A-39,B-7,C-73),(IB-4128,A-39,B-7,C-74),(IB-4129,A-39,B-7,C-75),(IB-4130,A-39,B-7,C-76), (IB-4131,A-39,B-7,C-77),(IB-4132,A-39,B-7,C-78),(IB-4133,A-39,B-7,C-79),(IB-4134,A-39,B-7,C-80),(IB-4135, A-39,B-7,C-81),(IB-4136,A-39,B-7,C-82),(IB-4137,A-39, B-7,C-83),(IB-4138,A-39,B-7,C-84),(IB-4139,A-39,B-7,C-85),(IB-4140,A-39,B-7,C-86),(IB-4141,A-39,B-7,C-87), (IB-4142,A-39,B-7,C-88),(IB-4143,A-39,B-7,C-89),(IB-4144,A-39,B-7,C-90),(IB-4145,A-39,B-7,C-91),(IB-4146, A-39,B-7,C-92),(IB-4147,A-39,B-7,C-93),(IB-4148,A-39,

B-7,C-94),(IB-4149,A-39,B-7,C-95),(IB-4150,A-39,B-7,C-96),(IB-4151,A-39,B-7,C-97),(IB-4152,A-39,B-7,C-98),(IB-4153,A-39,B-7,C-99),(IB-4154,A-39,B-7,C-100),(IB-4155,A-39,B-7,C-101),(IB-4156,A-39,B-7,C-102),(IB-4157,A-39,B-7,C-103),(IB-4158,A-39,B-7,C-104),(IB-4159,A-39,B-7,C-105),(IB-4160,A-39,B-7,C-106),(IB-4161,A-39,B-7,C-107),(IB-4162,A-39,B-7,C-108),(IB-4163,A-39,B-7,C-109),(IB-4164,A-39,B-7,C-110),(IB-4165,A-39,B-7,C-111),(IB-4166,A-39,B-7,C-112),(IB-4167,A-39,B-7,C-113),(IB-4168,A-39,B-7,C-114),(IB-4169,A-39,B-7,C-115),(IB-4170,A-39,B-7,C-116),(IB-4171,A-39,B-7,C-117),(IB-4172,A-39,B-7,C-118),(IB-4173,A-39,B-7,C-119),(IB-4174,A-39,B-7,C-120),(IB-4175,A-39,B-7,C-121),(IB-4176,A-39,B-7,C-122),(IB-4177,A-39,B-7,C-123),(IB-4178,A-39,B-7,C-124),(IB-4179,A-39,B-7,C-125),(IB-4180,A-39,B-7,C-126),(IB-4181,A-39,B-7,C-127),(IB-4182,A-39,B-7,C-128),(IB-4183,A-39,B-7,C-129),(IB-4184,A-39,B-7,C-130),(IB-4185,A-39,B-7,C-131),(IB-4186,A-39,B-7,C-132),(IB-4187,A-39,B-7,C-133),(IB-4188,A-39,B-7,C-134),(IB-4189,A-39,B-7,C-135),(IB-4190,A-39,B-7,C-136),(IB-4191,A-39,B-7,C-137),(IB-4192,A-39,B-7,C-138),(IB-4193,A-39,B-7,C-139),(IB-4194,A-39,B-7,C-140),(IB-4195,A-39,B-7,C-141),(IB-4196,A-39,B-7,C-142),(IB-4197,A-39,B-7,C-143),(IB-4198,A-39,B-7,C-144),(IB-4199,A-39,B-7,C-145),(IB-4200,A-39,B-7,C-146),(IB-4201,A-39,B-7,C-147),(IB-4202,A-39,B-7,C-148),(IB-4203,A-39,B-7,C-149),(IB-4204,A-39,B-7,C-150),(IB-4205,A-39,B-7,C-151),(IB-4206,A-39,B-7,C-152),(IB-4207,A-39,B-7,C-153),(IB-4208,A-39,B-7,C-154),(IB-4209,A-39,B-7,C-155),(IB-4210,A-39,B-7,C-156),(IB-4211,A-39,B-7,C-157),(IB-4212,A-39,B-7,C-158),(IB-4213,A-39,B-7,C-159),(IB-4214,A-39,B-7,C-160),(IB-4215,A-39,B-7,C-161),(IB-4216,A-39,B-7,C-162),(IB-4217,A-39,B-7,C-163),(IB-4218,A-39,B-7,C-164),(IB-4219,A-39,B-7,C-165),(IB-4220,A-39,B-7,C-166),(IB-4221,A-39,B-7,C-167),(IB-4222,A-39,B-7,C-168),(IB-4223,A-39,B-7,C-169),(IB-4224,A-39,B-7,C-170),(IB-4225,A-39,B-7,C-171),(IB-4226,A-39,B-7,C-172),(IB-4227,A-39,B-7,C-173),(IB-4228,A-39,B-7,C-174),(IB-4229,A-39,B-7,C-175),(IB-4230,A-39,B-7,C-176),(IB-4231,A-39,B-7,C-177),(IB-4232,A-39,B-7,C-178),(IB-4233,A-39,B-7,C-179),(IB-4234,A-39,B-7,C-180),(IB-4235,A-39,B-7,C-181),(IB-4236,A-39,B-7,C-182),(IB-4237,A-39,B-7,C-183),(IB-4238,A-39,B-7,C-184),(IB-4239,A-39,B-7,C-185),(IB-4240,A-39,B-7,C-186),(IB-4241,A-39,B-7,C-187),(IB-4242,A-39,B-7,C-188),(IB-4243,A-39,B-7,C-189),(IB-4244,A-39,B-7,C-190),(IB-4245,A-39,B-7,C-191),(IB-4246,A-39,B-7,C-192),(IB-4247,A-39,B-7,C-193),(IB-4248,A-39,B-7,C-194),(IB-4249,A-39,B-7,C-195),(IB-4250,A-39,B-7,C-196),(IB-4251,A-39,B-7,C-197),(IB-4252,A-39,B-7,C-198),(IB-4253,A-39,B-7,C-199),(IB-4254,A-39,B-7,C-200),(IB-4255,A-39,B-7,C-201),(IB-4256,A-39,B-7,C-202),(IB-4257,A-39,B-7,C-203),(IB-4258,A-39,B-7,C-204),(IB-4259,A-39,B-7,C-205),(IB-4260,A-39,B-7,C-206),(IB-4261,A-39,B-7,C-207),(IB-4262,A-39,B-7,C-208),(IB-4263,A-39,B-7,C-209),(IB-4264,A-39,B-7,C-210),(IB-4265,A-39,B-7,C-211),(IB-4266,A-39,B-7,C-212),(IB-4267,A-39,B-7,C-213),(IB-4268,A-39,B-7,C-214),(IB-4269,A-39,B-8,C-15),(IB-4270,A-39,B-9,C-15),(IB-4271,A-39,B-10, 0-15),(IB-4272,A-39,B-10,C-52),(IB-4273,A-40,B-1,C-15),(IB-4274,A-40,B-2,C-15),(IB-4275,A-40,B-3,C-15),(IB-4276,A-40,B-4,C-15),(IB-4277,A-40,B-5,C-15),(IB-4278,A-40,B-6,C-15),(IB-4279,A-40,B-7,C-15),(IB-4280,A-40,B-7,C-52),(IB-4281,A-40,B-8,C-15),(IB-4282,A-40,B-9,C-15),(IB-4283,A-40,B-10,C-15),(IB-4284,A-40,B-10,C-52),(IB-4285,A-41,B-1,C-15),(IB-4286,A-41,B-2,C-15),(IB-4287,A-41,B-3,C-15),(IB-4288,A-41,B-4,C-15),(IB-4289,A-41,B-5,C-15),(IB-4290,A-41,B-6,C-15),(IB-4291,A-41,B-7,C-15),(IB-4292,A-41,B-7,C-52),(IB-4293,A-41,B-8,C-15),(IB-4294,A-41,B-9,C-15),(IB-4295,A-41,B-10,C-15),(IB-4296,A-41,B-10,C-52),(IB-4297,A-42,B-1,C-15),(IB-4298,A-42,B-2,C-15),(IB-4299,A-42,B-3,C-15),(IB-4300,A-42,B-4,C-15),(IB-4301,A-42,B-5,C-15),(IB-4302,A-42,B-6,C-15),(IB-4303,A-42,B-7,C-15),(IB-4304,A-42,B-7,C-52),(IB-4305,A-42,B-8,C-15),(IB-4306,A-42,B-9,C-15),(IB-4307,A-42,B-10,C-15),(IB-4308,A-42,B-10,C-52),(IB-4309,A-43,B-1,C-15),(IB-4310,A-43,B-2,C-15),(IB-4311,A-43,B-3,C-15),(IB-4312,A-43,B-4,C-15),(IB-4313,A-43,B-5,C-15),(IB-4314,A-43,B-6,C-15),(IB-4315,A-43,B-7,C-15),(IB-4316,A-43,B-7,C-52),(IB-4317,A-43,B-8,C-15),(IB-4318,A-43,B-9,C-15),(IB-4319,A-43,B-10,C-15),(IB-4320,A-43,B-10,C-52),(IB-4321,A-44,B-7,C-15),(IB-4322,A-44,B-10,C-15),(IB-4323,A-45,B-7,C-15),(IB-4324,A-45,B-10,C-15),(IB-4325,A-46,B-7,C-15),(IB-4326,A-46,B-10,C-15),(IB-4327,A-47,B-7,C-15),(IB-4328,A-47,B-10,C-15),(IB-4329,A-48,B-7,C-15),(IB-4330,A-48,B-10,C-15),(IB-4331,A-49,B-7,C-15),(IB-4332,A-49,B-10,C-15),(IB-4333,A-50,B-7,C-15),(IB-4334,A-50,B-10,C-15),(IB-4335,A-51,B-7,C-15),(IB-4336,A-51,B-10,C-15),(IB-4337,A-52,B-7,C-15),(IB-4338,A-52,B-10,C-15),(IB-4339,A-53,B-7,C-15),(IB-4340,A-53,B-10,C-15),(IB-4341,A-54,B-7,C-15),(IB-4342,A-54,B-10,C-15),(IB-4343,A-55,B-7,C-15),(IB-4344,A-55,B-10,C-15),(IB-4345,A-56,B-7,C-15),(IB-4346,A-56,B-10,C-15),(IB-4347,A-57,B-7,C-15),(IB-4348,A-57,B-10,C-15),(IB-4349,A-58,B-7,C-15),(IB-4350,A-58,B-10,C-15),(IB-4351,A-59,B-7,C-15),(IB-4352,A-59,B-10,C-15),(IB-4353,A-60,B-7,C-15),(IB-4354,A-60,B-10,C-15),(IB-4355,A-61,B-7,C-15),(IB-4356,A-61,B-10,C-15),(IB-4357,A-62,B-7,C-15),(IB-4358,A-62,B-10,C-15),(IB-4359,A-63,B-7,C-15),(IB-4360,A-63,B-10,C-15),(IB-4361,A-64,B-7,C-15),(IB-4362,A-64,B-10,C-15),(IB-4363,A-65,B-7,C-15),(IB-4364,A-65,B-10,C-15),(IB-4365,A-66,B-7,C-15),(IB-4366,A-66,B-10,C-15),(IB-4367,A-67,B-7,C-15),(IB-4368,A-67,B-10,C-15),(IB-4369,A-68,B-7,C-15),(IB-4370,A-68,B-10,C-15),(IB-4371,A-69,B-7,C-15),(IB-4372,A-69,B-10,C-15),(IB-4373,A-70,B-7,C-15),(IB-4374,A-70,B-10,C-15),(IB-4375,A-71,B-7,C-15),(IB-4376,A-71,B-10,C-15),(IB-4377,A-72,B-7,C-15),(IB-4378,A-72,B-10,C-15),(IB-4379,A-73,B-7,C-15),(IB-4380,A-73,B-10,C-15),(IB-4381,A-74,B-7,C-15),(IB-4382,A-74,B-10,C-15),(IB-4383,A-75,B-7,C-15),(IB-4384,A-75,B-10,C-15),(IB-4385,A-76,B-7,C-15),(IB-4386,A-76,B-10,C-15),(IB-4387,A-77,B-7,C-15),(IB-4388,A-77,B-10,C-15),(IB-4389,A-78,B-7,C-15),(IB-4390,A-78,B-10,C-15),(IB-4391,A-79,B-7,C-15),(IB-4392,A-79,B-10,C-15),(IB-4393,A-80,B-7,C-15),(IB-4394,A-80,B-10,C-15),(IB-4395,A-81,B-7,C-15),(IB-4396,A-81,B-10,C-15),(IB-4397,A-82,B-7,C-15),(IB-4398,A-82,B-10,C-15),(IB-4399,A-83,B-7,C-15),(IB-4400,A-83,B-10,C-15),(IB-4401,A-84,B-7,C-15),(IB-4402,A-84,B-10,C-15),(IB-4403,A-85,B-7,C-15),(IB-4404,A-85,B-10,C-15),(IB-4405,A-86,B-7,C-15),(IB-4406,A-86,B-10,C-15),(IB-4407,A-87,B-7,C-15),(IB-4408,A-87,B-10,C-15),(IB-4409,A-88,B-7,C-15),(IB-4410,A-88,B-10,C-15),(IB-4411,A-89,B-7,C-15),(IB-4412,A-89,B-10,C-15),(IB-4413,A-90,B-7,C-15),(IB-4414,A-90,B-10,C-15),(IB-4415,A-91,B-7,C-15),(IB-4416,A-91,B-10,C-15),(IB-4417,A-92,B-7,C-15),(IB-4418,A-92,B-10,C-15),(IB-4419,A-93,B-7,C-15),(IB-4420,A-93,B-10,C-15),(IB-4421,A-94,B-7,C-15),(IB-4422,A-94,B-10,C-15),(IB-4423,A-95,B-7,C-15),(IB-4424,A-95,B-10,C-15),(IB-4425,A-96,B-7,C-15),(IB-4426,A-96,B-10,C-15),(IB-4427,A-97,B-7,C-15),(IB-4428,A-97,B-10,C-15),(IB-4429,A-98,B-7,C-

15),(IB-4430,A-98,B-10,C-15),(IB-4431,A-99,B-7,C-15),
(IB-4432,A-99,B-10,C-15),(IB-4433,A-100,B-7,C-15),(IB-4434,A-100,B-10,C-15),(IB-4435,A-101,B-7,C-15),(IB-4436,A-101,B-10,C-15),(IB-4437,A-102,B-7,C-15),(IB-4438,A-102,B-10,C-15),(IB-4439,A-103,B-7,C-15),(IB-4440,A-103,B-10,C-15),(IB-4441,A-104,B-7,C-15),(IB-4442,A-104,B-10,C-15),(IB-4443,A-105,B-7,C-15),(IB-4444,A-105,B-10,C-15),(IB-4445,A-106,B-7,C-15),(IB-4446,A-106,B-10,C-15),(IB-4447,A-107,B-7,C-15),(IB-4448,A-107,B-10,C-15),(IB-4449,A-108,B-7,C-15),(IB-4450,A-108,B-10,C-15),(IB-4451,A-109,B-7,C-15),(IB-4452,A-109,B-10,C-15),(IB-4453,A-110,B-7,C-15),(IB-4454,A-110,B-10,C-15),(IB-4455,A-111,B-7,C-15),(IB-4456,A-111,B-10,C-15),(IB-4457,A-112,B-7,C-15),(IB-4458,A-112,B-10,C-15),(IB-4459,A-113,B-7,C-15),(IB-4460,A-113,B-10,C-15),(IB-4461,A-114,B-7,C-15),(IB-4462,A-114,B-10,C-15),(IB-4463,A-115,B-7,C-15),(IB-4464,A-115,B-10,C-15),(IB-4465,A-116,B-7,C-15),(IB-4466,A-116,B-10,C-15),(IB-4467,A-117,B-7,C-15),(IB-4468,A-117,B-10,C-15),(IB-4469,A-118,B-7,C-15),(IB-4470,A-118,B-10,C-15),(IB-4471,A-119,B-7,C-4472,A-119,B-10,C-15),(IB-4473,A-120,B-7,C-15),(IB-4474,A-120,B-10,C-15),(IB-4475,A-121,B-7,C-15),(IB-4476,A-121,B-10,C-15),(IB-4477,A-122,B-7,C-15),(IB-4478,A-122,B-10,C-15),(IB-4479,A-123,B-7,C-15),(IB-4480,A-123,B-10,C-15),(IB-4481,A-124,B-7,C-15),(IB-4482,A-124,B-10,C-15),(IB-4483,A-125,B-7,C-15),(IB-4484,A-125,B-10,C-15),(IB-4485,A-126,B-7,C-15),(IB-4486,A-126,B-10,C-15),(IB-4487,A-127,B-7,C-15),(IB-4488,A-127,B-10,C-15),(IB-4489,A-128,B-7,C-15),(IB-4490,A-128,B-10,C-15),(IB-4491,A-129,B-7,C-15),(IB-4492,A-129,B-10,C-15),(IB-4493,A-130,B-7,C-15),(IB-4494,A-130,B-10,C-15),(IB-4495,A-131,B-7,C-15),(IB-4496,A-131,B-10,C-15),(IB-4497,A-132,B-7,C-15),(IB-4498,A-132,B-10,C-15),(IB-4499,A-133,B-7,C-15),(IB-4500,A-133,B-10,C-15),(IB-4501,A-134,B-7,C-15),(IB-4502,A-134,B-10,C-15),(IB-4503,A-135,B-7,C-15),(IB-4504,A-135,B-10,C-15),(IB-4505,A-136,B-7,C-15),(IB-4506,A-136,B-10,C-15),(IB-4507,A-137,B-7,C-15),(IB-4508,A-137,B-10,C-15),(IB-4509,A-138,B-7,C-15),(IB-4510,A-138,B-10,C-15),(IB-4511,A-139,B-7,C-15),(IB-4512,A-139,B-10,C-15),(IB-4513,A-140,B-7,C-15),(IB-4514,A-140,B-10,C-7,C-15),(IB-4516,A-141,B-10,C-15),(IB-4517,A-142,B-7,C-15),(IB-4518,A-142,B-10,C-15),(IB-4519,A-143,B-7,C-15),(IB-4520,A-143,B-10,C-15),(IB-4521,A-144,B-7,C-15),(IB-4522,A-144,B-10,C-15),(IB-4523,A-145,B-7,C-15),(IB-4524,A-145,B-10,C-15),(IB-4525,A-146,B-7,C-15),(IB-4526,A-146,B-10,C-15),(IB-4527,A-147,B-7,C-15),(IB-4528,A-147,B-10,C-15),(IB-4529,A-148,B-7,C-15),(IB-4530,A-148,B-10,C-15),(IB-4531,A-149,B-7,C-15),(IB-4532,A-149,B-10,C-15),(IB-4533,A-150,B-7,C-15),(IB-4534,A-150,B-10,C-15),(IB-4535,A-151,B-7,C-15),(IB-4536,A-151,B-10,C-15),(IB-4537,A-152,B-7,C-15),(IB-4538,A-152,B-10,C-15),(IB-4539,A-153,B-7,C-15),(IB-4540,A-153,B-10,C-15),(IB-4541,A-154,B-7,C-15),(IB-4542,A-154,B-10,C-15),(IB-4543,A-155,B-7,C-15),(IB-4544,A-155,B-10,C-15),(IB-4545,A-156,B-7,C-15),(IB-4546,A-156,B-10,C-15),(IB-4547,A-157,B-7,C-15),(IB-4548,A-157,B-10,C-15),(IB-4549,A-158,B-7,C-15),(IB-4550,A-158,B-10,C-15),(IB-4551,A-159,B-7,C-15),(IB-4552,A-159,B-10,C-15),(IB-4553,A-160,B-7,C-15),(IB-4554,A-160,B-10,C-15),(IB-4555,A-161,B-7,C-15),(IB-4556,A-161,B-10,C-15),(IB-4557,A-162,B-7,C-15),(IB-4558,A-162,B-10,C-15),(IB-4559,A-163,B-7,C-15),(IB-4560,A-163,B-10,C-15),(IB-4561,A-164,B-7,C-15),(IB-4562,A-164,B-10,C-15),(IB-4563,A-165,B-7,C-15),(IB-4564,A-165,B-10,C-15),(IB-4565,A-166,B-7,C-15),(IB-4566,A-166,B-10,C-15),(IB-4567,A-167,B-7,C-15),(IB-4568,A-167,B-10,C-15),(IB-4569,A-168,B-7,C-15),(IB-4570,A-168,B-10,C-15),(IB-4571,A-169,B-7,C-15),(IB-4572,A-169,B-10,C-15),(IB-4573,A-170,B-7,C-15),(IB-4574,A-170,B-10,C-15),(IB-4575,A-171,B-7,C-15),(IB-4576,A-171,B-10,C-15),(IB-4577,A-172,B-7,C-15),(IB-4578,A-172,B-10,C-15),(IB-4579,A-173,B-7,C-15),(IB-4580,A-173,B-10,C-15),(IB-4581,A-174,B-7,C-15),(IB-4582,A-174,B-10,C-15),(IB-4583,A-175,B-7,C-15),(IB-4584,A-175,B-10,C-15),(IB-4585,A-176,B-7,C-15),(IB-4586,A-176,B-10,C-15),(IB-4587,A-177,B-7,C-15),(IB-4588,A-177,B-10,C-15),(IB-4589,A-178,B-7,C-15),(IB-4590,A-178,B-10,C-15),(IB-4591,A-179,B-7,C-15),(IB-4592,A-179,B-10,C-15),(IB-4593,A-180,B-7,C-15),(IB-4594,A-180,B-10,C-15),(IB-4595,A-181,B-7,C-15),(IB-4596,A-181,B-10,C-15),(IB-4597,A-182,B-7,C,-15),(IB-4598,A-182,B-10,C-15),(IB-4599,A-183,B-7,C-15),(IB-4600,A-183,B-10,C-15),(IB-4601,A-184,B-7,C-15),(IB-4602,A-184,B-10,C-15),(IB-4603,A-185,B-7,C-15),(IB-4604,A-185,B-10,C-15),(IB-4605,A-186,B-7,C-15),(IB-4606,A-186,B-10,C-15),(IB-4607,A-187,B-7,C-15),(IB-4608,A-187,B-10,C-15),(IB-4609,A-188,B-7,C-15),(IB-4610,A-188,B-10,C-15),(IB-4611,A-189,B-7,C-15),(IB-4612,A-189,B-10,C-15),(IB-4613,A-190,B-7,C-15),(IB-4614,A-190,B-10,C-15),(IB-4615,A-191,B-7,C-15),(IB-4616,A-191,B-10,C-15),(IB-4617,A-192,B-7,C-15),(IB-4618,A-192,B-10,C-15),(IB-4619,A-193,B-7,C-15),(IB-4620,A-193,B-10,C-15),(IB-4621,A-194,B-7,C-15),(IB-4622,A-194,B-10,C-15),(IB-4623,A-195,B-7,C-15),(IB-4624,A-195,B-10,C-15),(IB-4625,A-196,B-7,C-15),(IB-4626,A-196,B-10,C-15),(IB-4627,A-197,B-7,C-15),(IB-4628,A-197,B-10,C-15),(IB-4629,A-198,B-7,C-15),(IB-4630,A-198,B-10,C-15),(IB-4631,A-199,B-7,C-15),(IB-4632,A-199,B-10,C-15),(IB-4633,A-200,B-7,C-15),(IB-4634,A-200,B-10,C-15),(IB-4635,A-201,B-7,C-15),(IB-4636,A-201,B-10,C-15),(IB-4637,A-202,B-7,C-15),(IB-4638,A-202,B-10,C-15),(IB-4639,A-203,B-7,C-15),(IB-4640,A-203,B-10,C-15),(IB-4641,A-204,B-7,C-15),(IB-4642,A-204,B-10,C-15),(IB-4643,A-205,B-7,C-15),(IB-4644,A-205,B-10,C-15),(IB-4645,A-206,B-7,C-15),(IB-4646,A-206,B-10,C-15),(IB-4647,A-207,B-7,C-15),(IB-4648,A-207,B-10,C-15),(IB-4649,A-208,B-7,C-15),(IB-4650,A-208,B-10,C-15),(IB-4651,A-209,B-7,C-15),(IB-4652,A-209,B-10,C-15),(IB-4653,A-210,B-7,C-15),(IB-4654,A-210,B-10,C-15),(IB-4655,A-211,B-7,C-15),(IB-4656,A-211,B-10,C-15),(IB-4657,A-212,B-7,C-15),(IB-4658,A-212,B-10,C-15),(IB-4659,A-213,B-7,C-15),(IB-4660,A-213,B-10,C-15),(IB-4661,A-214,B-7,C-15),(IB-4662,A-214,B-10,C-15),(IB-4663,A-215,B-7,C-15),(IB-4664,A-215,B-10,C-15),(IB-4665,A-216,B-7,C-15),(IB-4666,A-216,B-10,C-15),(IB-4667,A-217,B-7,C-15),(IB-4668,A-217,B-10,C-15),(IB-4669,A-218,B-7,C-15),(IB-4670,A-218,B-10,C-15),(IB-4671,A-219,B-7,C-15),(IB-4672,A-219,B-10,C-15),(IB-4673,A-220,B-7,C-15),(IB-4674,A-220,B-10,C-15),(IB-4675,A-221,B-7,C-15),(IB-4676,A-221,B-10,C-15),(IB-4677,A-222,B-7,C-15),(IB-4678,A-222,B-10,C-15),(IB-4679,A-223,B-7,C-15),(IB-4680,A-223,B-10,C-15),(IB-4681,A-224,B-7,C-15),(IB-4682,A-224,B-10,C-15),(IB-4683,A-225,B-7,C-15),(IB-4684,A-225,B-10,C-15),(IB-4685,A-226,B-7,C-15),(IB-4686,A-226,B-10,C-15),(IB-4687,A-227,B-7,C-15),(IB-4688,A-227,B-10,C-15),(IB-4689,A-228,B-7,C-15),(IB-4690,A-228,B-10,C-15),(IB-4691,A-229,B-7,C-15),(IB-4692,A-229,B-10,C-15),(IB-4693,A-230,B-7,C-15),(IB-4694,A-230,B-10,C-C-15),(IB-4696,A-231,B-10,C-15),(IB-4697,A-232,B-7,C-15),(IB-4698,A-232,B-10,C-15),(IB-4699,A-233,B-7,C-15),(IB-4700,A-

233,B-10,C-15),(IB-4701,A-234,B-7,C-15),(IB-4702,A-234,B-10,C-15),(IB-4703,A-235,B-7,C-15),(IB-4705,A-236,B-7,C-15),(IB-4706,A-236,B-10,C-15),(IB-4707,A-237,B-7,C-15),(IB-4708,A-237,B-10,C-15),(IB-4709,A-238,B-7,C-15),(IB-4710,A-238,B-10,C-15),(IB-4711,A-239,B-7,C-15),(IB-4712,A-239,B-10,C-15),(IB-4713,A-240,B-7,C-15),(IB-4714,A-240,B-10,C-15),(IB-4715,A-241,B-7,C-15),(IB-4716,A-241,B-10,C-15),(IB-4717,A-242,B-7,C-15),(IB-4718,A-242,B-10,C-15),(IB-4719,A-243,B-7,C-15),(IB-4720,A-243,B-10,C-15),(IB-4721,A-244,B-7,C-15),(IB-4722,A-244,B-10,C-15),(IB-4723,A-245,B-7,C-15),(IB-4724,A-245,B-10,C-15),(IB-4725,A-246,B-7,C-15),(IB-4726,A-246,B-10,C-15),(IB-4727,A-247,B-7,C-15),(IB-4728,A-247,B-10,C-15),(IB-4729,A-248,B-7,C-15),(IB-4730,A-248,B-10,C-15),(IB-4731,A-249,B-7,C-15),(IB-4732,A-249,B-10,C-15),(IB-4733,A-250,B-7,C-15),(IB-4734,A-250,B-10,C-15),(IB-4735,A-251,B-7,C-15),(IB-4736,A-251,B-10,C-15),(IB-4737,A-252,B-7,C-15),(IB-4738,A-252,B-10,C-15),(IB-4739,A-253,B-7,C-15),(IB-4740,A-253,B-10,C-15),(IB-4741,A-254,B-7,C-15),(IB-4742,A-254,B-10,C-15),(IB-4743,A-255,B-7,C-15),(IB-4744,A-255,B-10,C-15),(IB-4745,A-256,B-7,C-15),(IB-4746,A-256,B-10, C-15),(IB-4747,A-257,B-7,C-15),(IB-4748,A-257,B-10,C-15),(IB-4749,A-258,B-7,C-15),(IB-4750,A-258,B-10,C-15),(IB-4751,A-259,B-7,C-15),(IB-4752,A-259,B-10,C-15),(IB-4753,A-260,B-7,C-15),(IB-4754,A-260,B-10,C-15),(IB-4755,A-261,B-7,C-15),(IB-4756,A-261,B-10,C-15),(IB-4757,A-262,B-7,C-15),(IB-4758,A-262,B-10,C-15),(IB-4759,A-263,B-7,C-15),(IB-4760,A-263,B-10,C-15),(IB-4761,A-264,B-7,C-15),(IB-4762,A-264,B-10,C-15),(IB-4763,A-265,B-7,C-15),(IB-4764,A-265,B-10,C-15),(IB-4765,A-266,B-7,C-15),(IB-4766,A-266,B-10,C-15),(IB-4767,A-267,B-7,C-15),(IB-4768,A-267,B-10,C-15),(IB-4769,A-268,B-7,C-15),(IB-4770,A-268,B-10,C-15),(IB-4771,A-269,B-7,C-15),(IB-4772,A-269,B-10,C-15),(IB-4773,A-270,B-7,C-15),(IB-4774,A-270,B-10,C-15)

Test Example 1

DP Inhibitory Activity In Vitro

1) Preparation of Platelet and a Method of cAMP Assay 30 mL of peripheral blood was collected from a healthy volunteer using a syringe containing one ninth amount of 3.8% sodium citrate. After being centrifuged at 180 g for 10 minutes at room temperature, a supernatant was collected and used as Platelet Rich Plasma (PRP). The resulting PRP was washed with wash buffer and centrifuged three times (Washed Platelet: WP) and platelets were counted by a micro-cell counter. WP was added to a plate in amount of $1.5 \times 10^8$/assay and the plate was treated with 3-isobutyl-1-methylxanthin (IBMX; 0.5 mM) for 5 minutes. A reaction was initiated by adding 100 nM of PGD2 5 min after an addition of a test compound. The reaction was terminated with an addition of 1N hydrochloric acid after 2 minutes and the cells were destructed using 12% triton X-100. An amount of cAMP in the supernatant was assayed by Homogeneous Trangient Fluorescence (HTRF)

2) Receptor Binding Assay

A prepared WP was homogenated and a membrane fraction was collected with high-speed centrifugation. A compound of the present invention or a reference compound A (No. IC-73 in WO 2003/097598) was added to the plate and [$^3$H]-PGD2 was also added. A platelet membrane, a protein concentration is 2 mg/mL, was added and mixed in the plate, and placed on ice for 2 hours. The reaction solution was transferred to a low protein-adsorptive filter and washed with a wash solution eight times using a cell harvester. After the final washing, water was removed sufficiently, and scintillator was added. DP inhibitory activity was investigated by measuring [$^3$H] by using Micro Beta.

50% DP-inhibitory concentrations (IC-50) in the cAMP assay and Ki values in the receptor binding assay were shown in Table 61.

3) Prostanoid Agonist and Antagonist Assay

Agonistic and antagonistic activities of the compounds of the present invention against prostanoid receptors were evaluated based on intracellular calcium flux or cAMP-production as an indicator using HEK 293 cells expressing human EP1, EP2, EP3, EP4, FP, TP and IP respectively. Any compounds did not show an agonistic activity against each prostanoid. In the other hand, more than twenty times potent antagonistic activity (IC-50) was found in every compound compared with IC-50 of cAMP assay with WP.

TABLE 61

| Comd. No. | IC50 (μM) | Ki (μM) |
|---|---|---|
| I-7 | 2.4 | |
| I-8 | 2.1 | |
| I-10 | 2.7 | 30 |
| I-11 | 3.0 | |
| I-12 | 4.2 | |
| I-18 | 1.6 | |
| I-30 | 0.51 | |
| I-31 | 0.16 | 3.6 |
| II-8 | 4.6 | |
| II-10 | 0.41 | 0.65 |
| II-11 | 2.3 | |
| II-13 | 0.28 | 0.81 |
| II-16 | 0.25 | 0.87 |
| II-17 | 0.23 | 0.57 |
| II-18 | 4.9 | |
| II-19 | 1.1 | 2.0 |
| II-20 | 4.3 | |
| II-24 | 0.51 | 1.7 |
| II-25 | 0.67 | 1.6 |
| II-26 | 0.43 | 0.63 |
| II-27 | 1.0 | 1.4 |
| II-28 | 2.5 | 3.8 |
| II-29 | 0.38 | 0.74 |
| II-31 | 0.81 | 3.7 |
| II-33 | 0.30 | 1.9 |
| II-35 | 0.47 | 3.1 |
| II-37 | 1.5 | |
| II-38 | 0.65 | 0.25 |
| II-41 | 3.5 | |
| II-43 | 0.74 | 2.3 |
| II-44 | 0.69 | 1.6 |
| II-46 | 0.79 | 0.87 |
| II-47 | 3.1 | 2.2 |
| II-48 | 4.6 | |
| II-51 | 0.64 | 0.52 |
| II-53 | 2.3 | |
| II-54 | 0.42 | 0.27 |
| II-55 | 3.0 | |
| II-57 | 1.2 | |
| II-58 | 3.5 | |
| II-59 | 4.3 | |
| II-60 | 0.88 | 2.6 |
| II-61 | 2.1 | 1.4 |
| II-62 | 1.1 | 4.7 |
| II-65 | 0.14 | 16 |
| II-67 | 1.7 | |
| II-68 | 17 | |
| II-69 | 1.4 | |
| II-71 | 4.1 | |
| II-73 | 1.0 | 1.1 |
| II-74 | 0.52 | 0.24 |
| II-75 | 0.58 | 0.58 |
| II-77 | 3.6 | |

TABLE 61-continued

| Comd. No. | IC50 (μM) | Ki (μM) |
|---|---|---|
| II-79 | 2.3 | |
| II-80 | 0.20 | 0.23 |
| II-81 | 1.8 | 2.6 |
| II-82 | 1.1 | 5.0 |
| II-83 | 2.0 | 20 |
| II-84 | 0.18 | 0.33 |
| II-85 | 0.51 | 1.7 |
| II-88 | 0.23 | 1.5 |
| II-89 | 2.1 | 20 |
| II-90 | 0.59 | |
| II-91 | 1.3 | |
| II-92 | 0.36 | 0.58 |
| II-94 | 2.0 | 1.7 |
| II-95 | 2.4 | 4.7 |
| II-96 | 0.29 | 0.33 |
| II-99 | 0.59 | 11 |
| II-100 | 2.4 | 12.8 |
| II-101 | 0.21 | 22 |
| II-105 | 1.5 | 16 |
| II-106 | 1.6 | 19 |
| II-108 | 0.13 | 13 |
| II-110 | 0.36 | 9.8 |
| II-111 | 0.70 | 36 |
| II-112 | 0.12 | 9.3 |
| II-134 | 2.7 | 8.5 |
| II-135 | 0.13 | 0.49 |

Results were shown in Table 62.

TABLE 62

| Comd. No. | dose (mg/kg) | inhibition rate (%) | | |
|---|---|---|---|---|
| | | airway hyperresponsiveness | infiltration of inflammatory cells | mucus-secretion |
| II-1 | 10 | 59 | 76 | 79 |
| II-3 | 10 | 50 | 78 | 78 |
| II-13 | 10 | 99 | 46 | 47 |
| II-16 | 10 | 131 | 67 | 76 |
| II-17 | 10 | 89 | 53 | 49 |
| II-19 | 10 | 54 | 51 | 59 |
| II-24 | 10 | 77 | 67 | 89 |
| II-26 | 10 | 97 | 37 | 121 |
| II-27 | 10 | 49 | 49 | 118 |
| II-29 | 10 | 89 | 60 | 110 |
| II-33 | 10 | 72 | 57 | 76 |
| II-35 | 10 | 88 | 60 | 84 |
| II-38 | 10 | 39 | 69 | 71 |
| II-43 | 10 | 56 | 33 | 98 |
| II-54 | 10 | 119 | 39 | 106 |
| II-63 | 10 | 41 | 59 | 79 |
| II-74 | 10 | 111 | 65 | 92 |
| II-80 | 10 | 39 | 57 | 82 |
| II-84 | 10 | 82 | 54 | 56 |
| II-92 | 10 | 53 | 46 | 44 |
| II-96 | 10 | 105 | 46 | 52 |

Test Example 2

Test Using OVA Asthma Model of Rat

Brown Norway (BN) Rats were sensitized by i.p. administration of 0.1 mg/mL of ovalbumin (OVA) and 1 mg of aluminum hydroxide gel. A solution of 1% OVA was aerosolized by ultrasonic nebulizer (NE-U17) and the rats were subjected to inhalation exposure of the aerosol for 30 minutes in an exposing chamber 12, 19, 26 and 33 days after the sensitization. One hour before the 4th exposure of the antigen, compounds of the present invention were administered in a dose of 10 mg/kg p.o. once a day for three days consecutively. In a control group, 0.5% of methyl cellulose was administered in place of the compound of the present invention.

Under pentobarbital anesthesia (80 mg/kg, i.p.), acetylcholine (3.9, 7.8, 15.6, 31.3, 62.5, 125, 250 and 500 μg/kg) was injected to jugular vein of the rats successively from a lower dose at intervals of 5 minutes three days after the fourth exposure to the antigen, and immediate contractile reaction of airways (an increase of insufflation pressure) was measured by a modified method of Konnzett & Rössler. Inhibition rate of airway hyperresponsiveness against the control group was calculated based on area under the curve (AUC) obtained from concentration-response curve of acetylcholine.

After the measurement of increased hyperresponsive airway was completed, bronchoalveoli of the rats were washed with 5 mL of saline three times. Total cell number in the washings was counted by a hemacytometer under light microscope, and inhibition rates of infiltration of inflammatory cells against the control group were calculated. Further, mucin in the airway lavage fluid was measured by ELISA method using jacalin, a mucin-binding lectin, and the inhibition rates of mucus-secretion against the control group were calculated.

Test Example 3

Test Using Nasal Congestion Model of Guinea Pig

Methods of measuring nasal airway resistance and evaluating anti-nasal congestion activity using a guinea pig were illustrated below.

A 1% solution of ovalbumin (OVA) was aerosolized by ultrasonic nebulizer, male Hartley guinea pigs were sensitized by inhalation of the aerosol for 10 minutes twice at an interval of a week and a reaction was initiated by exposure to the antigen 7 days later. Trachea of the guinea pig was incised under pentobarbital anesthesia (30 mg/kg, i.p.), and cannulae were fitted at the sides of nasal cavity and lung respectively. To the lung side, a ventilator supplying 4 mL of air every time at a rate of 60 times/min was connected. Spontaneous breathing of the guinea pig was stopped by the administration of gallamine (2 mg/kg, i.v.) and 4 mL of air every time was supplied at a rate of 70 times/minute to rostrum of nose through the cannula of the nasal side using a ventilator. Air pressure necessary for supplying the air was measured by a transducer fitted at the side branch and used as an indicator for resistance of nasal cavity. Exposure to the antigen was performed by generating the aerosol of 3% OVA solution between the ventilator and the nasal cavity cannula for three minutes. Compounds of the present invention were administered intravenously 10 minutes before the exposure to the antigen. Resistance of nasal cavity was continuously measured during a period from 0 to 30 minutes, and the inhibition rate against the vehicle was obtained based on AUC of the 30 minutes, which was recorded with resistance of nasal cavity (cm $H_2O$) as a longitudinal axis, and time (from 0 to 30 min.) as an abscissa axis.

Formulation Example

The following formulating examples 1-8 are just for illustrative purposes and not intended to limit the range of the present invention. A term of "active ingredient" means the compounds of the present invention, pharmaceutically acceptable salt or hydrate thereof.

Formulation Example 1

A hard-gelatin capsule is prepared with the following ingredients;

|  | Amount (mg/capsule) |
| --- | --- |
| active ingredient | 250 |
| starch (dried) | 200 |
| magnesium stearate | 10 |
| Total | 460 mg |

Formulation Example 2

A tablet is prepared with the following ingredients;

|  | Amount (mg/tablet) |
| --- | --- |
| active ingredient | 250 |
| cellulose (micro crystalline) | 400 |
| silicon dioxide (fume) | 10 |
| stearic acid | 5 |
| Total | 665 mg |

The ingredients above are mixed and compressed to give a tablet weighing 665 mg/tablet.

Formulation Example 3

An aerosol solution is prepared with the following ingredients;

|  | weight |
| --- | --- |
| active ingredient | 0.25 |
| ethanol | 25.75 |
| propellant 22 (chlorodifluoroethane) | 74.00 |
| Total | 100.00 |

The active ingredient and ethanol are mixed and the mixture is added to a part of propellant 22, and the resulting solution is transferred to a filling apparatus after being cooled to −30° C. Next, the necessary amount is provided to a stainless-steel vessel and the content is diluted with the remaining propellant. A valve unit is fitted to the vessel.

Formulation Example 4

A tablet containing 60 mg of an active ingredient is prepared as follows;

| active ingredient | 60 mg |
| --- | --- |
| starch | 45 mg |
| microcrystalline cellulose | 35 mg |
| polyvinylpyrrolidone (10% aq. solution) | 4 mg |
| sodium carboxymethylstarch | 4.5 mg |
| magnesium stearate | 0.5 mg |
| talc | 1 mg |
| Total | 150 mg |

The active ingredient, starch and cellulose are put through a sieve of No. 45 mesh US and mixed sufficiently. The resulting powder is mixed with a solution containing polyvinylpyrrolidone and the mixture is put through a sieve of No. 14 mesh US. The granulated powder is dried at 50° C. and put through a sieve of No. 18 mesh US. Sodium carboxymethylstarch, magnesium stearate and talc are put through a sieve of No. 60 mesh US in advance and added to the granulated powder, mixed and compressed by a tableting machine to give a tablet weighing 150 mg/tablet.

Formulation Example 5

A capsule containing 80 mg of an active ingredient is prepared as follows;

| active ingredient | 80 mg |
| --- | --- |
| starch | 59 mg |
| microcrystalline cellulose | 59 mg |
| magnesium stearate | 2 mg |
| Total | 200 mg |

The active ingredient, starch, cellulose and magnesium stearate are mixed, put through a sieve of No. 45 mesh US and filled in hard-gelatin capsules to give a capsule formulation containing 200 mg/capsule.

Formulation Example 6

A suppository containing 225 mg of an active ingredient is prepared as follows;

| active ingredient | 225 mg |
| --- | --- |
| saturated fatty acid gliceride | 2000 mg |
| Total | 2225 mg |

The active ingredient is put through a sieve of No. 60 mesh US and suspended in the saturated fatty acid gliceride melted by the least amount of heating. Then, the mixture was cooled in a mold of 2 g in appearance.

Formulation Example 7

A suspension containing 50 mg of an active ingredient is prepared as follows;

| active ingredient | 50 mg |
| --- | --- |
| sodium carboxymethylcellulose | 50 mg |
| syrup | 1.25 ml |
| solution of benzoic acid | 0.10 ml |
| flavor | q.v. |
| pigment | q.v. |
| Total (adding purified water) | 5 ml |

The active ingredient is put through a sieve of No. 45 mesh US and mixed with sodium carboxymethylcellulose and syrup to give a smooth paste. The solution of benzoic acid and flavor are diluted with a part of water and added to the paste and stirred. A necessary amount of water is added to give the objective suspension.

245
Formulation Example 8

A formulation for i.v. injection is prepared as follows;

| active ingredient | 100 mg |
| saturated fatty acid gliceride | 1000 ml |

The solution containing the active ingredient above is usually injected intravenously to a patient at a rate of 1 ml/min.

Industrial Applicability

It was found that a novel sulfonamide derivative had a DP receptor antagonistic activity and was effective on treating allergic diseases.

The invention claimed is:

1. A method for treating asthma, comprising administering an effective amount of a compound of the following formula to a patient in need thereof,

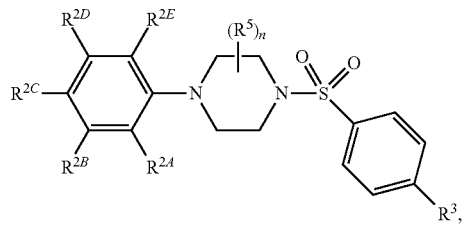

wherein:

$R^{2A}$ and $R^{2B}$ are each independently a hydrogen atom or

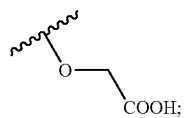

wherein at least one of $R^{2A}$ or $R^{2B}$ is

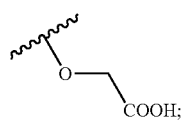

$R^{2C}$ is selected from the group consisting of:
a hydrogen atom, a halogen atom, $NO_2$, CN,

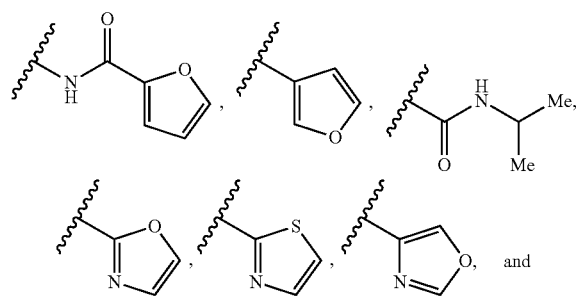

246
-continued

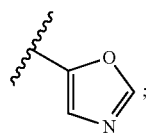

$R^{2D}$ is selected from the group consisting of:
a hydrogen atom, a halogen atom,

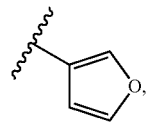

and $CF_3$;

$R^{2E}$ is a hydrogen atom;

$R^5$ is an alkyl group;

n is 0 or 1; and $R^3$ is optionally substituted alkoxy or optionally substituted alkylthio, or a pharmaceutically acceptable salt thereof.

2. A method for treating asthma, comprising administering an effective amount of a compound or a pharmaceutically acceptable salt thereof to a patient in need thereof, wherein the compound is selected from the group consisting of:

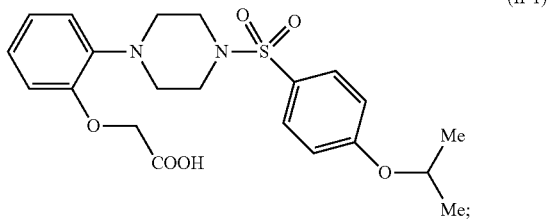
(II-1)

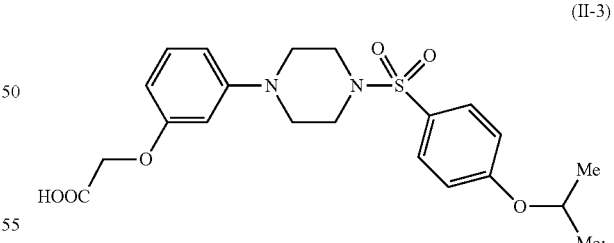
(II-3)

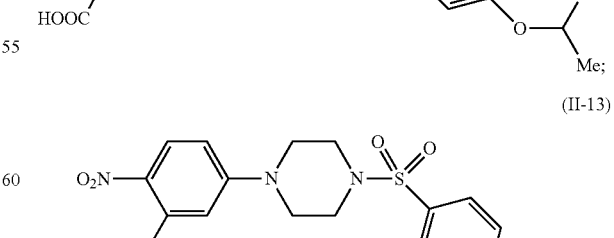
(II-13)

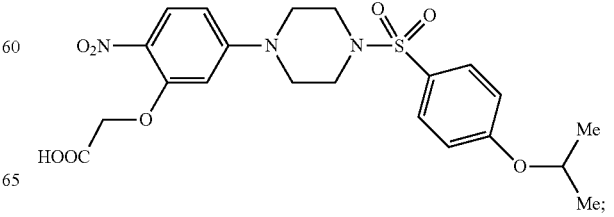

(II-16)
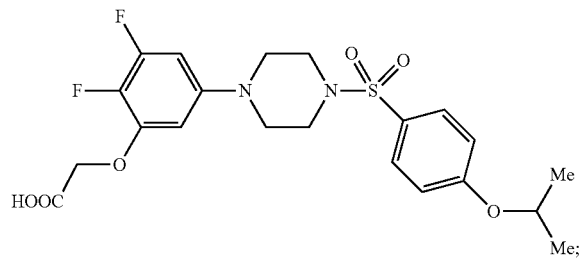
(II-17)
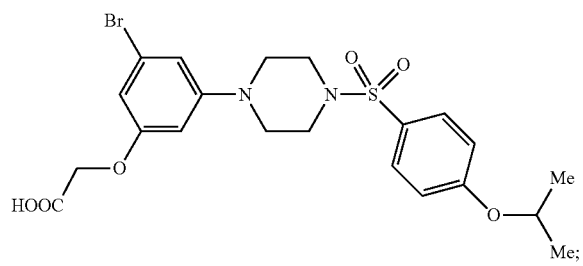
(II-19)
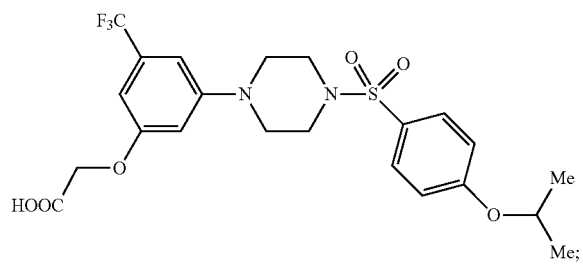
(II-24)
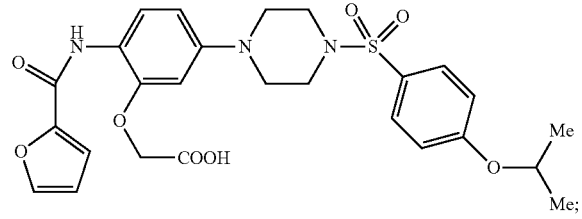
(II-26)
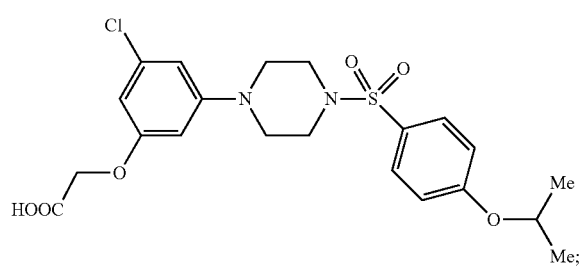
(II-29)
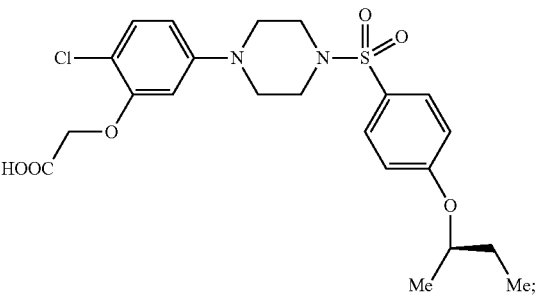
(II-33)
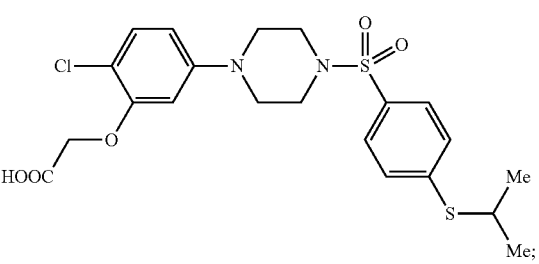
(II-35)
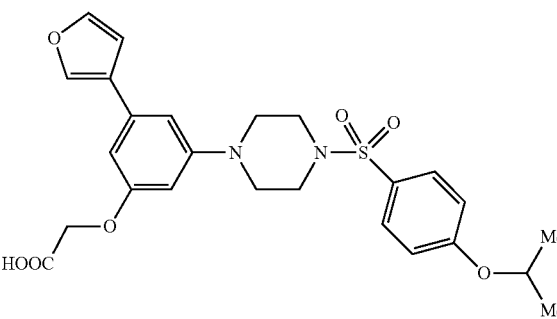
(II-38)
(II-43)
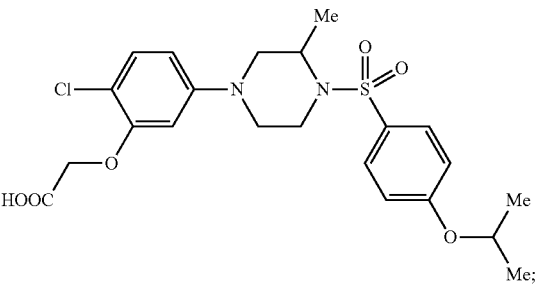

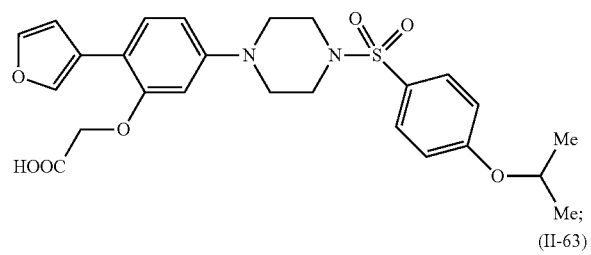
(II-54)

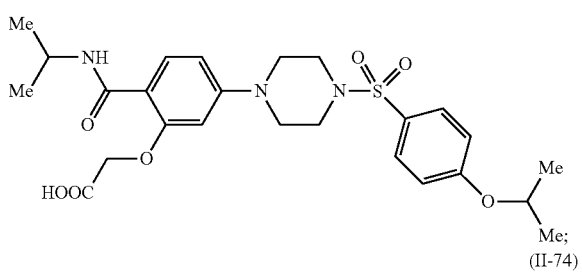
(II-63)

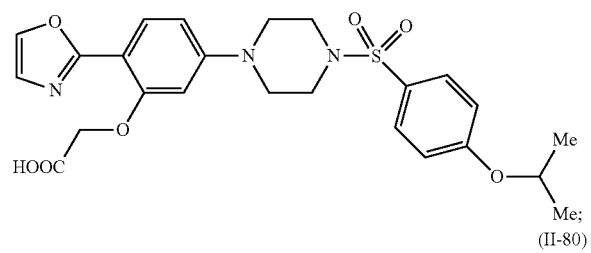
(II-74)

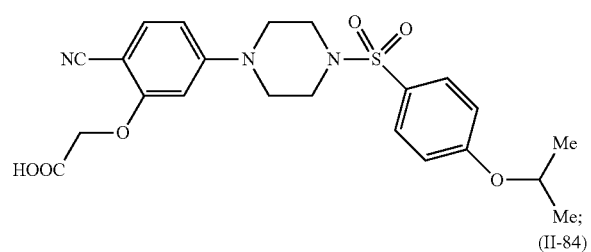
(II-80)

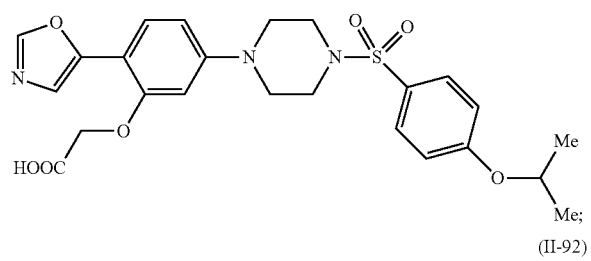
(II-84)

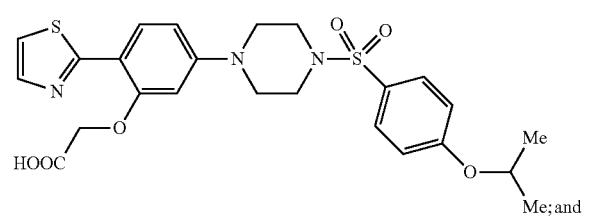
(II-92)

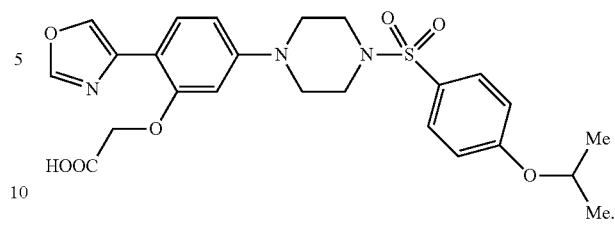
(II-96)

3. A method for treating asthma, comprising administering an effective amount of a compound of the formula

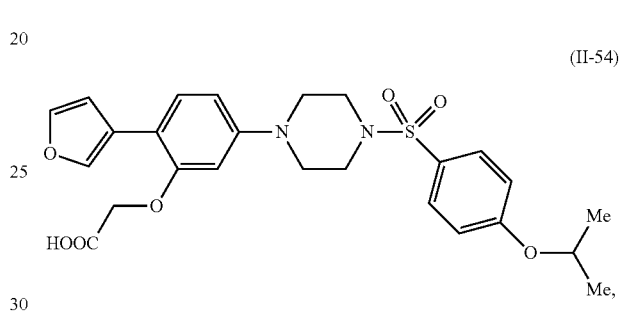
(II-54)

or a pharmaceutically acceptable salt thereof, to a patient in need thereof.

4. A method for treating asthma, comprising administering an effective amount of a compound of the formula

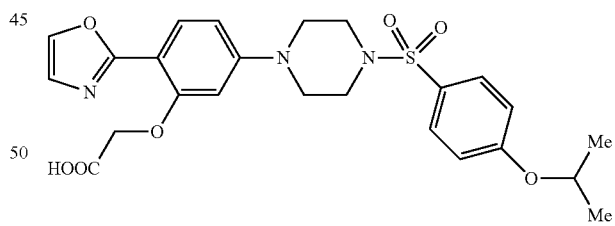

(II-74), or a pharmaceutically acceptable salt thereof, to a patient in need thereof.

* * * * *